US010023848B2

(12) United States Patent
Aman et al.

(10) Patent No.: US 10,023,848 B2
(45) Date of Patent: Jul. 17, 2018

(54) IMMUNOGENIC COMPOSITION COMPRISING PANTON-VALENTINE LEUKOCIDIN (PVL) DERIVED POLYPEPTIDES

(71) Applicant: Integrated BioTherapeutics, Inc., Gaithersburg, MD (US)

(72) Inventors: Mohammad Javad Aman, Rockville, MD (US); Rajan Prasad Adhikari, Gaithersburg, MD (US); Hatice Karauzum, Silver Spring, MD (US); Jawad Sarwar, Clarksburg, MD (US); Sergey Shulenin, Point of Rocks, MD (US); Sathya Venkataramani, Germantown, MD (US); Kelly Lyn Warfield, Adamstown, MD (US); Tam Luong Nguyen, Gaithersburg, MD (US)

(73) Assignee: INTEGRATED BIOTHERAPEUTICS, INC, Gaithersburg, MD (US)

( * ) Notice: Subject to any disclaimer, the term of this patent is extended or adjusted under 35 U.S.C. 154(b) by 123 days.

(21) Appl. No.: 14/362,298

(22) PCT Filed: Nov. 30, 2012

(86) PCT No.: PCT/US2012/067483

§ 371 (c)(1),
(2) Date: Jun. 2, 2014

(87) PCT Pub. No.: WO2013/082558

PCT Pub. Date: Jun. 6, 2013

(65) Prior Publication Data

US 2014/0308291 A1 Oct. 16, 2014

Related U.S. Application Data

(60) Provisional application No. 61/566,234, filed on Dec. 2, 2011.

(51) Int. Cl.

| | |
|---|---|
| ***C12N 9/10*** | (2006.01) |
| ***C07K 16/12*** | (2006.01) |
| ***C07K 16/40*** | (2006.01) |
| ***A61K 39/085*** | (2006.01) |
| ***C07K 14/31*** | (2006.01) |
| *A61K 39/00* | (2006.01) |

(52) U.S. Cl.

CPC .............. *C12N 9/10* (2013.01); *A61K 39/085* (2013.01); *C07K 14/31* (2013.01); *C07K 16/1271* (2013.01); *C07K 16/40* (2013.01); *A61K 2039/505* (2013.01); *A61K 2039/55505* (2013.01); *A61K 2039/55561* (2013.01); *A61K 2039/55566* (2013.01)

(58) Field of Classification Search

CPC .......... A61K 2039/55505; A61K 2039/55561; A61K 2039/55566; C07K 16/40; C07K 14/31; C12N 9/10

See application file for complete search history.

(56) References Cited

U.S. PATENT DOCUMENTS

| | | | | |
|---|---|---|---|---|
| 8,936,791 | B2 * | 1/2015 | Badiou | G01N 33/56938 424/234.1 |
| 2009/0074755 | A1 * | 3/2009 | Taylor et al. | 424/133.1 |
| 2010/0129839 | A1 * | 5/2010 | Badiou | G01N 33/56938 435/7.94 |
| 2010/0158871 | A1 | 6/2010 | Terman | |

FOREIGN PATENT DOCUMENTS

| | | | |
|---|---|---|---|
| WO | 2006/135912 | A2 | 12/2006 |
| WO | 2013/082558 | A1 | 6/2013 |

OTHER PUBLICATIONS

Bowie et al., Science, 1990; 257:1306-1310.*
Haddad et al., Applied and Environmental Microbiology, 2013; 79(8): 2828-2832.*
Kaneko et al., Biosci. Biotech. Biochem., 1997; 61(11): 1960-1962.*
Narita et al., Gene, 2001; 268: 195-206.*
Ma et al., Journal of Clinical Microbiology, 2008; 46(10): 3246-3258.*
Zhang et al., FEMS Microbiol. Lett, 2011; 323: 20-28.*
Adhikari et al., "Novel Structurally Designed Vaccine for *S. Aureus* a-Hemolysin: Protection against Bacteremia and Pneumonia", PLoS One, Jun. 6, 2012, pp. 1-11, vol. 7 Issue 6, e38567.
Alonzo et al., "*Staphylocuccus aureus* Luekocidin ED Contributes to Systemic Infection by Targeting Neutrophils and Promoting Bacterial Growth In Vivo", Molecular Microbiology, Jan. 2012, pp. 423-435, vol. 83 No. 2.
Aman et al., "Structural Model of the Pre-Pore Ring-Like Structure of Panton-Valentine Leukocidin: Providing Dimensionality to Biophysical and Mutational Data", Journal of Biomolecular Structure & Dynamics, 2010, pp. 1-12, vol. 28.
Appelbaum, "The Emergence of Vancomycin-Intermediate and Vancomycin-Resistant *Staphylococcus aureus*", European Society of Clinical Microbiology and Infectious Diseases, 2006, pp. 16-23, vol. 12 Supplement 1.
Brown et al., "Identification of a T-Cell Epitope in the *Staphylococcus aureus* Panton-Valentine LukS-PV Component", Open Journal of Immunology, 2012, pp. 111-115, vol. 2.
Bubeck Wardenburg et al., "Surface Proteins and Exotoxins are Required for the Pathogenesis of *Staphylococcus aureus* Pneumonia", Infection and Immunity, Feb. 2007, pp. 1040-1044, vol. 75 No. 2.

(Continued)

*Primary Examiner* — Gary B Nickol
*Assistant Examiner* — Lakia J Jackson-Tongue
(74) *Attorney, Agent, or Firm* — Thompson Coburn LLP

(57) ABSTRACT

The present disclosure provides immunogenic compositions useful in prevention and treatment of *Staphylococcus aureus* infection. In particular, the disclosure provides methods of inducing an immune response against a panton-valentine leukocidin (PVL)-expressing *S. aureus*, methods of preventing or treating *S. aureus* infections, and composition for preventing or treating *S. aureus* infections.

21 Claims, 19 Drawing Sheets

(56) References Cited

OTHER PUBLICATIONS

Chambers, "Community-Associated MRSA—Resistance and Virulence Converge", The New England Journal of Medicine, Apr. 7, 2005, pp. 1485-1487, vol. 352 No. 14.
Chambers, "Methicillin-Resistant *Staphylococci*", Clinical Microbiology Reviews, Apr. 1988, pp. 173-186, vol. 1 No. 2.
Coler et al., "A Synthetic Adjuvant to Enhance and Expand Immune Responses to Influenza Vaccines", PLoS One, Oct. 27, 2010, pp. 1-11, vol. 5 Issue 10, pp. e13677.
Coler et al., "Development and Characterization of Synthetic Glucopyranosyl Lipid Adjuvant System as a Vaccine Adjuvant", PLoS One, Jan. 26, 2011, pp. 1-12, vol. 6 Issue 1, pp. e16333.
Devi et al., "Disulfide Formation and Stability of a Cysteine-Rich Repeat Protein from Helicobacter Pylori", Biochemistry, 2006, pp. 1599-1607, vol. 45 No. 6.
Diep et al., "Complete Genome Sequence of USA300, an Epidemic Clone of Commuity-Aquired Meticillin-Resistant *Staphylococcus aureus*", Lancet, Mar. 4, 2006, pp. 731-739, vol. 367 No. 9512.
Diep et al., "The Role of Virulence Determinants in Community-Associated MRSA Pathogensis", Trends Mircrobiology, Aug. 2008, pp. 361-369, vol. 16 No. 8.
Enkhbaatar et al., "Novel Ovine Model of Methicillin-Resistant *Staphylococcus aureus*-Induced Pneumonia and Sepsis", Shock, 2008, pp. 642-649, vol. 29 No. 5.
Ericsson et al., "Thermofluor-based High-throughput Stability Optimization of Proteins for Structural Studies", Analytical Biochemistry, Aug. 10, 2006, pp. 289-298, vol. 357 No. 2.
Fattom et al., "A *Staphylococcus aureus* Capsular Polysaccharide (CP) Vaccine and CP-Specific Antibodies Protect Mice Against Bacterial Challenge", Infection and Immunity, May 1996, pp. 1659-1665, vol. 64 No. 5.
Ferreras et al., "The Interaction of *Staphylococcus aureus* Bi-Component g-Hemolysins and Leucocidins with Cells and Lipid Membranes", Biochimica et Biophysica Acta, Aug. 24, 1998, pp. 108-126, vol. 1414 No. 1-2.
GenBank accession No. NP_058465.1.
Guillet et al., "Crystal Structure of Leucotoxin S Component", Journal of Biological Chemistry, 2004, pp. 41028-41037, vol. 279, No. 39.
He et al., "High Throughput Thermostability Screening of Monoclonal Antibody Formulations", Journal of Pharmaceutical Sciences, Apr. 2010, pp. 1707-1720, vol. 99 No. 4.
International Search Report and Written Opinion for US/PCT2012/067483 dated Feb. 26, 2013.
Jayasinghe et al., "The Leukocidin Pore: Evidence for an Octamer with Four LukF Subunits and Four LukS Subunits Alternating Around a Central Axis", Protein Science, Jun. 25, 2005, pp. 2550-2561, vol. 14.
Kaneko et al., "Bacterial Two-Component and Hetero-Heptameric Pore-Forming Cytolytic Toxins: Structures, Pore-Forming Mechanism, and Organization of the Genes", Bioscience, Biotechnology, and Biochemistry, 2004, pp. 981-1003, vol. 68 No. 5.
Kaneko et al., "Complete Nucleotide Sequence and Molecular Characterization of the Temperate Staphylococcal Bacteriophage wPVL Carrying Panton-Valentine Leukocidin Genes", Gene, May 7, 1998, pp. 57-67, vol. 215 No. 1.
Karauzum et al., "Structurally Designed Attenuated Subunit Vaccines for *S. aureus* LukS-PV Confer Protection in a Mouse Bacteremia Model", PLOS One, Jun. 7, 2013, pp. e65384-e65384, vol. 8 No. 6.
Kephart et al., "Comparison of the Investigational Drug, LY146032, with Vancomycin in Experimental Pneumonia due to Methicillin-Resistant *Staphylococcus aureus*", Journal of Antimicrobial Chemotherapy, 1988, pp. 33-39, vol. 21.
Malachowa et al, "Global Changes in *Staphyloccus aureus* Gene Expression in Human Blood", PLoS One, Apr. 15, 2011, pp. 1-13, vol. 6 Issue 4, e18617.
McElroy et al., "Alpha-Toxin Damages the Air-Blood Barrier of the Lung in a Rat Model of *Staphlococcus aureus*-Induced Pneumonia", Infection and Immunity, Oct. 1999, pp. 5541-5544, vol. 67 No. 10.
Miles et al., "Assembly of the Bi-Component Leukocidin Pore Examined by Truncation Mutagenesis", Journal of Biological Chemistry, 2006, pp. 2205-2214, vol. 281.
Miles et al., "Subunit Composition of Bicomponent Toxin: Staphylococcal Leukocidin Forms an Octameric Transmembrane Pore", Protein Science, 2002, pp. 894-902, vol. 11 No. 4.
Mullen et al., "Phase 1 Trial of AMA1-C1/Alhydrogel Plus CPG 7909: An Asexual Blood-Stage Vaccine for Plasmodium Falciparum Malaria", PLoS One, Aug. 13, 2008, pp. 1-13, vol. 3 Issue 8, e2940.
Mulligan et al., "Methicillin-Resistant *Staphylococcus aureus*: A Consensus Review of the Microbiology, Pathogenesis, and Epidemiology With Implications for Prevention and Management", American Journal of Medicine, Mar. 1993, pp. 313-328, vol. 94.
Narita et al., "Phage Conversion of Panton-Valentine Leukocidin in *Staphylococcus aureus*: Molecular Analysis of a PVL-Converting Phage, fSLT", Gene, Feb. 13, 2001, pp. 195-206, vol. 268 No. 1-2.
Nguyen et al., "Single-Molecule Imaging of Cooperative Assembly of g-Hemolysin on Erythrocyte Membranes", The EMBO Journal, 2003, pp. 4968-4979, vol. 22 No. 19.
Pedelacq et al., "Crystal Structure of the F Component of the Panton-Valentine Leucocidin", Internal Journal of Medical Microbiology, 2000, pp. 395-401, vol. 290 No. 4-5.
Prevost et al., "Paton-Valentine Leucocidin and Gamma-Hemolysin from *Staphylococcus aureus* ATCC 49775 are Encoded by Distinct Genetic Loci and have Different Biological Activities", Infection and Immunity, Oct. 1995, pp. 4121-4129, vol. 63 No. 10.
Romero-Steiner et al., "Standardization of an Opsonophagocytic Assay for the Measurement of Functional Antibody Activity against *Streptococcus pneumoiae* Using Differentiated HL-60 Cells", Clinical and Diagnostic Laboratory Immunology, Jul. 1997, pp. 415-422, vol. 4 No. 4.
Ryding et al., "Antibody Response to *Staphylococcus aureus* Collagen Binding Protein in Patients with *S. aureus* Septicaemia and Collagen Binding Properties of Corresponding Strains", Journal of Medical Microbiology, 1995, pp. 328-334, vol. 43 No. 5.
Ventura et al., "Identification of a Novel *Staphyloccus aureus* Two-Component Leukotoxin Using Cell Surface Proteomics", PLoS One, Jul. 16, 2010, pp. 1-11, vol. 5 Issue 7, e11634.
Verghese et al., "LY146032 in a Hamster Model of *Staphylococcus aureus* Pneumonia—Effect on in vivo Clearance and Mortality and in vitro Opsonophagocytic Killing", Chemotherapy, 1988, pp. 497-503, vol. 34 No. 6.
Yamashita et al., "Crystal Structure of the Octameric Pore of Staphylococcal g-Hemolysin Reveals the b-Barrel Pore Formation Mechanism by Two Components", Proceedings of the National Academy of Sciences, Oct. 18, 2011, pp. 17314-17319, vol. 108 No. 42.

* cited by examiner

SEQUENCE LISTING

```
<160> NUMBER OF SEQ ID NOS: 143

<210> SEQ ID NO 1
<211> LENGTH: 60
<212> TYPE: PRT
<213> ORGANISM: Artificial Sequence
<220> FEATURE:
<223> OTHER INFORMATION: wild-type LukS-PV amino acid consensus sequence
      A
<220> FEATURE:
<221> NAME/KEY: misc_feature
<222> LOCATION: (1)..(1)
<223> OTHER INFORMATION: X can be Glu, Gln, or may be missing
<220> FEATURE:
<221> NAME/KEY: misc_feature
<222> LOCATION: (2)..(2)
<223> OTHER INFORMATION: X can be Asp, Gly, or may be missing
<220> FEATURE:
<221> NAME/KEY: misc_feature
<222> LOCATION: (3)..(3)
<223> OTHER INFORMATION: X can be Thr, Lys, Ile, Val, or may be missing
<220> FEATURE:
<221> NAME/KEY: misc_feature
<222> LOCATION: (4)..(4)
<223> OTHER INFORMATION: X can be Ser, Thr, Ala, or may be missing
<220> FEATURE:
<221> NAME/KEY: misc_feature
<222> LOCATION: (6)..(6)
<223> OTHER INFORMATION: X can be Asp, Lys, Asn, Arg, or may be missing
<220> FEATURE:
<221> NAME/KEY: misc_feature
<222> LOCATION: (7)..(7)
<223> OTHER INFORMATION: X can be Lys, Arg, or may be missing
<220> FEATURE:
<221> NAME/KEY: misc_feature
<222> LOCATION: (8)..(8)
<223> OTHER INFORMATION: X can be Trp, Leu, or may be missing
<220> FEATURE:
<221> NAME/KEY: misc_feature
<222> LOCATION: (9)..(9)
<223> OTHER INFORMATION: X can be Gly, Ala, or may be missing
<220> FEATURE:
<221> NAME/KEY: misc_feature
<222> LOCATION: (10)..(10)
<223> OTHER INFORMATION: X can be Val, Ile, or may be missing
<220> FEATURE:
<221> NAME/KEY: misc_feature
<222> LOCATION: (14)..(14)
<223> OTHER INFORMATION: X can be Ile, Val, or may be missing
<220> FEATURE:
<221> NAME/KEY: misc_feature
<222> LOCATION: (17)..(17)
<223> OTHER INFORMATION: X can be Asp, Gly, or may be missing
<220> FEATURE:
<221> NAME/KEY: misc_feature
<222> LOCATION: (19)..(19)
<223> OTHER INFORMATION: X can be Val or Met
<220> FEATURE:
<221> NAME/KEY: misc_feature
<222> LOCATION: (22)..(22)
<223> OTHER INFORMATION: X can be Lys, Thr, or Pro
<220> FEATURE:
<221> NAME/KEY: misc_feature
<222> LOCATION: (27)..(27)
<223> OTHER INFORMATION: X can be Asp, Asn, or Val
<220> FEATURE:
<221> NAME/KEY: misc_feature
```

<222> LOCATION: (30)..(30)
<223> OTHER INFORMATION: X can be Ile or Val
<220> FEATURE:
<221> NAME/KEY: misc_feature
<222> LOCATION: (31)..(31)
<223> OTHER INFORMATION: X can be Leu, Val, or Ile
<220> FEATURE:
<221> NAME/KEY: misc_feature
<222> LOCATION: (38)..(38)
<223> OTHER INFORMATION: X can be Asn, Ser, or Lys
<220> FEATURE:
<221> NAME/KEY: misc_feature
<222> LOCATION: (40)..(40)
<223> OTHER INFORMATION: X can be Lys or Arg
<220> FEATURE:
<221> NAME/KEY: misc_feature
<222> LOCATION: (42)..(42)
<223> OTHER INFORMATION: X can be Thr, Ser, or Ala
<220> FEATURE:
<221> NAME/KEY: misc_feature
<222> LOCATION: (43)..(43)
<223> OTHER INFORMATION: X can be Tyr or Phe
<220> FEATURE:
<221> NAME/KEY: misc_feature
<222> LOCATION: (44)..(44)
<223> OTHER INFORMATION: X can be Tyr, Ser, Asn, or Thr
<220> FEATURE:
<221> NAME/KEY: misc_feature
<222> LOCATION: (45)..(45)
<223> OTHER INFORMATION: X can be Asn or Asp
<220> FEATURE:
<221> NAME/KEY: misc_feature
<222> LOCATION: (46)..(46)
<223> OTHER INFORMATION: X can be Tyr, Val, Leu, Phe, or Ser
<220> FEATURE:
<221> NAME/KEY: misc_feature
<222> LOCATION: (48)..(48)
<223> OTHER INFORMATION: X can be Asn, Lys, Gly, or Gln
<220> FEATURE:
<221> NAME/KEY: misc_feature
<222> LOCATION: (49)..(49)
<223> OTHER INFORMATION: X can be Thr, Tyr, Ser, Asn, Lys, or Arg
<220> FEATURE:
<221> NAME/KEY: misc_feature
<222> LOCATION: (50)..(50)
<223> OTHER INFORMATION: X can be Gly or may be missing
<220> FEATURE:
<221> NAME/KEY: misc_feature
<222> LOCATION: (51)..(51)
<223> OTHER INFORMATION: X can be Tyr or may be missing
<220> FEATURE:
<221> NAME/KEY: misc_feature
<222> LOCATION: (52)..(52)
<223> OTHER INFORMATION: X can be Asp, Asn, Glu, Pro, or Arg
<220> FEATURE:
<221> NAME/KEY: misc_feature
<222> LOCATION: (53)..(53)
<223> OTHER INFORMATION: X can be His, Tyr, Leu, or Ala
<220> FEATURE:
<221> NAME/KEY: misc_feature
<222> LOCATION: (54)..(54)
<223> OTHER INFORMATION: X can be Ile, Thr, Val, or Asn
<220> FEATURE:
<221> NAME/KEY: misc_feature
<222> LOCATION: (56)..(56)
<223> OTHER INFORMATION: X can be Ala, Arg, or Ser
<220> FEATURE:
<221> NAME/KEY: misc_feature
<222> LOCATION: (57)..(57)
<223> OTHER INFORMATION: X can be Met, Ile, or Leu
<220> FEATURE:
<221> NAME/KEY: misc_feature
<222> LOCATION: (58)..(58)
<223> OTHER INFORMATION: X can be Arg, Ile, Val, or Leu

<400> SEQUENCE: 1

Xaa Xaa Xaa Xaa Ser Xaa Xaa Xaa Xaa Xaa Thr Gln Asn Xaa Gln Phe
1               5                   10                  15

```
Xaa Phe Xaa Lys Asp Xaa Lys Tyr Asn Lys Xaa Ala Leu Xaa Xaa Lys
            20                  25                  30

Met Gln Gly Phe Ile Xaa Ser Xaa Thr Xaa Xaa Xaa Xaa Xaa Lys Xaa
        35                  40                  45

Xaa Xaa Xaa Xaa Xaa Xaa Lys Xaa Xaa Xaa Trp Pro
    50                  55                  60


<210> SEQ ID NO 2
<211> LENGTH: 60
<212> TYPE: PRT
<213> ORGANISM: Artificial Sequence
<220> FEATURE:
<223> OTHER INFORMATION: wild-type LukS-PV amino acid consensus sequence
      B
<220> FEATURE:
<221> NAME/KEY: misc_feature
<222> LOCATION: (6)..(6)
<223> OTHER INFORMATION: X can be Gly, Ser, or Ala
<220> FEATURE:
<221> NAME/KEY: misc_feature
<222> LOCATION: (8)..(8)
<223> OTHER INFORMATION: X can be Lys, Thr, Ser, or Met
<220> FEATURE:
<221> NAME/KEY: misc_feature
<222> LOCATION: (9)..(9)
<223> OTHER INFORMATION: X can be Thr or Ser
<220> FEATURE:
<221> NAME/KEY: misc_feature
<222> LOCATION: (10)..(10)
<223> OTHER INFORMATION: X can be Asn or Lys
<220> FEATURE:
<221> NAME/KEY: misc_feature
<222> LOCATION: (12)..(12)
<223> OTHER INFORMATION: X can be Pro, Lys, Ser, or Gln
<220> FEATURE:
<221> NAME/KEY: misc_feature
<222> LOCATION: (13)..(13)
<223> OTHER INFORMATION: X can be Asn or Tyr
<220> FEATURE:
<221> NAME/KEY: misc_feature
<222> LOCATION: (14)..(14)
<223> OTHER INFORMATION: X can be Val, Thr, or Ile
<220> FEATURE:
<221> NAME/KEY: misc_feature
<222> LOCATION: (15)..(15)
<223> OTHER INFORMATION: X can be Asp, Ser, or Phe
<220> FEATURE:
<221> NAME/KEY: misc_feature
<222> LOCATION: (19)..(19)
<223> OTHER INFORMATION: X can be Ser or may be missing
<220> FEATURE:
<221> NAME/KEY: misc_feature
<222> LOCATION: (20)..(20)
<223> OTHER INFORMATION: X can be Ile or may be missing
<220> FEATURE:
<221> NAME/KEY: misc_feature
<222> LOCATION: (21)..(21)
<223> OTHER INFORMATION: X can be Tyr, His, or Thr
<220> FEATURE:
<221> NAME/KEY: misc_feature
<222> LOCATION: (25)..(25)
<223> OTHER INFORMATION: X can be Asn or Thr
<220> FEATURE:
<221> NAME/KEY: misc_feature
<222> LOCATION: (28)..(28)
<223> OTHER INFORMATION: X can be Asp or Glu
<220> FEATURE:
<221> NAME/KEY: misc_feature
<222> LOCATION: (29)..(29)
<223> OTHER INFORMATION: X can be Ser or Thr
<220> FEATURE:
<221> NAME/KEY: misc_feature
<222> LOCATION: (30)..(30)
<223> OTHER INFORMATION: X can be Val, Thr, Ala, or Ile
<220> FEATURE:
```

```
<221> NAME/KEY: misc_feature
<222> LOCATION: (31)..(31)
<223> OTHER INFORMATION: X can be Asn or Asp
<220> FEATURE:
<221> NAME/KEY: misc_feature
<222> LOCATION: (33)..(33)
<223> OTHER INFORMATION: X can be Ser or Gly
<220> FEATURE:
<221> NAME/KEY: misc_feature
<222> LOCATION: (35)..(35)
<223> OTHER INFORMATION: X can be Thr or Lys
<220> FEATURE:
<221> NAME/KEY: misc_feature
<222> LOCATION: (40)..(40)
<223> OTHER INFORMATION: X can be Ile or Val
<220> FEATURE:
<221> NAME/KEY: misc_feature
<222> LOCATION: (42)..(42)
<223> OTHER INFORMATION: X can be Gly or may be missing
<220> FEATURE:
<221> NAME/KEY: misc_feature
<222> LOCATION: (43)..(43)
<223> OTHER INFORMATION: X can be Asn, Lys, or may be missing
<220> FEATURE:
<221> NAME/KEY: misc_feature
<222> LOCATION: (44)..(44)
<223> OTHER INFORMATION: X can be Phe or may be missing
<220> FEATURE:
<221> NAME/KEY: misc_feature
<222> LOCATION: (45)..(45)
<223> OTHER INFORMATION: X can be Asn, Gln, or may be missing
<220> FEATURE:
<221> NAME/KEY: misc_feature
<222> LOCATION: (46)..(46)
<223> OTHER INFORMATION: X can be Ser, Thr, or may be missing
<220> FEATURE:
<221> NAME/KEY: misc_feature
<222> LOCATION: (47)..(47)
<223> OTHER INFORMATION: X can be Gly, Ala, Val, or may be missing
<220> FEATURE:
<221> NAME/KEY: misc_feature
<222> LOCATION: (48)..(48)
<223> OTHER INFORMATION: X can be Pro or may be missing
<220> FEATURE:
<221> NAME/KEY: misc_feature
<222> LOCATION: (49)..(49)
<223> OTHER INFORMATION: X can be Ser, Leu, or may be missing
<220> FEATURE:
<221> NAME/KEY: misc_feature
<222> LOCATION: (50)..(50)
<223> OTHER INFORMATION: X can be Thr, Leu, Ile, or may be missing
<220> FEATURE:
<221> NAME/KEY: misc_feature
<222> LOCATION: (51)..(51)
<223> OTHER INFORMATION: X can be Gly, Ala, or may be missing
<220> FEATURE:
<221> NAME/KEY: misc_feature
<222> LOCATION: (53)..(53)
<223> OTHER INFORMATION: X can be Asn, Ser, or Lys
<220> FEATURE:
<221> NAME/KEY: misc_feature
<222> LOCATION: (55)..(55)
<223> OTHER INFORMATION: X can be Ser, Ala, or Glu
<220> FEATURE:
<221> NAME/KEY: misc_feature
<222> LOCATION: (57)..(57)
<223> OTHER INFORMATION: X can be Asn or Ser

<400> SEQUENCE: 2

Phe Gln Tyr Asn Ile Xaa Leu Xaa Xaa Xaa Asp Xaa Xaa Xaa Xaa Leu
1               5                   10                  15

Ile Asn Xaa Xaa Xaa Leu Pro Lys Xaa Lys Ile Xaa Xaa Xaa Xaa Val
            20                  25                  30

Xaa Gln Xaa Leu Gly Tyr Asn Xaa Gly Xaa Xaa Xaa Xaa Xaa Xaa Xaa
        35                  40                  45
```

```
Xaa Xaa Xaa Gly Xaa Gly Xaa Phe Xaa Tyr Ser Lys
    50                  55                  60


<210> SEQ ID NO 3
<211> LENGTH: 60
<212> TYPE: PRT
<213> ORGANISM: Artificial Sequence
<220> FEATURE:
<223> OTHER INFORMATION: wild-type LukS-PV amino acid consensus sequence
      C
<220> FEATURE:
<221> NAME/KEY: misc_feature
<222> LOCATION: (2)..(2)
<223> OTHER INFORMATION: X can be Val or Ala
<220> FEATURE:
<221> NAME/KEY: misc_feature
<222> LOCATION: (3)..(3)
<223> OTHER INFORMATION: X can be Pro or Asp
<220> FEATURE:
<221> NAME/KEY: misc_feature
<222> LOCATION: (4)..(4)
<223> OTHER INFORMATION: X can be Asp or Asn
<220> FEATURE:
<221> NAME/KEY: misc_feature
<222> LOCATION: (5)..(5)
<223> OTHER INFORMATION: X can be Asn, Ser, or Asp
<220> FEATURE:
<221> NAME/KEY: misc_feature
<222> LOCATION: (6)..(6)
<223> OTHER INFORMATION: X can be Glu or Gln
<220> FEATURE:
<221> NAME/KEY: misc_feature
<222> LOCATION: (11)..(11)
<223> OTHER INFORMATION: X can be Val or Ile
<220> FEATURE:
<221> NAME/KEY: misc_feature
<222> LOCATION: (12)..(12)
<223> OTHER INFORMATION: X can be His, Gln, or Thr
<220> FEATURE:
<221> NAME/KEY: misc_feature
<222> LOCATION: (21)..(21)
<223> OTHER INFORMATION: X can be Ala or Thr
<220> FEATURE:
<221> NAME/KEY: misc_feature
<222> LOCATION: (23)..(23)
<223> OTHER INFORMATION: X can be Val or Leu
<220> FEATURE:
<221> NAME/KEY: misc_feature
<222> LOCATION: (27)..(27)
<223> OTHER INFORMATION: X can be Lys or Arg
<220> FEATURE:
<221> NAME/KEY: misc_feature
<222> LOCATION: (28)..(28)
<223> OTHER INFORMATION: X can be Gly or Asp
<220> FEATURE:
<221> NAME/KEY: misc_feature
<222> LOCATION: (29)..(29)
<223> OTHER INFORMATION: X can be Ser, Lys, or Thr
<220> FEATURE:
<221> NAME/KEY: misc_feature
<222> LOCATION: (30)..(30)
<223> OTHER INFORMATION: X can be Gly, Ser, or Lys
<220> FEATURE:
<221> NAME/KEY: misc_feature
<222> LOCATION: (31)..(31)
<223> OTHER INFORMATION: X can be Asp, Glu, or Leu
<220> FEATURE:
<221> NAME/KEY: misc_feature
<222> LOCATION: (32)..(32)
<223> OTHER INFORMATION: X can be Thr, Lys, or Ile
<220> FEATURE:
<221> NAME/KEY: misc_feature
<222> LOCATION: (33)..(33)
<223> OTHER INFORMATION: X can be Arg or may be missing
<220> FEATURE:
<221> NAME/KEY: misc_feature
<222> LOCATION: (34)..(34)
<223> OTHER INFORMATION: X can be Ser or Val
```

<220> FEATURE:
<221> NAME/KEY: misc_feature
<222> LOCATION: (35)..(35)
<223> OTHER INFORMATION: X can be Glu, Asp, or Asn
<220> FEATURE:
<221> NAME/KEY: misc_feature
<222> LOCATION: (36)..(36)
<223> OTHER INFORMATION: X can be Phe or Leu
<220> FEATURE:
<221> NAME/KEY: misc_feature
<222> LOCATION: (37)..(37)
<223> OTHER INFORMATION: X can be Glu or Lys
<220> FEATURE:
<221> NAME/KEY: misc_feature
<222> LOCATION: (38)..(38)
<223> OTHER INFORMATION: X can be Ile or Phe
<220> FEATURE:
<221> NAME/KEY: misc_feature
<222> LOCATION: (39)..(39)
<223> OTHER INFORMATION: X can be Thr, Ser, or Ala
<220> FEATURE:
<221> NAME/KEY: misc_feature
<222> LOCATION: (44)..(44)
<223> OTHER INFORMATION: X can be Met or Leu
<220> FEATURE:
<221> NAME/KEY: misc_feature
<222> LOCATION: (46)..(46)
<223> OTHER INFORMATION: X can be Val, Ala, Ile, or Thr
<220> FEATURE:
<221> NAME/KEY: misc_feature
<222> LOCATION: (48)..(48)
<223> OTHER INFORMATION: X can be His or Tyr
<220> FEATURE:
<221> NAME/KEY: misc_feature
<222> LOCATION: (50)..(50)
<223> OTHER INFORMATION: X can be Thr, Ile, or Tyr
<220> FEATURE:
<221> NAME/KEY: misc_feature
<222> LOCATION: (51)..(51)
<223> OTHER INFORMATION: X can be Arg, Lys, Val, Leu, or Phe
<220> FEATURE:
<221> NAME/KEY: misc_feature
<222> LOCATION: (52)..(52)
<223> OTHER INFORMATION: X can be Arg, Thr, Phe, or Leu
<220> FEATURE:
<221> NAME/KEY: misc_feature
<222> LOCATION: (53)..(53)
<223> OTHER INFORMATION: X can be Thr, Ser, Arg, or Pro
<220> FEATURE:
<221> NAME/KEY: misc_feature
<222> LOCATION: (54)..(54)
<223> OTHER INFORMATION: X can be Thr, His, Arg, Lys, or Pro
<220> FEATURE:
<221> NAME/KEY: misc_feature
<222> LOCATION: (55)..(55)
<223> OTHER INFORMATION: X can be His, Arg, Thr, Leu, or Gln
<220> FEATURE:
<221> NAME/KEY: misc_feature
<222> LOCATION: (56)..(56)
<223> OTHER INFORMATION: X can be Tyr or may be missing
<220> FEATURE:
<221> NAME/KEY: misc_feature
<222> LOCATION: (57)..(57)
<223> OTHER INFORMATION: X can be Gly or may be missing
<220> FEATURE:
<221> NAME/KEY: misc_feature
<222> LOCATION: (58)..(58)
<223> OTHER INFORMATION: X can be Asn or may be missing
<220> FEATURE:
<221> NAME/KEY: misc_feature
<222> LOCATION: (59)..(59)
<223> OTHER INFORMATION: X can be Ser or may be missing
<220> FEATURE:
<221> NAME/KEY: misc_feature
<222> LOCATION: (60)..(60)
<223> OTHER INFORMATION: X can be Tyr or Gly

<400> SEQUENCE: 3

-continued

```
Phe Xaa Xaa Xaa Xaa Xaa Leu Pro Pro Leu Xaa Xaa Ser Gly Phe Asn
1               5                   10                  15

Pro Ser Phe Ile Xaa Thr Xaa Ser His Glu Xaa Xaa Xaa Xaa Xaa Xaa
            20                  25                  30

Xaa Xaa Xaa Xaa Xaa Xaa Xaa Tyr Gly Arg Asn Xaa Asp Xaa Thr Xaa
        35                  40                  45

Ala Xaa Xaa Xaa Xaa Xaa Xaa Xaa Xaa Xaa Xaa Xaa
    50                  55                  60
```

<210> SEQ ID NO 4
<211> LENGTH: 60
<212> TYPE: PRT
<213> ORGANISM: Artificial Sequence
<220> FEATURE:
<223> OTHER INFORMATION: wild-type LukF-PV amino acid consensus sequence
<220> FEATURE:
<221> NAME/KEY: misc_feature
<222> LOCATION: (2)..(2)
<223> OTHER INFORMATION: X can be Val, Ile, or Ala
<220> FEATURE:
<221> NAME/KEY: misc_feature
<222> LOCATION: (4)..(4)
<223> OTHER INFORMATION: X can be Asp or His
<220> FEATURE:
<221> NAME/KEY: misc_feature
<222> LOCATION: (18)..(18)
<223> OTHER INFORMATION: X can be Asn or Gln
<220> FEATURE:
<221> NAME/KEY: misc_feature
<222> LOCATION: (20)..(20)
<223> OTHER INFORMATION: X can be Leu or Val
<220> FEATURE:
<221> NAME/KEY: misc_feature
<222> LOCATION: (23)..(23)
<223> OTHER INFORMATION: X can be Ser or Thr
<220> FEATURE:
<221> NAME/KEY: misc_feature
<222> LOCATION: (24)..(24)
<223> OTHER INFORMATION: X can be Phe or Tyr
<220> FEATURE:
<221> NAME/KEY: misc_feature
<222> LOCATION: (29)..(29)
<223> OTHER INFORMATION: X can be Ser or Asn
<220> FEATURE:
<221> NAME/KEY: misc_feature
<222> LOCATION: (31)..(31)
<223> OTHER INFORMATION: X can be Ser, Ile, Asn, or Thr
<220> FEATURE:
<221> NAME/KEY: misc_feature
<222> LOCATION: (32)..(32)
<223> OTHER INFORMATION: X can be Lys or Asn
<220> FEATURE:
<221> NAME/KEY: misc_feature
<222> LOCATION: (35)..(35)
<223> OTHER INFORMATION: X can be Ser or Thr
<220> FEATURE:
<221> NAME/KEY: misc_feature
<222> LOCATION: (38)..(38)
<223> OTHER INFORMATION: X can be Leu or Gly
<220> FEATURE:
<221> NAME/KEY: misc_feature
<222> LOCATION: (41)..(41)
<223> OTHER INFORMATION: X can be Ser or Asn
<220> FEATURE:
<221> NAME/KEY: misc_feature
<222> LOCATION: (42)..(42)
<223> OTHER INFORMATION: X can be Glu, Thr, or Lys
<220> FEATURE:
<221> NAME/KEY: misc_feature
<222> LOCATION: (43)..(43)
<223> OTHER INFORMATION: X can be Ser or Ala
<220> FEATURE:
<221> NAME/KEY: misc_feature
<222> LOCATION: (57)..(57)
<223> OTHER INFORMATION: X can be Thr or may be missing
<220> FEATURE:
<221> NAME/KEY: misc_feature
<222> LOCATION: (58)..(58)
<223> OTHER INFORMATION: X can be Thr or Ser
<220> FEATURE:
<221> NAME/KEY: misc_feature
<222> LOCATION: (59)..(59)
<223> OTHER INFORMATION: X can be Ile or Leu
<220> FEATURE:
<221> NAME/KEY: misc_feature
<222> LOCATION: (60)..(60)
<223> OTHER INFORMATION: X can be Asp or Ser

<400> SEQUENCE: 4

```
Asn Xaa Val Xaa Tyr Ala Pro Lys Asn Gln Asn Glu Glu Phe Gln Val
1               5                   10                  15

Gln Xaa Thr Xaa Gly Tyr Xaa Xaa Gly Gly Asp Ile Xaa Ile Xaa Xaa
            20                  25                  30

Gly Leu Xaa Gly Gly Xaa Asn Gly Xaa Xaa Xaa Phe Ser Glu Thr Ile
        35                  40                  45

Asn Tyr Lys Gln Glu Ser Tyr Arg Xaa Xaa Xaa Xaa
    50                  55                  60
```

<210> SEQ ID NO 5
<211> LENGTH: 312
<212> TYPE: PRT
<213> ORGANISM: Artificial Sequence
<220> FEATURE:
<223> OTHER INFORMATION: wild-type LukS-PV amino acid sequence (with signal peptide)

<400> SEQUENCE: 5

```
Met Val Lys Lys Arg Leu Leu Ala Ala Thr Leu Ser Leu Gly Ile Ile
1               5                   10                  15

Thr Pro Ile Ala Thr Ser Phe His Glu Ser Lys Ala Asp Asn Asn Ile
            20                  25                  30

Glu Asn Ile Gly Asp Gly Ala Glu Val Val Lys Arg Thr Glu Asp Thr
        35                  40                  45

Ser Ser Asp Lys Trp Gly Val Thr Gln Asn Ile Gln Phe Asp Phe Val
    50                  55                  60

Lys Asp Lys Lys Tyr Asn Lys Asp Ala Leu Ile Leu Lys Met Gln Gly
65                  70                  75                  80

Phe Ile Asn Ser Lys Thr Thr Tyr Tyr Asn Tyr Lys Asn Thr Asp His
                85                  90                  95

Ile Lys Ala Met Arg Trp Pro Phe Gln Tyr Asn Ile Gly Leu Lys Thr
            100                 105                 110

Asn Asp Pro Asn Val Asp Leu Ile Asn Tyr Leu Pro Lys Asn Lys Ile
        115                 120                 125

Asp Ser Val Asn Val Ser Gln Thr Leu Gly Tyr Asn Ile Gly Gly Asn
    130                 135                 140

Phe Asn Ser Gly Pro Ser Thr Gly Gly Asn Gly Ser Phe Asn Tyr Ser
145                 150                 155                 160

Lys Thr Ile Ser Tyr Asn Gln Gln Asn Tyr Ile Ser Glu Val Glu His
                165                 170                 175

Gln Asn Ser Lys Ser Val Gln Trp Gly Ile Lys Ala Asn Ser Phe Ile
            180                 185                 190

Thr Ser Leu Gly Lys Met Ser Gly His Asp Pro Asn Leu Phe Val Gly
        195                 200                 205

Tyr Lys Pro Tyr Ser Gln Asn Pro Arg Asp Tyr Phe Val Pro Asp Asn
    210                 215                 220
```

```
Glu Leu Pro Pro Leu Val His Ser Gly Phe Asn Pro Ser Phe Ile Ala
225                 230                 235                 240

Thr Val Ser His Glu Lys Gly Ser Gly Asp Thr Ser Glu Phe Glu Ile
                245                 250                 255

Thr Tyr Gly Arg Asn Met Asp Val Thr His Ala Thr Arg Arg Thr Thr
            260                 265                 270

His Tyr Gly Asn Ser Tyr Leu Glu Gly Ser Arg Ile His Asn Ala Phe
        275                 280                 285

Val Asn Arg Asn Tyr Thr Val Lys Tyr Glu Val Asn Trp Lys Thr His
    290                 295                 300

Glu Ile Lys Val Lys Gly His Asn
305                 310
```

```
<210> SEQ ID NO 6
<211> LENGTH: 284
<212> TYPE: PRT
<213> ORGANISM: Artificial Sequence
<220> FEATURE:
<223> OTHER INFORMATION: wild-type LukS-PV amino acid sequence (without
      signal peptide)

<400> SEQUENCE: 6

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
```

```
            260                 265                 270

Trp Lys Thr His Glu Ile Lys Val Lys Gly His Asn
        275                 280
```

<210> SEQ ID NO 7
<211> LENGTH: 284
<212> TYPE: PRT
<213> ORGANISM: Artificial Sequence
<220> FEATURE:
<223> OTHER INFORMATION: mutant LukS-PV amino acid sequence-Lys97Ala (K97A)

<400> SEQUENCE: 7

```
Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Ala Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280
```

<210> SEQ ID NO 8
<211> LENGTH: 284
<212> TYPE: PRT
<213> ORGANISM: Artificial Sequence
<220> FEATURE:
<223> OTHER INFORMATION: mutant LukS-PV amino acid sequence-Asp101Ala (D101A)

<400> SEQUENCE: 8

Asp Asn Asn Ile Glu Asn Ile Gly Asp Gly Ala Glu Val Val Lys Arg
1 5 10 15

Thr Glu Asp Thr Ser Ser Asp Lys Trp Gly Val Thr Gln Asn Ile Gln
20 25 30

Phe Asp Phe Val Lys Asp Lys Lys Tyr Asn Lys Asp Ala Leu Ile Leu
35 40 45

Lys Met Gln Gly Phe Ile Asn Ser Lys Thr Thr Tyr Tyr Asn Tyr Lys
50 55 60

Asn Thr Asp His Ile Lys Ala Met Arg Trp Pro Phe Gln Tyr Asn Ile
65 70 75 80

Gly Leu Lys Thr Asn Asp Pro Asn Val Asp Leu Ile Asn Tyr Leu Pro
85 90 95

Lys Asn Lys Ile Ala Ser Val Asn Val Ser Gln Thr Leu Gly Tyr Asn
100 105 110

Ile Gly Gly Asn Phe Asn Ser Gly Pro Ser Thr Gly Gly Asn Gly Ser
115 120 125

Phe Asn Tyr Ser Lys Thr Ile Ser Tyr Asn Gln Gln Asn Tyr Ile Ser
130 135 140

Glu Val Glu His Gln Asn Ser Lys Ser Val Gln Trp Gly Ile Lys Ala
145 150 155 160

Asn Ser Phe Ile Thr Ser Leu Gly Lys Met Ser Gly His Asp Pro Asn
165 170 175

Leu Phe Val Gly Tyr Lys Pro Tyr Ser Gln Asn Pro Arg Asp Tyr Phe
180 185 190

Val Pro Asp Asn Glu Leu Pro Pro Leu Val His Ser Gly Phe Asn Pro
195 200 205

Ser Phe Ile Ala Thr Val Ser His Glu Lys Gly Ser Gly Asp Thr Ser
210 215 220

Glu Phe Glu Ile Thr Tyr Gly Arg Asn Met Asp Val Thr His Ala Thr
225 230 235 240

Arg Arg Thr Thr His Tyr Gly Asn Ser Tyr Leu Glu Gly Ser Arg Ile
245 250 255

His Asn Ala Phe Val Asn Arg Asn Tyr Thr Val Lys Tyr Glu Val Asn
260 265 270

Trp Lys Thr His Glu Ile Lys Val Lys Gly His Asn
275 280

<210> SEQ ID NO 9
<211> LENGTH: 284
<212> TYPE: PRT
<213> ORGANISM: Artificial Sequence
<220> FEATURE:
<223> OTHER INFORMATION: mutant LukS-PV amino acid sequence-Tyr131Ala
(Y131A)

<400> SEQUENCE: 9

Asp Asn Asn Ile Glu Asn Ile Gly Asp Gly Ala Glu Val Val Lys Arg
1 5 10 15

Thr Glu Asp Thr Ser Ser Asp Lys Trp Gly Val Thr Gln Asn Ile Gln
20 25 30

Phe Asp Phe Val Lys Asp Lys Lys Tyr Asn Lys Asp Ala Leu Ile Leu
35 40 45

Lys Met Gln Gly Phe Ile Asn Ser Lys Thr Thr Tyr Tyr Asn Tyr Lys
50 55 60

Asn Thr Asp His Ile Lys Ala Met Arg Trp Pro Phe Gln Tyr Asn Ile
65 70 75 80

Gly Leu Lys Thr Asn Asp Pro Asn Val Asp Leu Ile Asn Tyr Leu Pro
85 90 95

Lys Asn Lys Ile Asp Ser Val Asn Val Ser Gln Thr Leu Gly Tyr Asn
100 105 110

Ile Gly Gly Asn Phe Asn Ser Gly Pro Ser Thr Gly Gly Asn Gly Ser
115 120 125

Phe Asn Ala Ser Lys Thr Ile Ser Tyr Asn Gln Gln Asn Tyr Ile Ser
130 135 140

Glu Val Glu His Gln Asn Ser Lys Ser Val Gln Trp Gly Ile Lys Ala
145 150 155 160

Asn Ser Phe Ile Thr Ser Leu Gly Lys Met Ser Gly His Asp Pro Asn
165 170 175

Leu Phe Val Gly Tyr Lys Pro Tyr Ser Gln Asn Pro Arg Asp Tyr Phe
180 185 190

Val Pro Asp Asn Glu Leu Pro Pro Leu Val His Ser Gly Phe Asn Pro
195 200 205

Ser Phe Ile Ala Thr Val Ser His Glu Lys Gly Ser Gly Asp Thr Ser
210 215 220

Glu Phe Glu Ile Thr Tyr Gly Arg Asn Met Asp Val Thr His Ala Thr
225 230 235 240

Arg Arg Thr Thr His Tyr Gly Asn Ser Tyr Leu Glu Gly Ser Arg Ile
245 250 255

His Asn Ala Phe Val Asn Arg Asn Tyr Thr Val Lys Tyr Glu Val Asn
260 265 270

Trp Lys Thr His Glu Ile Lys Val Lys Gly His Asn
275 280

<210> SEQ ID NO 10
<211> LENGTH: 284
<212> TYPE: PRT
<213> ORGANISM: Artificial Sequence
<220> FEATURE:
<223> OTHER INFORMATION: mutant LukS-PV amino acid sequence-Ser209Ala (S209A)

<400> SEQUENCE: 10

Asp Asn Asn Ile Glu Asn Ile Gly Asp Gly Ala Glu Val Val Lys Arg
1 5 10 15

Thr Glu Asp Thr Ser Ser Asp Lys Trp Gly Val Thr Gln Asn Ile Gln
20 25 30

Phe Asp Phe Val Lys Asp Lys Lys Tyr Asn Lys Asp Ala Leu Ile Leu
35 40 45

Lys Met Gln Gly Phe Ile Asn Ser Lys Thr Thr Tyr Tyr Asn Tyr Lys
50 55 60

Asn Thr Asp His Ile Lys Ala Met Arg Trp Pro Phe Gln Tyr Asn Ile
65 70 75 80

Gly Leu Lys Thr Asn Asp Pro Asn Val Asp Leu Ile Asn Tyr Leu Pro
85 90 95

Lys Asn Lys Ile Asp Ser Val Asn Val Ser Gln Thr Leu Gly Tyr Asn
100 105 110

Ile Gly Gly Asn Phe Asn Ser Gly Pro Ser Thr Gly Gly Asn Gly Ser
115 120 125

Phe Asn Tyr Ser Lys Thr Ile Ser Tyr Asn Gln Gln Asn Tyr Ile Ser
130 135 140

```
Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ala Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280


<210> SEQ ID NO 11
<211> LENGTH: 284
<212> TYPE: PRT
<213> ORGANISM: Artificial Sequence
<220> FEATURE:
<223> OTHER INFORMATION: mutant LukS-PV amino acid sequence-Thr28Phe
      (T28F)

<400> SEQUENCE: 11

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Phe Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
```

```
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280


<210> SEQ ID NO 12
<211> LENGTH: 284
<212> TYPE: PRT
<213> ORGANISM: Artificial Sequence
<220> FEATURE:
<223> OTHER INFORMATION: LukS-PV amino acid sequence-Thr28Phe/Tyr131Ala
      (T28F/Y131A)

<400> SEQUENCE: 12

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Phe Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Ala Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280
```

-continued

<210> SEQ ID NO 13
<211> LENGTH: 284
<212> TYPE: PRT
<213> ORGANISM: Artificial Sequence
<220> FEATURE:
<223> OTHER INFORMATION: mutant LukS-PV amino acid sequence-
Thr28Phe/Ser209Ala (T28F/S209A)

<400> SEQUENCE: 13

Asp Asn Asn Ile Glu Asn Ile Gly Asp Gly Ala Glu Val Val Lys Arg
1 5 10 15

Thr Glu Asp Thr Ser Ser Asp Lys Trp Gly Val Phe Gln Asn Ile Gln
20 25 30

Phe Asp Phe Val Lys Asp Lys Lys Tyr Asn Lys Asp Ala Leu Ile Leu
35 40 45

Lys Met Gln Gly Phe Ile Asn Ser Lys Thr Thr Tyr Tyr Asn Tyr Lys
50 55 60

Asn Thr Asp His Ile Lys Ala Met Arg Trp Pro Phe Gln Tyr Asn Ile
65 70 75 80

Gly Leu Lys Thr Asn Asp Pro Asn Val Asp Leu Ile Asn Tyr Leu Pro
85 90 95

Lys Asn Lys Ile Asp Ser Val Asn Val Ser Gln Thr Leu Gly Tyr Asn
100 105 110

Ile Gly Gly Asn Phe Asn Ser Gly Pro Ser Thr Gly Gly Asn Gly Ser
115 120 125

Phe Asn Tyr Ser Lys Thr Ile Ser Tyr Asn Gln Gln Asn Tyr Ile Ser
130 135 140

Glu Val Glu His Gln Asn Ser Lys Ser Val Gln Trp Gly Ile Lys Ala
145 150 155 160

Asn Ser Phe Ile Thr Ser Leu Gly Lys Met Ser Gly His Asp Pro Asn
165 170 175

Leu Phe Val Gly Tyr Lys Pro Tyr Ser Gln Asn Pro Arg Asp Tyr Phe
180 185 190

Val Pro Asp Asn Glu Leu Pro Pro Leu Val His Ser Gly Phe Asn Pro
195 200 205

Ala Phe Ile Ala Thr Val Ser His Glu Lys Gly Ser Gly Asp Thr Ser
210 215 220

Glu Phe Glu Ile Thr Tyr Gly Arg Asn Met Asp Val Thr His Ala Thr
225 230 235 240

Arg Arg Thr Thr His Tyr Gly Asn Ser Tyr Leu Glu Gly Ser Arg Ile
245 250 255

His Asn Ala Phe Val Asn Arg Asn Tyr Thr Val Lys Tyr Glu Val Asn
260 265 270

Trp Lys Thr His Glu Ile Lys Val Lys Gly His Asn
275 280

<210> SEQ ID NO 14
<211> LENGTH: 284
<212> TYPE: PRT
<213> ORGANISM: Artificial Sequence
<220> FEATURE:
<223> OTHER INFORMATION: mutant LukS-PV amino acid sequence-
Thr28Phe/Lys97Ala/Ser209Ala (T28F/K97A/S209A)

<400> SEQUENCE: 14

Asp Asn Asn Ile Glu Asn Ile Gly Asp Gly Ala Glu Val Val Lys Arg
1 5 10 15

```
Thr Glu Asp Thr Ser Ser Asp Lys Trp Gly Val Phe Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Ala Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ala Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280


<210> SEQ ID NO 15
<211> LENGTH: 311
<212> TYPE: PRT
<213> ORGANISM: Artificial Sequence
<220> FEATURE:
<223> OTHER INFORMATION: wild-type LukS-PV amino acid sequence

<400> SEQUENCE: 15

Met Val Lys Lys Arg Leu Leu Ala Ala Thr Leu Ser Leu Gly Ile Ile
1               5                   10                  15

Thr Pro Ile Ala Thr Ser Phe His Glu Ser Lys Ala Asp Asn Asn Ile
            20                  25                  30

Glu Asn Ile Gly Asp Gly Ala Glu Val Val Lys Arg Thr Glu Asp Thr
        35                  40                  45

Ser Ser Asp Lys Trp Gly Val Thr Gln Asn Ile Gln Phe Asp Phe Val
    50                  55                  60

Lys Asp Lys Lys Tyr Asn Lys Asp Ala Leu Ile Leu Lys Met Gln Gly
65                  70                  75                  80

Phe Ile Asn Ser Lys Thr Thr Tyr Tyr Asn Tyr Lys Asn Thr Asp His
                85                  90                  95
```

-continued

```
Ile Lys Ala Met Arg Trp Pro Phe Gln Tyr Asn Ile Gly Leu Lys Thr
            100                 105                 110

Asn Asp Pro Asn Val Asp Leu Ile Asn Tyr Leu Pro Lys Asn Lys Ile
        115                 120                 125

Asp Ser Val Asn Val Ser Gln Thr Leu Gly Tyr Asn Ile Gly Gly Asn
    130                 135                 140

Phe Asn Ser Gly Pro Ser Thr Gly Gly Asn Gly Ser Phe Asn Tyr Ser
145                 150                 155                 160

Lys Thr Ile Ser Tyr Asn Gln Gln Asn Tyr Ile Ser Glu Val Glu Arg
                165                 170                 175

Gln Asn Ser Lys Ser Val Gln Trp Gly Ile Lys Ala Asn Ser Phe Ile
            180                 185                 190

Thr Ser Leu Gly Lys Met Ser Gly His Asp Pro Asn Leu Phe Val Gly
        195                 200                 205

Tyr Lys Pro Tyr Ser Gln Asn Pro Arg Asp Tyr Phe Val Pro Asp Asn
    210                 215                 220

Glu Leu Pro Pro Leu Val His Ser Gly Phe Asn Pro Ser Phe Ile Ala
225                 230                 235                 240

Val Ser His Glu Lys Gly Ser Gly Asp Thr Ser Glu Phe Glu Ile Thr
                245                 250                 255

Tyr Gly Arg Asn Met Asp Val Thr His Ala Thr Arg Arg Thr Thr His
            260                 265                 270

Tyr Gly Asn Ser Tyr Leu Glu Gly Ser Arg Ile His Asn Ala Phe Val
        275                 280                 285

Asn Arg Asn Tyr Thr Val Lys Tyr Glu Val Asn Trp Lys Thr His Glu
    290                 295                 300

Ile Lys Val Lys Gly His Asn
305                 310


<210> SEQ ID NO 16
<211> LENGTH: 325
<212> TYPE: PRT
<213> ORGANISM: Artificial Sequence
<220> FEATURE:
<223> OTHER INFORMATION: wild-type LukF-PV amino acid sequence (with
      signal peptide)

<400> SEQUENCE: 16

Met Lys Lys Ile Val Lys Ser Ser Val Val Thr Ser Ile Ala Leu Leu
1               5                   10                  15

Leu Leu Ser Asn Thr Val Asp Ala Ala Gln His Ile Thr Pro Val Ser
            20                  25                  30

Glu Lys Lys Val Asp Asp Lys Ile Thr Leu Tyr Lys Thr Thr Ala Thr
        35                  40                  45

Ser Asp Ser Asp Lys Leu Lys Ile Ser Gln Ile Leu Thr Phe Asn Phe
    50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140
```

Asp Ile Asn Ile Ser Asn Gly Leu Ser Gly Gly Gly Asn Gly Ser Lys
145 150 155 160

Ser Phe Ser Glu Thr Ile Asn Tyr Lys Gln Glu Ser Tyr Arg Thr Ser
165 170 175

Leu Asp Lys Arg Thr Asn Phe Lys Lys Ile Gly Trp Asp Val Glu Ala
180 185 190

His Lys Ile Met Asn Asn Gly Trp Gly Pro Tyr Gly Arg Asp Ser Tyr
195 200 205

His Ser Thr Tyr Gly Asn Glu Met Phe Leu Gly Ser Arg Gln Ser Asn
210 215 220

Leu Asn Ala Gly Gln Asn Phe Leu Glu Tyr His Lys Met Pro Val Leu
225 230 235 240

Ser Arg Gly Asn Phe Asn Pro Glu Phe Ile Gly Val Leu Ser Arg Lys
245 250 255

Gln Asn Ala Ala Lys Lys Ser Lys Ile Thr Val Thr Tyr Gln Arg Glu
260 265 270

Met Asp Arg Tyr Thr Asn Phe Trp Asn Gln Leu His Trp Ile Gly Asn
275 280 285

Asn Tyr Lys Asp Glu Asn Arg Ala Thr His Thr Ser Ile Tyr Glu Val
290 295 300

Asp Trp Glu Asn His Thr Val Lys Leu Ile Asp Thr Gln Ser Lys Glu
305 310 315 320

Lys Asn Pro Met Ser
325

<210> SEQ ID NO 17
<211> LENGTH: 301
<212> TYPE: PRT
<213> ORGANISM: Artificial Sequence
<220> FEATURE:
<223> OTHER INFORMATION: wild-type LukF-PV amino acid sequence (without signal peptide)

<400> SEQUENCE: 17

Ala Gln His Ile Thr Pro Val Ser Glu Lys Lys Val Asp Asp Lys Ile
1 5 10 15

Thr Leu Tyr Lys Thr Thr Ala Thr Ser Asp Ser Asp Lys Leu Lys Ile
20 25 30

Ser Gln Ile Leu Thr Phe Asn Phe Ile Lys Asp Lys Ser Tyr Asp Lys
35 40 45

Asp Thr Leu Ile Leu Lys Ala Ala Gly Asn Ile Tyr Ser Gly Tyr Thr
50 55 60

Lys Pro Asn Pro Lys Asp Thr Ile Ser Ser Gln Phe Tyr Trp Gly Ser
65 70 75 80

Lys Tyr Asn Ile Ser Ile Asn Ser Asp Ser Asn Asp Ser Val Asn Val
85 90 95

Val Asp Tyr Ala Pro Lys Asn Gln Asn Glu Glu Phe Gln Val Gln Gln
100 105 110

Thr Val Gly Tyr Ser Tyr Gly Gly Asp Ile Asn Ile Ser Asn Gly Leu
115 120 125

Ser Gly Gly Gly Asn Gly Ser Lys Ser Phe Ser Glu Thr Ile Asn Tyr
130 135 140

Lys Gln Glu Ser Tyr Arg Thr Ser Leu Asp Lys Arg Thr Asn Phe Lys
145 150 155 160

Lys Ile Gly Trp Asp Val Glu Ala His Lys Ile Met Asn Asn Gly Trp

```
                165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
        195                 200                 205

Glu Tyr His Lys Met Pro Val Leu Ser Arg Gly Asn Phe Asn Pro Glu
    210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
                245                 250                 255

Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
        275                 280                 285

Leu Ile Asp Thr Gln Ser Lys Glu Lys Asn Pro Met Ser
    290                 295                 300


<210> SEQ ID NO 18
<211> LENGTH: 301
<212> TYPE: PRT
<213> ORGANISM: Artificial Sequence
<220> FEATURE:
<223> OTHER INFORMATION: mutant LukF-PV amino acid sequence-Lys102Ala
      (K102A)

<400> SEQUENCE: 18

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30

Ser Gln Ile Leu Thr Phe Asn Phe Ile Lys Asp Lys Ser Tyr Asp Lys
        35                  40                  45

Asp Thr Leu Ile Leu Lys Ala Ala Gly Asn Ile Tyr Ser Gly Tyr Thr
    50                  55                  60

Lys Pro Asn Pro Lys Asp Thr Ile Ser Ser Gln Phe Tyr Trp Gly Ser
65                  70                  75                  80

Lys Tyr Asn Ile Ser Ile Asn Ser Asp Ser Asn Asp Ser Val Asn Val
                85                  90                  95

Val Asp Tyr Ala Pro Ala Asn Gln Asn Glu Glu Phe Gln Val Gln Gln
            100                 105                 110

Thr Val Gly Tyr Ser Tyr Gly Gly Asp Ile Asn Ile Ser Asn Gly Leu
        115                 120                 125

Ser Gly Gly Gly Asn Gly Ser Lys Ser Phe Ser Glu Thr Ile Asn Tyr
    130                 135                 140

Lys Gln Glu Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
                165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
        195                 200                 205

Glu Tyr His Lys Met Pro Val Leu Ser Arg Gly Asn Phe Asn Pro Glu
    210                 215                 220
```

-continued

```
Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
                245                 250                 255

Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
        275                 280                 285

Leu Ile Asp Thr Gln Ser Lys Glu Lys Asn Pro Met Ser
    290                 295                 300


<210> SEQ ID NO 19
<211> LENGTH: 301
<212> TYPE: PRT
<213> ORGANISM: Artificial Sequence
<220> FEATURE:
<223> OTHER INFORMATION: mutant LukF-PV amino acid sequence-Asp121Ala
      (D121A)

<400> SEQUENCE: 19

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30

Ser Gln Ile Leu Thr Phe Asn Phe Ile Lys Asp Lys Ser Tyr Asp Lys
        35                  40                  45

Asp Thr Leu Ile Leu Lys Ala Ala Gly Asn Ile Tyr Ser Gly Tyr Thr
    50                  55                  60

Lys Pro Asn Pro Lys Asp Thr Ile Ser Ser Gln Phe Tyr Trp Gly Ser
65                  70                  75                  80

Lys Tyr Asn Ile Ser Ile Asn Ser Asp Ser Asn Asp Ser Val Asn Val
                85                  90                  95

Val Asp Tyr Ala Pro Lys Asn Gln Asn Glu Glu Phe Gln Val Gln Gln
            100                 105                 110

Thr Val Gly Tyr Ser Tyr Gly Gly Ala Ile Asn Ile Ser Asn Gly Leu
        115                 120                 125

Ser Gly Gly Gly Asn Gly Ser Lys Ser Phe Ser Glu Thr Ile Asn Tyr
    130                 135                 140

Lys Gln Glu Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
                165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
        195                 200                 205

Glu Tyr His Lys Met Pro Val Leu Ser Arg Gly Asn Phe Asn Pro Glu
    210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
                245                 250                 255

Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
        275                 280                 285
```

```
Leu Ile Asp Thr Gln Ser Lys Glu Lys Asn Pro Met Ser
    290                 295                 300


<210> SEQ ID NO 20
<211> LENGTH: 301
<212> TYPE: PRT
<213> ORGANISM: Artificial Sequence
<220> FEATURE:
<223> OTHER INFORMATION: mutant LukF-PV amino acid sequence-Glu147Ala
      (E147A)

<400> SEQUENCE: 20

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30

Ser Gln Ile Leu Thr Phe Asn Phe Ile Lys Asp Lys Ser Tyr Asp Lys
        35                  40                  45

Asp Thr Leu Ile Leu Lys Ala Ala Gly Asn Ile Tyr Ser Gly Tyr Thr
    50                  55                  60

Lys Pro Asn Pro Lys Asp Thr Ile Ser Ser Gln Phe Tyr Trp Gly Ser
65                  70                  75                  80

Lys Tyr Asn Ile Ser Ile Asn Ser Asp Ser Asn Asp Ser Val Asn Val
                85                  90                  95

Val Asp Tyr Ala Pro Lys Asn Gln Asn Glu Glu Phe Gln Val Gln Gln
            100                 105                 110

Thr Val Gly Tyr Ser Tyr Gly Gly Asp Ile Asn Ile Ser Asn Gly Leu
        115                 120                 125

Ser Gly Gly Gly Asn Gly Ser Lys Ser Phe Ser Glu Thr Ile Asn Tyr
    130                 135                 140

Lys Gln Ala Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
                165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
        195                 200                 205

Glu Tyr His Lys Met Pro Val Leu Ser Arg Gly Asn Phe Asn Pro Glu
    210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
                245                 250                 255

Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
        275                 280                 285

Leu Ile Asp Thr Gln Ser Lys Glu Lys Asn Pro Met Ser
    290                 295                 300


<210> SEQ ID NO 21
<211> LENGTH: 323
<212> TYPE: PRT
<213> ORGANISM: Artificial Sequence
<220> FEATURE:
<223> OTHER INFORMATION: wild-type LukF-PV amino acid sequence
```

<400> SEQUENCE: 21

Met Lys Lys Ile Val Lys Ser Ser Val Val Thr Ser Ile Ala Leu Leu
1               5                   10                  15

Leu Leu Ser Asn Thr Val Asp Ala Ala Gln His Ile Thr Pro Val Ser
            20                  25                  30

Glu Lys Lys Val Asp Asp Lys Ile Thr Leu Tyr Lys Thr Thr Ala Thr
        35                  40                  45

Ser Asp Ser Asp Lys Leu Lys Ile Ser Gln Ile Leu Thr Phe Asn Phe
    50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140

Asp Ile Asn Ile Ser Asn Gly Leu Ser Gly Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
        195                 200                 205

His Ser Thr Tyr Gly Asn Glu Met Phe Leu Gly Ser Arg Gln Ser Asn
    210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Arg Glu
            260                 265                 270

Met Asp Arg Tyr Thr Asn Phe Trp Asn Gln Leu His Trp Ile Gly Asn
        275                 280                 285

Asn Tyr Lys Asp Glu Asn Arg Ala Thr His Thr Ser Ile Tyr Glu Val
    290                 295                 300

Asp Trp Glu Asn His Thr Val Lys Leu Ile Asp Thr Gln Ser Lys Glu
305                 310                 315                 320

Lys Asn Pro

<210> SEQ ID NO 22
<211> LENGTH: 328
<212> TYPE: PRT
<213> ORGANISM: Artificial Sequence
<220> FEATURE:
<223> OTHER INFORMATION: wild-type LukF-PV amino acid sequence

<400> SEQUENCE: 22

Met Lys Lys Ile Val Lys Ser Ser Val Val Thr Ser Ile Ala Leu Leu
1               5                   10                  15

Leu Leu Ser Asn Thr Val Asp Ala Ala Gln His Ile Thr Pro Val Ser

```
            20                  25                  30

Glu Lys Lys Val Asp Asp Lys Ile Thr Leu Tyr Lys Thr Thr Ala Thr
        35                  40                  45

Ser Asp Ser Asp Lys Leu Lys Ile Ser Gln Ile Leu Thr Phe Asn Phe
    50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140

Asp Ile Asn Ile Ser Asn Gly Leu Ser Gly Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
        195                 200                 205

His Ser Thr Tyr Gly Asn Glu Met Phe Leu Gly Ser Arg Gln Ser Asn
    210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Arg Glu
            260                 265                 270

Met Asp Arg Tyr Thr Asn Phe Trp Asn Gln Leu His Trp Ile Gly Asn
        275                 280                 285

Asn Tyr Lys Asp Glu Asn Arg Ala Thr His Thr Ser Ile Tyr Glu Val
    290                 295                 300

Asp Trp Glu Asn His Thr Val Lys Leu Ile Asp Thr Gln Ser Lys Glu
305                 310                 315                 320

Lys Lys Ser Tyr Glu Leu Asn Arg
                325


<210> SEQ ID NO 23
<211> LENGTH: 324
<212> TYPE: PRT
<213> ORGANISM: Artificial Sequence
<220> FEATURE:
<223> OTHER INFORMATION: wild-type LukF-PV amino acid sequence

<400> SEQUENCE: 23

Met Lys Lys Ile Val Lys Ser Ser Val Val Thr Ser Ile Ala Leu Leu
1               5                   10                  15

Leu Leu Ser Asn Thr Val Asp Ala Ala Gln His Ile Thr Pro Val Ser
            20                  25                  30

Glu Lys Lys Val Asp Asp Lys Ile Thr Leu Tyr Lys Thr Thr Ala Thr
        35                  40                  45

Ser Asp Ser Asp Lys Leu Lys Ile Ser Gln Ile Leu Thr Phe Asn Phe
```

```
    50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140

Asp Ile Asn Ile Ser Asn Gly Leu Ser Gly Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
        195                 200                 205

His Ser Thr Tyr Gly Asn Glu Met Phe Leu Gly Ser Arg Gln Ser Asn
    210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Arg Glu
            260                 265                 270

Met Asp Arg Tyr Thr Asn Phe Trp Ile Asn Phe Asn Trp Ile Gly Asn
        275                 280                 285

Asn Tyr Lys Asp Glu Asn Arg Ala Thr His Thr Ser Ile Tyr Glu Val
    290                 295                 300

Asp Trp Glu Asn His Thr Val Lys Leu Ile Asp Thr Gln Ser Lys Glu
305                 310                 315                 320

Lys Asn Pro Met


<210> SEQ ID NO 24
<211> LENGTH: 327
<212> TYPE: PRT
<213> ORGANISM: Artificial Sequence
<220> FEATURE:
<223> OTHER INFORMATION: wild-type LukF-PV amino acid sequence

<400> SEQUENCE: 24

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95
```

```
Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Leu Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 25
<211> LENGTH: 322
<212> TYPE: PRT
<213> ORGANISM: Artificial Sequence
<220> FEATURE:
<223> OTHER INFORMATION: wild-type LukF-PV amino acid sequence

<400> SEQUENCE: 25

Met Lys Phe Lys Asn Ile Val Lys Ser Ser Val Ala Thr Ser Ile Thr
1               5                   10                  15

Leu Ile Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Ser Asp Lys Leu Lys Ile Ser Gln Ile Leu Thr Phe
    50                  55                  60

Asn Phe Ile Lys Asp Lys Ser Tyr Asp Lys Asp Thr Leu Ile Leu Lys
65                  70                  75                  80

Ala Ala Gly Asn Ile Tyr Ser Gly Tyr Thr Gln Pro Thr Ser Asp Ser
                85                  90                  95

Ser Ile Asn Ser Gln Phe Tyr Trp Gly Ala Lys Tyr Asn Val Phe Val
            100                 105                 110

Ser Ser Glu Ser Lys Asp Ser Val Asn Ile Val Asp Tyr Ala Pro Lys
        115                 120                 125
```

```
Asn Gln Asn Glu Glu Phe Gln Val Gln Gln Thr Leu Gly Tyr Ser Tyr
    130                 135                 140

Gly Gly Asp Ile Asn Ile Ile Asn Gly Leu Thr Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Ser Asp Ser Leu Tyr Gly Asn Glu Leu Phe Leu Gly Gly Arg Gln
    210                 215                 220

Ser Ser Ser Asn Ala Asn Gln Asn Phe Leu Pro Thr His Gln Met Pro
225                 230                 235                 240

Ile Leu Ala Arg Gly Asn Phe Asn Pro Glu Phe Ile Ser Val Leu Ser
                245                 250                 255

His Lys Gln Lys Asp Val Lys Lys Ser Lys Ile Lys Val Thr Tyr Gln
            260                 265                 270

Arg Glu Met Asp Arg Tyr Glu Asn Phe Trp Asn Asn Leu His Trp Ile
        275                 280                 285

Gly Tyr Asn Phe Lys Asn Gln Lys Arg Ala Thr His Thr Ser Ile Tyr
    290                 295                 300

Glu Ile Asp Trp Glu Lys His Thr Val Lys Leu Val Ala Ser Gln Ser
305                 310                 315                 320

Ser Glu


<210> SEQ ID NO 26
<211> LENGTH: 322
<212> TYPE: PRT
<213> ORGANISM: Artificial Sequence
<220> FEATURE:
<223> OTHER INFORMATION: wild-type LukF-PV amino acid sequence

<400> SEQUENCE: 26

Met Lys Phe Lys Asn Ile Val Lys Ser Ser Val Ala Thr Ser Ile Thr
1               5                   10                  15

Leu Ile Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Ser Asp Lys Leu Lys Ile Ser Gln Ile Leu Thr Phe
    50                  55                  60

Asn Phe Ile Lys Asp Lys Ser Tyr Asp Lys Asp Thr Leu Ile Leu Lys
65                  70                  75                  80

Ala Ala Gly Asn Ile Tyr Ser Gly Tyr Thr Gln Pro Thr Ser Asp Ser
                85                  90                  95

Ser Ile Asn Ser Gln Phe Tyr Trp Gly Ala Lys Tyr Asn Val Phe Val
            100                 105                 110

Ser Ser Glu Ser Lys Asp Ser Val Asn Ile Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ile Asn Gly Leu Thr Gly Gly Leu Asn Gly
145                 150                 155                 160
```

```
Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Ser Asp Ser Leu Tyr Gly Asn Glu Leu Phe Leu Gly Gly Arg Gln
    210                 215                 220

Ser Ser Ser Asn Ala Asn Gln Asn Phe Leu Pro Thr His Gln Met Pro
225                 230                 235                 240

Ile Leu Ala Arg Gly Asn Phe Asn Pro Glu Phe Ile Ser Val Leu Ser
                245                 250                 255

His Lys Gln Lys Asp Val Lys Lys Ser Lys Ile Lys Val Thr Tyr Gln
            260                 265                 270

Arg Glu Met Asp Arg Tyr Glu Asn Phe Trp Asn Asn Leu His Trp Ile
        275                 280                 285

Gly Tyr Asn Ile Lys Asn Gln Lys Arg Ala Thr His Thr Ser Ile Tyr
    290                 295                 300

Glu Ile Asp Trp Glu Lys His Thr Val Lys Leu Val Ala Ser Gln Ser
305                 310                 315                 320

Ser Glu


<210> SEQ ID NO 27
<211> LENGTH: 322
<212> TYPE: PRT
<213> ORGANISM: Artificial Sequence
<220> FEATURE:
<223> OTHER INFORMATION: wild-type LukF-PV amino acid sequence

<400> SEQUENCE: 27

Met Lys Ile Lys Asn Ile Val Lys Ser Ser Val Ala Thr Ser Ile Thr
1               5                   10                  15

Phe Ile Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Ser Asp Lys Leu Lys Ile Ser Gln Ile Leu Thr Phe
    50                  55                  60

Asn Phe Ile Lys Asp Lys Ser Tyr Asp Lys Asp Thr Leu Ile Leu Lys
65                  70                  75                  80

Ala Ala Gly Asn Ile Tyr Ser Gly Tyr Thr Gln Pro Thr Ser Asp Ser
                85                  90                  95

Ser Ile Asn Ser Gln Phe Tyr Trp Gly Ala Lys Tyr Asn Val Phe Val
            100                 105                 110

Ser Ser Glu Ser Lys Asp Ser Val Asn Ile Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ile Asn Gly Leu Thr Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Ile Asn His Lys Leu Ile Gly Trp Gly Val
            180                 185                 190

Glu Ala His Lys Ile Met Asn Asn Gly Trp Gly Pro Tyr Gly Arg Asp
```

```
        195                 200                 205

Ser Ser Asp Ser Leu Tyr Gly Asn Glu Leu Phe Leu Gly Gly Arg Gln
    210                 215                 220

Ser Ser Ser Asn Ala Asn Gln Asn Phe Leu Pro Thr His Gln Met Pro
225                 230                 235                 240

Ile Leu Ala Arg Gly Asn Phe Asn Pro Glu Phe Ile Ser Val Leu Ser
                245                 250                 255

His Lys Gln Lys Asp Val Lys Lys Ser Lys Ile Lys Val Thr Tyr Gln
            260                 265                 270

Arg Gln Met Asp Arg Tyr Glu Asn Phe Trp Asn Asn Leu His Trp Ile
        275                 280                 285

Gly Tyr Asn Ile Lys Asn Gln Lys Arg Ala Thr His Thr Ser Ile Tyr
    290                 295                 300

Glu Ile Asp Trp Glu Lys His Thr Val Lys Leu Val Ala Ser Gln Ser
305                 310                 315                 320

Ser Glu


<210> SEQ ID NO 28
<211> LENGTH: 315
<212> TYPE: PRT
<213> ORGANISM: Artificial Sequence
<220> FEATURE:
<223> OTHER INFORMATION: Panton-Valentine leukocidin chain S precursor
      amino acid sequence

<400> SEQUENCE: 28

Met Ile Phe Met Val Lys Lys Arg Leu Leu Ala Ala Thr Leu Ser Leu
1               5                   10                  15

Gly Ile Ile Thr Pro Ile Ala Thr Ser Phe His Glu Ser Lys Ala Asp
            20                  25                  30

Asn Asn Ile Glu Asn Ile Gly Asp Gly Ala Glu Val Val Lys Arg Thr
        35                  40                  45

Glu Asp Thr Ser Ser Asp Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Asn Ser Lys Thr Thr Tyr Tyr Asn Tyr Lys Asn
                85                  90                  95

Thr Asp His Ile Lys Ala Met Arg Trp Pro Phe Gln Tyr Asn Ile Gly
            100                 105                 110

Leu Lys Thr Asn Asp Pro Asn Val Asp Leu Ile Asn Tyr Leu Pro Lys
        115                 120                 125

Asn Lys Ile Asp Ser Val Asn Val Ser Gln Thr Leu Gly Tyr Asn Ile
    130                 135                 140

Gly Gly Asn Phe Asn Ser Gly Pro Ser Thr Gly Gly Asn Gly Ser Phe
145                 150                 155                 160

Asn Tyr Ser Lys Thr Ile Ser Tyr Asn Gln Gln Asn Tyr Ile Ser Glu
                165                 170                 175

Val Glu His Gln Asn Ser Lys Ser Val Gln Trp Gly Ile Lys Ala Asn
            180                 185                 190

Ser Phe Ile Thr Ser Leu Gly Lys Met Ser Gly His Asp Pro Asn Leu
        195                 200                 205

Phe Val Gly Tyr Lys Pro Tyr Ser Gln Asn Pro Arg Asp Tyr Phe Val
    210                 215                 220

Pro Asp Asn Glu Leu Pro Pro Leu Val His Ser Gly Phe Asn Pro Ser
```

```
225                 230                 235                 240

Phe Ile Ala Thr Val Ser His Glu Lys Gly Ser Gly Asp Thr Ser Glu
                245                 250                 255

Phe Glu Ile Thr Tyr Gly Arg Asn Met Asp Val Thr His Ala Thr Arg
            260                 265                 270

Arg Thr Thr His Tyr Gly Asn Ser Tyr Leu Glu Gly Ser Arg Ile His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly His Asn
305                 310                 315


<210> SEQ ID NO 29
<211> LENGTH: 315
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 29

Met Leu Lys Asn Lys Met Leu Ala Thr Thr Leu Ser Ile Ser Leu Ile
1               5                   10                  15

Ala Pro Leu Ala Thr Pro Leu Phe Glu Asn Ala Lys Ala Ala Asn Asp
            20                  25                  30

Thr Glu Asp Ile Gly Lys Gly Ser Asp Val Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Ala Tyr Tyr Asn Tyr Lys Lys
                85                  90                  95

Ser Asn His Val Lys Ala Met Arg Trp Pro Phe Gln Tyr Asn Ile Gly
            100                 105                 110

Leu Lys Thr Asn Asp Pro Asn Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Gly Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Gly Asp Thr Ser Glu
                245                 250                 255

Phe Glu Ile Thr Tyr Gly Arg Asn Met Asp Val Thr His Ala Ile Lys
            260                 265                 270
```

```
Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 30
<211> LENGTH: 315
<212> TYPE: PRT
<213> ORGANISM: Artificial Sequence
<220> FEATURE:
<223> OTHER INFORMATION: Leukocidin S subunit amino acid sequence

<400> SEQUENCE: 30

Met Leu Lys Asn Lys Ile Leu Ala Thr Thr Leu Ser Val Ser Leu Leu
1               5                   10                  15

Ala Pro Leu Ala Asn Pro Leu Leu Glu Lys Ala Lys Ala Ala Asn Asp
            20                  25                  30

Thr Glu Asp Ile Gly Lys Gly Asn Asp Val Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Asn
                85                  90                  95

Thr Asn His Ile Lys Ser Met Arg Trp Pro Phe Gln Tyr Asn Ile Gly
            100                 105                 110

Leu Lys Thr Asn Asp Pro Asn Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Val Thr Ala Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Gly Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Ile His
        275                 280                 285

Asn Ala Phe Lys Asn Arg Asn Tyr Thr Val Lys Tyr Glu Val Asn Trp
    290                 295                 300

Lys Thr His Glu Ile Lys Val Lys Gly Gln Asn
305                 310                 315
```

```
<210> SEQ ID NO 31
<211> LENGTH: 318
<212> TYPE: PRT
<213> ORGANISM: Artificial Sequence
<220> FEATURE:
<223> OTHER INFORMATION: Panton-Valentine leukocidin subunit S amino
      acid sequence

<400> SEQUENCE: 31

Met Lys Leu Met Leu Lys Asn Lys Ile Leu Ala Thr Thr Leu Ser Val
1               5                   10                  15

Ser Leu Leu Ala Pro Leu Ala Asn Pro Leu Leu Glu Asn Ala Lys Ala
            20                  25                  30

Ala Asn Asp Thr Glu Asp Ile Gly Lys Gly Ser Asp Ile Glu Ile Ile
        35                  40                  45

Lys Arg Thr Glu Asp Lys Thr Ser Asn Lys Trp Gly Val Thr Gln Asn
    50                  55                  60

Ile Gln Phe Asp Phe Val Lys Asp Lys Lys Tyr Asn Lys Asp Ala Leu
65                  70                  75                  80

Ile Leu Lys Met Gln Gly Phe Ile Ser Ser Arg Thr Thr Tyr Tyr Asn
                85                  90                  95

Tyr Lys Asn Thr Asn His Ile Lys Ser Met Arg Trp Pro Phe Gln Tyr
            100                 105                 110

Asn Ile Gly Leu Lys Thr Asn Asp Ser Asn Val Ser Leu Ile Asn Tyr
        115                 120                 125

Leu Pro Lys Asn Lys Ile Glu Ser Thr Asn Val Ser Gln Thr Leu Gly
    130                 135                 140

Tyr Asn Ile Gly Gly Asn Phe Gln Ser Ala Pro Ser Leu Gly Gly Asn
145                 150                 155                 160

Gly Ser Phe Asn Tyr Ser Lys Ser Ile Ser Tyr Thr Gln Gln Asn Tyr
                165                 170                 175

Val Ser Glu Val Glu Gln Gln Asn Ser Lys Ser Val Leu Trp Gly Val
            180                 185                 190

Lys Ala Asn Ser Phe Val Thr Ala Ser Gly Gln Lys Ser Ala Phe Asp
        195                 200                 205

Ser Asp Leu Phe Val Gly Tyr Lys Pro Asn Ser Lys Asp Pro Arg Asp
    210                 215                 220

Tyr Phe Val Pro Asp Ser Glu Leu Pro Pro Leu Val Gln Ser Gly Phe
225                 230                 235                 240

Asn Pro Ser Phe Ile Ala Thr Val Ser His Glu Lys Gly Ser Gly Asp
                245                 250                 255

Thr Ser Glu Phe Glu Ile Thr Tyr Gly Arg Asn Met Asp Val Thr His
            260                 265                 270

Ala Ile Lys Arg Ser Thr His Tyr Gly Asn Ser Tyr Leu Asp Gly His
        275                 280                 285

Arg Val His Asn Ala Phe Val Asn Arg Asn Tyr Thr Val Lys Tyr Glu
    290                 295                 300

Val Asn Trp Lys Thr His Glu Ile Lys Val Lys Gly Gln Asn
305                 310                 315


<210> SEQ ID NO 32
<211> LENGTH: 315
<212> TYPE: PRT
<213> ORGANISM: Artificial Sequence
<220> FEATURE:
<223> OTHER INFORMATION: gamma-hemolysin component C amino acid
      sequence
```

-continued

<400> SEQUENCE: 32

```
Met Leu Lys Asn Lys Ile Leu Ala Ala Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Lys
                85                  90                  95

Thr Asn His Val Lys Ala Met Arg Trp Pro Phe Gln Tyr Asn Ile Gly
            100                 105                 110

Leu Lys Thr Asn Asp Pro Asn Ile Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315
```

<210> SEQ ID NO 33
<211> LENGTH: 315
<212> TYPE: PRT
<213> ORGANISM: Artificial Sequence
<220> FEATURE:
<223> OTHER INFORMATION: Leukocidin S subunit amino acid sequence

<400> SEQUENCE: 33

```
Met Leu Lys Asn Lys Ile Leu Ala Thr Thr Ile Ser Val Ser Leu Leu
1               5                   10                  15

Ala Pro Leu Ala Asn Pro Leu Leu Glu Asn Ala Lys Ala Ala Asn Asp
            20                  25                  30
```

```
Thr Glu Asp Ile Gly Lys Gly Asn Asp Val Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Asn
                85                  90                  95

Thr Asn His Ile Lys Ser Met Arg Trp Pro Phe Gln Tyr Asn Ile Gly
            100                 105                 110

Leu Lys Thr Asn Asp Pro Asn Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Val Thr Ala Ser Gly Gln Lys Ser Ala Phe Asp Ser Asp Leu
        195                 200                 205

Phe Val Gly Tyr Lys Pro Asn Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Gly Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Lys Asn Arg Asn Tyr Thr Val Lys Tyr Glu Val Asn Trp
    290                 295                 300

Lys Thr His Glu Ile Lys Val Lys Gly Gln Asn
305                 310                 315
```

<210> SEQ ID NO 34
<211> LENGTH: 315
<212> TYPE: PRT
<213> ORGANISM: Artificial Sequence
<220> FEATURE:
<223> OTHER INFORMATION: gamma-hemolysin component C amino acid sequence

<400> SEQUENCE: 34

```
Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80
```

Met Gln Gly Phe Ile Ser Ser Arg Thr Thr Tyr Tyr Asn Tyr Lys Lys
85 90 95

Thr Asn His Val Lys Ala Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Thr Leu Gly Tyr Asn Ile
130 135 140

Gly Gly Asn Phe Gln Ser Ala Pro Ser Leu Gly Gly Asn Gly Ser Phe
145 150 155 160

Asn Tyr Ser Lys Ser Ile Ser Tyr Thr Gln Gln Asn Tyr Val Ser Glu
165 170 175

Val Glu Gln Gln Asn Ser Lys Ser Val Leu Trp Gly Val Lys Ala Asn
180 185 190

Ser Phe Ala Thr Glu Ser Gly Gln Lys Ser Ala Phe Asp Ser Asp Leu
195 200 205

Phe Val Gly Tyr Lys Pro His Ser Lys Asp Pro Arg Asp Tyr Phe Val
210 215 220

Pro Asp Ser Glu Leu Pro Pro Leu Val Gln Ser Gly Phe Asn Pro Ser
225 230 235 240

Phe Ile Ala Thr Val Ser His Glu Lys Gly Ser Ser Asp Thr Ser Glu
245 250 255

Phe Glu Ile Thr Tyr Gly Arg Asn Met Asp Val Thr His Ala Ile Lys
260 265 270

Arg Ser Thr His Tyr Gly Asn Ser Tyr Leu Asp Gly His Arg Val His
275 280 285

Asn Ala Phe Val Asn Arg Asn Tyr Thr Val Lys Tyr Glu Val Asn Trp
290 295 300

Lys Thr His Glu Ile Lys Val Lys Gly Gln Asn
305 310 315

<210> SEQ ID NO 35
<211> LENGTH: 315
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 35

Met Leu Lys Asn Lys Ile Leu Ala Thr Thr Leu Ser Val Ser Leu Leu
1 5 10 15

Ala Pro Leu Ala Asn Pro Leu Leu Glu Asn Ala Lys Ala Ala Asn Asp
20 25 30

Thr Glu Glu Ile Gly Lys Gly Ser Asp Ile Glu Ile Ile Lys Arg Thr
35 40 45

Glu Asp Lys Thr Ser Asn Lys Trp Gly Val Thr Gln Asn Ile Gln Phe
50 55 60

Asp Phe Val Lys Asp Lys Lys Tyr Asn Lys Asp Ala Leu Ile Leu Lys
65 70 75 80

Met Gln Gly Phe Ile Ser Ser Arg Thr Thr Tyr Tyr Asn Tyr Lys Lys
85 90 95

Thr Asn His Val Lys Ala Met Arg Trp Pro Phe Gln Tyr Asn Ile Gly
100 105 110

Leu Lys Thr Asn Asp Lys Tyr Val Ser Leu Ile Asn Tyr Leu Pro Lys

```
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 36
<211> LENGTH: 315
<212> TYPE: PRT
<213> ORGANISM: Artificial Sequence
<220> FEATURE:
<223> OTHER INFORMATION: Leukocidin S subunit amino acid sequence

<400> SEQUENCE: 36

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Lys
                85                  90                  95

Thr Asn His Val Lys Ala Met Arg Trp Pro Phe Gln Tyr Asn Ile Ala
            100                 105                 110

Leu Lys Thr Asn Asp Lys Tyr Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
```

```
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 37
<211> LENGTH: 315
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 37

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Lys
                85                  90                  95

Thr Asn His Ile Lys Ala Met Arg Trp Pro Phe Gln Tyr Asn Ile Ser
            100                 105                 110

Leu Lys Thr Asn Asp Lys Tyr Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205
```

```
Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 38
<211> LENGTH: 318
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 38

Met Lys Leu Met Leu Lys Asn Lys Ile Leu Thr Thr Thr Leu Ser Val
1               5                   10                  15

Ser Leu Leu Ala Pro Leu Ala Asn Pro Leu Leu Glu Asn Ala Lys Ala
            20                  25                  30

Ala Asn Asp Thr Glu Asp Ile Gly Lys Gly Ser Asp Ile Glu Ile Ile
        35                  40                  45

Lys Arg Thr Glu Asp Lys Thr Ser Asn Lys Trp Gly Val Thr Gln Asn
    50                  55                  60

Ile Gln Phe Asp Phe Val Lys Asp Lys Lys Tyr Asn Lys Asp Ala Leu
65                  70                  75                  80

Ile Leu Lys Met Gln Gly Phe Ile Ser Ser Arg Thr Thr Tyr Tyr Asn
                85                  90                  95

Tyr Lys Lys Thr Asn His Val Lys Ala Met Arg Trp Pro Phe Gln Tyr
            100                 105                 110

Asn Ile Gly Leu Lys Thr Asn Asp Lys Tyr Val Ser Leu Ile Asn Tyr
        115                 120                 125

Leu Pro Lys Asn Lys Ile Glu Ser Thr Asn Val Ser Gln Thr Leu Gly
    130                 135                 140

Tyr Asn Ile Gly Gly Asn Phe Gln Ser Ala Pro Ser Leu Gly Gly Asn
145                 150                 155                 160

Gly Ser Phe Asn Tyr Ser Lys Ser Ile Ser Tyr Thr Gln Gln Asn Tyr
                165                 170                 175

Val Ser Glu Val Glu Gln Gln Asn Ser Lys Ser Val Leu Trp Gly Val
            180                 185                 190

Lys Ala Asn Ser Phe Ala Thr Glu Ser Gly Gln Lys Ser Ala Phe Asp
        195                 200                 205

Ser Asp Leu Phe Val Gly Tyr Lys Pro His Ser Lys Asp Pro Arg Asp
    210                 215                 220

Tyr Phe Val Pro Asp Ser Glu Leu Pro Pro Leu Val Gln Ser Gly Phe
225                 230                 235                 240

Asn Pro Ser Phe Ile Ala Thr Val Ser His Glu Lys Gly Ser Ser Asp
                245                 250                 255
```

```
Thr Ser Glu Phe Glu Ile Thr Tyr Gly Arg Asn Met Asp Val Thr His
            260                 265                 270

Ala Ile Lys Arg Ser Thr His Tyr Gly Asn Ser Tyr Leu Asp Gly His
        275                 280                 285

Arg Val His Asn Ala Phe Val Asn Arg Asn Tyr Thr Val Lys Tyr Glu
    290                 295                 300

Val Asn Trp Lys Thr His Glu Ile Lys Val Lys Gly Gln Asn
305                 310                 315


<210> SEQ ID NO 39
<211> LENGTH: 315
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 39

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Lys
                85                  90                  95

Thr Asn His Val Lys Ala Met Arg Trp Pro Phe Gln Tyr Asn Ile Gly
            100                 105                 110

Leu Lys Thr Asn Asp Lys Tyr Val Ser Leu Ile Asn His Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
```

290 295 300

Lys Thr His Glu Ile Lys Val Lys Gly Gln Asn
305 310 315

<210> SEQ ID NO 40
<211> LENGTH: 318
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 40

Met Lys Ile Met Leu Lys Asn Lys Ile Leu Ala Thr Thr Leu Ser Val
1 5 10 15

Ser Leu Leu Ala Pro Leu Ala Asn Pro Leu Leu Glu Asn Ala Lys Ala
20 25 30

Ala Asn Asp Thr Glu Asp Ile Gly Lys Gly Asn Asp Val Glu Ile Ile
35 40 45

Lys Arg Thr Glu Asp Lys Thr Ser Asn Lys Trp Gly Val Thr Gln Asn
50 55 60

Ile Gln Phe Asp Phe Val Lys Asp Lys Lys Tyr Asn Lys Asp Ala Leu
65 70 75 80

Ile Leu Lys Met Gln Gly Phe Ile Ser Ser Arg Thr Thr Tyr Tyr Asn
85 90 95

Tyr Lys Asn Thr Asn His Ile Lys Ser Met Arg Trp Pro Phe Gln Tyr
100 105 110

Asn Ile Gly Leu Lys Thr Asn Asp Lys Tyr Val Ser Leu Ile Asn Tyr
115 120 125

Leu Pro Lys Asn Lys Ile Glu Ser Thr Asn Val Ser Gln Thr Leu Gly
130 135 140

Tyr Asn Ile Gly Gly Asn Phe Gln Ser Ala Pro Ser Leu Gly Gly Asn
145 150 155 160

Gly Ser Phe Asn Tyr Ser Lys Ser Ile Ser Tyr Thr Gln Gln Asn Tyr
165 170 175

Val Ser Glu Val Glu Gln Gln Asn Ser Lys Ser Val Leu Trp Gly Val
180 185 190

Lys Ala Asn Ser Phe Ala Thr Glu Ser Gly Gln Lys Ser Ala Phe Asp
195 200 205

Ser Asp Leu Phe Val Gly Tyr Lys Pro His Ser Lys Asp Pro Arg Asp
210 215 220

Tyr Phe Val Pro Asp Ser Glu Leu Pro Pro Leu Val Gln Ser Gly Phe
225 230 235 240

Asn Pro Ser Phe Ile Ala Thr Val Ser His Glu Lys Gly Ser Ser Asp
245 250 255

Thr Ser Glu Phe Glu Ile Thr Tyr Gly Arg Asn Met Asp Val Thr His
260 265 270

Ala Ile Lys Arg Ser Thr His Tyr Gly Asn Ser Tyr Leu Asp Gly His
275 280 285

Arg Val His Asn Ala Phe Lys Asn Arg Asn Tyr Thr Val Lys Tyr Glu
290 295 300

Val Asn Trp Lys Thr His Glu Ile Lys Val Lys Gly Gln Asn
305 310 315

<210> SEQ ID NO 41
<211> LENGTH: 315

<212> TYPE: PRT
<213> ORGANISM: Artificial Sequence
<220> FEATURE:
<223> OTHER INFORMATION: gamma-hemolysin component C precursor amino acid sequence

<400> SEQUENCE: 41

Met Leu Lys Asn Lys Ile Leu Thr Thr Thr Leu Ser Val Ser Leu Leu
1 5 10 15

Ala Pro Leu Ala Asn Pro Leu Leu Glu Asn Ala Lys Ala Ala Asn Asp
20 25 30

Thr Glu Asp Ile Gly Lys Gly Ser Asp Ile Glu Ile Ile Lys Arg Thr
35 40 45

Glu Asp Lys Thr Ser Asn Lys Trp Gly Val Thr Gln Asn Ile Gln Phe
50 55 60

Asp Phe Val Lys Asp Lys Lys Tyr Asn Lys Asp Ala Leu Ile Leu Lys
65 70 75 80

Met Gln Gly Phe Ile Ser Ser Arg Thr Thr Tyr Tyr Asn Tyr Lys Lys
85 90 95

Thr Asn His Val Lys Ala Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Thr Leu Gly Tyr Asn Ile
130 135 140

Gly Gly Asn Phe Gln Ser Ala Pro Ser Leu Gly Gly Asn Gly Ser Phe
145 150 155 160

Asn Tyr Ser Lys Ser Ile Ser Tyr Thr Gln Gln Asn Tyr Val Ser Glu
165 170 175

Val Glu Gln Gln Asn Ser Lys Ser Val Leu Trp Gly Val Lys Ala Asn
180 185 190

Ser Phe Ala Thr Glu Ser Gly Gln Lys Ser Ala Phe Asp Ser Asp Leu
195 200 205

Phe Val Gly Tyr Lys Pro His Ser Lys Asp Pro Arg Asp Tyr Phe Val
210 215 220

Pro Asp Ser Glu Leu Pro Pro Leu Val Gln Ser Gly Phe Asn Pro Ser
225 230 235 240

Phe Ile Ala Thr Val Ser His Glu Lys Gly Ser Ser Asp Thr Ser Glu
245 250 255

Phe Glu Ile Thr Tyr Gly Arg Asn Met Asp Val Thr His Ala Ile Lys
260 265 270

Arg Ser Thr His Tyr Gly Asn Ser Tyr Leu Asp Gly His Arg Val His
275 280 285

Asn Ala Phe Val Asn Arg Asn Tyr Thr Val Lys Tyr Glu Val Asn Trp
290 295 300

Lys Thr His Glu Ile Lys Val Lys Gly Gln Asn
305 310 315

<210> SEQ ID NO 42
<211> LENGTH: 315
<212> TYPE: PRT
<213> ORGANISM: Artificial Sequence
<220> FEATURE:
<223> OTHER INFORMATION: Leukocidin S subunit amino acid sequence

<400> SEQUENCE: 42

Met Leu Lys Asn Lys Ile Leu Ala Thr Thr Leu Ser Val Ser Leu Leu

-continued

```
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Ser Asp Ile Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Thr Lys Tyr Asn Lys Asp Ala Leu Ile Leu Lys
65                  70                  75                  80

Met Gln Gly Phe Ile Ser Ser Arg Thr Thr Tyr Tyr Asn Tyr Lys Lys
                85                  90                  95

Thr Asn His Val Lys Ala Met Arg Trp Pro Phe Gln Tyr Asn Ile Gly
            100                 105                 110

Leu Lys Thr Asn Asp Lys Tyr Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 43
<211> LENGTH: 315
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 43

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Asn Asp Val Glu Ile Ile Lys Arg Thr
        35                  40                  45
```

Glu Asp Lys Thr Ser Asn Lys Trp Gly Val Thr Gln Asn Ile Gln Phe
50 55 60

Asp Phe Val Lys Asp Lys Lys Tyr Asn Lys Asp Ala Leu Ile Leu Lys
65 70 75 80

Met Gln Gly Phe Ile Ser Ser Arg Thr Thr Tyr Tyr Asn Tyr Lys Asn
85 90 95

Thr Asn His Ile Lys Ser Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Thr Leu Gly Tyr Asn Ile
130 135 140

Gly Gly Asn Phe Gln Ser Ala Pro Ser Leu Gly Gly Asn Gly Ser Phe
145 150 155 160

Asn Tyr Ser Lys Ser Ile Ser Tyr Thr Gln Gln Asn Tyr Val Ser Glu
165 170 175

Val Glu Gln Gln Asn Ser Lys Ser Val Leu Trp Gly Val Lys Ala Asn
180 185 190

Ser Phe Ala Thr Glu Ser Gly Gln Lys Ser Ala Phe Asp Ser Asp Leu
195 200 205

Phe Val Gly Tyr Lys Pro His Ser Lys Asp Pro Arg Asp Tyr Phe Val
210 215 220

Pro Asp Ser Glu Leu Pro Pro Leu Val Gln Ser Gly Phe Asn Pro Ser
225 230 235 240

Phe Ile Ala Thr Val Ser His Glu Lys Gly Ser Ser Asp Thr Ser Glu
245 250 255

Phe Glu Ile Thr Tyr Gly Arg Asn Met Asp Val Thr His Ala Ile Lys
260 265 270

Arg Ser Thr His Tyr Gly Asn Ser Tyr Leu Asp Gly His Arg Val His
275 280 285

Asn Ala Phe Lys Asn Arg Asn Tyr Thr Val Lys Tyr Glu Val Asn Trp
290 295 300

Lys Thr His Glu Ile Lys Val Lys Gly Gln Asn
305 310 315

<210> SEQ ID NO 44
<211> LENGTH: 315
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 44

Met Leu Lys Asn Lys Ile Leu Ala Thr Thr Leu Ser Val Ser Leu Leu
1 5 10 15

Ala Pro Leu Ala Asn Pro Leu Leu Glu Asn Ala Lys Ala Ala Asn Asp
20 25 30

Thr Glu Asp Ile Gly Lys Gly Ser Asp Ile Glu Ile Ile Lys Arg Thr
35 40 45

Glu Asp Lys Thr Ser Asn Lys Trp Gly Val Thr Gln Asn Ile Gln Phe
50 55 60

Asp Phe Val Lys Asp Lys Lys Tyr Asn Lys Asn Ala Leu Ile Leu Lys
65 70 75 80

Met Gln Gly Phe Ile Ser Ser Arg Thr Thr Tyr Tyr Asn Tyr Lys Lys
85 90 95

Thr Asn His Ile Lys Ala Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Thr Leu Gly Tyr Asn Ile
130 135 140

Gly Gly Asn Phe Gln Ser Ala Pro Ser Leu Gly Gly Asn Gly Ser Phe
145 150 155 160

Ser Tyr Ser Lys Ser Ile Ser Tyr Thr Gln Gln Asn Tyr Val Ser Glu
165 170 175

Val Glu Gln Gln Asn Ser Lys Ser Val Leu Trp Gly Val Lys Ala Asn
180 185 190

Ser Phe Ala Thr Glu Ser Gly Gln Lys Ser Ala Phe Asp Ser Asp Leu
195 200 205

Phe Val Gly Tyr Lys Pro His Ser Lys Asp Pro Arg Asp Tyr Phe Val
210 215 220

Pro Asp Ser Glu Leu Pro Pro Leu Val Gln Ser Gly Phe Asn Pro Ser
225 230 235 240

Phe Ile Ala Thr Val Ser His Glu Lys Gly Ser Ser Asp Thr Ser Glu
245 250 255

Phe Glu Ile Thr Tyr Gly Arg Asn Met Asp Val Thr His Ala Ile Lys
260 265 270

Arg Ser Thr His Tyr Gly Asn Ser Tyr Leu Asp Gly His Arg Val His
275 280 285

Asn Ala Phe Val Asn Arg Asn Tyr Thr Val Lys Tyr Glu Val Asn Trp
290 295 300

Lys Thr His Glu Ile Lys Val Lys Gly Gln Asn
305 310 315

<210> SEQ ID NO 45
<211> LENGTH: 315
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 45

Met Leu Lys Asn Lys Ile Leu Thr Thr Thr Leu Ser Val Ser Leu Leu
1 5 10 15

Ala Pro Leu Ala Asn Pro Leu Leu Glu Asn Ala Lys Ala Ala Asn Asp
20 25 30

Thr Glu Asp Ile Gly Lys Gly Ser Asp Ile Glu Ile Ile Lys Arg Thr
35 40 45

Glu Asp Lys Thr Ser Asn Lys Trp Gly Val Thr Gln Asn Ile Gln Phe
50 55 60

Asp Phe Val Lys Asp Lys Lys Tyr Asn Lys Asp Ala Leu Ile Leu Lys
65 70 75 80

Met Gln Gly Phe Ile Ser Ser Arg Thr Thr Tyr Tyr Asn Tyr Lys Lys
85 90 95

Thr Asn His Val Lys Ala Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Ile Leu Gly Tyr Asn Ile

```
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Val Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 46
<211> LENGTH: 315
<212> TYPE: PRT
<213> ORGANISM: Artificial Sequence
<220> FEATURE:
<223> OTHER INFORMATION: S component of leucocodin R amino acid sequence

<400> SEQUENCE: 46

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Asn Asp Val Glu Ile Ile Lys Arg Thr
        35                  40                  45

Glu Asp Lys Thr Ser Asn Lys Trp Gly Val Thr Gln Asn Ile Gln Phe
    50                  55                  60

Asp Phe Val Lys Asp Lys Lys Tyr Asn Lys Asp Ala Leu Ile Leu Lys
65                  70                  75                  80

Met Gln Gly Phe Ile Ser Ser Arg Thr Thr Tyr Tyr Asn Ser Lys Asn
                85                  90                  95

Thr Asn His Ile Lys Ser Met Arg Trp Pro Phe Gln Tyr Asn Ile Gly
            100                 105                 110

Leu Lys Thr Asn Asp Lys Tyr Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
```

```
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Lys Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 47
<211> LENGTH: 315
<212> TYPE: PRT
<213> ORGANISM: Artificial Sequence
<220> FEATURE:
<223> OTHER INFORMATION: hlgC-like ORFamino acid sequence

<400> SEQUENCE: 47

Met Leu Lys Asn Lys Ile Leu Ala Thr Thr Leu Ser Val Ser Leu Leu
1               5                   10                  15

Ala Pro Leu Ala Asn Pro Leu Leu Glu Asn Ala Lys Ala Ala Asn Asp
            20                  25                  30

Thr Glu Asp Ile Gly Lys Gly Asn Asp Val Glu Ile Ile Lys Arg Thr
        35                  40                  45

Glu Asp Lys Thr Ser Asn Lys Trp Gly Val Thr Gln Asn Ile Gln Phe
    50                  55                  60

Gly Phe Val Lys Asp Lys Lys Tyr Asn Lys Val Ala Leu Ile Leu Lys
65                  70                  75                  80

Met Gln Gly Phe Ile Ser Ser Arg Thr Thr Tyr Tyr Asn Tyr Lys Asn
                85                  90                  95

Thr Asn His Ile Lys Ser Met Arg Trp Pro Phe Gln Tyr Asn Ile Gly
            100                 105                 110

Leu Lys Thr Asn Asp Lys Tyr Val Ser Leu Ile Asn Tyr Leu Pro Lys
        115                 120                 125

Asn Lys Ile Glu Ser Thr Asn Val Ser Gln Thr Leu Gly Tyr Asn Ile
    130                 135                 140

Gly Gly Asn Phe Gln Ser Ala Pro Ser Leu Gly Gly Asn Gly Ser Phe
145                 150                 155                 160

Asn Tyr Ser Lys Ser Ile Ser Tyr Thr Gln Gln Asn Tyr Val Ser Glu
                165                 170                 175

Val Glu Gln Gln Asn Ser Lys Ser Val Leu Trp Gly Val Lys Ala Asn
            180                 185                 190

Ser Phe Ala Thr Glu Ser Gly Gln Lys Ser Ala Phe Asp Ser Asp Leu
        195                 200                 205

Phe Val Gly Tyr Lys Pro His Ser Lys Asp Pro Arg Asp Tyr Phe Val
    210                 215                 220

Pro Asp Ser Glu Leu Pro Pro Leu Val Gln Ser Gly Phe Asn Pro Ser
```

-continued

```
225                 230                 235                 240

Phe Ile Ala Thr Val Ser His Glu Lys Gly Ser Ser Asp Thr Ser Glu
                245                 250                 255

Phe Glu Ile Thr Tyr Gly Arg Asn Met Asp Val Thr His Ala Ile Lys
            260                 265                 270

Arg Ser Thr His Tyr Gly Asn Ser Tyr Leu Asp Gly His Arg Val His
        275                 280                 285

Asn Ala Phe Lys Asn Arg Asn Tyr Thr Val Lys Tyr Glu Val Asn Trp
    290                 295                 300

Lys Thr His Glu Ile Lys Val Lys Gly Gln Asn
305                 310                 315


<210> SEQ ID NO 48
<211> LENGTH: 286
<212> TYPE: PRT
<213> ORGANISM: Artificial Sequence
<220> FEATURE:
<223> OTHER INFORMATION: Leukocidin LukS component amino acid sequence

<400> SEQUENCE: 48

Ala Asn Asp Thr Glu Asp Ile Gly Lys Gly Ser Asp Ile Glu Ile Ile
1               5                   10                  15

Lys Arg Thr Glu Asp Lys Thr Ser Asn Lys Trp Gly Val Thr Gln Asn
            20                  25                  30

Ile Gln Phe Asp Phe Val Lys Asp Lys Lys Tyr Asn Lys Asp Ala Leu
        35                  40                  45

Ile Leu Lys Met Gln Gly Phe Ile Ser Ser Arg Thr Thr Tyr Tyr Asn
    50                  55                  60

Tyr Lys Lys Thr Asn His Val Lys Ala Met Arg Trp Pro Phe Gln Tyr
65                  70                  75                  80

Asn Ile Gly Leu Lys Thr Asn Asp Lys Tyr Val Ser Leu Ile Asn Tyr
                85                  90                  95

Leu Pro Lys Asn Lys Ile Glu Ser Thr Asn Val Ser Gln Thr Leu Gly
            100                 105                 110

Tyr Asn Ile Gly Gly Asn Phe Gln Ser Ala Pro Ser Leu Gly Gly Asn
        115                 120                 125

Gly Ser Phe Asn Tyr Ser Lys Ser Ile Ser Tyr Thr Gln Gln Asn Tyr
    130                 135                 140

Val Ser Glu Val Glu Gln Gln Asn Ser Lys Ser Val Leu Trp Gly Val
145                 150                 155                 160

Lys Ala Asn Ser Phe Ala Thr Glu Ser Gly Gln Lys Ser Ala Phe Asp
                165                 170                 175

Ser Asp Leu Phe Val Gly Tyr Lys Pro His Ser Lys Asp Pro Arg Asp
            180                 185                 190

Tyr Phe Val Pro Asp Ser Glu Leu Pro Pro Leu Val Gln Ser Gly Phe
        195                 200                 205

Asn Pro Ser Phe Ile Ala Thr Val Ser His Glu Lys Gly Ser Ser Asp
    210                 215                 220

Thr Ser Glu Phe Glu Ile Thr Tyr Gly Arg Asn Met Asp Val Thr His
225                 230                 235                 240

Ala Ile Lys Arg Ser Thr His Tyr Gly Asn Ser Tyr Leu Asp Gly His
                245                 250                 255

Arg Val His Asn Ala Phe Val Asn Arg Asn Tyr Thr Val Lys Tyr Glu
            260                 265                 270

Val Asn Trp Lys Thr His Glu Ile Lys Glu Lys Gly Gln Asn
```

275 280 285

<210> SEQ ID NO 49
<211> LENGTH: 305
<212> TYPE: PRT
<213> ORGANISM: Artificial Sequence
<220> FEATURE:
<223> OTHER INFORMATION: gamma-hemolysin component C amino acid sequence

<400> SEQUENCE: 49

Met Leu Lys Asn Lys Ile Leu Ala Thr Thr Leu Ser Val Ser Leu Leu
1 5 10 15

Ala Pro Leu Ala Asn Pro Leu Leu Glu Asn Ala Lys Ala Ala Asn Asp
20 25 30

Thr Glu Asp Ile Gly Lys Gly Asn Asp Val Glu Ile Ile Lys Arg Thr
35 40 45

Glu Asp Lys Thr Ser Asn Lys Trp Gly Val Thr Gln Asn Ile Gln Phe
50 55 60

Asp Phe Val Lys Asp Lys Lys Tyr Asn Lys Asp Ala Leu Ile Leu Lys
65 70 75 80

Met Gln Gly Phe Ile Ser Ser Arg Thr Thr Tyr Tyr Asn Tyr Lys Asn
85 90 95

Thr Asn His Ile Lys Ser Met Arg Trp Pro Phe Gln Tyr Asn Ile Gly
100 105 110

Leu Lys Thr Asn Asp Lys Tyr Val Ser Leu Ile Asn Tyr Leu Pro Lys
115 120 125

Asn Lys Ile Glu Ser Thr Asn Val Ser Gln Thr Leu Gly Tyr Asn Ile
130 135 140

Gly Gly Asn Gly Ser Phe Asn Tyr Ser Lys Ser Ile Ser Tyr Thr Gln
145 150 155 160

Gln Asn Tyr Val Ser Glu Val Glu Gln Gln Asn Ser Lys Ser Val Leu
165 170 175

Trp Gly Val Lys Ala Asn Ser Phe Ala Thr Glu Ser Gly Gln Lys Ser
180 185 190

Ala Phe Asp Ser Asp Leu Phe Val Gly Tyr Lys Pro His Ser Lys Asp
195 200 205

Pro Arg Asp Tyr Phe Val Pro Asp Ser Glu Leu Pro Pro Leu Val Gln
210 215 220

Ser Gly Phe Asn Pro Ser Phe Ile Ala Thr Val Ser His Glu Lys Gly
225 230 235 240

Ser Ser Asp Thr Ser Glu Phe Glu Ile Thr Tyr Gly Arg Asn Met Asp
245 250 255

Val Thr His Ala Ile Lys Arg Ser Thr His Tyr Gly Asn Ser Tyr Leu
260 265 270

Asp Gly His Arg Val His Asn Ala Phe Lys Asn Arg Asn Tyr Thr Val
275 280 285

Lys Tyr Glu Val Asn Trp Lys Thr His Glu Ile Lys Val Lys Gly Gln
290 295 300

Asn
305

<210> SEQ ID NO 50
<211> LENGTH: 311
<212> TYPE: PRT
<213> ORGANISM: Artificial Sequence
<220> FEATURE:
<223> OTHER INFORMATION: gamma-hemolysin component A amino acid sequence

<400> SEQUENCE: 50

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Ser Gly Ser Ala Arg Glu Tyr Phe Val
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 51
<211> LENGTH: 314
<212> TYPE: PRT
<213> ORGANISM: Artificial Sequence
<220> FEATURE:
<223> OTHER INFORMATION: Leukotoxin S-subunit amino acid sequence

<400> SEQUENCE: 51

Met Lys Leu Met Phe Lys Lys Lys Met Leu Ala Ala Thr Leu Ser Val
1               5                   10                  15

Gly Leu Ile Ala Pro Leu Ala Ser Pro Ile Gln Glu Ser Arg Ala Asn
            20                  25                  30

```
Thr Asn Ile Glu Asn Ile Gly Asp Gly Ala Glu Val Ile Lys Arg Thr
        35                  40                  45

Glu Asp Val Ser Ser Lys Lys Trp Gly Val Thr Gln Asn Val Gln Phe
    50                  55                  60

Asp Phe Val Lys Asp Lys Lys Tyr Asn Lys Asp Ala Leu Ile Val Lys
65                  70                  75                  80

Met Gln Gly Phe Ile Asn Ser Arg Thr Ser Phe Ser Asp Val Lys Gly
                85                  90                  95

Ser Gly Tyr Glu Leu Thr Lys Arg Met Ile Trp Pro Phe Gln Tyr Asn
            100                 105                 110

Ile Gly Leu Thr Thr Lys Asp Pro Asn Val Ser Leu Ile Asn Tyr Leu
        115                 120                 125

Pro Lys Asn Lys Ile Glu Thr Thr Asp Val Gly Gln Thr Leu Gly Tyr
    130                 135                 140

Asn Ile Gly Gly Asn Phe Gln Ser Ala Pro Ser Ile Gly Gly Asn Gly
145                 150                 155                 160

Ser Phe Asn Tyr Ser Lys Thr Ile Ser Tyr Thr Gln Lys Ser Tyr Val
                165                 170                 175

Ser Glu Val Asp Lys Gln Asn Ser Lys Ser Val Lys Trp Gly Val Lys
            180                 185                 190

Ala Asn Glu Phe Val Thr Pro Asp Gly Lys Lys Ser Ala His Asp Arg
        195                 200                 205

Tyr Leu Phe Val Gln Ser Pro Asn Gly Pro Thr Gly Ser Ala Arg Glu
    210                 215                 220

Tyr Phe Ala Pro Asp Asn Gln Leu Pro Pro Leu Val Gln Ser Gly Phe
225                 230                 235                 240

Asn Pro Ser Phe Ile Thr Thr Leu Ser His Glu Lys Gly Ser Ser Asp
                245                 250                 255

Thr Ser Glu Phe Glu Ile Ser Tyr Gly Arg Asn Leu Asp Ile Thr Tyr
            260                 265                 270

Ala Thr Leu Phe Pro Arg Thr Gly Ile Tyr Ala Glu Arg Lys His Asn
        275                 280                 285

Ala Phe Val Asn Arg Asn Phe Val Val Arg Tyr Glu Val Asn Trp Lys
    290                 295                 300

Thr His Glu Ile Lys Val Lys Gly His Asn
305                 310


<210> SEQ ID NO 52
<211> LENGTH: 311
<212> TYPE: PRT
<213> ORGANISM: Artificial Sequence
<220> FEATURE:
<223> OTHER INFORMATION: Leukotoxin S-subunit amino acid sequence

<400> SEQUENCE: 52

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80
```

```
Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310
```

<210> SEQ ID NO 53
<211> LENGTH: 311
<212> TYPE: PRT
<213> ORGANISM: Artificial Sequence
<220> FEATURE:
<223> OTHER INFORMATION: Leukocidin LukE precursor amino acid sequence

<400> SEQUENCE: 53

```
Met Phe Lys Lys Lys Met Leu Ala Ala Thr Leu Ser Val Gly Leu Ile
1               5                   10                  15

Ala Pro Leu Ala Ser Pro Ile His Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Met Thr Lys Asp Pro Asn Val Ser Leu Ile Asn Tyr Leu Pro Lys Asn
        115                 120                 125
```

-continued

```
Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Ser Gly Ser Ala Arg Glu Tyr Phe Ala
    210                 215                 220

Pro Asp Asn Gln Leu Pro Pro Leu Ile Gln Ser Gly Phe Asn Pro Ser
225                 230                 235                 240

Phe Ile Thr Thr Ile Ser His Glu Lys Gly Thr Ser Glu Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310
```

<210> SEQ ID NO 54
<211> LENGTH: 311
<212> TYPE: PRT
<213> ORGANISM: Artificial Sequence
<220> FEATURE:
<223> OTHER INFORMATION: LukNS amino acid sequence

<400> SEQUENCE: 54

```
Met Phe Lys Lys Gln Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175
```

```
Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310


<210> SEQ ID NO 55
<211> LENGTH: 311
<212> TYPE: PRT
<213> ORGANISM: Artificial Sequence
<220> FEATURE:
<223> OTHER INFORMATION: Leukocidin/Hemolysin toxin family protein amino
      acid sequence

<400> SEQUENCE: 55

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ala Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Ser Gly Ser Ala Arg Glu Tyr Phe Ala
    210                 215                 220
```

Pro Asp Asn Gln Leu Pro Pro Leu Val Gln Ser Gly Phe Asn Pro Ser
225 230 235 240

Phe Ile Thr Thr Leu Ser His Glu Lys Gly Ser Ser Asp Thr Ser Glu
245 250 255

Phe Glu Ile Ser Tyr Gly Arg Asn Leu Asp Ile Thr Tyr Ala Thr Leu
260 265 270

Phe Pro Arg Thr Gly Ile Tyr Ala Glu Arg Lys His Asn Ala Phe Val
275 280 285

Asn Arg Asn Phe Val Val Arg Tyr Glu Val Asn Trp Lys Thr His Glu
290 295 300

Ile Lys Val Lys Gly His Asn
305 310

<210> SEQ ID NO 56
<211> LENGTH: 311
<212> TYPE: PRT
<213> ORGANISM: Artificial Sequence
<220> FEATURE:
<223> OTHER INFORMATION: Leukotoxin E-subunit amino acid sequence

<400> SEQUENCE: 56

Met Phe Lys Lys Lys Met Leu Ala Ala Thr Leu Ser Val Gly Leu Ile
1 5 10 15

Ala Pro Leu Ala Ser Pro Ile Gln Glu Ser Arg Ala Asn Thr Asn Ile
20 25 30

Glu Asn Ile Gly Asp Gly Ala Glu Val Ile Lys Arg Thr Glu Asp Val
35 40 45

Ser Ser Lys Lys Trp Gly Val Thr Gln Asn Val Gln Phe Asp Phe Val
50 55 60

Lys Asp Lys Lys Tyr Asn Lys Asp Ala Leu Ile Val Lys Met Gln Gly
65 70 75 80

Phe Ile Asn Ser Arg Thr Ser Phe Ser Asp Val Lys Gly Ser Gly Tyr
85 90 95

Glu Leu Thr Lys Arg Met Ile Trp Pro Phe Gln Tyr Asn Ile Gly Leu
100 105 110

Ser Thr Lys Asp Pro Tyr Val Ser Leu Ile Asn Tyr Leu Pro Lys Asn
115 120 125

Lys Ile Glu Thr Thr Asp Val Gly Gln Thr Leu Gly Tyr Asn Ile Gly
130 135 140

Gly Asn Phe Gln Ser Ala Pro Ser Ile Gly Gly Asn Gly Ser Phe Asn
145 150 155 160

Tyr Ser Lys Thr Ile Ser Tyr Thr Gln Lys Ser Tyr Val Ser Glu Val
165 170 175

Asp Lys Gln Asn Ser Lys Ser Val Lys Trp Gly Val Lys Ala Asn Ala
180 185 190

Phe Val Thr Pro Asp Gly Lys Lys Ser Ala His Asp Arg Tyr Leu Phe
195 200 205

Val Gln Ser Pro Asn Gly Pro Ser Gly Ser Ala Arg Glu Tyr Phe Val
210 215 220

Pro Asp Asn Gln Leu Pro Pro Leu Val Gln Ser Gly Phe Asn Pro Ser
225 230 235 240

Phe Ile Thr Thr Leu Ser His Glu Lys Gly Ser Ser Asp Thr Ser Glu
245 250 255

Phe Glu Ile Ser Tyr Gly Arg Asn Leu Asp Ile Thr Tyr Ala Thr Leu
260 265 270

Phe Pro Arg Thr Gly Ile Tyr Ala Glu Arg Lys His Asn Ala Phe Val
275 280 285

Asn Arg Asn Phe Val Val Arg Tyr Glu Val Asn Trp Lys Thr His Glu
290 295 300

Ile Lys Val Lys Gly His Asn
305 310

<210> SEQ ID NO 57
<211> LENGTH: 311
<212> TYPE: PRT
<213> ORGANISM: Artificial Sequence
<220> FEATURE:
<223> OTHER INFORMATION: Leukotoxin S-subunit amino acid sequence

<400> SEQUENCE: 57

Met Phe Lys Lys Lys Met Leu Ala Ala Thr Leu Ser Val Gly Leu Ile
1 5 10 15

Ala Pro Leu Ala Ser Pro Ile Gln Glu Ser Arg Ala Asn Thr Asn Ile
20 25 30

Glu Asn Ile Gly Asp Gly Ala Glu Val Ile Lys Arg Thr Glu Asp Val
35 40 45

Ser Ser Lys Lys Trp Gly Val Thr Gln Asn Val Gln Phe Asp Phe Val
50 55 60

Lys Asp Lys Lys Tyr Asn Lys Asp Ala Leu Ile Val Lys Met Gln Gly
65 70 75 80

Phe Ile Asn Ser Arg Thr Ser Phe Ser Asp Val Lys Gly Ser Gly Tyr
85 90 95

Glu Leu Thr Lys Arg Met Ile Trp Pro Phe Gln Tyr Asn Ile Gly Leu
100 105 110

Thr Thr Lys Asp Pro Asn Val Ser Leu Ile Asn Tyr Leu Pro Lys Asn
115 120 125

Lys Ile Glu Thr Thr Asp Val Gly Gln Thr Leu Gly Tyr Asn Ile Gly
130 135 140

Gly Asn Phe Gln Ser Ala Pro Ser Ile Gly Gly Asn Gly Ser Phe Asn
145 150 155 160

Tyr Ser Lys Thr Ile Ser Tyr Thr Gln Lys Ser Tyr Val Ser Glu Val
165 170 175

Asp Lys Gln Asn Ser Lys Ser Val Lys Trp Gly Val Lys Ala Asn Glu
180 185 190

Phe Val Thr Pro Asp Gly Lys Lys Ser Ala His Asp Arg Tyr Leu Phe
195 200 205

Val Gln Ser Pro Asn Gly Pro Thr Gly Ser Ala Arg Glu Tyr Phe Ala
210 215 220

Pro Asp Asn Gln Leu Pro Pro Leu Val Gln Ser Gly Phe Asn Pro Ser
225 230 235 240

Phe Ile Thr Thr Leu Ser His Glu Arg Gly Ser Ser Asp Thr Ser Glu
245 250 255

Phe Glu Ile Ser Tyr Gly Arg Asn Leu Asp Ile Thr Tyr Ala Thr Leu
260 265 270

Phe Pro Arg Thr Gly Ile Tyr Ala Glu Arg Lys His Asn Ala Phe Val
275 280 285

Asn Arg Asn Phe Val Val Arg Tyr Glu Val Asn Trp Lys Thr His Glu
290 295 300

Ile Lys Val Lys Gly His Asn
305 310

<210> SEQ ID NO 58
<211> LENGTH: 311
<212> TYPE: PRT
<213> ORGANISM: Artificial Sequence
<220> FEATURE:
<223> OTHER INFORMATION: Beta-channel forming cytolysin amino acid sequence

<400> SEQUENCE: 58

```
Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Ala Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310
```

<210> SEQ ID NO 59
<211> LENGTH: 311
<212> TYPE: PRT
<213> ORGANISM: Artificial Sequence
<220> FEATURE:
<223> OTHER INFORMATION: Gamma-hemolysin component A amino acid sequence

<400> SEQUENCE: 59

```
Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Ala Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310
```

<210> SEQ ID NO 60
<211> LENGTH: 311
<212> TYPE: PRT
<213> ORGANISM: Artificial Sequence
<220> FEATURE:
<223> OTHER INFORMATION: Leukotoxin E-subunit amino acid sequence

<400> SEQUENCE: 60

```
Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30
```

Glu Asn Ile Gly Asp Gly Ala Glu Val Ile Lys Arg Thr Glu Gly Val
35 40 45

Ser Ser Lys Lys Trp Gly Val Thr Gln Asn Val Gln Phe Asp Phe Val
50 55 60

Lys Asp Lys Lys Tyr Asn Lys Asp Ala Leu Ile Val Lys Met Gln Gly
65 70 75 80

Phe Ile Asn Ser Arg Thr Ser Phe Ser Asp Val Lys Gly Ser Gly Tyr
85 90 95

Glu Leu Thr Lys Arg Met Ile Trp Pro Phe Gln Tyr Asn Ile Gly Leu
100 105 110

Thr Thr Lys Asp Pro Asn Val Ser Leu Ile Asn Tyr Leu Pro Lys Asn
115 120 125

Lys Ile Glu Thr Thr Asp Val Gly Gln Thr Leu Gly Tyr Asn Ile Gly
130 135 140

Gly Asn Phe Gln Ser Ala Pro Ser Ile Gly Gly Asn Gly Ser Phe Asn
145 150 155 160

Tyr Ser Lys Thr Ile Ser Tyr Thr Gln Lys Ser Tyr Val Ser Glu Val
165 170 175

Asp Lys Gln Asn Ser Lys Ser Val Lys Trp Gly Val Lys Ala Asn Glu
180 185 190

Phe Val Thr Pro Asp Gly Lys Lys Ser Ala His Asp Arg Tyr Leu Phe
195 200 205

Val Gln Ser Pro Asn Gly Pro Ser Gly Ser Ala Arg Glu Tyr Phe Ala
210 215 220

Pro Asp Asn Gln Leu Pro Pro Leu Val Gln Ser Gly Phe Asn Pro Ser
225 230 235 240

Phe Ile Thr Thr Leu Ser His Glu Lys Gly Ser Ser Asp Thr Ser Glu
245 250 255

Phe Glu Ile Ser Tyr Gly Arg Asn Leu Asp Ile Thr Tyr Ala Thr Leu
260 265 270

Phe Pro Arg Thr Gly Ile Tyr Ala Glu Arg Lys His Asn Ala Phe Val
275 280 285

Asn Arg Asn Phe Val Val Arg Tyr Glu Val Asn Trp Lys Thr His Glu
290 295 300

Ile Lys Val Lys Gly His Asn
305 310

<210> SEQ ID NO 61
<211> LENGTH: 249
<212> TYPE: PRT
<213> ORGANISM: Artificial Sequence
<220> FEATURE:
<223> OTHER INFORMATION: Leukotoxin S-subunit amino acid sequence

<400> SEQUENCE: 61

Met Lys Asp Lys Lys Tyr Asn Lys Asp Ala Leu Ile Leu Lys Met Gln
1 5 10 15

Gly Phe Ile Ser Ser Arg Thr Thr Tyr Tyr Asn Tyr Lys Lys Thr Asn
20 25 30

His Val Lys Ala Met Arg Trp Pro Phe Gln Tyr Asn Ile Gly Leu Lys
35 40 45

Thr Asn Asp Lys Tyr Val Ser Leu Ile Asn Tyr Leu Pro Lys Asn Lys
50 55 60

Ile Glu Ser Thr Asn Val Ser Gln Thr Leu Gly Tyr Asn Ile Gly Gly
65 70 75 80

-continued

```
Asn Phe Gln Ser Ala Pro Ser Leu Gly Gly Asn Gly Ser Phe Asn Tyr
                85                  90                  95

Ser Lys Ser Ile Ser Tyr Thr Gln Gln Asn Tyr Val Ser Glu Val Glu
            100                 105                 110

Gln Gln Asn Ser Lys Ser Val Leu Trp Gly Val Lys Ala Asn Ser Phe
        115                 120                 125

Ala Thr Glu Ser Gly Gln Lys Ser Ala Phe Asp Ser Asp Leu Phe Val
    130                 135                 140

Gly Tyr Lys Pro His Ser Lys Asp Pro Arg Asp Tyr Phe Val Pro Asp
145                 150                 155                 160

Ser Glu Leu Pro Pro Leu Val Gln Ser Gly Phe Asn Pro Ser Phe Ile
                165                 170                 175

Ala Thr Val Ser His Glu Lys Gly Ser Ser Asp Thr Ser Glu Phe Glu
            180                 185                 190

Ile Thr Tyr Gly Arg Asn Met Asp Val Thr His Ala Ile Lys Arg Ser
        195                 200                 205

Thr His Tyr Gly Asn Ser Tyr Leu Asp Gly His Arg Val His Asn Ala
    210                 215                 220

Phe Val Asn Arg Asn Tyr Thr Val Lys Tyr Glu Val Asn Trp Lys Thr
225                 230                 235                 240

His Glu Ile Lys Val Lys Gly Gln Asn
                245
```

<210> SEQ ID NO 62
<211> LENGTH: 306
<212> TYPE: PRT
<213> ORGANISM: Artificial Sequence
<220> FEATURE:
<223> OTHER INFORMATION: Leukotoxin S-subunit amino acid sequence

<400> SEQUENCE: 62

```
Met Leu Ala Ala Thr Leu Ser Val Gly Leu Ile Ala Pro Leu Ala Ser
1               5                   10                  15

Pro Ile Gln Glu Ser Arg Ala Asn Thr Asn Ile Glu Asn Ile Gly Asp
            20                  25                  30

Gly Ala Glu Val Ile Lys Arg Thr Glu Asp Val Ser Ser Lys Lys Trp
        35                  40                  45

Gly Val Thr Gln Asn Val Gln Phe Asp Phe Val Lys Asp Lys Lys Tyr
    50                  55                  60

Asn Lys Asp Ala Leu Ile Val Lys Met Gln Gly Phe Ile Asn Ser Arg
65                  70                  75                  80

Thr Ser Phe Ser Asp Val Lys Gly Ser Gly Tyr Glu Leu Thr Lys Arg
                85                  90                  95

Met Ile Trp Pro Phe Gln Tyr Asn Ile Gly Leu Thr Thr Lys Asp Pro
            100                 105                 110

Asn Val Ser Leu Ile Asn Tyr Leu Pro Lys Asn Lys Ile Glu Thr Thr
        115                 120                 125

Asp Val Gly Gln Thr Leu Gly Tyr Asn Ile Gly Gly Asn Phe Gln Ser
    130                 135                 140

Ala Pro Ser Ile Gly Gly Asn Gly Ser Phe Asn Tyr Ser Lys Thr Ile
145                 150                 155                 160

Ser Tyr Thr Gln Lys Ser Tyr Val Ser Glu Val Asp Lys Gln Asn Ser
                165                 170                 175

Lys Ser Val Lys Trp Gly Val Lys Ala Asn Glu Phe Val Thr Pro Asp
            180                 185                 190
```

```
Gly Lys Lys Ser Ala His Asp Arg Tyr Leu Phe Val Gln Ser Pro Asn
        195                 200                 205

Gly Pro Thr Gly Ser Ala Arg Glu Tyr Phe Ala Pro Asp Asn Gln Leu
    210                 215                 220

Pro Pro Leu Val Gln Ser Gly Phe Asn Pro Ser Phe Ile Thr Thr Leu
225                 230                 235                 240

Ser His Glu Lys Gly Ser Ser Asp Thr Ser Glu Phe Glu Ile Ser Tyr
                245                 250                 255

Gly Arg Asn Leu Asp Ile Thr Tyr Ala Thr Leu Phe Pro Arg Thr Gly
            260                 265                 270

Ile Tyr Ala Glu Arg Lys His Asn Ala Phe Val Asn Arg Asn Phe Val
        275                 280                 285

Val Arg Tyr Glu Val Asn Trp Lys Thr His Glu Ile Lys Val Lys Gly
    290                 295                 300

His Asn
305


<210> SEQ ID NO 63
<211> LENGTH: 306
<212> TYPE: PRT
<213> ORGANISM: Artificial Sequence
<220> FEATURE:
<223> OTHER INFORMATION: Leukotoxin E-subunit amino acid sequence

<400> SEQUENCE: 63

Met Leu Ala Ala Thr Leu Ser Val Gly Leu Ile Ala Pro Leu Ala Ser
1               5                   10                  15

Pro Ile Gln Glu Ser Arg Ala Asn Thr Asn Ile Glu Asn Ile Gly Asp
            20                  25                  30

Gly Ala Glu Val Ile Lys Arg Thr Glu Asp Val Ser Ser Lys Lys Trp
        35                  40                  45

Gly Val Thr Gln Asn Val Gln Phe Asp Phe Val Lys Asp Lys Lys Tyr
    50                  55                  60

Asn Lys Asp Ala Leu Ile Val Lys Met Gln Gly Phe Ile Asn Ser Arg
65                  70                  75                  80

Thr Ser Phe Ser Asp Val Lys Gly Ser Gly Tyr Glu Leu Thr Lys Arg
                85                  90                  95

Met Ile Trp Pro Phe Gln Tyr Asn Ile Gly Leu Ser Thr Lys Asp Pro
            100                 105                 110

Tyr Val Ser Leu Ile Asn Tyr Leu Pro Lys Asn Lys Ile Glu Thr Thr
        115                 120                 125

Asp Val Gly Gln Thr Leu Gly Tyr Asn Ile Gly Gly Asn Phe Gln Ser
    130                 135                 140

Ala Pro Ser Ile Gly Gly Asn Gly Ser Phe Asn Tyr Ser Lys Thr Ile
145                 150                 155                 160

Ser Tyr Thr Gln Lys Ser Tyr Val Ser Glu Val Asp Lys Gln Asn Ser
                165                 170                 175

Lys Ser Val Lys Trp Gly Val Lys Ala Asn Ala Phe Val Thr Pro Asp
            180                 185                 190

Gly Lys Lys Ser Ala His Asp Arg Tyr Leu Phe Val Gln Ser Pro Asn
        195                 200                 205

Gly Pro Ser Gly Ser Ala Arg Glu Tyr Phe Val Pro Asp Asn Gln Leu
    210                 215                 220

Pro Pro Leu Val Gln Ser Gly Phe Asn Pro Ser Phe Ile Thr Thr Leu
225                 230                 235                 240
```

Ser His Glu Lys Gly Ser Ser Asp Thr Ser Glu Phe Glu Ile Ser Tyr
245 250 255

Gly Arg Asn Leu Asp Ile Thr Tyr Ala Thr Leu Phe Pro Arg Thr Gly
260 265 270

Ile Tyr Ala Glu Arg Lys His Asn Ala Phe Val Asn Arg Asn Phe Val
275 280 285

Val Arg Tyr Glu Val Asn Trp Lys Thr His Glu Ile Lys Val Lys Gly
290 295 300

His Asn
305

<210> SEQ ID NO 64
<211> LENGTH: 306
<212> TYPE: PRT
<213> ORGANISM: Artificial Sequence
<220> FEATURE:
<223> OTHER INFORMATION: Gamma-hemolysin component A amino acid sequence

<400> SEQUENCE: 64

Met Leu Ala Ala Thr Leu Ser Val Gly Leu Ile Ala Pro Leu Ala Ser
1 5 10 15

Pro Ile Gln Glu Ser Arg Ala Asn Thr Asn Ile Glu Asn Ile Gly Asp
20 25 30

Gly Ala Glu Val Ile Lys Arg Met Glu Asp Val Ser Ser Lys Lys Trp
35 40 45

Gly Val Thr Gln Asn Val Gln Phe Asp Phe Val Lys Asp Lys Lys Tyr
50 55 60

Asn Lys Asp Ala Leu Ile Val Lys Met Gln Gly Phe Ile Asn Ser Arg
65 70 75 80

Thr Ser Phe Ser Asp Val Lys Gly Ser Gly Tyr Glu Leu Thr Lys Arg
85 90 95

Met Ile Trp Pro Phe Gln Tyr Asn Ile Gly Leu Thr Thr Lys Asp Pro
100 105 110

Asn Val Ser Leu Ile Asn Tyr Leu Pro Lys Asn Lys Ile Glu Thr Thr
115 120 125

Asp Val Gly Gln Thr Leu Gly Tyr Asn Ile Gly Gly Asn Phe Gln Ser
130 135 140

Ala Pro Ser Ile Gly Gly Asn Gly Ser Phe Asn Tyr Ser Lys Thr Ile
145 150 155 160

Ser Tyr Thr Gln Lys Ser Tyr Val Ser Glu Val Asp Lys Gln Asn Ser
165 170 175

Lys Ser Val Lys Trp Gly Val Lys Ala Asn Glu Phe Val Thr Pro Asp
180 185 190

Gly Lys Lys Ser Ala His Asp Arg Tyr Leu Phe Val Gln Ser Pro Asn
195 200 205

Gly Pro Ser Gly Ser Ala Arg Glu Tyr Phe Ala Pro Asp Asn Gln Leu
210 215 220

Pro Pro Leu Val Gln Ser Gly Phe Asn Pro Ser Phe Ile Thr Thr Leu
225 230 235 240

Ser His Glu Lys Gly Ser Ser Asp Thr Ser Glu Phe Glu Ile Ser Tyr
245 250 255

Gly Arg Asn Leu Asp Ile Thr Tyr Ala Thr Leu Phe Pro Arg Thr Gly
260 265 270

Ile Tyr Ala Glu Arg Lys His Asn Ala Phe Val Asn Arg Asn Phe Val
275 280 285

```
Val Arg Tyr Glu Val Asn Trp Lys Thr His Glu Ile Lys Val Lys Gly
    290                 295                 300

His Asn
305


<210> SEQ ID NO 65
<211> LENGTH: 306
<212> TYPE: PRT
<213> ORGANISM: Artificial Sequence
<220> FEATURE:
<223> OTHER INFORMATION: Gamma-hemolysin component A amino acid sequence

<400> SEQUENCE: 65

Met Leu Ala Ala Thr Leu Ser Val Gly Leu Ile Ala Pro Leu Ala Ser
1               5                   10                  15

Pro Ile His Glu Ser Arg Ala Asn Thr Asn Ile Glu Asn Ile Gly Asp
            20                  25                  30

Gly Ala Glu Val Ile Lys Arg Thr Glu Asp Val Ser Ser Lys Lys Trp
        35                  40                  45

Gly Val Thr Gln Asn Val Gln Phe Asp Phe Val Lys Asp Lys Lys Tyr
    50                  55                  60

Asn Lys Asp Ala Leu Ile Val Lys Met Gln Gly Phe Ile Asn Ser Arg
65                  70                  75                  80

Thr Ser Phe Ser Asp Val Lys Gly Ser Gly Tyr Glu Leu Thr Lys Arg
                85                  90                  95

Met Ile Trp Pro Phe Gln Tyr Asn Ile Gly Leu Ser Thr Lys Asp Pro
            100                 105                 110

Tyr Val Ser Leu Ile Asn Tyr Leu Pro Lys Asn Lys Ile Glu Thr Thr
        115                 120                 125

Asp Val Gly Gln Thr Leu Gly Tyr Asn Ile Gly Gly Asn Phe Gln Ser
    130                 135                 140

Ala Pro Ser Ile Gly Gly Asn Gly Ser Phe Asn Tyr Ser Lys Thr Ile
145                 150                 155                 160

Ser Tyr Thr Gln Lys Ser Tyr Val Ser Glu Val Asp Lys Gln Asn Ser
                165                 170                 175

Lys Ser Val Lys Trp Gly Val Lys Ala Asn Glu Phe Val Thr Pro Asp
            180                 185                 190

Gly Lys Lys Ser Ala Gln Asp Arg Tyr Leu Phe Val Gln Ser Pro Asn
        195                 200                 205

Gly Pro Ser Gly Ser Ala Arg Glu Tyr Phe Ala Pro Asp Asn Gln Leu
    210                 215                 220

Pro Pro Leu Val Gln Ser Gly Phe Asn Pro Ser Phe Ile Thr Thr Leu
225                 230                 235                 240

Ser His Glu Lys Gly Ser Ser Asp Thr Ser Glu Phe Glu Ile Ser Tyr
                245                 250                 255

Gly Arg Asn Leu Asp Ile Thr Tyr Ala Thr Leu Phe Pro Arg Thr Gly
            260                 265                 270

Ile Tyr Ala Glu Arg Lys His Asn Ala Phe Val Asn Arg Asn Phe Val
        275                 280                 285

Val Arg Tyr Glu Val Asn Trp Lys Thr His Glu Ile Lys Val Lys Gly
    290                 295                 300

His Asn
305


<210> SEQ ID NO 66
<211> LENGTH: 308
```

```
<212> TYPE: PRT
<213> ORGANISM: Artificial Sequence
<220> FEATURE:
<223> OTHER INFORMATION: Leukocidin chain lukM precursor amino acid
      sequence

<400> SEQUENCE: 66

Met Phe Lys Arg Lys Leu Leu Val Thr Thr Leu Ser Leu Gly Leu Ile
1               5                   10                  15

Val Pro Ile Ala Thr Pro Phe Gln Gly Ser Lys Ala Thr Thr Asn Ala
            20                  25                  30

Glu Asp Ile Gly Asp Asp Ala Glu Val Ile Lys Arg Thr Glu Asp Val
        35                  40                  45

Ser Ser Arg Lys Trp Gly Val Thr Gln Asn Val Gln Phe Asp Phe Val
    50                  55                  60

Lys Asp Lys Lys Tyr Asn Lys Asp Ala Leu Ile Ile Lys Met Gln Gly
65                  70                  75                  80

Phe Ile Asn Ser Arg Thr Thr Phe Asn Asp Val Lys Gln Asn Arg Ala
                85                  90                  95

Asn Lys Arg Met Val Trp Pro Phe Gln Tyr Asn Ile Gly Leu Thr Ser
            100                 105                 110

Lys Asp Gln Asn Thr Ser Leu Ile Asn Tyr Leu Pro Lys Asn Lys Ile
        115                 120                 125

Glu Thr Val Asp Val Gly Gln Thr Leu Gly Tyr Asn Ile Gly Gly Lys
    130                 135                 140

Phe Gln Ser Ala Pro Ser Ile Gly Gly Asn Gly Ser Phe Asn Tyr Ser
145                 150                 155                 160

Lys Ser Ile Lys Tyr Ser Gln Lys Ser Tyr Val Ser Glu Val Glu Gln
                165                 170                 175

Gln Ser Ser Lys Thr Ile Lys Trp Gly Val Lys Ala Asn Ser Phe Val
            180                 185                 190

Ile Ala Gly His Arg Trp Ser Ala Tyr Asp Glu Leu Leu Phe Ile Arg
        195                 200                 205

Asn Thr Thr Arg Gly Pro Asn Ala Arg Asp Tyr Phe Val Asp Asp Asn
    210                 215                 220

Glu Leu Pro Pro Leu Ile Thr Ser Gly Phe Asn Pro Ser Phe Ile Ala
225                 230                 235                 240

Thr Val Ser His Glu Lys Asp Ser Gly Asp Thr Ser Glu Phe Glu Ile
                245                 250                 255

Thr Tyr Gly Arg Asn Met Asp Val Thr Tyr Ala Thr Tyr Leu Pro Lys
            260                 265                 270

Gln Gly Leu Tyr Pro Glu Arg Lys His Asn Glu Phe Val Asn Arg Asn
        275                 280                 285

Phe Val Val Lys Tyr Glu Val Asn Trp Lys Thr His Glu Ile Lys Val
    290                 295                 300

Lys Gly His Asn
305


<210> SEQ ID NO 67
<211> LENGTH: 308
<212> TYPE: PRT
<213> ORGANISM: Artificial Sequence
<220> FEATURE:
<223> OTHER INFORMATION: Leukocidin chain lukM precursor amino acid
      sequence

<400> SEQUENCE: 67
```

```
Met Phe Lys Arg Lys Leu Leu Val Thr Thr Leu Ser Leu Gly Leu Ile
1               5                   10                  15

Val Pro Ile Ala Thr Pro Phe Gln Gly Ser Lys Ala Thr Thr Asn Ala
            20                  25                  30

Glu Asp Ile Gly Asp Asp Ala Glu Val Ile Lys Arg Thr Glu Asp Val
        35                  40                  45

Ser Ser Arg Lys Trp Gly Val Thr Gln Asn Val Gln Phe Asp Phe Val
    50                  55                  60

Lys Asp Lys Lys Tyr Asn Lys Asp Ala Leu Ile Ile Lys Met Gln Gly
65                  70                  75                  80

Phe Ile Asn Ser Arg Thr Thr Phe Asn Asp Val Lys Gln Asn Arg Ala
                85                  90                  95

Asn Lys Arg Met Val Trp Pro Phe Gln Tyr Asn Ile Gly Leu Thr Ser
            100                 105                 110

Lys Asp Gln Asn Thr Ser Leu Ile Asn Tyr Leu Pro Lys Asn Lys Ile
        115                 120                 125

Glu Thr Val Asp Val Gly Gln Thr Leu Gly Tyr Asn Ile Gly Gly Lys
    130                 135                 140

Phe Gln Ser Ala Pro Ser Ile Gly Gly Asn Gly Ser Phe Asn Tyr Ser
145                 150                 155                 160

Lys Ser Ile Lys Tyr Ser Gln Lys Ser Tyr Val Ser Glu Val Glu Gln
                165                 170                 175

Gln Ser Ser Lys Thr Ile Lys Trp Gly Val Lys Ala Asn Ser Phe Val
            180                 185                 190

Ile Ala Gly His Arg Trp Ser Ala Tyr Asp Glu Leu Leu Phe Ile Arg
        195                 200                 205

Asn Thr Thr Arg Gly Pro Asn Ala Arg Asp Tyr Phe Val Asp Asp Asn
    210                 215                 220

Glu Leu Pro Pro Leu Ile Thr Ser Gly Phe Asn Pro Ser Phe Ile Ala
225                 230                 235                 240

Thr Val Ser His Glu Lys Asp Ser Gly Asp Thr Ser Glu Phe Glu Ile
                245                 250                 255

Thr Tyr Gly Arg Asn Met Asp Val Thr Tyr Ala Thr Tyr Leu Pro Lys
            260                 265                 270

Leu Gly Leu Tyr Pro Glu Arg Lys His Asn Glu Phe Val Asn Arg Asn
        275                 280                 285

Phe Val Val Lys Tyr Glu Val Asn Trp Lys Thr Tyr Glu Ile Lys Val
    290                 295                 300

Lys Gly His Asn
305


<210> SEQ ID NO 68
<211> LENGTH: 308
<212> TYPE: PRT
<213> ORGANISM: Artificial Sequence
<220> FEATURE:
<223> OTHER INFORMATION: LukM precursor amino acid sequence

<400> SEQUENCE: 68

Met Phe Lys Arg Lys Leu Leu Val Thr Thr Leu Ser Leu Gly Leu Ile
1               5                   10                  15

Val Pro Ile Ala Thr Pro Phe Gln Gly Ser Lys Ala Thr Thr Asn Ala
            20                  25                  30

Glu Asp Ile Gly Asp Asp Ala Glu Val Ile Lys Arg Thr Glu Asp Val
        35                  40                  45
```

```
Ser Ser Arg Lys Trp Gly Val Thr Gln Asn Val Gln Phe Asp Phe Val
    50                  55                  60

Lys Asp Lys Lys Tyr Asn Lys Asp Ala Leu Ile Ile Lys Met Gln Gly
65                  70                  75                  80

Phe Ile Asn Ser Arg Thr Thr Phe Asn Asp Val Lys Gln Asn Arg Ala
                85                  90                  95

Asn Lys Arg Met Val Trp Pro Phe Gln Tyr Asn Ile Gly Leu Thr Ser
            100                 105                 110

Lys Asp Gln Asn Thr Ser Leu Ile Asn Tyr Leu Pro Lys Asn Lys Ile
        115                 120                 125

Glu Thr Val Asp Val Gly Gln Thr Leu Gly Tyr Asn Ile Gly Gly Lys
    130                 135                 140

Phe Gln Ser Val Pro Ser Ile Gly Gly Asn Gly Ser Phe Asn Tyr Ser
145                 150                 155                 160

Lys Ser Ile Lys Tyr Ser Gln Lys Ser Tyr Val Ser Glu Val Glu Gln
                165                 170                 175

Gln Ser Ser Lys Thr Ile Lys Trp Gly Val Lys Ala Asn Ser Phe Val
            180                 185                 190

Ile Ala Gly His Arg Trp Ser Ala Tyr Asp Glu Leu Leu Phe Ile Arg
        195                 200                 205

Asn Thr Thr Arg Gly Pro Asn Ala Arg Asp Tyr Phe Val Asp Asp Asn
    210                 215                 220

Glu Leu Pro Pro Leu Ile Thr Ser Gly Phe Asn Pro Ser Phe Ile Ala
225                 230                 235                 240

Thr Val Ser His Glu Lys Asp Ser Gly Asp Thr Ser Glu Phe Glu Ile
                245                 250                 255

Thr Tyr Gly Arg Asn Met Asp Val Thr Tyr Ala Thr Tyr Leu Pro Lys
            260                 265                 270

Leu Gly Leu Tyr Pro Glu Arg Lys His Asn Glu Phe Val Asn Arg Asn
        275                 280                 285

Phe Val Val Lys Tyr Glu Val Asn Trp Lys Thr Tyr Glu Ile Lys Val
    290                 295                 300

Lys Gly His Asn
305
```

<210> SEQ ID NO 69
<211> LENGTH: 309
<212> TYPE: PRT
<213> ORGANISM: Artificial Sequence
<220> FEATURE:
<223> OTHER INFORMATION: gamma-hemolysin component A precursor amino acid sequence

<400> SEQUENCE: 69

```
Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95
```

Tyr Ile Lys Arg Met Ile Trp Pro Phe Gln Tyr Asn Ile Ser Leu Lys
100 105 110

Thr Lys Asp Pro Asn Val Asp Leu Ile Asn Tyr Leu Pro Lys Asn Lys
115 120 125

Ile Asp Ser Ala Asp Val Ser Gln Lys Leu Gly Tyr Asn Ile Gly Gly
130 135 140

Asn Phe Gln Thr Ala Pro Ser Ile Gly Gly Ser Gly Ser Phe Asn Tyr
145 150 155 160

Ser Lys Thr Ile Ser Tyr Asn Gln Lys Asn Tyr Val Thr Glu Val Glu
165 170 175

Ser Gln Asn Ser Lys Gly Val Lys Trp Gly Ile Lys Ala Asn Ser Phe
180 185 190

Val Thr Pro Asn Gly Gln Val Ser Ala Tyr Asp Gln Tyr Leu Phe Ala
195 200 205

Gln Asp Pro Thr Gly Pro Ala Ala Arg Asp Tyr Phe Val Pro Asp Asn
210 215 220

Gln Leu Pro Pro Leu Ile Gln Ser Gly Phe Asn Pro Ser Phe Ile Thr
225 230 235 240

Thr Leu Ser His Glu Arg Gly Lys Gly Asp Lys Ser Glu Phe Glu Ile
245 250 255

Thr Tyr Gly Arg Asn Met Asp Ala Thr Tyr Ala Tyr Val Thr Arg His
260 265 270

Arg Leu Ala Val Asp Arg Lys His Asp Ala Phe Lys Asn Arg Asn Val
275 280 285

Thr Val Lys Tyr Glu Val Asn Trp Lys Thr His Glu Val Lys Ile Lys
290 295 300

Ser Ile Thr Pro Lys
305

<210> SEQ ID NO 70
<211> LENGTH: 321
<212> TYPE: PRT
<213> ORGANISM: Artificial Sequence
<220> FEATURE:
<223> OTHER INFORMATION: gamma-hemolysin component A precursor amino acid sequence

<400> SEQUENCE: 70

Met Asn Leu Lys Leu Asn Arg Lys Lys Val Ile Ser Met Ile Lys Asn
1 5 10 15

Lys Ile Leu Thr Ala Thr Leu Ala Val Gly Leu Ile Ala Pro Leu Ala
20 25 30

Asn Pro Phe Ile Glu Ile Ser Lys Ala Glu Asn Lys Ile Glu Asp Ile
35 40 45

Gly Gln Gly Ala Glu Ile Ile Lys Arg Thr Gln Asp Ile Thr Ser Lys
50 55 60

Arg Leu Ala Ile Thr Gln Asn Ile Gln Phe Asp Phe Val Lys Asp Lys
65 70 75 80

Lys Tyr Asn Lys Asp Ala Leu Val Val Lys Met Gln Gly Phe Ile Ser
85 90 95

Ser Arg Thr Thr Tyr Ser Asp Phe Lys Lys Tyr Pro Tyr Ile Lys Arg
100 105 110

Met Ile Trp Pro Phe Gln Tyr Asn Ile Ser Leu Lys Thr Lys Asp Ser
115 120 125

Asn Val Asp Leu Ile Asn Tyr Leu Pro Lys Asn Lys Ile Asp Ser Ala 130 135 140

Asp Val Ser Gln Lys Leu Gly Tyr Asn Ile Gly Gly Asn Phe Gln Ser
145 150 155 160

Ala Pro Ser Ile Gly Gly Ser Gly Ser Phe Asn Tyr Ser Lys Thr Ile
165 170 175

Ser Tyr Asn Gln Lys Asn Tyr Val Thr Glu Val Glu Ser Gln Asn Ser
180 185 190

Lys Gly Val Lys Trp Gly Val Lys Ala Asn Ser Phe Val Thr Pro Asn
195 200 205

Gly Gln Val Ser Ala Tyr Asp Gln Tyr Leu Phe Ala Gln Asp Pro Thr
210 215 220

Gly Pro Ala Ala Arg Asp Tyr Phe Val Pro Asp Asn Gln Leu Pro Pro
225 230 235 240

Leu Ile Gln Ser Gly Phe Asn Pro Ser Phe Ile Thr Thr Leu Ser His
245 250 255

Glu Arg Gly Lys Gly Asp Lys Ser Glu Phe Glu Ile Thr Tyr Gly Arg
260 265 270

Asn Met Asp Ala Thr Tyr Ala Tyr Val Thr Arg His Arg Leu Ala Val
275 280 285

Asp Arg Lys His Asp Ala Phe Lys Asn Arg Asn Val Thr Val Lys Tyr
290 295 300

Glu Val Asn Trp Lys Thr His Glu Val Lys Ile Lys Ser Ile Thr Pro
305 310 315 320

Lys

<210> SEQ ID NO 71
<211> LENGTH: 321
<212> TYPE: PRT
<213> ORGANISM: Artificial Sequence
<220> FEATURE:
<223> OTHER INFORMATION: beta-channel forming cytolysin amino acid sequence

<400> SEQUENCE: 71

Met Asn Leu Lys Leu Asn Arg Lys Lys Val Ile Ser Met Ile Lys Asn
1 5 10 15

Lys Ile Leu Thr Ala Thr Leu Ala Val Gly Leu Ile Ala Pro Leu Ala
20 25 30

Asn Pro Phe Thr Glu Ile Ser Lys Ala Glu Asn Lys Ile Glu Asp Ile
35 40 45

Gly Gln Gly Ala Glu Ile Ile Lys Arg Thr Gln Asp Ile Thr Ser Lys
50 55 60

Arg Leu Ala Ile Thr Gln Asn Ile Gln Phe Asp Phe Val Lys Asp Lys
65 70 75 80

Lys Tyr Asn Lys Asp Ala Leu Val Val Lys Met Gln Gly Phe Ile Ser
85 90 95

Ser Arg Thr Thr Tyr Ser Asp Leu Lys Lys Tyr Pro Tyr Ile Lys Arg
100 105 110

Met Ile Trp Pro Phe Gln Tyr Asn Ile Ser Leu Lys Thr Lys Asp Ser
115 120 125

Asn Val Asp Leu Ile Asn Tyr Leu Pro Lys Asn Lys Ile Asp Ser Ala
130 135 140

Asp Val Ser Gln Lys Leu Gly Tyr Asn Ile Gly Gly Asn Phe Gln Ser
145 150 155 160

Ala Pro Ser Ile Gly Gly Ser Gly Ser Phe Asn Tyr Ser Lys Thr Ile

```
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Lys Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285

Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys


<210> SEQ ID NO 72
<211> LENGTH: 309
<212> TYPE: PRT
<213> ORGANISM: Artificial Sequence
<220> FEATURE:
<223> OTHER INFORMATION: gamma hemolysin amino acid sequence

<400> SEQUENCE: 72

Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140

Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205
```

```
Gln Asp Pro Thr Gly Pro Ala Ala Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Lys Gly Lys Gly Asp Lys Ser Glu Phe Glu Ile
                245                 250                 255

Thr Tyr Gly Arg Asn Met Asp Ala Thr Tyr Ala Tyr Val Thr Arg His
            260                 265                 270

Arg Leu Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305


<210> SEQ ID NO 73
<211> LENGTH: 309
<212> TYPE: PRT
<213> ORGANISM: Artificial Sequence
<220> FEATURE:
<223> OTHER INFORMATION: gamma-hemolysin component A precursor amino
      acid sequence

<400> SEQUENCE: 73

Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140

Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205

Gln Asp Pro Thr Gly Pro Ala Ala Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Lys Gly Lys Gly Asp Lys Ser Glu Phe Glu Ile
```

```
                245                 250                 255

Thr Tyr Gly Arg Asn Met Asp Thr Thr Tyr Ala Tyr Val Thr Arg His
            260                 265                 270

Arg Leu Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305


<210> SEQ ID NO 74
<211> LENGTH: 321
<212> TYPE: PRT
<213> ORGANISM: Artificial Sequence
<220> FEATURE:
<223> OTHER INFORMATION: gamma-hemolysin component A precursor amino
      acid sequence

<400> SEQUENCE: 74

Met Asn Leu Lys Leu Asn Arg Lys Lys Val Ile Ser Met Ile Lys Asn
1               5                   10                  15

Lys Ile Leu Thr Ala Thr Leu Ala Val Gly Leu Ile Ala Pro Leu Ala
            20                  25                  30

Asn Pro Phe Ile Glu Ile Ser Lys Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Pro Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Lys Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285
```

```
Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys


<210> SEQ ID NO 75
<211> LENGTH: 309
<212> TYPE: PRT
<213> ORGANISM: Artificial Sequence
<220> FEATURE:
<223> OTHER INFORMATION: gamma-hemolysin component A precursor amino
      acid sequence

<400> SEQUENCE: 75

Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Ala Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140

Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205

Gln Asp Pro Thr Gly Pro Ala Ala Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Arg Gly Lys Gly Asp Lys Ser Glu Phe Glu Ile
                245                 250                 255

Thr Tyr Gly Arg Asn Met Asp Ala Thr Tyr Ala Tyr Val Thr Arg His
            260                 265                 270

Arg Leu Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305
```

<210> SEQ ID NO 76
<211> LENGTH: 309
<212> TYPE: PRT
<213> ORGANISM: Artificial Sequence
<220> FEATURE:
<223> OTHER INFORMATION: gamma-hemolysin chain II precursor amino acid sequence

<400> SEQUENCE: 76

```
Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140

Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205

Gln Asp Pro Thr Gly Pro Ala Ala Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Arg Gly Lys Gly Asp Lys Ser Glu Phe Glu Ile
                245                 250                 255

Thr Tyr Gly Arg Asn Met Asp Ala Thr Tyr Ala Tyr Val Thr Arg His
            260                 265                 270

Arg Leu Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305
```

<210> SEQ ID NO 77
<211> LENGTH: 321
<212> TYPE: PRT
<213> ORGANISM: Artificial Sequence
<220> FEATURE:
<223> OTHER INFORMATION: beta-channel forming cytolysin amino acid sequence

<400> SEQUENCE: 77

Met Asn Leu Lys Leu Asn Arg Lys Lys Val Ile Ser Met Ile Lys Asn
1               5                   10                  15

Lys Ile Leu Thr Ala Thr Leu Ala Val Gly Leu Ile Ala Pro Leu Ala
            20                  25                  30

Asn Pro Phe Ile Glu Ile Ser Lys Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Pro Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Arg Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285

Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys

<210> SEQ ID NO 78
<211> LENGTH: 321
<212> TYPE: PRT
<213> ORGANISM: Artificial Sequence
<220> FEATURE:
<223> OTHER INFORMATION: beta-channel forming cytolysin amino acid sequence

<400> SEQUENCE: 78

Met Asn Leu Lys Leu Asn Arg Lys Lys Val Ile Ser Met Ile Lys Asn
1               5                   10                  15

```
Lys Ile Leu Thr Ala Thr Leu Ala Val Gly Leu Ile Ala Pro Leu Ala
            20                  25                  30

Asn Pro Phe Ile Glu Ile Ser Lys Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Leu Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Arg Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285

Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys
```

<210> SEQ ID NO 79
<211> LENGTH: 308
<212> TYPE: PRT
<213> ORGANISM: Artificial Sequence
<220> FEATURE:
<223> OTHER INFORMATION: preLukM amino acid sequence

<400> SEQUENCE: 79

```
Met Phe Asn Arg Lys Leu Leu Val Thr Thr Leu Ser Leu Gly Leu Ile
1               5                   10                  15

Val Pro Ile Ala Thr Pro Phe Gln Gly Ser Lys Ala Thr Thr Asn Ala
            20                  25                  30

Glu Asp Ile Gly Asp Asp Ala Glu Val Ile Lys Arg Thr Glu Asp Val
        35                  40                  45

Ser Ser Arg Lys Trp Gly Val Thr Gln Asn Val Gln Phe Asp Phe Val
```

```
    50                  55                  60

Lys Asp Lys Lys Tyr Asn Lys Asp Ala Leu Ile Ile Lys Met Gln Gly
65                  70                  75                  80

Phe Ile Asn Ser Arg Thr Thr Phe Asn Asp Val Lys Gln Asn Arg Ala
                85                  90                  95

Asn Lys Arg Met Val Trp Pro Phe Gln Tyr Asn Ile Gly Leu Thr Ser
            100                 105                 110

Lys Asp Gln Asn Thr Ser Leu Ile Asn Tyr Leu Pro Lys Asn Lys Ile
        115                 120                 125

Glu Thr Val Asp Val Gly Gln Thr Leu Gly Tyr Asn Ile Gly Gly Lys
    130                 135                 140

Phe Gln Ser Val Pro Ser Ile Gly Gly Asn Gly Ser Phe Asn Tyr Ser
145                 150                 155                 160

Lys Ser Ile Lys Tyr Ser Gln Lys Ser Tyr Val Ser Glu Val Glu Gln
                165                 170                 175

Gln Ser Ser Lys Thr Ile Lys Trp Gly Val Lys Ala Asn Ser Phe Val
            180                 185                 190

Ile Ala Gly His Arg Trp Ser Ala Tyr Asp Glu Leu Leu Phe Ile Arg
        195                 200                 205

Asn Thr Thr Arg Gly Pro Asn Ala Arg Asp Tyr Phe Val Asp Asp Asn
    210                 215                 220

Glu Leu Pro Pro Leu Ile Thr Ser Gly Phe Asn Pro Ser Phe Ile Ala
225                 230                 235                 240

Thr Val Ser His Glu Lys Asp Ser Gly Asp Thr Ser Glu Phe Glu Ile
                245                 250                 255

Thr Tyr Gly Arg Asn Met Asp Val Thr Tyr Ala Thr Tyr Leu Pro Lys
            260                 265                 270

Leu Gly Leu Tyr Pro Glu Arg Lys His Asn Glu Phe Val Asn Arg Asn
        275                 280                 285

Leu Val Val Lys Tyr Glu Val Asn Trp Lys Thr Ser Glu Leu Lys Val
    290                 295                 300

Arg Gly His Asn
305
```

<210> SEQ ID NO 80
<211> LENGTH: 309
<212> TYPE: PRT
<213> ORGANISM: Artificial Sequence
<220> FEATURE:
<223> OTHER INFORMATION: gamma-hemolysin component A precursor amino acid sequence

<400> SEQUENCE: 80

```
Met Ile Lys Asn Lys Ile Leu Thr Ala Thr Leu Ala Val Gly Leu Met
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95
```

```
Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140

Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205

Gln Asp Pro Thr Gly Pro Ala Thr Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Arg Gly Lys Gly Asp Lys Ser Glu Phe Glu Ile
                245                 250                 255

Thr Tyr Gly Arg Asn Met Asp Ala Thr Tyr Ala Tyr Val Thr Arg His
            260                 265                 270

Arg Leu Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305
```

```
<210> SEQ ID NO 81
<211> LENGTH: 309
<212> TYPE: PRT
<213> ORGANISM: Artificial Sequence
<220> FEATURE:
<223> OTHER INFORMATION: Leukocidin-S subunit amino acid sequence

<400> SEQUENCE: 81

Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
        115                 120                 125

Ile Asp Ser Ala Asp Val Ser Gln Lys Leu Gly Tyr Asn Ile Gly Gly
    130                 135                 140
```

```
Asn Phe Gln Ser Ala Pro Ser Ile Gly Gly Ser Gly Ser Phe Asn Tyr
145                 150                 155                 160

Ser Lys Thr Ile Ser Tyr Asn Gln Lys Asn Tyr Val Thr Glu Val Glu
                165                 170                 175

Ser Gln Asn Ser Lys Gly Val Lys Trp Gly Val Lys Ala Asn Ser Phe
            180                 185                 190

Val Thr Pro Asn Gly Gln Val Ser Ala Tyr Asp Gln Tyr Leu Phe Ala
        195                 200                 205

Gln Asp Pro Thr Gly Pro Ala Ala Arg Asp Tyr Phe Val Pro Asp Asn
    210                 215                 220

Gln Leu Pro Pro Leu Ile Gln Ser Gly Phe Asn Pro Ser Phe Ile Thr
225                 230                 235                 240

Thr Leu Ser His Glu Arg Gly Lys Gly Asp Lys Ser Glu Phe Glu Ile
                245                 250                 255

Thr Tyr Gly Arg Asn Met Asp Ala Thr Tyr Ala Tyr Val Thr Arg His
            260                 265                 270

Arg Phe Ala Val Asp Arg Lys His Asp Ala Phe Lys Asn Arg Asn Val
        275                 280                 285

Thr Val Lys Tyr Glu Val Asn Trp Lys Thr His Glu Val Lys Ile Lys
    290                 295                 300

Ser Ile Thr Pro Lys
305
```

<210> SEQ ID NO 82
<211> LENGTH: 321
<212> TYPE: PRT
<213> ORGANISM: Artificial Sequence
<220> FEATURE:
<223> OTHER INFORMATION: hlgA-like ORF amino acid sequence

<400> SEQUENCE: 82

```
Met Asn Leu Lys Leu Asn Arg Lys Lys Val Ile Ser Met Ile Lys Asn
1               5                   10                  15

Lys Ile Leu Thr Ala Thr Leu Ala Val Gly Leu Ile Ala Pro Leu Ala
            20                  25                  30

Asn Pro Phe Ile Glu Ile Ser Lys Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Pro Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190
```

```
Lys Gly Gly Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Lys Gly Lys Gly Asp Lys Ser Glu Phe Glu Ile Thr Tyr Gly Arg
            260                 265                 270

Asn Met Asp Ala Thr Tyr Ala Tyr Val Thr Arg Pro Arg Leu Ala Val
        275                 280                 285

Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys


<210> SEQ ID NO 83
<211> LENGTH: 321
<212> TYPE: PRT
<213> ORGANISM: Artificial Sequence
<220> FEATURE:
<223> OTHER INFORMATION: gamma-hemolysin component A precursor amino
      acid sequence

<400> SEQUENCE: 83

Met Asn Leu Lys Leu Asn Arg Lys Lys Val Ile Ser Met Ile Lys Asn
1               5                   10                  15

Lys Ile Leu Thr Ala Thr Leu Ala Val Gly Leu Ile Ala Pro Leu Ala
            20                  25                  30

Asn Pro Phe Ile Glu Ile Ser Arg Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Pro Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Pro Thr
    210                 215                 220
```

Gly Pro Ala Ala Arg Asp Tyr Phe Val Pro Asp Asn Gln Leu Pro Pro
225 230 235 240

Leu Ile Gln Ser Gly Phe Asn Pro Ser Phe Ile Thr Thr Leu Ser His
245 250 255

Glu Arg Gly Lys Gly Asp Lys Ser Asp Phe Glu Ile Thr Tyr Gly Arg
260 265 270

Asn Met Asp Ala Thr Tyr Ala Tyr Val Thr Arg His Arg Leu Ala Val
275 280 285

Asp Arg Lys His Asp Ala Phe Lys Asn Arg Asn Val Thr Val Lys Tyr
290 295 300

Glu Val Asn Trp Lys Thr His Glu Val Lys Ile Lys Ser Ile Thr Pro
305 310 315 320

Lys

<210> SEQ ID NO 84
<211> LENGTH: 321
<212> TYPE: PRT
<213> ORGANISM: Artificial Sequence
<220> FEATURE:
<223> OTHER INFORMATION: gamma-hemolysin component A precursor amino acid sequence

<400> SEQUENCE: 84

Met Asn Leu Lys Leu Asn Arg Lys Lys Val Ile Ser Met Ile Lys Asn
1 5 10 15

Lys Ile Leu Thr Ala Thr Leu Ala Val Gly Leu Ile Ala Pro Leu Ala
20 25 30

Asn Pro Phe Ile Glu Ile Ser Lys Ala Glu Asn Lys Ile Glu Asp Ile
35 40 45

Gly Gln Gly Ala Glu Ile Ile Lys Arg Thr Gln Asp Ile Thr Ser Lys
50 55 60

Arg Leu Ala Ile Thr Gln Asn Ile Gln Phe Asp Phe Val Lys Asp Lys
65 70 75 80

Lys Tyr Asn Lys Asp Ala Leu Val Val Lys Met Gln Gly Phe Ile Ser
85 90 95

Ser Arg Thr Thr Tyr Ser Asp Leu Lys Lys Tyr Pro Tyr Ile Lys Arg
100 105 110

Met Ile Trp Pro Phe Gln Tyr Asn Ile Ser Leu Lys Thr Lys Asp Ser
115 120 125

Asn Val Asp Leu Ile Asn Tyr Leu Pro Lys Asn Lys Ile Asp Ser Ala
130 135 140

Asp Val Ser Gln Lys Leu Gly Tyr Asn Ile Gly Gly Asn Phe Gln Ser
145 150 155 160

Ala Pro Ser Ile Gly Gly Ser Gly Ser Phe Asn Tyr Ser Lys Thr Ile
165 170 175

Ser Tyr Asn Gln Lys Asn Tyr Val Thr Glu Val Glu Ser Gln Asn Ser
180 185 190

Lys Gly Val Lys Arg Gly Val Lys Ala Asn Ser Phe Val Thr Pro Asn
195 200 205

Gly Gln Val Ser Ala Tyr Asp Gln Tyr Leu Phe Ala Gln Asp Pro Thr
210 215 220

Gly Pro Ala Ala Arg Asp Tyr Phe Val Pro Asp Asn Gln Leu Pro Pro
225 230 235 240

Leu Ile Gln Ser Gly Phe Asn Pro Ser Phe Ile Thr Thr Leu Ser His
245 250 255

```
Glu Lys Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285

Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys


<210> SEQ ID NO 85
<211> LENGTH: 321
<212> TYPE: PRT
<213> ORGANISM: Artificial Sequence
<220> FEATURE:
<223> OTHER INFORMATION: gamma-hemolysin component A precursor amino
      acid sequence

<400> SEQUENCE: 85

Met Asn Leu Lys Leu Asn Arg Lys Lys Val Ile Ser Met Ile Lys Asn
1               5                   10                  15

Lys Ile Leu Thr Ala Thr Leu Ala Val Gly Leu Ile Ala Pro Leu Ala
            20                  25                  30

Asn Pro Phe Ile Glu Ile Ser Arg Ala Glu Asn Lys Ile Glu Asp Ile
        35                  40                  45

Gly Gln Gly Ala Glu Ile Ile Lys Arg Thr Gln Asp Ile Thr Ser Lys
    50                  55                  60

Arg Leu Ala Ile Thr Gln Asn Ile Gln Phe Asp Phe Val Lys Asp Lys
65                  70                  75                  80

Lys Tyr Asn Lys Asp Ala Leu Val Val Lys Met Gln Gly Phe Ile Ser
                85                  90                  95

Ser Arg Thr Thr Tyr Ser Asp Leu Lys Lys Tyr Pro Tyr Ile Lys Arg
            100                 105                 110

Met Ile Trp Pro Phe Gln Tyr Asn Ile Ser Leu Lys Thr Lys Asp Ser
        115                 120                 125

Asn Val Asp Leu Ile Asn Tyr Leu Pro Lys Asn Lys Ile Asp Ser Ala
    130                 135                 140

Asp Val Ser Gln Lys Leu Gly Tyr Asn Ile Gly Gly Asn Phe Gln Ser
145                 150                 155                 160

Ala Pro Ser Ile Gly Gly Ser Gly Ser Phe Asn Tyr Ser Lys Thr Ile
                165                 170                 175

Ser Tyr Asn Gln Lys Asn Tyr Val Thr Glu Val Glu Ser Gln Asn Ser
            180                 185                 190

Lys Gly Val Lys Trp Gly Val Lys Ala Asn Ser Phe Val Thr Pro Asn
        195                 200                 205

Gly Gln Val Ser Ala Tyr Asp Gln Tyr Leu Phe Ala Gln Asp Gln Thr
    210                 215                 220

Gly Pro Ala Ala Arg Asp Tyr Phe Val Pro Asp Asn Gln Leu Pro Pro
225                 230                 235                 240

Leu Ile Gln Ser Gly Phe Asn Pro Ser Phe Ile Thr Thr Leu Ser His
                245                 250                 255

Glu Arg Gly Lys Gly Asp Lys Ser Glu Phe Glu Ile Thr Tyr Gly Arg
            260                 265                 270

Asn Met Asp Ala Thr Tyr Ala Tyr Val Thr Arg His Arg Leu Ala Val
        275                 280                 285
```

```
Asp Arg Lys His Asp Ala Phe Lys Asn Arg Asn Val Thr Val Lys Tyr
    290                 295                 300

Glu Val Asn Trp Lys Thr His Glu Val Lys Ile Lys Ser Ile Thr Pro
305                 310                 315                 320

Lys


<210> SEQ ID NO 86
<211> LENGTH: 310
<212> TYPE: PRT
<213> ORGANISM: Artificial Sequence
<220> FEATURE:
<223> OTHER INFORMATION: Synergohymenotropic toxin amino acid
      sequenceSynergohymenotropic toxin amino acid sequence

<400> SEQUENCE: 86

Met Val Lys Asn Lys Leu Leu Ala Ala Thr Leu Ser Ile Ser Leu Ile
1               5                   10                  15

Leu Pro Leu Ile Thr Pro Tyr Ser Glu Glu Ala Lys Ala Ala Asn Thr
            20                  25                  30

Ile Glu Glu Ile Gly Glu Gly Ala Gln Ile Ile Lys Arg Thr Glu Asp
        35                  40                  45

Val Ser Ser Arg Lys Trp Gly Val Thr Gln Asn Ile Gln Phe Asp Phe
    50                  55                  60

Val Lys Asp Pro Lys Tyr Asn Lys Asp Ala Leu Ile Ile Lys Met Gln
65                  70                  75                  80

Gly Phe Ile Lys Ser Arg Thr Ser Phe Thr Asp Val Lys Gly Lys Gly
                85                  90                  95

Tyr Glu Ser Thr Lys Arg Ile Leu Trp Pro Phe Gln Tyr Asn Ile Ala
            100                 105                 110

Leu Lys Thr Asn Asp Pro Asn Val Phe Leu Ile Asn Tyr Leu Pro Lys
        115                 120                 125

Asn Lys Ile Glu Ser Ile Asp Val Ser Gln Thr Leu Gly Tyr Asn Val
    130                 135                 140

Gly Gly Asn Phe Gln Ser Ala Pro Leu Leu Gly Gly Lys Gly Glu Phe
145                 150                 155                 160

Asn Tyr Ser Lys Lys Ile Ser Tyr Thr Gln Lys Asn Tyr Ile Ser Glu
                165                 170                 175

Val Ala Gln Gln Asn Ser Lys Asn Ile Arg Trp Glu Val Lys Ala Asn
            180                 185                 190

Ser Phe Asn Thr Glu Asn Gly Gln Val Ser Ala Tyr Asp Arg His Leu
        195                 200                 205

Phe Val Arg Ser Pro Ile Gly Pro Asn Ala Arg Asp Phe Phe Val Pro
    210                 215                 220

Asn Asp Glu Leu Pro Pro Leu Ile Gln Ser Gly Phe Asn Pro Ser Phe
225                 230                 235                 240

Ile Ala Thr Val Ser His Glu Lys Asp Lys Gly Asp Thr Ser Glu Phe
                245                 250                 255

Glu Ile Ala Tyr Gly Arg Asn Leu Asp Ile Thr Tyr Ala Thr Phe Phe
            260                 265                 270

Pro Arg Thr Gly Ile Phe Ala Glu Arg Arg His Asn Ala Leu Met Asn
        275                 280                 285

Arg Asn Leu Val Thr Lys Tyr Glu Val Asn Trp Lys Thr His Glu Ile
    290                 295                 300

Lys Val Lys Gly His Asn
305                 310
```

<210> SEQ ID NO 87
<211> LENGTH: 314
<212> TYPE: PRT
<213> ORGANISM: Artificial Sequence
<220> FEATURE:
<223> OTHER INFORMATION: Leukotoxin LukEamino acid sequence

<400> SEQUENCE: 87

Met Phe Lys Lys Lys Met Leu Ala Ala Ser Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Arg Gly Tyr
                85                  90                  95

Glu Leu Thr Lys Arg Leu Ile Trp Pro Phe Gln Tyr Asn Ile Gly Leu
            100                 105                 110

Thr Thr Lys Asp Pro Asn Val Ser Leu Ile Asn Ser Ile Thr Leu Pro
        115                 120                 125

Lys Thr Lys Ile Glu Thr Thr Asp Val Gly Gln Thr Leu Gly Tyr Asn
    130                 135                 140

Ile Gly Gly Asn Phe Gln Ser Ala Pro Ser Ile Gly Gly Asn Gly Ser
145                 150                 155                 160

Phe Asn Tyr Ser Lys Thr Ile Ser Tyr Thr Gln Lys Ser Tyr Val Ser
                165                 170                 175

Glu Val Asp Lys Gln Asn Ser Lys Ser Val Lys Trp Gly Val Lys Ala
            180                 185                 190

Asn Lys Phe Val Thr Pro Asp Gly Lys Lys Phe Ala His Asp Arg Tyr
        195                 200                 205

Leu Phe Val Gln Ser Pro Asn Gly Pro Thr Gly Ser Ala Arg Glu Tyr
    210                 215                 220

Phe Ala Pro Asp Asn Gln Leu Pro Pro Leu Val Gln Ser Gly Phe Asn
225                 230                 235                 240

Pro Ser Phe Ile Thr Thr Leu Ser His Glu Lys Gly Ser Lys Leu Ile
                245                 250                 255

Arg Val Asn Leu Lys Phe Ser Tyr Gly Arg Asn Leu Asp Ile Thr Tyr
            260                 265                 270

Ala Thr Leu Phe Pro Arg Thr Gly Ile Tyr Ala Glu Arg Lys His Asn
        275                 280                 285

Ala Phe Val Asn Arg Asn Phe Val Val Arg Tyr Lys Val Asn Trp Lys
    290                 295                 300

Thr His Glu Ile Lys Val Lys Gly His Asn
305                 310

<210> SEQ ID NO 88
<211> LENGTH: 290
<212> TYPE: PRT
<213> ORGANISM: Artificial Sequence
<220> FEATURE:
<223> OTHER INFORMATION: Chain B, crystal structure of octameric pore
      form of gamma-hemolysin amino acid sequence

<400> SEQUENCE: 88

Met Gly His His His His His His Ala Met Glu Asn Lys Ile Glu Asp
1               5                   10                  15

Ile Gly Gln Gly Ala Glu Ile Ile Lys Arg Thr Gln Asp Ile Thr Ser
            20                  25                  30

Lys Arg Leu Ala Ile Thr Gln Asn Ile Gln Phe Asp Phe Val Lys Asp
        35                  40                  45

Lys Lys Tyr Asn Lys Asp Ala Leu Val Val Lys Met Gln Gly Phe Ile
    50                  55                  60

Ser Ser Arg Thr Thr Tyr Ser Asp Leu Lys Lys Tyr Pro Tyr Ile Lys
65                  70                  75                  80

Arg Met Ile Trp Pro Phe Gln Tyr Asn Ile Ser Leu Lys Thr Lys Asp
                85                  90                  95

Ser Asn Val Asp Leu Ile Asn Tyr Leu Pro Lys Asn Lys Ile Asp Ser
            100                 105                 110

Ala Asp Val Ser Gln Lys Leu Gly Tyr Asn Ile Gly Gly Asn Phe Gln
        115                 120                 125

Ser Ala Pro Ser Ile Gly Gly Ser Gly Ser Phe Asn Tyr Ser Lys Thr
    130                 135                 140

Ile Ser Tyr Asn Gln Lys Asn Tyr Val Thr Glu Val Glu Ser Gln Asn
145                 150                 155                 160

Ser Lys Gly Val Lys Trp Gly Val Lys Ala Asn Ser Phe Val Thr Pro
                165                 170                 175

Asn Gly Gln Val Ser Ala Tyr Asp Gln Tyr Leu Phe Ala Gln Asp Pro
            180                 185                 190

Thr Gly Pro Ala Ala Arg Asp Tyr Phe Val Pro Asp Asn Gln Leu Pro
        195                 200                 205

Pro Leu Ile Gln Ser Gly Phe Asn Pro Ser Phe Ile Thr Thr Leu Ser
    210                 215                 220

His Glu Arg Gly Lys Gly Asp Lys Ser Glu Phe Glu Ile Thr Tyr Gly
225                 230                 235                 240

Arg Asn Met Asp Ala Thr Tyr Ala Tyr Val Thr Arg His Arg Leu Ala
                245                 250                 255

Val Asp Arg Lys His Asp Ala Phe Lys Asn Arg Asn Val Thr Val Lys
            260                 265                 270

Tyr Glu Val Asn Trp Lys Thr His Glu Val Lys Ile Lys Ser Ile Thr
        275                 280                 285

Pro Lys
    290

<210> SEQ ID NO 89
<211> LENGTH: 203
<212> TYPE: PRT
<213> ORGANISM: Artificial Sequence
<220> FEATURE:
<223> OTHER INFORMATION: gamma-hemolysin component C amino acid sequence

<400> SEQUENCE: 89

Leu Lys Thr Asn Asp Lys Tyr Val Ser Leu Ile Asn Tyr Leu Pro Lys
1               5                   10                  15

Asn Lys Ile Glu Ser Thr Asn Val Ser Gln Thr Leu Gly Tyr Asn Ile
            20                  25                  30

Gly Gly Asn Phe Gln Ser Ala Pro Ser Leu Gly Gly Asn Gly Ser Phe
        35                  40                  45

Asn Tyr Ser Lys Ser Ile Ser Tyr Thr Gln Gln Asn Tyr Val Ser Glu

```
    50                  55                  60

Val Glu Gln Gln Asn Ser Lys Ser Val Leu Trp Gly Val Lys Ala Asn
65                  70                  75                  80

Ser Phe Ala Thr Glu Ser Gly Gln Lys Ser Ala Phe Asp Ser Asp Leu
                85                  90                  95

Phe Val Gly Tyr Lys Pro His Ser Lys Asp Pro Arg Asp Tyr Phe Val
            100                 105                 110

Pro Asp Ser Glu Leu Pro Pro Leu Val Gln Ser Gly Phe Asn Pro Ser
        115                 120                 125

Phe Ile Ala Thr Val Ser His Glu Lys Gly Ser Ser Asp Thr Ser Glu
    130                 135                 140

Phe Glu Ile Thr Tyr Gly Arg Asn Met Asp Val Thr His Ala Ile Lys
145                 150                 155                 160

Arg Ser Thr His Tyr Gly Asn Ser Tyr Leu Asp Gly His Arg Val His
                165                 170                 175

Asn Ala Phe Val Asn Arg Asn Tyr Thr Val Lys Tyr Glu Val Asn Trp
            180                 185                 190

Lys Thr His Glu Ile Lys Val Lys Gly Gln Asn
        195                 200


<210> SEQ ID NO 90
<211> LENGTH: 325
<212> TYPE: PRT
<213> ORGANISM: Artificial Sequence
<220> FEATURE:
<223> OTHER INFORMATION: Leucocidin F amino acid sequence

<400> SEQUENCE: 90

Met Lys Lys Ile Val Lys Ser Arg Glu Val Thr Ser Ile Ala Leu Leu
1               5                   10                  15

Leu Leu Ser Asn Thr Leu Asp Ala Ala Gln His Ile Thr Pro Val Ser
            20                  25                  30

Glu Lys Lys Val Asp Asp Lys Ile Thr Leu Tyr Lys Thr Thr Ala Thr
        35                  40                  45

Ser Asp Ser Asp Lys Leu Lys Ile Ser Gln Ile Leu Thr Phe Asn Phe
    50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140

Asp Ile Asn Ile Ser Asn Gly Leu Ser Gly Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
        195                 200                 205

His Ser Thr Tyr Gly Asn Glu Met Phe Leu Gly Ser Arg Gln Ser Asn
```

```
    210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Ser Glu
            260                 265                 270

Met Asp Arg Tyr Thr Asn Phe Trp Ile Asn Phe Asn Trp Ile Gly Asn
        275                 280                 285

Asn Tyr Lys Asp His Ile Arg Ala Thr His Thr Ser Ile Tyr Glu Val
    290                 295                 300

Asp Trp Glu Asn His Thr Val Lys Leu Ile Asp Thr Gln Ser Lys Glu
305                 310                 315                 320

Lys Asn Pro Met Ser
                325


<210> SEQ ID NO 91
<211> LENGTH: 327
<212> TYPE: PRT
<213> ORGANISM: Artificial Sequence
<220> FEATURE:
<223> OTHER INFORMATION: gamma-hemolysin component B amino acid sequence

<400> SEQUENCE: 91

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Leu Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
```

```
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 92
<211> LENGTH: 327
<212> TYPE: PRT
<213> ORGANISM: Artificial Sequence
<220> FEATURE:
<223> OTHER INFORMATION: gamma-hemolysin component B amino acid sequence

<400> SEQUENCE: 92

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
```

```
        275                 280                 285

Gly Asn Asn Tyr Lys Asn Gln Asn Thr Ala Thr Phe Thr Ser Thr Tyr
    290                 295                 300

Glu Val Asp Trp Gln Asn His Thr Val Lys Leu Ile Ser Thr Asp Ser
305                 310                 315                 320

Lys Glu Thr Asn Pro Gly Val
                325


<210> SEQ ID NO 93
<211> LENGTH: 327
<212> TYPE: PRT
<213> ORGANISM: Artificial Sequence
<220> FEATURE:
<223> OTHER INFORMATION: Leukocidin/Hemolysin toxin family protein amino
      acid sequence

<400> SEQUENCE: 93

Met Lys Met Lys Lys Leu Val Lys Ser Ser Val Ala Thr Ser Ile Ala
1               5                   10                  15

Leu Ile Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Tyr Phe Tyr Trp Gly Ala Lys Tyr Asn Val Ser Val
            100                 105                 110

Ser Ser Glu Ser Asn Asp Ser Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Thr Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Glu Ala Lys Lys Ser Lys Ile Lys Val Thr Tyr Gln
            260                 265                 270

Arg Glu Met Asp Arg Tyr Thr Asn Tyr Trp Asn Arg Leu His Trp Ile
        275                 280                 285

Gly Asn Asn His Lys Asn Gln Asn Thr Val Thr Phe Thr Ser Thr Tyr
    290                 295                 300
```

```
Glu Val Asp Trp His Asn His Thr Val Lys Leu Ile Asp Thr Asn Ser
305                 310                 315                 320

Lys Glu Thr Asn Pro Gly Val
                325


<210> SEQ ID NO 94
<211> LENGTH: 327
<212> TYPE: PRT
<213> ORGANISM: Artificial Sequence
<220> FEATURE:
<223> OTHER INFORMATION: Leukotoxin, LukD amino acid sequence

<400> SEQUENCE: 94

Met Lys Met Lys Lys Leu Val Lys Ser Ser Val Ala Thr Ser Ile Ala
1               5                   10                  15

Leu Leu Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

<210> SEQ ID NO 95
<211> LENGTH: 327
<212> TYPE: PRT
<213> ORGANISM: Artificial Sequence
<220> FEATURE:
<223> OTHER INFORMATION: Leukotoxin, LukD amino acid sequence

<400> SEQUENCE: 95

```
Met Lys Met Lys Lys Leu Val Lys Ser Ser Val Ala Thr Ser Ile Ala
1               5                   10                  15

Leu Leu Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Val Asn Ser Gly Tyr Lys Lys Pro Asn Pro Lys Asp
                85                  90                  95

Tyr Asp Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

<210> SEQ ID NO 96
<211> LENGTH: 327
<212> TYPE: PRT
<213> ORGANISM: Artificial Sequence
<220> FEATURE:

<223> OTHER INFORMATION: Leukotoxin, LukD amino acid sequence

<400> SEQUENCE: 96

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 97
<211> LENGTH: 327
<212> TYPE: PRT
<213> ORGANISM: Artificial Sequence
<220> FEATURE:
<223> OTHER INFORMATION: Leukotoxin amino acid sequence

<400> SEQUENCE: 97

Met Lys Met Lys Lys Leu Val Lys Ser Ser Val Ala Ser Ser Ile Ala
1               5                   10                  15

```
Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 98
<211> LENGTH: 327
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 98

Met Lys Met Lys Lys Leu Ile Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
```

```
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 99
<211> LENGTH: 327
<212> TYPE: PRT
<213> ORGANISM: Artificial Sequence
<220> FEATURE:
<223> OTHER INFORMATION: gamma-hemolysin component B amino acid sequence

<400> SEQUENCE: 99

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
```

```
65                  70                  75                  80

Ala Ala Gly Asn Ile Asn Ser Gly Tyr Lys Lys Pro Asn Pro Arg Asp
                85                  90                  95

Tyr Asp Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Ser Thr Asp Ser
305                 310                 315                 320

Lys Glu Thr Asn Pro Gly Val
                325


<210> SEQ ID NO 100
<211> LENGTH: 327
<212> TYPE: PRT
<213> ORGANISM: Artificial Sequence
<220> FEATURE:
<223> OTHER INFORMATION: Leukotoxin D subunit amino acid sequence

<400> SEQUENCE: 100

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Arg Asp
                85                  90                  95

Tyr Asp Tyr Ser Gln Phe Tyr Trp Gly Gly Lys Tyr Asn Val Ser Val
```

```
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 101
<211> LENGTH: 327
<212> TYPE: PRT
<213> ORGANISM: Artificial Sequence
<220> FEATURE:
<223> OTHER INFORMATION: Leukotoxin D subunit amino acid sequence

<400> SEQUENCE: 101

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Asn Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Arg Asp
                85                  90                  95

Tyr Asp Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
```

```
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 102
<211> LENGTH: 327
<212> TYPE: PRT
<213> ORGANISM: Artificial Sequence
<220> FEATURE:
<223> OTHER INFORMATION: gamma-hemolysin component B amino acid sequence

<400> SEQUENCE: 102

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val His Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
```

```
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Ile
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 103
<211> LENGTH: 327
<212> TYPE: PRT
<213> ORGANISM: Artificial Sequence
<220> FEATURE:
<223> OTHER INFORMATION: Leukotoxin LukD amino acid sequence

<400> SEQUENCE: 103

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Ser Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
```

```
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 104
<211> LENGTH: 327
<212> TYPE: PRT
<213> ORGANISM: Artificial Sequence
<220> FEATURE:
<223> OTHER INFORMATION: Leukotoxin LukD amino acid sequence

<400> SEQUENCE: 104

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Phe Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
```

```
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325


<210> SEQ ID NO 105
<211> LENGTH: 326
<212> TYPE: PRT
<213> ORGANISM: Artificial Sequence
<220> FEATURE:
<223> OTHER INFORMATION: Leukocidin/hemolysin toxin family protein amino
      acid sequence

<400> SEQUENCE: 105

Met Lys Met Lys Lys Leu Val Lys Ser Ser Val Ala Thr Ser Ile Ala
1               5                   10                  15

Leu Ile Met Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Tyr Phe Tyr Trp Gly Ala Lys Tyr Asn Val Ser Val
            100                 105                 110

Ser Ser Glu Ser Asn Asp Ser Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Asn Gly Leu Ser Gly Gly Leu Asn Gly Ser
145                 150                 155                 160

Lys Ser Phe Ser Glu Thr Ile Asn Tyr Lys Gln Glu Ser Tyr Arg Thr
                165                 170                 175

Thr Ile Asp Arg Lys Thr Asn His Lys Ser Ile Gly Trp Gly Val Glu
            180                 185                 190

Ala His Lys Ile Met Asn Asn Gly Trp Gly Pro Tyr Gly Arg Asp Ser
        195                 200                 205

Tyr Asp Pro Thr Tyr Gly Asn Glu Leu Phe Leu Gly Gly Arg Gln Ser
    210                 215                 220

Ser Ser Asn Ala Gly Gln Asn Phe Leu Pro Thr His Gln Met Pro Leu
225                 230                 235                 240

Leu Ala Arg Gly Asn Phe Asn Pro Glu Phe Ile Ser Val Leu Ser His
                245                 250                 255
```

```
Lys Gln Asn Glu Ala Lys Lys Ser Lys Ile Lys Val Thr Tyr Gln Arg
            260                 265                 270

Glu Met Asp Arg Tyr Thr Asn Tyr Trp Asn Arg Leu His Trp Ile Gly
        275                 280                 285

Asn Asn His Lys Asn Gln Asn Thr Val Thr Phe Thr Ser Thr Tyr Glu
    290                 295                 300

Val Asp Trp His Asn His Thr Val Lys Leu Ile Asp Thr Asn Ser Lys
305                 310                 315                 320

Glu Thr Asn Pro Gly Val
                325


<210> SEQ ID NO 106
<211> LENGTH: 327
<212> TYPE: PRT
<213> ORGANISM: Artificial Sequence
<220> FEATURE:
<223> OTHER INFORMATION: Leukotoxin, LukD amino acid sequence

<400> SEQUENCE: 106

Met Lys Ile Glu Lys Leu Gly Lys Ser Ser Val Ala Ser Ser Ile Ala
1               5                   10                  15

Leu Leu Leu Leu Ser Asn Thr Val Asp Ala Ala Gln Asn Ile Thr Pro
            20                  25                  30

Lys Arg Glu Lys Lys Val Asp Asp Lys Ile Thr Leu Tyr Lys Thr Thr
        35                  40                  45

Ala Thr Ser Asp Asn Asp Lys Leu Asn Ile Phe Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Asn Ser Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Asp Lys
    210                 215                 220

Ser Ser Ser Asn Ala Gly Gln Asn Phe Leu Pro Thr His Gln Ile Pro
225                 230                 235                 240

Leu Leu Ala Arg Gly Asn Phe Asn Pro Glu Phe Ile Ser Val Leu Ser
                245                 250                 255

His Lys Leu Phe Asp Thr Lys Lys Ser Lys Ile Lys Val Thr Tyr Gln
            260                 265                 270

Arg Glu Met Asp Arg Tyr Thr Asn Gln Trp Asn Arg Ser His Trp Val
        275                 280                 285
```

```
Gly Asn Asn Tyr Lys Asn Gln Asn Thr Val Thr Phe Thr Ser Thr Tyr
    290                 295                 300

Glu Val Asp Trp Gln Asn Ile Leu Leu Lys Leu Ile Gly Thr Asp Ser
305                 310                 315                 320

Lys Glu Thr Asn Pro Gly Val
                325


<210> SEQ ID NO 107
<211> LENGTH: 326
<212> TYPE: PRT
<213> ORGANISM: Artificial Sequence
<220> FEATURE:
<223> OTHER INFORMATION: Gamma-hemolysin component B amino acid sequence

<400> SEQUENCE: 107

Met Lys Ile Ser Lys Val Ile Lys Ala Ala Thr Ala Thr Ser Val Ala
1               5                   10                  15

Leu Met Leu Phe Ser Asn Pro Val Tyr Ala Ala Asn Gln Ile Thr Pro
            20                  25                  30

Val Ser Glu Lys Lys Val Asp Asp Lys Ile Thr Leu Tyr Lys Thr Thr
        35                  40                  45

Ala Thr Ala Asp Ser Asp Lys Leu Asn Ile Ser Gln Leu Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Ser Pro Asn Pro Asn Asp
                85                  90                  95

Tyr Ile Tyr Ser Ser Phe Tyr Trp Gly Ala Lys Tyr Asn Val Ser Ile
            100                 105                 110

Ser Ala Glu Ser Lys Gly Ala Val Asn Val Val Asp Tyr Ala Pro Lys
        115                 120                 125

Asn Gln Asn Glu Glu Phe Gln Val Gln Asn Thr Leu Gly Tyr Ser Phe
    130                 135                 140

Gly Gly Asp Ile Ser Ile Ser Lys Gly Leu Ser Gly Gly Leu Asn Gly
145                 150                 155                 160

Ser Glu Ser Phe Ser Glu Thr Ile Asn Tyr Lys Gln Glu Ser Tyr Arg
                165                 170                 175

Thr Thr Ile Asp Lys His Thr Asp Asn Lys Thr Ile Gly Trp Gly Val
            180                 185                 190

Glu Ala His Lys Ile Met Asn Ala Gly Trp Gly Pro Tyr Gly Arg Asp
        195                 200                 205

Ser Phe His Asp Leu Tyr Gly Asn Glu Leu Phe Leu Gly Gly Arg Gln
    210                 215                 220

Ser Lys Leu Asn Ala Gly Gln Asn Phe Leu Pro Thr Ser Gln Met Pro
225                 230                 235                 240

Leu Leu Ala Arg Gly Asn Phe Asn Pro Glu Phe Leu Ser Val Leu Ser
                245                 250                 255

His Lys Pro Asn Gly Ala Lys Thr Ser Lys Ile Lys Val Thr Tyr Gln
            260                 265                 270

Arg Glu Met Asp Glu Tyr Thr Asn Tyr Trp Asn Gly Phe His Trp Met
        275                 280                 285

Gly Thr Asn Tyr Lys Asn Gln Asn Asn Ala Thr Phe Thr Ser Phe Tyr
    290                 295                 300

Glu Ile Asp Trp Asp Gln His Thr Val Lys Leu Ile Lys Thr His Ser
305                 310                 315                 320
```

```
Asp Glu Lys Asn Pro Ser
                325


<210> SEQ ID NO 108
<211> LENGTH: 326
<212> TYPE: PRT
<213> ORGANISM: Artificial Sequence
<220> FEATURE:
<223> OTHER INFORMATION: Synergohymenotropic toxin amino acid sequence

<400> SEQUENCE: 108

Met Lys Ile Ser Lys Val Ile Lys Ala Ala Thr Ala Thr Ser Val Ala
1               5                   10                  15

Leu Met Leu Phe Ser Asn Pro Val Tyr Ala Ala Asn Gln Ile Thr Pro
            20                  25                  30

Val Ser Glu Lys Lys Val Asp Asp Lys Ile Thr Leu Tyr Lys Thr Thr
        35                  40                  45

Ala Thr Ala Asp Ser Asp Asn Leu Asn Ile Ser Gln Leu Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Ser Pro Asn Pro Asn Asp
                85                  90                  95

Tyr Ile Tyr Ser Ser Phe Tyr Trp Gly Ala Lys Tyr Asn Val Ser Ile
            100                 105                 110

Ser Ala Glu Ser Lys Gly Ala Val Asn Val Val Asp Tyr Ala Pro Lys
        115                 120                 125

Asn Gln Asn Glu Glu Phe Gln Val Gln Asn Thr Leu Gly Tyr Ser Phe
    130                 135                 140

Gly Gly Asp Ile Ser Ile Ser Lys Gly Leu Ser Gly Gly Leu Asn Gly
145                 150                 155                 160

Ser Glu Ser Phe Ser Glu Thr Ile Asn Tyr Lys Gln Glu Ser Tyr Arg
                165                 170                 175

Thr Thr Ile Asp Lys His Thr Asp Asn Lys Thr Ile Gly Trp Gly Val
            180                 185                 190

Glu Ala His Lys Ile Met Asn Ala Gly Trp Gly Pro Tyr Gly Arg Asp
        195                 200                 205

Ser Phe His Asp Leu Tyr Gly Asn Glu Leu Phe Leu Gly Gly Arg Gln
    210                 215                 220

Ser Lys Leu Asn Ala Gly Gln Asn Phe Leu Pro Thr Arg Gln Met Pro
225                 230                 235                 240

Leu Leu Ala Arg Gly Asn Phe Asn Pro Glu Phe Leu Ser Val Leu Ser
                245                 250                 255

His Lys Pro Asn Gly Ala Lys Thr Ser Lys Ile Lys Val Thr Tyr Gln
            260                 265                 270

Arg Glu Met Asp Glu Tyr Thr Asn Tyr Trp Asn Gly Phe His Trp Met
        275                 280                 285

Gly Thr Asn Tyr Lys Asn Gln Asn Asn Ala Thr Phe Thr Ser Phe Tyr
    290                 295                 300

Glu Ile Asp Trp Asp Gln His Thr Val Lys Leu Ile Lys Thr His Ser
305                 310                 315                 320

Asp Glu Lys Asn Pro Ser
                325


<210> SEQ ID NO 109
<211> LENGTH: 325
```

<212> TYPE: PRT
<213> ORGANISM: Artificial Sequence
<220> FEATURE:
<223> OTHER INFORMATION: gamma-hemolysin component C precursor amino acid sequence

<400> SEQUENCE: 109

```
Met Lys Met Asn Lys Leu Val Lys Ser Ser Val Ala Thr Ser Met Ala
1               5                   10                  15

Leu Leu Leu Leu Ser Asn Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Glu Lys Pro Asn Pro Lys Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ser Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Lys Gln Asn Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Ile Asn Lys
                325
```

<210> SEQ ID NO 110
<211> LENGTH: 325
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 110

Met Asn Met Asn Lys Leu Val Lys Ser Ser Val Ala Thr Ser Met Ala
1               5                   10                  15

Leu Leu Leu Leu Ser Asn Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Glu Arg Pro Asn Pro Lys Asp
                85                  90                  95

Tyr Asp Phe Ser Lys Ile Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Tyr Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Ile Asn Lys
                325

<210> SEQ ID NO 111
<211> LENGTH: 325
<212> TYPE: PRT
<213> ORGANISM: Artificial Sequence
<220> FEATURE:
<223> OTHER INFORMATION: gamma-hemolysin component C precursor amino acid sequence

<400> SEQUENCE: 111

Met Asn Met Asn Lys Leu Val Lys Ser Ser Val Ala Thr Ser Met Ala
1               5                   10                  15

```
Leu Leu Leu Leu Ser Asn Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Glu Arg Pro Asn Pro Lys Asp
                85                  90                  95

Tyr Asp Phe Ser Lys Ile Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 112
<211> LENGTH: 281
<212> TYPE: PRT
<213> ORGANISM: Artificial Sequence
<220> FEATURE:
<223> OTHER INFORMATION: gamma-hemolysin component B amino acid sequence

<400> SEQUENCE: 112

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45
```

```
Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln
        275                 280


<210> SEQ ID NO 113
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 113

Met Asn Met Asn Lys Leu Val Lys Ser Ser Val Ala Thr Ser Met Ala
1               5                   10                  15

Leu Leu Leu Leu Ser Asn Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125
```

```
Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 114
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 114

Met Lys Met Asn Lys Leu Val Lys Ser Ser Val Ala Thr Ser Met Ala
1               5                   10                  15

Leu Leu Leu Leu Ser Asn Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160
```

```
Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 115
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 115

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190
```

```
Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Cys Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 116
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 116

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Arg Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220
```

```
Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 117
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 117

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255
```

```
His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 118
<211> LENGTH: 325
<212> TYPE: PRT
<213> ORGANISM: Artificial Sequence
<220> FEATURE:
<223> OTHER INFORMATION: gamma-hemolysin component C precursor amino
      acid sequence

<400> SEQUENCE: 118

Met Lys Met Asn Lys Leu Val Lys Ser Ser Val Thr Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
```

```
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325


<210> SEQ ID NO 119
<211> LENGTH: 325
<212> TYPE: PRT
<213> ORGANISM: Artificial Sequence
<220> FEATURE:
<223> OTHER INFORMATION: gamma-hemolysin component B amino acid sequence

<400> SEQUENCE: 119

Met Asn Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Glu Arg Pro Asn Pro Lys Asp
                85                  90                  95

Tyr Asp Phe Ser Lys Ile Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Ile Phe Leu Ala Gly Arg Gln
    210                 215                 220

Ser Ser Ser Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Gly Thr Lys Glu
```

```
305                 310                 315                 320

Thr Glu Asn Asn Lys
                325


<210> SEQ ID NO 120
<211> LENGTH: 323
<212> TYPE: PRT
<213> ORGANISM: Artificial Sequence
<220> FEATURE:
<223> OTHER INFORMATION: Leukocidin-F subunit amino acid sequence

<400> SEQUENCE: 120

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Ala Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Leu Ser Arg Asn Thr Asn Tyr Lys Asn Val Gly Trp Gly Val Glu
            180                 185                 190

Ala His Lys Ile Met Asn Gly Trp Gly Pro Tyr Gly Arg Asp Ser Phe
        195                 200                 205

His Pro Thr Tyr Gly Asn Glu Leu Phe Leu Ala Gly Arg Gln Ser Ser
    210                 215                 220

Ala Tyr Ala Gly Gln Asn Phe Ile Ala Gln His Gln Met Pro Leu Leu
225                 230                 235                 240

Ser Arg Ser Asn Phe Asn Pro Glu Phe Leu Ser Val Leu Ser His Arg
                245                 250                 255

Gln Asp Arg Ala Lys Lys Ser Lys Ile Thr Val Thr Tyr Gln Arg Glu
            260                 265                 270

Met Asp Leu Tyr Gln Ile Arg Trp Asn Gly Phe Tyr Trp Ala Gly Ala
        275                 280                 285

Asn Tyr Lys Asn Phe Lys Thr Arg Thr Phe Lys Ser Thr Tyr Glu Ile
    290                 295                 300

Asp Trp Glu Asn His Lys Val Lys Leu Leu Asp Thr Lys Glu Thr Glu
305                 310                 315                 320

Asn Asn Lys


<210> SEQ ID NO 121
```

<211> LENGTH: 268
<212> TYPE: PRT
<213> ORGANISM: Artificial Sequence
<220> FEATURE:
<223> OTHER INFORMATION: gamma-hemolysin component B amino acid sequence

<400> SEQUENCE: 121

```
Met Lys Met Asn Lys Leu Val Lys Ser Ser Val Ala Thr Ser Met Ala
1               5                   10                  15

Leu Leu Leu Leu Ser Ser Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ile Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Asn Leu Lys Leu Gln
            260                 265
```

<210> SEQ ID NO 122
<211> LENGTH: 236
<212> TYPE: PRT
<213> ORGANISM: Artificial Sequence
<220> FEATURE:
<223> OTHER INFORMATION: gamma-hemolysin component B amino acid sequence

<400> SEQUENCE: 122

```
Met Lys Pro Asn Pro Asn Asp Tyr Asp Phe Ser Lys Leu Tyr Trp Gly
1               5                   10                  15

Ala Lys Tyr Asn Val Ser Ile Ser Ser Gln Ser Asn Asp Ser Val Asn
            20                  25                  30

Val Val Asp Tyr Ala Pro Lys Asn Gln Asn Glu Glu Phe Gln Val Gln
        35                  40                  45

Asn Thr Leu Gly Tyr Thr Phe Gly Gly Asp Ile Ser Ile Ser Asn Gly
```

```
    50                  55                  60

Leu Ser Gly Gly Leu Asn Gly Asn Thr Ala Phe Ser Glu Thr Ile Asn
65                  70                  75                  80

Tyr Lys Gln Glu Ser Tyr Arg Thr Thr Leu Ser Arg Asn Thr Asn Tyr
                85                  90                  95

Lys Asn Val Gly Trp Gly Val Glu Ala His Lys Ile Met Asn Asn Gly
            100                 105                 110

Trp Gly Pro Tyr Gly Arg Asp Ser Phe His Pro Thr Tyr Gly Asn Glu
        115                 120                 125

Leu Phe Leu Ala Gly Arg Gln Ser Ser Ala Tyr Ala Gly Gln Asn Phe
    130                 135                 140

Ile Ala Gln His Gln Met Pro Leu Leu Ser Arg Ser Asn Phe Asn Pro
145                 150                 155                 160

Glu Phe Leu Ser Val Leu Ser His Arg Gln Asp Gly Ala Lys Lys Ser
                165                 170                 175

Lys Ile Thr Val Thr Tyr Gln Arg Glu Met Asp Leu Tyr Gln Ile Arg
            180                 185                 190

Trp Asn Gly Phe Tyr Trp Ala Gly Ala Asn Tyr Lys Asn Phe Lys Thr
        195                 200                 205

Arg Thr Phe Lys Ser Thr Tyr Glu Ile Asp Trp Glu Asn His Lys Val
    210                 215                 220

Lys Leu Leu Asp Thr Lys Glu Thr Glu Asn Asn Lys
225                 230                 235
```

<210> SEQ ID NO 123
<211> LENGTH: 4304
<212> TYPE: DNA
<213> ORGANISM: Artificial Sequence
<220> FEATURE:
<223> OTHER INFORMATION: plasmid construct encoding the wild-type LukS-PV

<400> SEQUENCE: 123

```
ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtgggggt cacacaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctaa aaataaaata gattcagtaa atgttagtca aacattaggt    480

tataacatag gtggtaattt taatagtggt ccatcaacag gaggtaatgg ttcatttaat    540

tattcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tccttcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020
```

cctgcagcca agcttaatta gctgagcttg gactcctgtt gatagatcca gtaatgacct 1080
cagaactcca tctggatttg ttcagaacgc tcggttgccg ccgggcgttt tttattggtg 1140
agaatccaag ctagcttggc gagattttca ggagctaagg aagctaaaat ggagaaaaaa 1200
atcactggat ataccaccgt tgatatatcc caatggcatc gtaaagaaca ttttgaggca 1260
tttcagtcag ttgctcaatg tacctataac cagaccgttc agctggatat tacggccttt 1320
ttaaagaccg taaagaaaaa taagcacaag ttttatccgg cctttattca cattcttgcc 1380
cgcctgatga atgctcatcc ggaatttcgt atggcaatga aagacggtga gctggtgata 1440
tgggatagtg ttcacccttg ttacaccgtt ttccatgagc aaactgaaac gttttcatcg 1500
ctctggagtg aataccacga cgatttccgg cagtttctac acatatattc gcaagatgtg 1560
gcgtgttacg gtgaaaacct ggcctatttc cctaaagggt ttattgagaa tatgtttttc 1620
gtctcagcca atccctgggt gagtttcacc agttttgatt taaacgtggc caatatggac 1680
aacttcttcg cccccgtttt caccatgggc aaatattata cgcaaggcga caaggtgctg 1740
atgccgctgg cgattcaggt tcatcatgcc gtttgtgatg gcttccatgt cggcagaatg 1800
cttaatgaat tacaacagta ctgcgatgag tggcagggcg gggcgtaatt tttttaaggc 1860
agttattggt gcccttaaac gcctggggta atgactctct agcttgaggc atcaaataaa 1920
acgaaaggct cagtcgaaag actgggcctt tcgttttatc tgttgtttgt cggtgaacgc 1980
tctcctgagt aggacaaatc cgccctctag agctgcctcg cgcgtttcgg tgatgacggt 2040
gaaaacctct gacacatgca gctcccggag acggtcacag cttgtctgta agcggatgcc 2100
gggagcagac aagcccgtca gggcgcgtca gcgggtgttg gcgggtgtcg gggcgcagcc 2160
atgacccagt cacgtagcga tagcggagtg tatactggct taactatgcg gcatcagagc 2220
agattgtact gagagtgcac catatgcggt gtgaaatacc gcacagatgc gtaaggagaa 2280
aataccgcat caggcgctct tccgcttcct cgctcactga ctcgctgcgc tcggtcgttc 2340
ggctgcggcg agcggtatca gctcactcaa aggcggtaat acggttatcc acagaatcag 2400
gggataacgc aggaaagaac atgtgagcaa aaggccagca aaaggccagg aaccgtaaaa 2460
aggccgcgtt gctggcgttt ttccataggc tccgcccccc tgacgagcat cacaaaaatc 2520
gacgctcaag tcagaggtgg cgaaacccga caggactata aagataccag gcgtttcccc 2580
ctggaagctc cctcgtgcgc tctcctgttc cgaccctgcc gcttaccgga tacctgtccg 2640
cctttctccc ttcgggaagc gtggcgcttt ctcatagctc acgctgtagg tatctcagtt 2700
cggtgtaggt cgttcgctcc aagctgggct gtgtgcacga accccccgtt cagcccgacc 2760
gctgcgcctt atccggtaac tatcgtcttg agtccaaccc ggtaagacac gacttatcgc 2820
cactggcagc agccactggt aacaggatta gcagagcgag gtatgtaggc ggtgctacag 2880
agttcttgaa gtggtggcct aactacggct acactagaag gacagtattt ggtatctgcg 2940
ctctgctgaa gccagttacc ttcggaaaaa gagttggtag ctcttgatcc ggcaaacaaa 3000
ccaccgctgg tagcggtggt ttttttgttt gcaagcagca gattacgcgc agaaaaaaag 3060
gatctcaaga agatcctttg atcttttcta cggggtctga cgctcagtgg aacgaaaact 3120
cacgttaagg gattttggtc atgagattat caaaaaggat cttcacctag atccttttaa 3180
attaaaaatg aagttttaaa tcaatctaaa gtatatatga gtaaacttgg tctgacagtt 3240
accaatgctt aatcagtgag gcacctatct cagcgatctg tctatttcgt tcatccatag 3300
ttgcctgact ccccgtcgtg tagataacta cgatacggga gggcttacca tctggcccca 3360

```
gtgctgcaat gataccgcga gacccacgct caccggctcc agatttatca gcaataaacc   3420
agccagccgg aagggccgag cgcagaagtg gtcctgcaac tttatccgcc tccatccagt   3480
ctattaattg ttgccgggaa gctagagtaa gtagttcgcc agttaatagt ttgcgcaacg   3540
ttgttgccat tgctacaggc atcgtggtgt cacgctcgtc gtttggtatg gcttcattca   3600
gctccggttc ccaacgatca aggcgagtta catgatcccc catgttgtgc aaaaaagcgg   3660
ttagctcctt cggtcctccg atcgttgtca gaagtaagtt ggccgcagtg ttatcactca   3720
tggttatggc agcactgcat aattctctta ctgtcatgcc atccgtaaga tgcttttctg   3780
tgactggtga gtactcaacc aagtcattct gagaatagtg tatgcggcga ccgagttgct   3840
cttgcccggc gtcaatacgg gataataccg cgccacatag cagaacttta aaagtgctca   3900
tcattggaaa acgttcttcg gggcgaaaac tctcaaggat cttaccgctg ttgagatcca   3960
gttcgatgta acccactcgt gcacccaact gatcttcagc atcttttact ttcaccagcg   4020
tttctgggtg agcaaaaaca ggaaggcaaa atgccgcaaa aaagggaata agggcgacac   4080
ggaaatgttg aatactcata ctcttccttt ttcaatatta ttgaagcatt tatcagggtt   4140
attgtctcat gagcggatac atatttgaat gtatttagaa aaataaacaa ataggggttc   4200
cgcgcacatt tccccgaaaa gtgccacctg acgtctaaga aaccattatt atcatgacat   4260
taacctataa aaataggcgt atcacgaggc cctttcgtct tcac                   4304
```

<210> SEQ ID NO 124
<211> LENGTH: 4304
<212> TYPE: DNA
<213> ORGANISM: Artificial Sequence
<220> FEATURE:
<223> OTHER INFORMATION: plasmid construct encoding the mutant (K97A)
      LukS-PV

<400> SEQUENCE: 124

```
ctcgagaaat cataaaaaat ttatttgctt tgtgagcgga taacaattat aatagattca     60
attgtgagcg gataacaatt tcacacagaa ttcattaaag aggagaaatt aactatgaga    120
ggatcgcatc accatcacca tcacggatcc gataacaata ttgagaatat tggtgatggc    180
gctgaggtag tcaaaagaac agaagataca agtagcgata agtggggggt cacacaaaat    240
attcagtttg attttgttaa agataaaaag tataacaaag acgctttgat tttaaaaatg    300
caaggtttta tcaattcaaa gactacttat tacaattaca aaaacacaga tcatataaaa    360
gcaatgaggt ggcctttcca atacaatatt ggtctcaaaa caaatgaccc caatgtagat    420
ttaataaatt atctacctgc aaataaaata gattcagtaa atgttagtca aacattaggt    480
tataacatag gtggtaattt taatagtggt ccatcaacag gaggtaatgg ttcatttaat    540
tattcaaaaa caattagtta taatcaacaa aactatatca gtgaagtaga acatcaaaat    600
tcaaaaagtg ttcaatgggg aataaaagct aattcattta tcacatcatt aggtaaaatg    660
tctggacatg atccaaattt atttgttgga tataaaccat atagtcaaaa tccgagagac    720
tattttgtgc cagacaatga attacccccca ttagtacaca gtggtttcaa tccttcattt    780
attgcaactg tttctcatga aaaaggctca ggagatacaa gtgaatttga aataacgtat    840
ggcagaaata tggatgttac tcatgctact agaagaacaa cacactatgg caatagttat    900
ttagaaggat ctagaataca caacgcattt gtaaacagaa attacacagt taaatatgaa    960
gtgaactgga aaactcatga aattaaagtg aaaggacata attgaggtac cccgggtcga   1020
cctgcagcca agcttaatta gctgagcttg gactcctgtt gatagatcca gtaatgacct   1080
```

-continued

```
cagaactcca tctggatttg ttcagaacgc tcggttgccg ccgggcgttt tttattggtg   1140
agaatccaag ctagcttggc gagattttca ggagctaagg aagctaaaat ggagaaaaaa   1200
atcactggat ataccaccgt tgatatatcc caatggcatc gtaaagaaca ttttgaggca   1260
tttcagtcag ttgctcaatg tacctataac cagaccgttc agctggatat tacggccttt   1320
ttaaagaccg taaagaaaaa taagcacaag ttttatccgg cctttattca cattcttgcc   1380
cgcctgatga atgctcatcc ggaatttcgt atggcaatga aagacggtga gctggtgata   1440
tgggatagtg ttcacccttg ttacaccgtt ttccatgagc aaactgaaac gttttcatcg   1500
ctctggagtg aataccacga cgatttccgg cagtttctac acatatattc gcaagatgtg   1560
gcgtgttacg gtgaaaacct ggcctatttc cctaaagggt ttattgagaa tatgtttttc   1620
gtctcagcca atccctgggt gagtttcacc agttttgatt taaacgtggc caatatggac   1680
aacttcttcg cccccgtttt caccatgggc aaatattata cgcaaggcga caaggtgctg   1740
atgccgctgg cgattcaggt tcatcatgcc gtttgtgatg gcttccatgt cggcagaatg   1800
cttaatgaat tacaacagta ctgcgatgag tggcagggcg gggcgtaatt tttttaaggc   1860
agttattggt gcccttaaac gcctggggta atgactctct agcttgaggc atcaaataaa   1920
acgaaaggct cagtcgaaag actgggcctt tcgttttatc tgttgtttgt cggtgaacgc   1980
tctcctgagt aggacaaatc cgccctctag agctgcctcg cgcgtttcgg tgatgacggt   2040
gaaaacctct gacacatgca gctcccggag acggtcacag cttgtctgta agcggatgcc   2100
gggagcagac aagcccgtca gggcgcgtca gcgggtgttg gcgggtgtcg gggcgcagcc   2160
atgacccagt cacgtagcga tagcggagtg tatactggct taactatgcg gcatcagagc   2220
agattgtact gagagtgcac catatgcggt gtgaaatacc gcacagatgc gtaaggagaa   2280
aataccgcat caggcgctct tccgcttcct cgctcactga ctcgctgcgc tcggtcgttc   2340
ggctgcggcg agcggtatca gctcactcaa aggcggtaat acggttatcc acagaatcag   2400
gggataacgc aggaaagaac atgtgagcaa aaggccagca aaaggccagg aaccgtaaaa   2460
aggccgcgtt gctggcgttt ttccataggc tccgcccccc tgacgagcat cacaaaaatc   2520
gacgctcaag tcagaggtgg cgaaacccga caggactata aagataccag gcgtttcccc   2580
ctggaagctc cctcgtgcgc tctcctgttc cgaccctgcc gcttaccgga tacctgtccg   2640
cctttctccc ttcgggaagc gtggcgcttt ctcatagctc acgctgtagg tatctcagtt   2700
cggtgtaggt cgttcgctcc aagctgggct gtgtgcacga accccccgtt cagcccgacc   2760
gctgcgcctt atccggtaac tatcgtcttg agtccaaccc ggtaagacac gacttatcgc   2820
cactggcagc agccactggt aacaggatta gcagagcgag gtatgtaggc ggtgctacag   2880
agttcttgaa gtggtggcct aactacggct acactagaag gacagtattt ggtatctgcg   2940
ctctgctgaa gccagttacc ttcggaaaaa gagttggtag ctcttgatcc ggcaaacaaa   3000
ccaccgctgg tagcggtggt ttttttgttt gcaagcagca gattacgcgc agaaaaaaag   3060
gatctcaaga agatcctttg atcttttcta cggggtctga cgctcagtgg aacgaaaact   3120
cacgttaagg gattttggtc atgagattat caaaaaggat cttcacctag atccttttaa   3180
attaaaaatg aagttttaaa tcaatctaaa gtatatatga gtaaacttgg tctgacagtt   3240
accaatgctt aatcagtgag gcacctatct cagcgatctg tctatttcgt tcatccatag   3300
ttgcctgact ccccgtcgtg tagataacta cgatacggga gggcttacca tctggcccca   3360
gtgctgcaat gataccgcga gacccacgct caccggctcc agatttatca gcaataaacc   3420
agccagccgg aagggccgag cgcagaagtg gtcctgcaac tttatccgcc tccatccagt   3480
```

```
ctattaattg ttgccgggaa gctagagtaa gtagttcgcc agttaatagt ttgcgcaacg   3540

ttgttgccat tgctacaggc atcgtggtgt cacgctcgtc gtttggtatg gcttcattca   3600

gctccggttc ccaacgatca aggcgagtta catgatcccc catgttgtgc aaaaaagcgg   3660

ttagctcctt cggtcctccg atcgttgtca gaagtaagtt ggccgcagtg ttatcactca   3720

tggttatggc agcactgcat aattctctta ctgtcatgcc atccgtaaga tgcttttctg   3780

tgactggtga gtactcaacc aagtcattct gagaatagtg tatgcggcga ccgagttgct   3840

cttgcccggc gtcaatacgg gataataccg cgccacatag cagaacttta aaagtgctca   3900

tcattggaaa acgttcttcg gggcgaaaac tctcaaggat cttaccgctg ttgagatcca   3960

gttcgatgta acccactcgt gcacccaact gatcttcagc atcttttact ttcaccagcg   4020

tttctgggtg agcaaaaaca ggaaggcaaa atgccgcaaa aaagggaata agggcgacac   4080

ggaaatgttg aatactcata ctcttccttt ttcaatatta ttgaagcatt tatcagggtt   4140

attgtctcat gagcggatac atatttgaat gtatttagaa aaataaacaa ataggggttc   4200

cgcgcacatt tccccgaaaa gtgccacctg acgtctaaga aaccattatt atcatgacat   4260

taacctataa aaataggcgt atcacgaggc cctttcgtct tcac                    4304


<210> SEQ ID NO 125
<211> LENGTH: 4304
<212> TYPE: DNA
<213> ORGANISM: Artificial Sequence
<220> FEATURE:
<223> OTHER INFORMATION: plasmid construct encoding the mutant (D102A)
      LukS-PV

<400> SEQUENCE: 125

ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtgggggt cacacaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctaa aaataaaata gcttcagtaa atgttagtca aacattaggt    480

tataacatag gtggtaattt taatagtggt ccatcaacag gaggtaatgg ttcatttaat    540

tattcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tccttcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020

cctgcagcca agcttaatta gctgagcttg gactcctgtt gatagatcca gtaatgacct   1080

cagaactcca tctggatttg ttcagaacgc tcggttgccg ccgggcgttt tttattggtg   1140

agaatccaag ctagcttggc gagattttca ggagctaagg aagctaaaat ggagaaaaaa   1200
```

atcactggat ataccaccgt tgatatatcc caatggcatc gtaaagaaca ttttgaggca 1260
tttcagtcag ttgctcaatg tacctataac cagaccgttc agctggatat tacggccttt 1320
ttaaagaccg taaagaaaaa taagcacaag ttttatccgg cctttattca cattcttgcc 1380
cgcctgatga atgctcatcc ggaatttcgt atggcaatga aagacggtga gctggtgata 1440
tgggatagtg ttcacccttg ttacaccgtt ttccatgagc aaactgaaac gttttcatcg 1500
ctctggagtg aataccacga cgatttccgg cagtttctac acatatattc gcaagatgtg 1560
gcgtgttacg gtgaaaacct ggcctatttc cctaaagggt ttattgagaa tatgtttttc 1620
gtctcagcca atccctgggt gagtttcacc agttttgatt taaacgtggc caatatggac 1680
aacttcttcg cccccgtttt caccatgggc aaatattata cgcaaggcga caaggtgctg 1740
atgccgctgg cgattcaggt tcatcatgcc gtttgtgatg gcttccatgt cggcagaatg 1800
cttaatgaat tacaacagta ctgcgatgag tggcagggcg gggcgtaatt tttttaaggc 1860
agttattggt gcccttaaac gcctggggta atgactctct agcttgaggc atcaaataaa 1920
acgaaaggct cagtcgaaag actgggcctt tcgttttatc tgttgtttgt cggtgaacgc 1980
tctcctgagt aggacaaatc cgccctctag agctgcctcg cgcgtttcgg tgatgacggt 2040
gaaaacctct gacacatgca gctcccggag acggtcacag cttgtctgta agcggatgcc 2100
gggagcagac aagcccgtca gggcgcgtca gcgggtgttg gcgggtgtcg gggcgcagcc 2160
atgacccagt cacgtagcga tagcggagtg tatactggct taactatgcg gcatcagagc 2220
agattgtact gagagtgcac catatgcggt gtgaaatacc gcacagatgc gtaaggagaa 2280
aataccgcat caggcgctct tccgcttcct cgctcactga ctcgctgcgc tcggtcgttc 2340
ggctgcggcg agcggtatca gctcactcaa aggcggtaat acggttatcc acagaatcag 2400
gggataacgc aggaaagaac atgtgagcaa aaggccagca aaaggccagg aaccgtaaaa 2460
aggccgcgtt gctggcgttt ttccataggc tccgcccccc tgacgagcat cacaaaaatc 2520
gacgctcaag tcagaggtgg cgaaacccga caggactata aagataccag gcgtttcccc 2580
ctggaagctc cctcgtgcgc tctcctgttc cgaccctgcc gcttaccgga tacctgtccg 2640
cctttctccc ttcgggaagc gtggcgcttt ctcatagctc acgctgtagg tatctcagtt 2700
cggtgtaggt cgttcgctcc aagctgggct gtgtgcacga accccccgtt cagcccgacc 2760
gctgcgcctt atccggtaac tatcgtcttg agtccaaccc ggtaagacac gacttatcgc 2820
cactggcagc agccactggt aacaggatta gcagagcgag gtatgtaggc ggtgctacag 2880
agttcttgaa gtggtggcct aactacggct acactagaag gacagtattt ggtatctgcg 2940
ctctgctgaa gccagttacc ttcggaaaaa gagttggtag ctcttgatcc ggcaaacaaa 3000
ccaccgctgg tagcggtggt ttttttgttt gcaagcagca gattacgcgc agaaaaaaag 3060
gatctcaaga agatcctttg atcttttcta cggggtctga cgctcagtgg aacgaaaact 3120
cacgttaagg gattttggtc atgagattat caaaaaggat cttcacctag atccttttaa 3180
attaaaaatg aagttttaaa tcaatctaaa gtatatatga gtaaacttgg tctgacagtt 3240
accaatgctt aatcagtgag gcacctatct cagcgatctg tctatttcgt tcatccatag 3300
ttgcctgact ccccgtcgtg tagataacta cgatacggga gggcttacca tctggcccca 3360
gtgctgcaat gataccgcga gacccacgct caccggctcc agatttatca gcaataaacc 3420
agccagccgg aagggccgag cgcagaagtg gtcctgcaac tttatccgcc tccatccagt 3480
ctattaattg ttgccgggaa gctagagtaa gtagttcgcc agttaatagt ttgcgcaacg 3540
ttgttgccat tgctacaggc atcgtggtgt cacgctcgtc gtttggtatg gcttcattca 3600
gctccggttc ccaacgatca aggcgagtta catgatcccc catgttgtgc aaaaaagcgg 3660
ttagctcctt cggtcctccg atcgttgtca gaagtaagtt ggccgcagtg ttatcactca 3720
tggttatggc agcactgcat aattctctta ctgtcatgcc atccgtaaga tgcttttctg 3780
tgactggtga gtactcaacc aagtcattct gagaatagtg tatgcggcga ccgagttgct 3840
cttgcccggc gtcaatacgg gataataccg cgccacatag cagaacttta aaagtgctca 3900
tcattggaaa acgttcttcg gggcgaaaac tctcaaggat cttaccgctg ttgagatcca 3960
gttcgatgta acccactcgt gcacccaact gatcttcagc atcttttact ttcaccagcg 4020
tttctgggtg agcaaaaaca ggaaggcaaa atgccgcaaa aaagggaata agggcgacac 4080
ggaaatgttg aatactcata ctcttccttt ttcaatatta ttgaagcatt tatcagggtt 4140
attgtctcat gagcggatac atatttgaat gtatttagaa aaataaacaa ataggggttc 4200
cgcgcacatt tccccgaaaa gtgccacctg acgtctaaga aaccattatt atcatgacat 4260
taacctataa aaataggcgt atcacgaggc cctttcgtct tcac 4304

<210> SEQ ID NO 126
<211> LENGTH: 4304
<212> TYPE: DNA
<213> ORGANISM: Artificial Sequence
<220> FEATURE:
<223> OTHER INFORMATION: plasmid construct encoding the mutant (Y131A)
LukS-PV

<400> SEQUENCE: 126
ctcgagaaat cataaaaaat ttatttgctt tgtgagcgga taacaattat aatagattca 60
attgtgagcg gataacaatt tcacacagaa ttcattaaag aggagaaatt aactatgaga 120
ggatcgcatc accatcacca tcacggatcc gataacaata ttgagaatat tggtgatggc 180
gctgaggtag tcaaaagaac agaagataca agtagcgata agtgggggt cacacaaaat 240 attcagtttg attttgttaa agataaaaag tataacaaag acgctttgat tttaaaaatg 300
caaggtttta tcaattcaaa gactacttat tacaattaca aaaacacaga tcatataaaa 360
gcaatgaggt ggcctttcca atacaatatt ggtctcaaaa caaatgaccc caatgtagat 420
ttaataaatt atctacctaa aaataaaata gattcagtaa atgttagtca aacattaggt 480
tataacatag gtggtaattt taatagtggt ccatcaacag gaggtaatgg ttcatttaat 540
gcatcaaaaa caattagtta taatcaacaa aactatatca gtgaagtaga acatcaaaat 600
tcaaaaagtg ttcaatgggg aataaaagct aattcattta tcacatcatt aggtaaaatg 660
tctggacatg atccaaattt atttgttgga tataaaccat atagtcaaaa tccgagagac 720
tattttgtgc cagacaatga attaccccca ttagtacaca gtggtttcaa tccttcattt 780
attgcaactg tttctcatga aaaaggctca ggagatacaa gtgaatttga aataacgtat 840
ggcagaaata tggatgttac tcatgctact agaagaacaa cacactatgg caatagttat 900
ttagaaggat ctagaataca caacgcattt gtaaacagaa attacacagt taaatatgaa 960
gtgaactgga aaactcatga aattaaagtg aaaggacata attgaggtac cccgggtcga 1020
cctgcagcca agcttaatta gctgagcttg gactcctgtt gatagatcca gtaatgacct 1080
cagaactcca tctggatttg ttcagaacgc tcggttgccg ccgggcgttt tttattggtg 1140
agaatccaag ctagcttggc gagattttca ggagctaagg aagctaaaat ggagaaaaaa 1200
atcactggat ataccaccgt tgatatatcc caatggcatc gtaaagaaca ttttgaggca 1260

-continued

```
tttcagtcag ttgctcaatg tacctataac cagaccgttc agctggatat tacggccttt   1320
ttaaagaccg taaagaaaaa taagcacaag ttttatccgg cctttattca cattcttgcc   1380
cgcctgatga atgctcatcc ggaatttcgt atggcaatga aagacggtga gctggtgata   1440
tgggatagtg ttcacccttg ttacaccgtt ttccatgagc aaactgaaac gttttcatcg   1500
ctctggagtg aataccacga cgatttccgg cagtttctac acatatattc gcaagatgtg   1560
gcgtgttacg gtgaaaacct ggcctatttc cctaaagggt ttattgagaa tatgtttttc   1620
gtctcagcca atccctgggt gagtttcacc agttttgatt taaacgtggc caatatggac   1680
aacttcttcg cccccgtttt caccatgggc aaatattata cgcaaggcga caaggtgctg   1740
atgccgctgg cgattcaggt tcatcatgcc gtttgtgatg gcttccatgt cggcagaatg   1800
cttaatgaat tacaacagta ctgcgatgag tggcagggcg gggcgtaatt tttttaaggc   1860
agttattggt gcccttaaac gcctggggta atgactctct agcttgaggc atcaaataaa   1920
acgaaaggct cagtcgaaag actgggcctt tcgttttatc tgttgtttgt cggtgaacgc   1980
tctcctgagt aggacaaatc cgccctctag agctgcctcg cgcgtttcgg tgatgacggt   2040
gaaaacctct gacacatgca gctcccggag acggtcacag cttgtctgta agcggatgcc   2100
gggagcagac aagcccgtca gggcgcgtca gcgggtgttg gcgggtgtcg gggcgcagcc   2160
atgacccagt cacgtagcga tagcggagtg tatactggct taactatgcg gcatcagagc   2220
agattgtact gagagtgcac catatgcggt gtgaaatacc gcacagatgc gtaaggagaa   2280
aataccgcat caggcgctct tccgcttcct cgctcactga ctcgctgcgc tcggtcgttc   2340
ggctgcggcg agcggtatca gctcactcaa aggcggtaat acggttatcc acagaatcag   2400
gggataacgc aggaaagaac atgtgagcaa aaggccagca aaaggccagg aaccgtaaaa   2460
aggccgcgtt gctggcgttt ttccataggc tccgcccccc tgacgagcat cacaaaaatc   2520
gacgctcaag tcagaggtgg cgaaacccga caggactata aagataccag gcgtttcccc   2580
ctggaagctc cctcgtgcgc tctcctgttc cgaccctgcc gcttaccgga tacctgtccg   2640
cctttctccc ttcgggaagc gtggcgcttt ctcatagctc acgctgtagg tatctcagtt   2700
cggtgtaggt cgttcgctcc aagctgggct gtgtgcacga accccccgtt cagcccgacc   2760
gctgcgcctt atccggtaac tatcgtcttg agtccaaccc ggtaagacac gacttatcgc   2820
cactggcagc agccactggt aacaggatta gcagagcgag gtatgtaggc ggtgctacag   2880
agttcttgaa gtggtggcct aactacggct acactagaag gacagtattt ggtatctgcg   2940
ctctgctgaa gccagttacc ttcggaaaaa gagttggtag ctcttgatcc ggcaaacaaa   3000
ccaccgctgg tagcggtggt ttttttgttt gcaagcagca gattacgcgc agaaaaaaag   3060
gatctcaaga agatcctttg atcttttcta cggggtctga cgctcagtgg aacgaaaact   3120
cacgttaagg gattttggtc atgagattat caaaaaggat cttcacctag atccttttaa   3180
attaaaaatg aagttttaaa tcaatctaaa gtatatatga gtaaacttgg tctgacagtt   3240
accaatgctt aatcagtgag gcacctatct cagcgatctg tctatttcgt tcatccatag   3300
ttgcctgact ccccgtcgtg tagataacta cgatacggga gggcttacca tctggcccca   3360
gtgctgcaat gataccgcga gacccacgct caccggctcc agatttatca gcaataaacc   3420
agccagccgg aagggccgag cgcagaagtg gtcctgcaac tttatccgcc tccatccagt   3480
ctattaattg ttgccgggaa gctagagtaa gtagttcgcc agttaatagt ttgcgcaacg   3540
ttgttgccat tgctacaggc atcgtggtgt cacgctcgtc gtttggtatg gcttcattca   3600
gctccggttc ccaacgatca aggcgagtta catgatcccc catgttgtgc aaaaaagcgg   3660
```

```
ttagctcctt cggtcctccg atcgttgtca gaagtaagtt ggccgcagtg ttatcactca   3720

tggttatggc agcactgcat aattctctta ctgtcatgcc atccgtaaga tgcttttctg   3780

tgactggtga gtactcaacc aagtcattct gagaatagtg tatgcggcga ccgagttgct   3840

cttgcccggc gtcaatacgg gataataccg cgccacatag cagaacttta aaagtgctca   3900

tcattggaaa acgttcttcg gggcgaaaac tctcaaggat cttaccgctg ttgagatcca   3960

gttcgatgta acccactcgt gcacccaact gatcttcagc atcttttact ttcaccagcg   4020

tttctgggtg agcaaaaaca ggaaggcaaa atgccgcaaa aaagggaata agggcgacac   4080

ggaaatgttg aatactcata ctcttccttt ttcaatatta ttgaagcatt tatcagggtt   4140

attgtctcat gagcggatac atatttgaat gtatttagaa aaataaacaa ataggggttc   4200

cgcgcacatt tccccgaaaa gtgccacctg acgtctaaga aaccattatt atcatgacat   4260

taacctataa aaataggcgt atcacgaggc cctttcgtct tcac                    4304
```

<210> SEQ ID NO 127
<211> LENGTH: 4304
<212> TYPE: DNA
<213> ORGANISM: Artificial Sequence
<220> FEATURE:
<223> OTHER INFORMATION: plasmid construct encoding the mutant (S209A) LukS-PV

<400> SEQUENCE: 127

```
ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtgggggt cacacaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctaa aaataaaata gattcagtaa atgttagtca aacattaggt    480

tataacatag gtggtaattt taatagtggt ccatcaacag gaggtaatgg ttcatttaat    540

gcatcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tcctgcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020

cctgcagcca agcttaatta gctgagcttg gactcctgtt gatagatcca gtaatgacct   1080

cagaactcca tctggatttg ttcagaacgc tcggttgccg ccgggcgttt tttattggtg   1140

agaatccaag ctagcttggc gagattttca ggagctaagg aagctaaaat ggagaaaaaa   1200

atcactggat ataccaccgt tgatatatcc caatggcatc gtaaagaaca ttttgaggca   1260

tttcagtcag ttgctcaatg tacctataac cagaccgttc agctggatat tacggccttt   1320

ttaaagaccg taaagaaaaa taagcacaag ttttatccgg cctttattca cattcttgcc   1380
```

cgcctgatga atgctcatcc ggaatttcgt atggcaatga aagacggtga gctggtgata 1440
tgggatagtg ttcacccttg ttacaccgtt ttccatgagc aaactgaaac gttttcatcg 1500
ctctggagtg aataccacga cgatttccgg cagtttctac acatatattc gcaagatgtg 1560
gcgtgttacg gtgaaaacct ggcctatttc cctaaagggt ttattgagaa tatgtttttc 1620
gtctcagcca atccctgggt gagtttcacc agttttgatt taaacgtggc caatatggac 1680
aacttcttcg cccccgtttt caccatgggc aaatattata cgcaaggcga caaggtgctg 1740
atgccgctgg cgattcaggt tcatcatgcc gtttgtgatg gcttccatgt cggcagaatg 1800
cttaatgaat tacaacagta ctgcgatgag tggcagggcg gggcgtaatt tttttaaggc 1860
agttattggt gcccttaaac gcctggggta atgactctct agcttgaggc atcaaataaa 1920
acgaaaggct cagtcgaaag actgggcctt tcgttttatc tgttgtttgt cggtgaacgc 1980
tctcctgagt aggacaaatc cgccctctag agctgcctcg cgcgtttcgg tgatgacggt 2040
gaaaacctct gacacatgca gctcccggag acggtcacag cttgtctgta agcggatgcc 2100
gggagcagac aagcccgtca gggcgcgtca gcgggtgttg gcgggtgtcg gggcgcagcc 2160
atgacccagt cacgtagcga tagcggagtg tatactggct taactatgcg gcatcagagc 2220
agattgtact gagagtgcac catatgcggt gtgaaatacc gcacagatgc gtaaggagaa 2280
aataccgcat caggcgctct tccgcttcct cgctcactga ctcgctgcgc tcggtcgttc 2340
ggctgcggcg agcggtatca gctcactcaa aggcggtaat acggttatcc acagaatcag 2400
gggataacgc aggaaagaac atgtgagcaa aaggccagca aaaggccagg aaccgtaaaa 2460
aggccgcgtt gctggcgttt ttccataggc tccgcccccc tgacgagcat cacaaaaatc 2520
gacgctcaag tcagaggtgg cgaaacccga caggactata aagataccag gcgtttcccc 2580
ctggaagctc cctcgtgcgc tctcctgttc cgaccctgcc gcttaccgga tacctgtccg 2640
cctttctccc ttcgggaagc gtggcgcttt ctcatagctc acgctgtagg tatctcagtt 2700
cggtgtaggt cgttcgctcc aagctgggct gtgtgcacga accccccgtt cagcccgacc 2760
gctgcgcctt atccggtaac tatcgtcttg agtccaaccc ggtaagacac gacttatcgc 2820
cactggcagc agccactggt aacaggatta gcagagcgag gtatgtaggc ggtgctacag 2880
agttcttgaa gtggtggcct aactacggct acactagaag gacagtattt ggtatctgcg 2940
ctctgctgaa gccagttacc ttcggaaaaa gagttggtag ctcttgatcc ggcaaacaaa 3000
ccaccgctgg tagcggtggt ttttttgttt gcaagcagca gattacgcgc agaaaaaaag 3060
gatctcaaga agatcctttg atcttttcta cggggtctga cgctcagtgg aacgaaaact 3120
cacgttaagg gattttggtc atgagattat caaaaaggat cttcacctag atccttttaa 3180
attaaaaatg aagttttaaa tcaatctaaa gtatatatga gtaaacttgg tctgacagtt 3240
accaatgctt aatcagtgag gcacctatct cagcgatctg tctatttcgt tcatccatag 3300
ttgcctgact ccccgtcgtg tagataacta cgatacggga gggcttacca tctggcccca 3360
gtgctgcaat gataccgcga gacccacgct caccggctcc agatttatca gcaataaacc 3420
agccagccgg aagggccgag cgcagaagtg gtcctgcaac tttatccgcc tccatccagt 3480
ctattaattg ttgccgggaa gctagagtaa gtagttcgcc agttaatagt ttgcgcaacg 3540
ttgttgccat tgctacaggc atcgtggtgt cacgctcgtc gtttggtatg gcttcattca 3600
gctccggttc ccaacgatca aggcgagtta catgatcccc catgttgtgc aaaaaagcgg 3660
ttagctcctt cggtcctccg atcgttgtca gaagtaagtt ggccgcagtg ttatcactca 3720
tggttatggc agcactgcat aattctctta ctgtcatgcc atccgtaaga tgcttttctg 3780
tgactggtga gtactcaacc aagtcattct gagaatagtg tatgcggcga ccgagttgct 3840
cttgcccggc gtcaatacgg gataataccg cgccacatag cagaacttta aaagtgctca 3900
tcattggaaa acgttcttcg gggcgaaaac tctcaaggat cttaccgctg ttgagatcca 3960
gttcgatgta acccactcgt gcacccaact gatcttcagc atcttttact ttcaccagcg 4020
tttctgggtg agcaaaaaca ggaaggcaaa atgccgcaaa aaagggaata agggcgacac 4080
ggaaatgttg aatactcata ctcttccttt ttcaatatta ttgaagcatt tatcagggtt 4140
attgtctcat gagcggatac atatttgaat gtatttagaa aaataaacaa ataggggttc 4200
cgcgcacatt tccccgaaaa gtgccacctg acgtctaaga aaccattatt atcatgacat 4260
taacctataa aaataggcgt atcacgaggc cctttcgtct tcac 4304

<210> SEQ ID NO 128
<211> LENGTH: 4184
<212> TYPE: DNA
<213> ORGANISM: Artificial Sequence
<220> FEATURE:
<223> OTHER INFORMATION: plasmid construct encoding the mutant (T28F) LukS-PV

<400> SEQUENCE: 128
ctcgagaaat cataaaaaat ttatttgctt tgtgagcgga taacaattat aatagattca 60
attgtgagcg gataacaatt tcacacagaa ttcattaaag aggagaaatt aactatgaga 120
ggatcgcatc accatcacca tcacggatcc gataacaata ttgagaatat tggtgatggc 180
gctgaggtag tcaaaagaac agaagataca agtagcgata agtggggggt ctttcaaaat 240
attcagtttg attttgttaa agataaaaag tataacaaag acgctttgat tttaaaaatg 300
caaggtttta tcaattcaaa gactacttat tacaattaca aaaacacaga tcatataaaa 360
gcaatgaggt ggcctttcca atacaatatt ggtctcaaaa caaatgaccc caatgtagat 420
ttaataaatt atctacctaa aaataaaata gattcagtaa atgttagtca aacattaggt 480
tataacatag gtggtaattt taatagtggt ccatcaacag gaggtaatgg ttcatttaat 540
tattcaaaaa caattagtta taatcaacaa aactatatca gtgaagtaga acatcaaaat 600
tcaaaaagtg ttcaatgggg aataaaagct aattcattta tcacatcatt aggtaaaatg 660
tctggacatg atccaaattt atttgttgga tataaaccat atagtcaaaa tccgagagac 720
tattttgtgc cagacaatga attacccccca ttagtacaca gtggtttcaa tccttcattt 780
attgcaactg tttctcatga aaaaggctca ggagatacaa gtgaatttga aataacgtat 840
ggcagaaata tggatgttac tcatgctact agaagaacaa cacactatgg caatagttat 900
ttagaaggat ctagaataca caacgcattt gtaaacagaa attacacagt taaatatgaa 960
gtgaactgga aaactcatga aattaaagtg aaaggacata attgaggtac cccgggtcga 1020
cctgcagcca agcttaatta gctgagcttg gactcctgtt gatagatcca gtaatgacct 1080
cagaactcca tctggatttg ttcagaacgc tcggttgccg ccgggcgttt tttattggtg 1140
agaatccaag ctagcttggc gagattttca ggagctaagg aagctaaaat ggagaaaaaa 1200
atcactggat ataccaccgt tgatatatcc caatggcatc gtaaagaaca ttttgaggca 1260
tttcagtcag ttgctcaatg tacctataac cagaccgttc agctggatat tacggccttt 1320
ttaaagaccg taaagaaaaa taagcacaag ttttatccgg cctttattca cattcttgcc 1380
cgcctgatga atgctcatcc ggaatttcgt atggcaatga aagacggtga gctggtgata 1440
tgggatagtg ttcacccttg ttacaccgtt ttccatgagc aaactgaaac gttttcatcg 1500
ctctggagtg aataccacga cgatttccgg cagtttctac acatatattc gcaagatgtg 1560
gcgtgttacg gtgaaaacct ggcctatttc cctaaagggt ttattgagaa tatgtttttc 1620
gtctcagcca atccctgggt gagtttcacc agttttgatt taaacgtggc caatatggac 1680
aacttcttcg cccccgtttt caccatgggc aaatattata cgcaaggcga caaggtgctg 1740
atgccgctgg cgattcaggt tcatcatgcc gtttgtgatg gcttccatgt cggcagaatg 1800
cttaatgaat tacaacagta ctgcgatgag tggcagggcg gggcgtaatt tttttaaggc 1860
agttattggt gcccttaaac gcctggggta atgactctct agcttgaggc atcaaataaa 1920
acgaaaggct cagtcgaaag actgggcctt tcgttttatc tgttgtttgt cggtgaacgc 1980
tctcctgagt aggacaaatc cgccctctag agctgcctcg cgcgtttcgg tgatgacggt 2040
gaaaacctct gacacatgca gctcccggag acggtcacag cttgtctgta agcggatgcc 2100
gggagcagac aagcccgtca gggcgcgtca gcgggtgttg gcgggtgtcg gggcgcagcc 2160
atgacccagt cacgtagcga tagcggagtg tatactggct taactatgcg gcatcagagc 2220
aataccgcat caggcgctct tccgcttcct cgctcactga ctcgctgcgc tcggtcgttc 2280
ggctgcggcg agcggtatca gctcactcaa aggcggtaat acggttatcc acagaatcag 2340
gggataacgc aggaaagaac atgtgagcaa aaggccagca aaaggccagg aaccgtaaaa 2400
aggccgcgtt gctggcgttt ttccataggc tccgcccccc tgacgagcat cacaaaaatc 2460
gacgctcaag tcagaggtgg cgaaacccga caggactata aagataccag gcgtttcccc 2520
ctggaagctc cctcgtgcgc tctcctgttc cgaccctgcc gcttaccgga tacctgtccg 2580
cggtgtaggt cgttcgctcc aagctgggct gtgtgcacga accccccgtt cagcccgacc 2640
gctgcgcctt atccggtaac tatcgtcttg agtccaaccc ggtaagacac gacttatcgc 2700
cactggcagc agccactggt aacaggatta gcagagcgag gtatgtaggc ggtgctacag 2760
agttcttgaa gtggtggcct aactacggct acactagaag gacagtattt ggtatctgcg 2820
ctctgctgaa gccagttacc ttcggaaaaa gagttggtag ctcttgatcc ggcaaacaaa 2880
ccaccgctgg tagcggtggt ttttttgttt gcaagcagca gattacgcgc agaaaaaaag 2940
gatctcaaga agatcctttg atcttttcta cggggtctga cgctcagtgg aacgaaaact 3000
cacgttaagg gattttggtc atgagattat caaaaaggat cttcacctag atccttttaa 3060
attaaaaatg aagttttaaa tcaatctaaa gtatatatga gtaaacttgg tctgacagtt 3120
accaatgctt aatcagtgag gcacctatct cagcgatctg tctatttcgt tcatccatag 3180
ttgcctgact ccccgtcgtg tagataacta cgatacggga gggcttacca tctggcccca 3240
gtgctgcaat gataccgcga gacccacgct caccggctcc agatttatca gcaataaacc 3300
agccagccgg aagggccgag cgcagaagtg gtcctgcaac tttatccgcc tccatccagt 3360
ctattaattg ttgccgggaa gctagagtaa gtagttcgcc agttaatagt ttgcgcaacg 3420
ttgttgccat tgctacaggc atcgtggtgt cacgctcgtc gtttggtatg gcttcattca 3480
gctccggttc ccaacgatca aggcgagtta catgatcccc catgttgtgc aaaaaagcgg 3540
ttagctcctt cggtcctccg atcgttgtca gaagtaagtt ggccgcagtg ttatcactca 3600
tggttatggc agcactgcat aattctctta ctgtcatgcc atccgtaaga tgcttttctg 3660
tgactggtga gtactcaacc aagtcattct gagaatagtg tatgcggcga ccgagttgct 3720
cttgcccggc gtcaatacgg gataataccg cgccacatag cagaacttta aaagtgctca 3780
tcattggaaa acgttcttcg gggcgaaaac tctcaaggat cttaccgctg ttgagatcca 3840

```
gttcgatgta acccactcgt gcacccaact gatcttcagc atcttttact ttcaccagcg   3900

tttctgggtg agcaaaaaca ggaaggcaaa atgccgcaaa aaagggaata agggcgacac   3960

ggaaatgttg aatactcata ctcttccttt ttcaatatta ttgaagcatt tatcagggtt   4020

attgtctcat gagcggatac atatttgaat gtatttagaa aaataaacaa ataggggttc   4080

cgcgcacatt tccccgaaaa gtgccacctg acgtctaaga aaccattatt atcatgacat   4140

taacctataa aaataggcgt atcacgaggc cctttcgtct tcac                    4184
```

<210> SEQ ID NO 129
<211> LENGTH: 4304
<212> TYPE: DNA
<213> ORGANISM: Artificial Sequence
<220> FEATURE:
<223> OTHER INFORMATION: plasmid construct encoding the mutant (T28F/Y131A) LukS-PV

<400> SEQUENCE: 129

```
ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtggggggt ctttcaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctaa aaataaaata gcttcagtaa atgttagtca aacattaggt    480

tataacatag gtggtaattt taatagtggt ccatcaacag gaggtaatgg ttcatttaat    540

tattcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tccttcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020

cctgcagcca agcttaatta gctgagcttg gactcctgtt gatagatcca gtaatgacct   1080

cagaactcca tctggatttg ttcagaacgc tcggttgccg ccgggcgttt tttattggtg   1140

agaatccaag ctagcttggc gagattttca ggagctaagg aagctaaaat ggagaaaaaa   1200

atcactggat ataccaccgt tgatatatcc caatggcatc gtaaagaaca ttttgaggca   1260

tttcagtcag ttgctcaatg tacctataac cagaccgttc agctggatat tacggccttt   1320

ttaaagaccg taaagaaaaa taagcacaag ttttatccgg cctttattca cattcttgcc   1380

cgcctgatga atgctcatcc ggaatttcgt atggcaatga aagacggtga gctggtgata   1440

tgggatagtg ttcacccttg ttacaccgtt ttccatgagc aaactgaaac gttttcatcg   1500

ctctggagtg aataccacga cgatttccgg cagtttctac acatatattc gcaagatgtg   1560

gcgtgttacg gtgaaaacct ggcctatttc cctaaagggt ttattgagaa tatgtttttc   1620

gtctcagcca atccctgggt gagtttcacc agttttgatt taaacgtggc caatatggac   1680
```

```
aacttcttcg cccccgtttt caccatgggc aaatattata cgcaaggcga caaggtgctg   1740
atgccgctgg cgattcaggt tcatcatgcc gtttgtgatg gcttccatgt cggcagaatg   1800
cttaatgaat tacaacagta ctgcgatgag tggcagggcg gggcgtaatt tttttaaggc   1860
agttattggt gcccttaaac gcctggggta atgactctct agcttgaggc atcaaataaa   1920
acgaaaggct cagtcgaaag actgggcctt tcgttttatc tgttgtttgt cggtgaacgc   1980
tctcctgagt aggacaaatc cgccctctag agctgcctcg cgcgtttcgg tgatgacggt   2040
gaaaacctct gacacatgca gctcccggag acggtcacag cttgtctgta agcggatgcc   2100
gggagcagac aagcccgtca gggcgcgtca gcgggtgttg gcgggtgtcg gggcgcagcc   2160
atgacccagt cacgtagcga tagcggagtg tatactggct taactatgcg gcatcagagc   2220
agattgtact gagagtgcac catatgcggt gtgaaatacc gcacagatgc gtaaggagaa   2280
aataccgcat caggcgctct tccgcttcct cgctcactga ctcgctgcgc tcggtcgttc   2340
ggctgcggcg agcggtatca gctcactcaa aggcggtaat acggttatcc acagaatcag   2400
gggataacgc aggaaagaac atgtgagcaa aaggccagca aaaggccagg aaccgtaaaa   2460
aggccgcgtt gctggcgttt ttccataggc tccgcccccc tgacgagcat cacaaaaatc   2520
gacgctcaag tcagaggtgg cgaaacccga caggactata aagataccag gcgtttcccc   2580
ctggaagctc cctcgtgcgc tctcctgttc cgaccctgcc gcttaccgga tacctgtccg   2640
cctttctccc ttcgggaagc gtggcgcttt ctcatagctc acgctgtagg tatctcagtt   2700
cggtgtaggt cgttcgctcc aagctgggct gtgtgcacga accccccgtt cagcccgacc   2760
gctgcgcctt atccggtaac tatcgtcttg agtccaaccc ggtaagacac gacttatcgc   2820
cactggcagc agccactggt aacaggatta gcagagcgag gtatgtaggc ggtgctacag   2880
agttcttgaa gtggtggcct aactacggct acactagaag gacagtattt ggtatctgcg   2940
ctctgctgaa gccagttacc ttcggaaaaa gagttggtag ctcttgatcc ggcaaacaaa   3000
ccaccgctgg tagcggtggt ttttttgttt gcaagcagca gattacgcgc agaaaaaaag   3060
gatctcaaga agatcctttg atcttttcta cggggtctga cgctcagtgg aacgaaaact   3120
cacgttaagg gattttggtc atgagattat caaaaaggat cttcacctag atccttttaa   3180
attaaaaatg aagttttaaa tcaatctaaa gtatatatga gtaaacttgg tctgacagtt   3240
accaatgctt aatcagtgag gcacctatct cagcgatctg tctatttcgt tcatccatag   3300
ttgcctgact ccccgtcgtg tagataacta cgatacggga gggcttacca tctggcccca   3360
gtgctgcaat gataccgcga gacccacgct caccggctcc agatttatca gcaataaacc   3420
agccagccgg aagggccgag cgcagaagtg gtcctgcaac tttatccgcc tccatccagt   3480
ctattaattg ttgccgggaa gctagagtaa gtagttcgcc agttaatagt ttgcgcaacg   3540
ttgttgccat tgctacaggc atcgtggtgt cacgctcgtc gtttggtatg gcttcattca   3600
gctccggttc ccaacgatca aggcgagtta catgatcccc catgttgtgc aaaaaagcgg   3660
ttagctcctt cggtcctccg atcgttgtca gaagtaagtt ggccgcagtg ttatcactca   3720
tggttatggc agcactgcat aattctctta ctgtcatgcc atccgtaaga tgcttttctg   3780
tgactggtga gtactcaacc aagtcattct gagaatagtg tatgcggcga ccgagttgct   3840
cttgcccggc gtcaatacgg gataataccg cgccacatag cagaacttta aaagtgctca   3900
tcattggaaa acgttcttcg gggcgaaaac tctcaaggat cttaccgctg ttgagatcca   3960
gttcgatgta acccactcgt gcacccaact gatcttcagc atcttttact ttcaccagcg   4020
```

```
tttctgggtg agcaaaaaca ggaaggcaaa atgccgcaaa aaagggaata agggcgacac   4080

ggaaatgttg aatactcata ctcttccttt ttcaatatta ttgaagcatt tatcagggtt   4140

attgtctcat gagcggatac atatttgaat gtatttagaa aaataaacaa ataggggttc   4200

cgcgcacatt tccccgaaaa gtgccacctg acgtctaaga aaccattatt atcatgacat   4260

taacctataa aaataggcgt atcacgaggc cctttcgtct tcac                    4304


<210> SEQ ID NO 130
<211> LENGTH: 4304
<212> TYPE: DNA
<213> ORGANISM: Artificial Sequence
<220> FEATURE:
<223> OTHER INFORMATION: plasmid construct encoding the mutant
      (T28F/S209A) LukS-PV

<400> SEQUENCE: 130

ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtggggggt ctttcaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctaa aaataaaata gattcagtaa atgttagtca aacattaggt    480

tataacatag gtggtaattt taatagtggt ccatcaacag gaggtaatgg ttcatttaat    540

tattcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tcctgcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020

cctgcagcca agcttaatta gctgagcttg gactcctgtt gatagatcca gtaatgacct   1080

cagaactcca tctggatttg ttcagaacgc tcggttgccg ccgggcgttt tttattggtg   1140

agaatccaag ctagcttggc gagattttca ggagctaagg aagctaaaat ggagaaaaaa   1200

atcactggat ataccaccgt tgatatatcc caatggcatc gtaaagaaca ttttgaggca   1260

tttcagtcag ttgctcaatg tacctataac cagaccgttc agctggatat tacggccttt   1320

ttaaagaccg taaagaaaaa taagcacaag ttttatccgg cctttattca cattcttgcc   1380

cgcctgatga atgctcatcc ggaatttcgt atggcaatga aagacggtga gctggtgata   1440

tgggatagtg ttcacccttg ttacaccgtt ttccatgagc aaactgaaac gttttcatcg   1500

ctctggagtg aataccacga cgatttccgg cagtttctac acatatattc gcaagatgtg   1560

gcgtgttacg gtgaaaacct ggcctatttc cctaaagggt ttattgagaa tatgtttttc   1620

gtctcagcca atccctgggt gagtttcacc agttttgatt taaacgtggc caatatggac   1680

aacttcttcg cccccgtttt caccatgggc aaatattata cgcaaggcga caaggtgctg   1740
```

-continued

```
atgccgctgg cgattcaggt tcatcatgcc gtttgtgatg gcttccatgt cggcagaatg   1800
cttaatgaat tacaacagta ctgcgatgag tggcagggcg gggcgtaatt tttttaaggc   1860
agttattggt gcccttaaac gcctggggta atgactctct agcttgaggc atcaaataaa   1920
acgaaaggct cagtcgaaag actgggcctt tcgttttatc tgttgtttgt cggtgaacgc   1980
tctcctgagt aggacaaatc cgccctctag agctgcctcg cgcgtttcgg tgatgacggt   2040
gaaaacctct gacacatgca gctcccggag acggtcacag cttgtctgta agcggatgcc   2100
gggagcagac aagcccgtca gggcgcgtca gcgggtgttg gcgggtgtcg gggcgcagcc   2160
atgacccagt cacgtagcga tagcggagtg tatactggct taactatgcg gcatcagagc   2220
agattgtact gagagtgcac catatgcggt gtgaaatacc gcacagatgc gtaaggagaa   2280
aataccgcat caggcgctct tccgcttcct cgctcactga ctcgctgcgc tcggtcgttc   2340
ggctgcggcg agcggtatca gctcactcaa aggcggtaat acggttatcc acagaatcag   2400
gggataacgc aggaaagaac atgtgagcaa aaggccagca aaaggccagg aaccgtaaaa   2460
aggccgcgtt gctggcgttt ttccataggc tccgcccccc tgacgagcat cacaaaaatc   2520
gacgctcaag tcagaggtgg cgaaacccga caggactata aagataccag gcgtttcccc   2580
ctggaagctc cctcgtgcgc tctcctgttc cgaccctgcc gcttaccgga tacctgtccg   2640
cctttctccc ttcgggaagc gtggcgcttt ctcatagctc acgctgtagg tatctcagtt   2700
cggtgtaggt cgttcgctcc aagctgggct gtgtgcacga accccccgtt cagcccgacc   2760
gctgcgcctt atccggtaac tatcgtcttg agtccaaccc ggtaagacac gacttatcgc   2820
cactggcagc agccactggt aacaggatta gcagagcgag gtatgtaggc ggtgctacag   2880
agttcttgaa gtggtggcct aactacggct acactagaag gacagtattt ggtatctgcg   2940
ctctgctgaa gccagttacc ttcggaaaaa gagttggtag ctcttgatcc ggcaaacaaa   3000
ccaccgctgg tagcggtggt ttttttgttt gcaagcagca gattacgcgc agaaaaaaag   3060
gatctcaaga agatcctttg atcttttcta cggggtctga cgctcagtgg aacgaaaact   3120
cacgttaagg gattttggtc atgagattat caaaaaggat cttcacctag atccttttaa   3180
attaaaaatg aagttttaaa tcaatctaaa gtatatatga gtaaacttgg tctgacagtt   3240
accaatgctt aatcagtgag gcacctatct cagcgatctg tctatttcgt tcatccatag   3300
ttgcctgact ccccgtcgtg tagataacta cgatacggga gggcttacca tctggcccca   3360
gtgctgcaat gataccgcga gacccacgct caccggctcc agatttatca gcaataaacc   3420
agccagccgg aagggccgag cgcagaagtg gtcctgcaac tttatccgcc tccatccagt   3480
ctattaattg ttgccgggaa gctagagtaa gtagttcgcc agttaatagt ttgcgcaacg   3540
ttgttgccat tgctacaggc atcgtggtgt cacgctcgtc gtttggtatg gcttcattca   3600
gctccggttc ccaacgatca aggcgagtta catgatcccc catgttgtgc aaaaaagcgg   3660
ttagctcctt cggtcctccg atcgttgtca gaagtaagtt ggccgcagtg ttatcactca   3720
tggttatggc agcactgcat aattctctta ctgtcatgcc atccgtaaga tgcttttctg   3780
tgactggtga gtactcaacc aagtcattct gagaatagtg tatgcggcga ccgagttgct   3840
cttgcccggc gtcaatacgg gataataccg cgccacatag cagaacttta aaagtgctca   3900
tcattggaaa acgttcttcg gggcgaaaac tctcaaggat cttaccgctg ttgagatcca   3960
gttcgatgta acccactcgt gcacccaact gatcttcagc atcttttact ttcaccagcg   4020
tttctgggtg agcaaaaaca ggaaggcaaa atgccgcaaa aaagggaata agggcgacac   4080
ggaaatgttg aatactcata ctcttccttt ttcaatatta ttgaagcatt tatcagggtt   4140
```

```
attgtctcat gagcggatac atatttgaat gtatttagaa aaataaacaa ataggggttc   4200

cgcgcacatt tccccgaaaa gtgccacctg acgtctaaga aaccattatt atcatgacat   4260

taacctataa aaataggcgt atcacgaggc cctttcgtct tcac                    4304


<210> SEQ ID NO 131
<211> LENGTH: 4304
<212> TYPE: DNA
<213> ORGANISM: Artificial Sequence
<220> FEATURE:
<223> OTHER INFORMATION: plasmid construct encoding the mutant
      (T28F/K97A/Y131A) LukS-PV

<400> SEQUENCE: 131

ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gataacaata ttgagaatat tggtgatggc    180

gctgaggtag tcaaaagaac agaagataca agtagcgata agtgggggt ctttcaaaat    240

attcagtttg attttgttaa agataaaaag tataacaaag acgctttgat tttaaaaatg    300

caaggtttta tcaattcaaa gactacttat tacaattaca aaaacacaga tcatataaaa    360

gcaatgaggt ggcctttcca atacaatatt ggtctcaaaa caaatgaccc caatgtagat    420

ttaataaatt atctacctgc aaataaaata gattcagtaa atgttagtca aacattaggt    480

tataacatag gtggtaattt taatagtggt ccatcaacag gaggtaatgg ttcatttaat    540

tattcaaaaa caattagtta taatcaacaa aactatatca gtgaagtaga acatcaaaat    600

tcaaaaagtg ttcaatgggg aataaaagct aattcattta tcacatcatt aggtaaaatg    660

tctggacatg atccaaattt atttgttgga tataaaccat atagtcaaaa tccgagagac    720

tattttgtgc cagacaatga attacccccca ttagtacaca gtggtttcaa tcctgcattt    780

attgcaactg tttctcatga aaaaggctca ggagatacaa gtgaatttga aataacgtat    840

ggcagaaata tggatgttac tcatgctact agaagaacaa cacactatgg caatagttat    900

ttagaaggat ctagaataca caacgcattt gtaaacagaa attacacagt taaatatgaa    960

gtgaactgga aaactcatga aattaaagtg aaaggacata attgaggtac cccgggtcga   1020

cctgcagcca agcttaatta gctgagcttg gactcctgtt gatagatcca gtaatgacct   1080

cagaactcca tctggatttg ttcagaacgc tcggttgccg ccgggcgttt tttattggtg   1140

agaatccaag ctagcttggc gagattttca ggagctaagg aagctaaaat ggagaaaaaa   1200

atcactggat ataccaccgt tgatatatcc caatggcatc gtaaagaaca ttttgaggca   1260

tttcagtcag ttgctcaatg tacctataac cagaccgttc agctggatat tacggccttt   1320

ttaaagaccg taaagaaaaa taagcacaag ttttatccgg cctttattca cattcttgcc   1380

cgcctgatga atgctcatcc ggaatttcgt atggcaatga aagacggtga gctggtgata   1440

tgggatagtg ttcacccttg ttacaccgtt ttccatgagc aaactgaaac gttttcatcg   1500

ctctggagtg aataccacga cgatttccgg cagtttctac acatatattc gcaagatgtg   1560

gcgtgttacg gtgaaaacct ggcctatttc cctaaagggt ttattgagaa tatgtttttc   1620

gtctcagcca atccctgggt gagtttcacc agttttgatt taaacgtggc caatatggac   1680

aacttcttcg cccccgtttt caccatgggc aaatattata cgcaaggcga caaggtgctg   1740

atgccgctgg cgattcaggt tcatcatgcc gtttgtgatg gcttccatgt cggcagaatg   1800

cttaatgaat tacaacagta ctgcgatgag tggcagggcg gggcgtaatt tttttaaggc   1860
```

-continued agttattggt gcccttaaac gcctggggta atgactctct agcttgaggc atcaaataaa 1920
acgaaaggct cagtcgaaag actgggcctt tcgttttatc tgttgtttgt cggtgaacgc 1980
tctcctgagt aggacaaatc cgccctctag agctgcctcg cgcgtttcgg tgatgacggt 2040
gaaaacctct gacacatgca gctcccggag acggtcacag cttgtctgta agcggatgcc 2100
gggagcagac aagcccgtca gggcgcgtca gcgggtgttg gcgggtgtcg gggcgcagcc 2160
atgacccagt cacgtagcga tagcggagtg tatactggct taactatgcg gcatcagagc 2220
agattgtact gagagtgcac catatgcggt gtgaaatacc gcacagatgc gtaaggagaa 2280
aataccgcat caggcgctct tccgcttcct cgctcactga ctcgctgcgc tcggtcgttc 2340
ggctgcggcg agcggtatca gctcactcaa aggcggtaat acggttatcc acagaatcag 2400
gggataacgc aggaaagaac atgtgagcaa aaggccagca aaaggccagg aaccgtaaaa 2460
aggccgcgtt gctggcgttt ttccataggc tccgcccccc tgacgagcat cacaaaaatc 2520
gacgctcaag tcagaggtgg cgaaacccga caggactata aagataccag gcgtttcccc 2580
ctggaagctc cctcgtgcgc tctcctgttc cgaccctgcc gcttaccgga tacctgtccg 2640
cctttctccc ttcgggaagc gtggcgcttt ctcatagctc acgctgtagg tatctcagtt 2700
cggtgtaggt cgttcgctcc aagctgggct gtgtgcacga accccccgtt cagcccgacc 2760
gctgcgcctt atccggtaac tatcgtcttg agtccaaccc ggtaagacac gacttatcgc 2820
cactggcagc agccactggt aacaggatta gcagagcgag gtatgtaggc ggtgctacag 2880
agttcttgaa gtggtggcct aactacggct acactagaag gacagtattt ggtatctgcg 2940
ctctgctgaa gccagttacc ttcggaaaaa gagttggtag ctcttgatcc ggcaaacaaa 3000
ccaccgctgg tagcggtggt ttttttgttt gcaagcagca gattacgcgc agaaaaaaag 3060
gatctcaaga agatcctttg atcttttcta cggggtctga cgctcagtgg aacgaaaact 3120
cacgttaagg gattttggtc atgagattat caaaaaggat cttcacctag atccttttaa 3180
attaaaaatg aagttttaaa tcaatctaaa gtatatatga gtaaacttgg tctgacagtt 3240
accaatgctt aatcagtgag gcacctatct cagcgatctg tctatttcgt tcatccatag 3300
ttgcctgact ccccgtcgtg tagataacta cgatacggga gggcttacca tctggcccca 3360
gtgctgcaat gataccgcga gacccacgct caccggctcc agatttatca gcaataaacc 3420
agccagccgg aagggccgag cgcagaagtg gtcctgcaac tttatccgcc tccatccagt 3480
ctattaattg ttgccgggaa gctagagtaa gtagttcgcc agttaatagt ttgcgcaacg 3540
ttgttgccat tgctacaggc atcgtggtgt cacgctcgtc gtttggtatg gcttcattca 3600
gctccggttc ccaacgatca aggcgagtta catgatcccc catgttgtgc aaaaaagcgg 3660
ttagctcctt cggtcctccg atcgttgtca gaagtaagtt ggccgcagtg ttatcactca 3720
tggttatggc agcactgcat aattctctta ctgtcatgcc atccgtaaga tgcttttctg 3780
tgactggtga gtactcaacc aagtcattct gagaatagtg tatgcggcga ccgagttgct 3840
cttgcccggc gtcaatacgg gataataccg cgccacatag cagaacttta aaagtgctca 3900
tcattggaaa acgttcttcg gggcgaaaac tctcaaggat cttaccgctg ttgagatcca 3960
gttcgatgta acccactcgt gcacccaact gatcttcagc atcttttact ttcaccagcg 4020
tttctgggtg agcaaaaaca ggaaggcaaa atgccgcaaa aaagggaata agggcgacac 4080
ggaaatgttg aatactcata ctcttccttt ttcaatatta ttgaagcatt tatcagggtt 4140
attgtctcat gagcggatac atatttgaat gtatttagaa aaataaacaa ataggggttc 4200

-continued

```
cgcgcacatt tccccgaaaa gtgccacctg acgtctaaga aaccattatt atcatgacat   4260

taacctataa aaataggcgt atcacgaggc cctttcgtct tcac                    4304


<210> SEQ ID NO 132
<211> LENGTH: 2375
<212> TYPE: DNA
<213> ORGANISM: Artificial Sequence
<220> FEATURE:
<223> OTHER INFORMATION: plasmid construct encoding the wild-type
      LukF-PV

<400> SEQUENCE: 132

tcagtcgaaa gactgggcct ttcgttttat ctgttgtttg tcggtgaacg ctctcctgag     60

taggacaaat ccgccctcta gagctgcctc gcgcgtttcg gtgatgacgg tgaaaacctc    120

tgacacatgc agctcccgga gacggtcaca gcttgtctgt aagcggatgc cgggagcaga    180

caagcccgtc agggcgcgtc agcgggtgtt ggcgggtgtc ggggcgcagc catgacccag    240

tcacgtagcg atagcggagt gtatactggc ttaactatgc ggcatcagag cagattgtac    300

tgagagtgca ccatatgcgg tgtgaaatac cgcacagatg cgtaaggaga aaataccgca    360

tcaggcgctc ttccgcttcc tcgctcactg actcgctgcg ctcggtcgtt cggctgcggc    420

gagcggtatc agctcactca aaggcggtaa tacggttatc cacagaatca ggggataacg    480

caggaaagaa catgtgagca aaaggccagc aaaaggccag gaaccgtaaa aaggccgcgt    540

tgctggcgtt tttccatagg ctccgccccc ctgacgagca tcacaaaaat cgacgctcaa    600

gtcagaggtg gcgaaacccg acaggactat aaagatacca ggcgtttccc cctggaagct    660

ccctcgtgcg ctctcctgtt ccgaccctgc cgcttaccgg atacctgtcc gcctttctcc    720

cttcgggaag cgtggcgctt tctcatagct cacgctgtag gtatctcagt tcggtgtagg    780

tcgttcgctc caagctgggc tgtgtgcacg aaccccccgt tcagcccgac cgctgcgcct    840

tatccggtaa ctatcgtctt gagtccaacc cggtaagaca cgacttatcg ccactggcag    900

cagccactgg taacaggatt agcagagcga ggtatgtagg cggtgctaca gagttcttga    960

agtggtggcc taactacggc tacactagaa ggacagtatt tggtatctgc gctctgctga   1020

agccagttac cttcggaaaa agagttggta gctcttgatc cggcaaacaa accaccgctg   1080

gtagcggtgg tttttttgtt tgcaagcagc agattacgcg cagaaaaaaa ggatctcaag   1140

aagatccttt gatcttttct acggggtctg acgctcagtg gaacgaaaac tcacgttaag   1200

ggattttggt catgagatta tcaaaaagga tcttcaccta gatcctttta aattaaaaat   1260

gaagttttaa atcaatctaa agtatatatg agtaaacttg gtctgacagt taccaatgct   1320

taatcagtga ggcacctatc tcagcgatct gtctatttcg ttcatccata gttgcctgac   1380

tccccgtcgt gtagataact acgatacggg agggcttacc atctggcccc agtgctgcaa   1440

tgataccgcg agacccacgc tcaccggctc cagatttatc agcaataaac cagccagccg   1500

gaagggccga gcgcagaagt ggtcctgcaa ctttatccgc ctccatccag tctattaatt   1560

gttgccggga agctagagta agtagttcgc cagttaatag tttgcgcaac gttgttgcca   1620

ttgctacagg catcgtggtg tcacgctcgt cgtttggtat ggcttcattc agctccggtt   1680

cccaacgatc aaggcgagtt acatgatccc ccatgttgtg caaaaaagcg gttagctcct   1740

tcggtcctcc gatcgttgtc agaagtaagt tggccgcagt gttatcactc atggttatgg   1800

cagcactgca taattctctt actgtcatgc catccgtaag atgcttttct gtgactggtg   1860

agtactcaac caagtcattc tgagaatagt gtatgcggcg accgagttgc tcttgcccgg   1920
```

```
cgtcaatacg ggataatacc gcgccacata gcagaacttt aaaagtgctc atcattggaa   1980

aacgttcttc ggggcgaaaa ctctcaagga tcttaccgct gttgagatcc agttcgatgt   2040

aacccactcg tgcacccaac tgatcttcag catcttttac tttcaccagc gtttctgggt   2100

gagcaaaaac aggaaggcaa aatgccgcaa aaaagggaat aagggcgaca cggaaatgtt   2160

gaatactcat actcttcctt tttcaatatt attgaagcat ttatcagggt tattgtctca   2220

tgagcggata catatttgaa tgtatttaga aaaataaaca aataggggtt ccgcgcacat   2280

ttccccgaaa agtgccacct gacgtctaag aaaccattat tatcatgaca ttaacctata   2340

aaaataggcg tatcacgagg ccctttcgtc ttcac                              2375


<210> SEQ ID NO 133
<211> LENGTH: 4355
<212> TYPE: DNA
<213> ORGANISM: Artificial Sequence
<220> FEATURE:
<223> OTHER INFORMATION: plasmid construct encoding the mutant (K102A)
      LukF-PV

<400> SEQUENCE: 133

ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gctcaacata tcacacctgt aagtgagaaa    180

aaggttgatg ataaaattac tttgtacaaa acaactgcaa catcagattc cgataagtta    240

aaaatttctc agattttaac ttttaatttt attaaagata aaagttatga taaagataca    300

ttaatactca aagctgctgg aaacatttat tctggctata caaagccaaa tccaaaagac    360

actattagtt ctcaatttta ttggggttct aagtacaaca tttcaattaa ttcagattct    420

aatgactcag taaacgttgt agattatgca cctgcaaatc aaaatgaaga atttcaagta    480

caacaaacgg taggttattc ttatggtgga gatattaata tctctaacgg cttatcaggt    540

ggaggtaatg gttcaaaatc tttttcagag acaattaact ataaacaaga aagctataga    600

actagcttag ataaaagaac taatttcaaa aaaattggtt gggatgttga agcacataaa    660

attatgaata atggttgggg accatatggc agagatagtt atcattcaac ttatggtaat    720

gaaatgtttt taggctcaag acaaagcaac ttaaatgctg gacaaaactt cttggaatat    780

cacaaaatgc cagtgttatc cagaggtaac ttcaatccag aatttattgg tgtcctatct    840

cgaaaacaaa acgctgcaaa aaaatcaaaa attactgtta cttatcaaag agaaatggat    900

agatatacaa acttttggaa tcaacttcac tggataggta ataattataa agatgaaaat    960

agagcaactc atacatcaat ttatgaagtt gattgggaaa atcatacagt taaattaata   1020

gatactcaat ctaaggaaaa aaatcctatg agctaaggta ccccgggtcg acctgcagcc   1080

aagcttaatt agctgagctt ggactcctgt tgatagatcc agtaatgacc tcagaactcc   1140

atctggattt gttcagaacg ctcggttgcc gccgggcgtt ttttattggt gagaatccaa   1200

gctagcttgg cgagattttc aggagctaag gaagctaaaa tggagaaaaa aatcactgga   1260

tataccaccg ttgatatatc ccaatggcat cgtaaagaac attttgaggc atttcagtca   1320

gttgctcaat gtacctataa ccagaccgtt cagctggata ttacggcctt tttaaagacc   1380

gtaaagaaaa ataagcacaa gttttatccg gcctttattc acattcttgc ccgcctgatg   1440

aatgctcatc cggaatttcg tatggcaatg aaagacggtg agctggtgat atgggatagt   1500

gttcaccctt gttacaccgt tttccatgag caaactgaaa cgttttcatc gctctggagt   1560
```

-continued

```
gaataccacg acgatttccg gcagtttcta cacatatatt cgcaagatgt ggcgtgttac   1620
ggtgaaaacc tggcctattt ccctaaaggg tttattgaga atatgttttt cgtctcagcc   1680
aatccctggg tgagtttcac cagttttgat ttaaacgtgg ccaatatgga caacttcttc   1740
gcccccgttt tcaccatggg caaatattat acgcaaggcg acaaggtgct gatgccgctg   1800
gcgattcagg ttcatcatgc cgtttgtgat ggcttccatg tcggcagaat gcttaatgaa   1860
ttacaacagt actgcgatga gtggcagggc ggggcgtaat ttttttaagg cagttattgg   1920
tgcccttaaa cgcctggggt aatgactctc tagcttgagg catcaaataa aacgaaaggc   1980
tcagtcgaaa gactgggcct ttcgttttat ctgttgtttg tcggtgaacg ctctcctgag   2040
taggacaaat ccgccctcta gagctgcctc gcgcgtttcg gtgatgacgg tgaaaacctc   2100
tgacacatgc agctcccgga gacggtcaca gcttgtctgt aagcggatgc cgggagcaga   2160
caagcccgtc agggcgcgtc agcgggtgtt ggcgggtgtc ggggcgcagc catgacccag   2220
tcacgtagcg atagcggagt gtatactggc ttaactatgc ggcatcagag cagattgtac   2280
tgagagtgca ccatatgcgg tgtgaaatac cgcacagatg cgtaaggaga aaataccgca   2340
tcaggcgctc ttccgcttcc tcgctcactg actcgctgcg ctcggtcgtt cggctgcggc   2400
gagcggtatc agctcactca aaggcggtaa tacggttatc cacagaatca ggggataacg   2460
caggaaagaa catgtgagca aaaggccagc aaaaggccag gaaccgtaaa aaggccgcgt   2520
tgctggcgtt tttccatagg ctccgccccc ctgacgagca tcacaaaaat cgacgctcaa   2580
gtcagaggtg gcgaaacccg acaggactat aaagatacca ggcgtttccc cctggaagct   2640
ccctcgtgcg ctctcctgtt ccgaccctgc cgcttaccgg atacctgtcc gcctttctcc   2700
cttcgggaag cgtggcgctt tctcatagct cacgctgtag gtatctcagt tcggtgtagg   2760
tcgttcgctc caagctgggc tgtgtgcacg aaccccccgt tcagcccgac cgctgcgcct   2820
tatccggtaa ctatcgtctt gagtccaacc cggtaagaca cgacttatcg ccactggcag   2880
cagccactgg taacaggatt agcagagcga ggtatgtagg cggtgctaca gagttcttga   2940
agtggtggcc taactacggc tacactagaa ggacagtatt tggtatctgc gctctgctga   3000
agccagttac cttcggaaaa agagttggta gctcttgatc cggcaaacaa accaccgctg   3060
gtagcggtgg tttttttgtt tgcaagcagc agattacgcg cagaaaaaaa ggatctcaag   3120
aagatccttt gatcttttct acggggtctg acgctcagtg gaacgaaaac tcacgttaag   3180
ggattttggt catgagatta tcaaaaagga tcttcaccta gatcctttta aattaaaaat   3240
gaagttttaa atcaatctaa agtatatatg agtaaacttg gtctgacagt taccaatgct   3300
taatcagtga ggcacctatc tcagcgatct gtctatttcg ttcatccata gttgcctgac   3360
tccccgtcgt gtagataact acgatacggg agggcttacc atctggcccc agtgctgcaa   3420
tgataccgcg agacccacgc tcaccggctc cagatttatc agcaataaac cagccagccg   3480
gaagggccga gcgcagaagt ggtcctgcaa ctttatccgc ctccatccag tctattaatt   3540
gttgccggga agctagagta agtagttcgc cagttaatag tttgcgcaac gttgttgcca   3600
ttgctacagg catcgtggtg tcacgctcgt cgtttggtat ggcttcattc agctccggtt   3660
cccaacgatc aaggcgagtt acatgatccc ccatgttgtg caaaaaagcg gttagctcct   3720
tcggtcctcc gatcgttgtc agaagtaagt tggccgcagt gttatcactc atggttatgg   3780
cagcactgca taattctctt actgtcatgc catccgtaag atgcttttct gtgactggtg   3840
agtactcaac caagtcattc tgagaatagt gtatgcggcg accgagttgc tcttgcccgg   3900
cgtcaatacg ggataatacc gcgccacata gcagaacttt aaaagtgctc atcattggaa   3960
```

aacgttcttc ggggcgaaaa ctctcaagga tcttaccgct gttgagatcc agttcgatgt 4020
aacccactcg tgcacccaac tgatcttcag catcttttac tttcaccagc gtttctgggt 4080
gagcaaaaac aggaaggcaa aatgccgcaa aaaagggaat aagggcgaca cggaaatgtt 4140
gaatactcat actcttcctt tttcaatatt attgaagcat ttatcagggt tattgtctca 4200
tgagcggata catatttgaa tgtatttaga aaaataaaca aataggggtt ccgcgcacat 4260
ttccccgaaa agtgccacct gacgtctaag aaaccattat tatcatgaca ttaacctata 4320
aaaataggcg tatcacgagg ccctttcgtc ttcac 4355

<210> SEQ ID NO 134
<211> LENGTH: 4354
<212> TYPE: DNA
<213> ORGANISM: Artificial Sequence
<220> FEATURE:
<223> OTHER INFORMATION: plasmid construct encoding the mutant (D121A) LukF-PV

<400> SEQUENCE: 134
ctcgagaaat cataaaaaat ttatttgctt tgtgagcgga taacaattat aatagattca 60
attgtgagcg gataacaatt tcacacagaa ttcattaaag aggagaaatt aactatgaga 120
ggatcgcatc accatcacca tcacggatcc gctcaacata tcacacctgt aagtgagaaa 180
aaggttgatg ataaaattac tttgtacaaa acaactgcaa catcagattc cgataagtta 240
aaaatttctc agattttaac ttttaatttt attaaagata aaagttatga taaagataca 300
ttaatactca aagctgctgg aaacatttat tctggctata caaagccaaa tccaaaagac 360
actattagtt ctcaatttta ttggggttct aagtacaaca tttcaattaa ttcagattct 420
aatgactcag taaacgttgt agattatgca cctaaaaatc aaaatgaaga atttcaagta 480
caacaaacgg taggttattc ttatggtgga gctattaata tctctaacgg cttatcaggt 540
ggaggtaatg gttcaaaatc tttttcagag acaattaact ataaacaaga agctatagaa 600
ctagcttaga taaaagaact aatttcaaaa aaattggttg ggatgttgaa gcacataaaa 660
ttatgaataa tggttgggga ccatatggca gagatagtta tcattcaact tatggtaatg 720
aaatgttttt aggctcaaga caaagcaact taaatgctgg acaaaacttc ttggaatatc 780
acaaaatgcc agtgttatcc agaggtaact tcaatccaga atttattggt gtcctatctc 840
gaaaacaaaa cgctgcaaaa aaatcaaaaa ttactgttac ttatcaaaga gaaatggata 900
gatatacaaa cttttggaat caacttcact ggataggtaa taattataaa gatgaaaata 960
gagcaactca tacatcaatt tatgaagttg attgggaaaa tcatacagtt aaattaatag 1020
atactcaatc taaggaaaaa aatcctatga gctaaggtac cccgggtcga cctgcagcca 1080
agcttaatta gctgagcttg gactcctgtt gatagatcca gtaatgacct cagaactcca 1140
tctggatttg ttcagaacgc tcggttgccg ccgggcgttt tttattggtg agaatccaag 1200
ctagcttggc gagattttca ggagctaagg aagctaaaat ggagaaaaaa atcactggat 1260
ataccaccgt tgatatatcc caatggcatc gtaaagaaca ttttgaggca tttcagtcag 1320
ttgctcaatg tacctataac cagaccgttc agctggatat tacggccttt ttaaagaccg 1380
taaagaaaaa taagcacaag ttttatccgg cctttattca cattcttgcc cgcctgatga 1440
atgctcatcc ggaatttcgt atggcaatga aagacggtga gctggtgata tgggatagtg 1500
ttcacccttg ttacaccgtt ttccatgagc aaactgaaac gttttcatcg ctctggagtg 1560
aataccacga cgatttccgg cagtttctac acatatattc gcaagatgtg gcgtgttacg 1620

-continued

```
gtgaaaacct ggcctatttc cctaaagggt ttattgagaa tatgtttttc gtctcagcca   1680

atccctgggt gagtttcacc agttttgatt taaacgtggc caatatggac aacttcttcg   1740

cccccgtttt caccatgggc aaatattata cgcaaggcga caaggtgctg atgccgctgg   1800

cgattcaggt tcatcatgcc gtttgtgatg gcttccatgt cggcagaatg cttaatgaat   1860

tacaacagta ctgcgatgag tggcagggcg gggcgtaatt tttttaaggc agttattggt   1920

gcccttaaac gcctggggta atgactctct agcttgaggc atcaaataaa acgaaaggct   1980

cagtcgaaag actgggcctt tcgttttatc tgttgtttgt cggtgaacgc tctcctgagt   2040

aggacaaatc cgccctctag agctgcctcg cgcgtttcgg tgatgacggt gaaaacctct   2100

gacacatgca gctcccggag acggtcacag cttgtctgta agcggatgcc gggagcagac   2160

aagcccgtca gggcgcgtca gcgggtgttg gcgggtgtcg gggcgcagcc atgacccagt   2220

cacgtagcga tagcggagtg tatactggct taactatgcg gcatcagagc agattgtact   2280

gagagtgcac catatgcggt gtgaaatacc gcacagatgc gtaaggagaa aataccgcat   2340

caggcgctct tccgcttcct cgctcactga ctcgctgcgc tcggtcgttc ggctgcggcg   2400

agcggtatca gctcactcaa aggcggtaat acggttatcc acagaatcag gggataacgc   2460

aggaaagaac atgtgagcaa aaggccagca aaaggccagg aaccgtaaaa aggccgcgtt   2520

gctggcgttt ttccataggc tccgcccccc tgacgagcat cacaaaaatc gacgctcaag   2580

tcagaggtgg cgaaacccga caggactata aagataccag gcgtttcccc ctggaagctc   2640

cctcgtgcgc tctcctgttc cgaccctgcc gcttaccgga tacctgtccg cctttctccc   2700

ttcgggaagc gtggcgcttt ctcatagctc acgctgtagg tatctcagtt cggtgtaggt   2760

cgttcgctcc aagctgggct gtgtgcacga accccccgtt cagcccgacc gctgcgcctt   2820

atccggtaac tatcgtcttg agtccaaccc ggtaagacac gacttatcgc cactggcagc   2880

agccactggt aacaggatta gcagagcgag gtatgtaggc ggtgctacag agttcttgaa   2940

gtggtggcct aactacggct acactagaag gacagtattt ggtatctgcg ctctgctgaa   3000

gccagttacc ttcggaaaaa gagttggtag ctcttgatcc ggcaaacaaa ccaccgctgg   3060

tagcggtggt ttttttgttt gcaagcagca gattacgcgc agaaaaaaag gatctcaaga   3120

agatcctttg atcttttcta cggggtctga cgctcagtgg aacgaaaact cacgttaagg   3180

gattttggtc atgagattat caaaaaggat cttcacctag atccttttaa attaaaaatg   3240

aagttttaaa tcaatctaaa gtatatatga gtaaacttgg tctgacagtt accaatgctt   3300

aatcagtgag gcacctatct cagcgatctg tctatttcgt tcatccatag ttgcctgact   3360

ccccgtcgtg tagataacta cgatacggga gggcttacca tctggcccca gtgctgcaat   3420

gataccgcga gacccacgct caccggctcc agatttatca gcaataaacc agccagccgg   3480

aagggccgag cgcagaagtg gtcctgcaac tttatccgcc tccatccagt ctattaattg   3540

ttgccgggaa gctagagtaa gtagttcgcc agttaatagt ttgcgcaacg ttgttgccat   3600

tgctacaggc atcgtggtgt cacgctcgtc gtttggtatg gcttcattca gctccggttc   3660

ccaacgatca aggcgagtta catgatcccc catgttgtgc aaaaaagcgg ttagctcctt   3720

cggtcctccg atcgttgtca gaagtaagtt ggccgcagtg ttatcactca tggttatggc   3780

agcactgcat aattctctta ctgtcatgcc atccgtaaga tgcttttctg tgactggtga   3840

gtactcaacc aagtcattct gagaatagtg tatgcggcga ccgagttgct cttgcccggc   3900

gtcaatacgg gataataccg cgccacatag cagaacttta aaagtgctca tcattggaaa   3960
```

acgttcttcg gggcgaaaac tctcaaggat cttaccgctg ttgagatcca gttcgatgta 4020
acccactcgt gcacccaact gatcttcagc atcttttact ttcaccagcg tttctgggtg 4080
agcaaaaaca ggaaggcaaa atgccgcaaa aaagggaata agggcgacac ggaaatgttg 4140
aatactcata ctcttccttt ttcaatatta ttgaagcatt tatcagggtt attgtctcat 4200
gagcggatac atatttgaat gtatttagaa aaataaacaa ataggggttc cgcgcacatt 4260
tccccgaaaa gtgccacctg acgtctaaga aaccattatt atcatgacat taacctataa 4320
aaataggcgt atcacgaggc cctttcgtct tcac 4354

<210> SEQ ID NO 135
<211> LENGTH: 4355
<212> TYPE: DNA
<213> ORGANISM: Artificial Sequence
<220> FEATURE:
<223> OTHER INFORMATION: plasmid construct encoding the mutant (E147A) LukF-PV

<400> SEQUENCE: 135
ctcgagaaat cataaaaaat ttatttgctt tgtgagcgga taacaattat aatagattca 60
attgtgagcg gataacaatt tcacacagaa ttcattaaag aggagaaatt aactatgaga 120
ggatcgcatc accatcacca tcacggatcc gctcaacata tcacacctgt aagtgagaaa 180
aaggttgatg ataaaattac tttgtacaaa acaactgcaa catcagattc cgataagtta 240
aaaatttctc agattttaac ttttaatttt attaaagata aaagttatga taaagataca 300
ttaatactca aagctgctgg aaacatttat tctggctata caaagccaaa tccaaaagac 360
actattagtt ctcaatttta ttggggttct aagtacaaca tttcaattaa ttcagattct 420
aatgactcag taaacgttgt agattatgca cctaaaaatc aaaatgaaga atttcaagta 480
caacaaacgg taggttattc ttatggtgga gatattaata tctctaacgg cttatcaggt 540
ggaggtaatg gttcaaaatc tttttcagag acaattaact ataaacaagc aagctataga 600
actagcttag ataaaagaac taatttcaaa aaaattggtt gggatgttga agcacataaa 660
attatgaata atggttgggg accatatggc agagatagtt atcattcaac ttatggtaat 720
gaaatgtttt taggctcaag acaaagcaac ttaaatgctg gacaaaactt cttggaatat 780
cacaaaatgc cagtgttatc cagaggtaac ttcaatccag aatttattgg tgtcctatct 840
cgaaaacaaa acgctgcaaa aaaatcaaaa attactgtta cttatcaaag agaaatggat 900
agatatacaa acttttggaa tcaacttcac tggataggta ataattataa agatgaaaat 960
agagcaactc atacatcaat ttatgaagtt gattgggaaa atcatacagt taaattaata 1020
gatactcaat ctaaggaaaa aaatcctatg agctaaggta ccccgggtcg acctgcagcc 1080
aagcttaatt agctgagctt ggactcctgt tgatagatcc agtaatgacc tcagaactcc 1140
atctggattt gttcagaacg ctcggttgcc gccgggcgtt ttttattggt gagaatccaa 1200
gctagcttgg cgagattttc aggagctaag gaagctaaaa tggagaaaaa aatcactgga 1260
tataccaccg ttgatatatc ccaatggcat cgtaaagaac attttgaggc atttcagtca 1320
gttgctcaat gtacctataa ccagaccgtt cagctggata ttacggcctt tttaaagacc 1380
gtaaagaaaa ataagcacaa gttttatccg gcctttattc acattcttgc ccgcctgatg 1440
aatgctcatc cggaatttcg tatggcaatg aaagacggtg agctggtgat atgggatagt 1500
gttcaccctt gttacaccgt tttccatgag caaactgaaa cgttttcatc gctctggagt 1560
gaataccacg acgatttccg gcagtttcta cacatatatt cgcaagatgt ggcgtgttac 1620
ggtgaaaacc tggcctattt ccctaaaggg tttattgaga atatgttttt cgtctcagcc 1680
aatccctggg tgagtttcac cagttttgat ttaaacgtgg ccaatatgga caacttcttc 1740
gcccccgttt tcaccatggg caaatattat acgcaaggcg acaaggtgct gatgccgctg 1800
gcgattcagg ttcatcatgc cgtttgtgat ggcttccatg tcggcagaat gcttaatgaa 1860
ttacaacagt actgcgatga gtggcagggc ggggcgtaat ttttttaagg cagttattgg 1920
tgcccttaaa cgcctggggt aatgactctc tagcttgagg catcaaataa aacgaaaggc 1980
tcagtcgaaa gactgggcct ttcgttttat ctgttgtttg tcggtgaacg ctctcctgag 2040
taggacaaat ccgccctcta gagctgcctc gcgcgtttcg gtgatgacgg tgaaaacctc 2100
tgacacatgc agctcccgga gacggtcaca gcttgtctgt aagcggatgc cgggagcaga 2160
caagcccgtc agggcgcgtc agcgggtgtt ggcgggtgtc ggggcgcagc catgacccag 2220
tcacgtagcg atagcggagt gtatactggc ttaactatgc ggcatcagag cagattgtac 2280
tgagagtgca ccatatgcgg tgtgaaatac cgcacagatg cgtaaggaga aaataccgca 2340
tcaggcgctc ttccgcttcc tcgctcactg actcgctgcg ctcggtcgtt cggctgcggc 2400
gagcggtatc agctcactca aaggcggtaa tacggttatc cacagaatca ggggataacg 2460
caggaaagaa catgtgagca aaaggccagc aaaaggccag gaaccgtaaa aaggccgcgt 2520
tgctggcgtt tttccatagg ctccgccccc ctgacgagca tcacaaaaat cgacgctcaa 2580
gtcagaggtg gcgaaacccg acaggactat aaagatacca ggcgtttccc cctggaagct 2640
ccctcgtgcg ctctcctgtt ccgaccctgc cgcttaccgg atacctgtcc gcctttctcc 2700
cttcgggaag cgtggcgctt tctcatagct cacgctgtag gtatctcagt tcggtgtagg 2760
tcgttcgctc caagctgggc tgtgtgcacg aaccccccgt tcagcccgac cgctgcgcct 2820
tatccggtaa ctatcgtctt gagtccaacc cggtaagaca cgacttatcg ccactggcag 2880
cagccactgg taacaggatt agcagagcga ggtatgtagg cggtgctaca gagttcttga 2940
agtggtggcc taactacggc tacactagaa ggacagtatt tggtatctgc gctctgctga 3000
agccagttac cttcggaaaa agagttggta gctcttgatc cggcaaacaa accaccgctg 3060
gtagcggtgg tttttttgtt tgcaagcagc agattacgcg cagaaaaaaa ggatctcaag 3120
aagatccttt gatcttttct acggggtctg acgctcagtg gaacgaaaac tcacgttaag 3180
ggattttggt catgagatta tcaaaaagga tcttcaccta gatcctttta aattaaaaat 3240
gaagttttaa atcaatctaa agtatatatg agtaaacttg gtctgacagt taccaatgct 3300
taatcagtga ggcacctatc tcagcgatct gtctatttcg ttcatccata gttgcctgac 3360
tccccgtcgt gtagataact acgatacggg agggcttacc atctggcccc agtgctgcaa 3420
tgataccgcg agacccacgc tcaccggctc cagatttatc agcaataaac cagccagccg 3480
gaagggccga gcgcagaagt ggtcctgcaa ctttatccgc ctccatccag tctattaatt 3540
gttgccggga agctagagta agtagttcgc cagttaatag tttgcgcaac gttgttgcca 3600
ttgctacagg catcgtggtg tcacgctcgt cgtttggtat ggcttcattc agctccggtt 3660
cccaacgatc aaggcgagtt acatgatccc ccatgttgtg caaaaaagcg gttagctcct 3720
tcggtcctcc gatcgttgtc agaagtaagt tggccgcagt gttatcactc atggttatgg 3780
cagcactgca taattctctt actgtcatgc catccgtaag atgcttttct gtgactggtg 3840
agtactcaac caagtcattc tgagaatagt gtatgcggcg accgagttgc tcttgcccgg 3900
cgtcaatacg ggataatacc gcgccacata gcagaacttt aaaagtgctc atcattggaa 3960
aacgttcttc ggggcgaaaa ctctcaagga tcttaccgct gttgagatcc agttcgatgt 4020
aacccactcg tgcacccaac tgatcttcag catcttttac tttcaccagc gtttctgggt 4080
gagcaaaaac aggaaggcaa aatgccgcaa aaaagggaat aagggcgaca cggaaatgtt 4140
gaatactcat actcttcctt tttcaatatt attgaagcat ttatcagggt tattgtctca 4200
tgagcggata catatttgaa tgtatttaga aaaataaaca aataggggtt ccgcgcacat 4260
ttccccgaaa agtgccacct gacgtctaag aaaccattat tatcatgaca ttaacctata 4320
aaaataggcg tatcacgagg ccctttcgtc ttcac 4355

<210> SEQ ID NO 136
<211> LENGTH: 301
<212> TYPE: PRT
<213> ORGANISM: Artificial Sequence
<220> FEATURE:
<223> OTHER INFORMATION: LukF-PV Triple Mutant

<400> SEQUENCE: 136

Ala Gln His Ile Thr Pro Val Ser Glu Lys Lys Val Asp Asp Lys Ile
1 5 10 15

Thr Leu Tyr Lys Thr Thr Ala Thr Ser Asp Ser Asp Lys Leu Lys Ile
20 25 30

Ser Gln Ile Leu Thr Phe Asn Phe Ile Lys Asp Lys Ser Tyr Asp Lys
35 40 45

Asp Thr Leu Ile Leu Lys Ala Ala Gly Asn Ile Tyr Ser Gly Tyr Thr
50 55 60

Lys Pro Asn Pro Lys Asp Thr Ile Ser Ser Gln Phe Tyr Trp Gly Ser
65 70 75 80

Lys Tyr Asn Ile Ser Ile Asn Ser Asp Ser Asn Asp Ser Val Asn Val
85 90 95

Val Asp Tyr Ala Pro Ala Asn Gln Asn Glu Glu Phe Gln Val Gln Gln
100 105 110

Thr Val Gly Tyr Ser Tyr Gly Gly Ala Ile Asn Ile Ser Asn Gly Leu
115 120 125

Ser Gly Gly Gly Asn Gly Ser Lys Ser Phe Ser Glu Thr Ile Asn Tyr
130 135 140

Lys Gln Ala Ser Tyr Arg Thr Ser Leu Asp Lys Arg Thr Asn Phe Lys
145 150 155 160

Lys Ile Gly Trp Asp Val Glu Ala His Lys Ile Met Asn Asn Gly Trp
165 170 175

Gly Pro Tyr Gly Arg Asp Ser Tyr His Ser Thr Tyr Gly Asn Glu Met
180 185 190

Phe Leu Gly Ser Arg Gln Ser Asn Leu Asn Ala Gly Gln Asn Phe Leu
195 200 205

Glu Tyr His Lys Met Pro Val Leu Ser Arg Gly Asn Phe Asn Pro Glu
210 215 220

Phe Ile Gly Val Leu Ser Arg Lys Gln Asn Ala Ala Lys Lys Ser Lys
225 230 235 240

Ile Thr Val Thr Tyr Gln Arg Glu Met Asp Arg Tyr Thr Asn Phe Trp
245 250 255

Asn Gln Leu His Trp Ile Gly Asn Asn Tyr Lys Asp Glu Asn Arg Ala
260 265 270

Thr His Thr Ser Ile Tyr Glu Val Asp Trp Glu Asn His Thr Val Lys
275 280 285

Leu Ile Asp Thr Gln Ser Lys Glu Lys Asn Pro Met Ser
290 295 300

<210> SEQ ID NO 137
<211> LENGTH: 948
<212> TYPE: DNA
<213> ORGANISM: Artificial Sequence
<220> FEATURE:
<223> OTHER INFORMATION: polynucleotide sequence of Triple PVLF

<400> SEQUENCE: 137
atgagaggat cgcatcacca tcaccatcac ggatccgctc aacatatcac acctgtaagt 60
gagaaaaagg ttgatgataa aattactttg tacaaaacaa ctgcaacatc agattccgat 120
aagttaaaaa tttctcagat tttaactttt aattttatta aagataaaag ttatgataaa 180
gatacattaa tactcaaagc tgctggaaac atttattctg gctatacaaa gccaaatcca 240
aaagacacta ttagttctca attttattgg ggttctaagt acaacatttc aattaattca 300
gattctaatg actcagtaaa cgttgtagat tatgcacctg caaatcaaaa tgaagaattt 360
caagtacaac aaacggtagg ttattcttat ggtggagcta ttaatatctc taacggctta 420
tcaggtggag gtaatggttc aaaatctttt tcagagacaa ttaactataa acaagcaagc 480
tatagaacta gcttagataa aagaactaat ttcaaaaaaa ttggttggga tgttgaagca 540
cataaaatta tgaataatgg ttggggacca tatggcagag atagttatca ttcaacttat 600
ggtaatgaaa tgtttttagg ctcaagacaa agcaacttaa atgctggaca aaacttcttg 660
gaatatcaca aaatgccagt gttatccaga ggtaacttca atccagaatt tattggtgtc 720
ctatctcgaa aacaaaacgc tgcaaaaaaa tcaaaaatta ctgttactta tcaaagagaa 780
atggatagat atacaaactt ttggaatcaa cttcactgga taggtaataa ttataaagat 840
gaaaatagag caactcatac atcaatttat gaagttgatt gggaaaatca tacagttaaa 900
ttaatagata ctcaatctaa ggaaaaaaat cctatgagct aaggtacc 948

<210> SEQ ID NO 138
<211> LENGTH: 280
<212> TYPE: PRT
<213> ORGANISM: Staphylococcus aureus

<400> SEQUENCE: 138

Glu Asn Lys Ile Glu Asp Ile Gly Gln Gly Ala Glu Ile Ile Lys Arg
1 5 10 15

Thr Gln Asp Ile Thr Ser Lys Arg Leu Ala Ile Thr Gln Asn Ile Gln
20 25 30

Phe Asp Phe Val Lys Asp Lys Lys Tyr Asn Lys Asp Ala Leu Val Val
35 40 45

Lys Met Gln Gly Phe Ile Ser Ser Arg Thr Thr Tyr Ser Asp Leu Lys
50 55 60

Lys Tyr Pro Tyr Ile Lys Arg Met Ile Trp Pro Phe Gln Tyr Asn Ile
65 70 75 80

Ser Leu Lys Thr Lys Asp Ser Asn Val Asp Leu Ile Asn Tyr Leu Pro
85 90 95

Lys Asn Lys Ile Asp Ser Ala Asp Val Ser Gln Lys Leu Gly Tyr Asn
100 105 110

Ile Gly Glu Asn Phe Gln Ser Ala Pro Ser Ile Gly Gly Ser Gly Ser
115 120 125

Phe Asn Tyr Ser Lys Thr Ile Ser Tyr Asn Gln Lys Asn Tyr Val Thr
130 135 140

Glu Val Glu Ser Gln Asn Ser Lys Gly Val Lys Trp Gly Val Lys Ala

```
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
        195                 200                 205

Phe Ile Thr Thr Leu Ser His Glu Arg Gly Lys Gly Asp Lys Ser Glu
    210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
            260                 265                 270

Lys Ile Lys Ser Ile Thr Pro Lys
        275                 280


<210> SEQ ID NO 139
<211> LENGTH: 283
<212> TYPE: PRT
<213> ORGANISM: Staphylococcus aureus

<400> SEQUENCE: 139

Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
            20                  25                  30

Phe Asp Phe Val Lys Asp Lys Lys Tyr Asn Lys Asp Ala Leu Ile Val
        35                  40                  45

Lys Met Gln Gly Phe Ile Asn Ser Arg Thr Ser Phe Ser Asp Val Lys
    50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
                85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
    130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gln Ser Pro Asn Gly Pro Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240
```

```
Tyr Ala Thr Leu Phe Pro Arg Thr Gly Ile Tyr Ala Glu Arg Lys His
                245                 250                 255

Asn Ala Phe Val Asn Arg Asn Phe Val Val Arg Tyr Glu Val Asn Trp
            260                 265                 270

Lys Thr His Glu Ile Lys Val Lys Gly His Asn
        275                 280


<210> SEQ ID NO 140
<211> LENGTH: 280
<212> TYPE: PRT
<213> ORGANISM: Staphylococcus aureus

<400> SEQUENCE: 140

Thr Thr Asn Ala Glu Asp Ile Gly Asp Asp Ala Glu Val Ile Lys Arg
1               5                   10                  15

Thr Glu Asp Val Ser Ser Arg Lys Trp Gly Val Thr Gln Asn Val Gln
            20                  25                  30

Phe Asp Phe Val Lys Asp Lys Lys Tyr Asn Lys Asp Ala Leu Ile Ile
        35                  40                  45

Lys Met Gln Gly Phe Ile Asn Ser Arg Thr Thr Phe Asn Asp Val Lys
    50                  55                  60

Gln Asn Arg Ala Asn Lys Arg Met Val Trp Pro Phe Gln Tyr Asn Ile
65                  70                  75                  80

Gly Leu Thr Ser Lys Asp Gln Asn Thr Ser Leu Ile Asn Tyr Leu Pro
                85                  90                  95

Lys Asn Lys Ile Glu Thr Val Asp Val Gly Gln Thr Leu Gly Tyr Asn
            100                 105                 110

Ile Gly Gly Lys Phe Gln Ser Ala Pro Ser Ile Gly Gly Asn Gly Ser
        115                 120                 125

Phe Asn Tyr Ser Lys Ser Ile Lys Tyr Ser Gln Lys Ser Tyr Val Ser
    130                 135                 140

Glu Val Glu Gln Gln Ser Ser Lys Thr Ile Lys Trp Gly Val Lys Ala
145                 150                 155                 160

Asn Ser Phe Val Ile Ala Gly His Arg Trp Ser Ala Tyr Asp Glu Leu
                165                 170                 175

Leu Phe Ile Arg Asn Thr Thr Arg Gly Pro Asn Ala Arg Asp Tyr Phe
            180                 185                 190

Val Asp Asp Asn Glu Leu Pro Pro Leu Ile Thr Ser Gly Phe Asn Pro
        195                 200                 205

Ser Phe Ile Ala Thr Val Ser His Glu Lys Asp Ser Gly Asp Thr Ser
    210                 215                 220

Glu Phe Glu Ile Thr Tyr Gly Arg Asn Met Asp Val Thr Tyr Ala Thr
225                 230                 235                 240

Tyr Leu Pro Lys Leu Gly Leu Tyr Pro Glu Arg Lys His Asn Glu Phe
                245                 250                 255

Val Asn Arg Asn Phe Val Val Lys Tyr Glu Val Asn Trp Lys Thr Tyr
            260                 265                 270

Glu Ile Lys Val Lys Gly His Asn
        275                 280


<210> SEQ ID NO 141
<211> LENGTH: 286
<212> TYPE: PRT
<213> ORGANISM: Staphylococcus aureus

<400> SEQUENCE: 141
```

```
Ala Asn Asp Thr Glu Asp Ile Gly Lys Gly Ser Asp Ile Glu Ile Ile
1               5                   10                  15

Lys Arg Thr Glu Asp Lys Thr Ser Asn Lys Trp Gly Val Thr Gln Asn
            20                  25                  30

Ile Gln Phe Asp Phe Val Lys Asp Lys Lys Tyr Asn Lys Asp Ala Leu
        35                  40                  45

Ile Leu Lys Met Gln Gly Phe Ile Ser Ser Arg Thr Thr Tyr Tyr Asn
    50                  55                  60

Tyr Lys Lys Thr Asn His Val Lys Ala Met Arg Trp Pro Phe Gln Tyr
65                  70                  75                  80

Asn Ile Gly Leu Lys Thr Asn Asp Lys Tyr Val Ser Leu Ile Asn Tyr
                85                  90                  95

Leu Pro Lys Asn Lys Ile Glu Ser Thr Asn Val Ser Gln Thr Leu Gly
            100                 105                 110

Tyr Asn Ile Gly Gly Asn Phe Gln Ser Ala Pro Ser Leu Gly Gly Asn
        115                 120                 125

Gly Ser Phe Asn Tyr Ser Lys Ser Ile Ser Tyr Thr Gln Gln Asn Tyr
    130                 135                 140

Val Ser Glu Val Glu Gln Gln Asn Ser Lys Ser Val Leu Trp Gly Val
145                 150                 155                 160

Lys Ala Asn Ser Phe Ala Thr Glu Ser Gly Gln Lys Ser Ala Phe Asp
                165                 170                 175

Ser Asp Leu Phe Val Gly Tyr Lys Pro His Ser Lys Asp Pro Arg Asp
            180                 185                 190

Tyr Phe Val Pro Asp Ser Glu Leu Pro Pro Leu Val Gln Ser Gly Phe
        195                 200                 205

Asn Pro Ser Phe Ile Ala Thr Val Ser His Glu Lys Gly Ser Ser Asp
    210                 215                 220

Thr Ser Glu Phe Glu Ile Thr Tyr Gly Arg Asn Met Asp Val Thr His
225                 230                 235                 240

Ala Ile Lys Arg Ser Thr His Tyr Gly Asn Ser Tyr Leu Asp Gly His
                245                 250                 255

Arg Val His Asn Ala Phe Val Asn Arg Asn Tyr Thr Val Lys Tyr Glu
            260                 265                 270

Val Asn Trp Lys Thr His Glu Ile Lys Glu Lys Gly Gln Asn
        275                 280                 285
```

<210> SEQ ID NO 142
<211> LENGTH: 284
<212> TYPE: PRT
<213> ORGANISM: Staphylococcus aureus

<400> SEQUENCE: 142

```
Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95
```

Lys Asn Lys Ile Asp Ser Val Asn Val Ser Gln Thr Leu Gly Tyr Asn
100 105 110

Ile Gly Gly Asn Phe Asn Ser Gly Pro Ser Thr Gly Gly Asn Gly Ser
115 120 125

Phe Asn Tyr Ser Lys Thr Ile Ser Tyr Asn Gln Gln Asn Tyr Ile Ser
130 135 140

Glu Val Glu His Gln Asn Ser Lys Ser Val Gln Trp Gly Ile Lys Ala
145 150 155 160

Asn Ser Phe Ile Thr Ser Leu Gly Lys Met Ser Gly His Asp Pro Asn
165 170 175

Leu Phe Val Gly Tyr Lys Pro Tyr Ser Gln Asn Pro Arg Asp Tyr Phe
180 185 190

Val Pro Asp Asn Glu Leu Pro Pro Leu Val His Ser Gly Phe Asn Pro
195 200 205

Ser Phe Ile Ala Thr Val Ser His Glu Lys Gly Ser Gly Asp Thr Ser
210 215 220

Glu Phe Glu Ile Thr Tyr Gly Arg Asn Met Asp Val Thr His Ala Thr
225 230 235 240

Arg Arg Thr Thr His Tyr Gly Asn Ser Tyr Leu Glu Gly Ser Arg Ile
245 250 255

His Asn Ala Phe Val Asn Arg Asn Tyr Thr Val Lys Tyr Glu Val Asn
260 265 270

Trp Lys Thr His Glu Ile Lys Val Lys Gly His Asn
275 280

<210> SEQ ID NO 143
<211> LENGTH: 253
<212> TYPE: PRT
<213> ORGANISM: Artificial Sequence
<220> FEATURE:
<223> OTHER INFORMATION: Synthetic

<400> SEQUENCE: 143

Asn Asn Ile Glu Asp Ile Gly Asp Gly Ala Glu Val Ile Lys Arg Thr
1 5 10 15

Glu Asp Val Ser Ser Lys Lys Trp Gly Val Thr Gln Asn Ile Gln Phe
20 25 30

Asp Phe Val Lys Asp Lys Lys Tyr Asn Lys Asp Ala Leu Ile Leu Lys
35 40 45

Met Gln Gly Phe Ile Asn Ser Arg Thr Thr Tyr Asp Val Lys Thr His
50 55 60

Ile Lys Arg Met Ile Trp Pro Phe Gln Tyr Asn Ile Gly Leu Lys Thr
65 70 75 80

Lys Asp Asn Val Ser Leu Ile Asn Tyr Leu Pro Lys Asn Lys Ile Glu
85 90 95

Ser Asp Val Ser Gln Thr Leu Gly Tyr Asn Ile Gly Gly Asn Phe Gln
100 105 110

Ser Ala Pro Ser Ile Gly Gly Asn Gly Ser Phe Asn Tyr Ser Lys Thr
115 120 125

Ile Ser Tyr Thr Gln Lys Asn Tyr Val Ser Glu Val Glu Gln Asn Ser
130 135 140

Lys Ser Val Lys Trp Gly Val Lys Ala Asn Ser Phe Val Thr Gly Lys
145 150 155 160

Ser Ala His Asp Leu Phe Val Ala Arg Asp Tyr Phe Val Pro Asp Asn
165 170 175

-continued

```
Glu Leu Pro Pro Leu Val Gln Ser Gly Phe Asn Pro Ser Phe Ile Ala
            180                 185                 190

Thr Val Ser His Glu Lys Gly Ser Gly Asp Thr Ser Glu Phe Glu Ile
        195                 200                 205

Thr Tyr Gly Arg Asn Met Asp Val Thr Tyr Ala Thr Leu Gly Glu Arg
    210                 215                 220

Lys His Asn Ala Phe Val Asn Arg Asn Phe Thr Val Lys Tyr Glu Val
225                 230                 235                 240

Asn Trp Lys Thr His Glu Ile Lys Val Lys Gly His Asn
                245                 250
```

IMMUNOGENIC COMPOSITION COMPRISING PANTON-VALENTINE LEUKOCIDIN (PVL) DERIVED POLYPEPTIDES

CROSS-REFERENCE TO RELATED APPLICATIONS

This application is a national stage application of International Patent Application No. PCT/US2012/067483, filed on Nov. 30, 2012, which claims the benefit of U.S. Provisional Application No. 61/566,234, filed on Dec. 2, 2011, both of which are incorporated herein by reference in their entireties.

STATEMENT REGARDING FEDERALLY SPONSORED RESEARCH OR DEVELOPMENT

This invention was made with government support under Grant # AI085665 awarded by National Institutes of Health (NIH). The government has certain rights in the invention.

REFERENCE TO SEQUENCE LISTING SUBMITTED ELECTRONICALLY

The content of the electronically submitted sequence listing in ASCII text file (Name: 57783_132826 Substitute Seq List_ST25.txt; Size: 434,217 bytes; and Date of Creation: Sep. 8, 2016, which is filed with this application is incorporated herein by reference in its entirety.

BACKGROUND

Field of the Disclosure

This disclosure relates to the treatment and prevention of *Staphylococcus aureus* (*S. aureus*) infection. In particular, the disclosure provides compositions and methods for preventing *S. aureus* infection and treating a disease caused by a leukocidin, e.g., Panton-Valentine leukocidin (PVL) or gamma-hemolysin expressing *S. aureus* infection.

Background of the Disclosure

*Staphylococcus aureus* (SA) is a gram positive human pathogen that is associated with or causes a wide range of pathologies ranging from skin and soft tissue infections to life-threatening systemic infections, e.g., minor skin infections such as pimples, impetigo, boils (furuncles), cellulitis folliculitis, carbuncles, scalded skin syndrome, and abscesses, to life-threatening deep infections such as pneumonia, sepsis, endocarditis, meningitis, post-operative wound infections, septicemia, and toxic shock syndrome (Nizet, V., J Allergy Clin Immunol, 2007. 120(1): p. 13-22; Kotzin, et al., Adv Immunol, 1993. 54: p. 99-166; Meyer et al., Int J Infect Dis, 2001. 5(3): p. 163-6; Schuberth et al., Vet Microbiol, 2001. 82(2): p. 187-99; and Silverstein et al., in Microbiology, Davis et al., eds. (Lippincott, Philadelphia, 1990), pp. 485-506).

Pneumonia is one of the most severe and prominent complications of *S. aureus* infection leading with 50,000 cases per year in the U.S. alone (Kuehnert, et al., *Emerg. Infect. Dis.* 11:868-872, 2005). *S. aureus* pneumonia has been traditionally ventilator associated but in recent years it has been recognized also as a major cause of community acquired pneumonia primarily in otherwise healthy children and young individuals.

The range of SA-associated pathologies reflects the diverse abilities of this microbe to escape the innate and adaptive immune response using multiple virulence factors including coagulase, capsular polysaccharides, adhesins, proteases, exoproteins that inactivate the complement system, pore-forming toxins, and other innate response mediators (Nizet, V., J Allergy Clin Immunol, 2007. 120(1): p. 13-22; Tristan et al., J Hosp Infect, 2007. 65 Suppl 2: p. 105-9). The rapid spread of methicillin resistant SA (MRSA) underscores the importance of developing vaccines for prevention or reduction of severity of MRSA infections. Most previous approaches for vaccine development have ignored the importance of including attenuated toxin components to disarm the immune evasion strategies of SA.

A significant increase in *S. aureus* isolates that exhibit resistance to most of the antibiotics currently available to treat infections has been observed in hospitals throughout the world. While MRSA strains were initially limited to health care settings, recent epidemics of community associated *S. aureus* (CA-MRSA) have been reported that cause severe disease in an otherwise healthy population. To date, five CA-MRSA clonal lineages are associated with these outbreaks: the Midwest clone (USA400, CC1), the European clone (CC80), the Southwest-Pacific Oceania clone (CC30), the Pacific clone (CC59), and the Pandemic clone (USA300, CC8). In addition to SCCmec IV, a characteristic feature of these major CA-MRSA lineages is that they have the lukPV operon encoding the Panton Valentine Leukocidin (PVL) (Diep, B. A. and M. Otto, Trends Microbiol, 2008. 16(8): p. 361-9), carried by the lysogenic phages ϕSLT, ϕPVL, ϕSA2MW and ϕSA2usa (Diep et al., Lancet, 2006. 367 (9512): p. 731-9; Kaneko et al., Gene, 1998. 215(1): p. 57-67; Narita et al., Gene, 2001. 268(1-2): p. 195-206). The development of penicillin to combat *S. aureus* was a major advance in infection control and treatment. Unfortunately, penicillin-resistant organisms quickly emerged and the need for new antibiotics was paramount. With the introduction of every new antibiotic, *S. aureus* has been able to counter with β-lactamases, altered penicillin-binding proteins, and mutated cell membrane proteins allowing the bacterium to persist. Consequently, methicillin-resistant *S. aureus* (MRSA) and multidrug resistant organisms have emerged and established major footholds in hospitals and nursing homes around the world. (Chambers, H. F., *Clin Microbiol Rev.,* 1:173, 1988; and Mulligan, M. E., et al., *Am J Med.,* 94:313, 1993). Today, almost half of the Staphylococcal strains causing nosocomial infections are resistant to all antibiotics except vancomycin and linezolid. Since many vancomycin intermediate resistant *S. aureus* (VISA) among MRSA, and a few vancomycin resistant *S. aureus*, have been reported in the literature, it appears to be only a matter of time before vancomycin will become ineffective as well. (Appelbaum P C., *Clin Microbiol Infect.,* 12 Suppl 1:16-23, 2006).

Natural immunity to *S. aureus* infections remains poorly understood. Typically, healthy humans and animals exhibit a high degree of innate resistance to *S. aureus* infections. Protection is attributed to intact epithelial and mucosal barriers and normal cellular and humoral responses. Titers of antibodies to *S. aureus* components are elevated after severe infections (Ryding et al., *J Med Microbiol,* 43(5):328-334, 1995), however to date there is no serological evidence of a correlation between these acquired antibody titers and human immunity.

Pore forming toxins that are secreted by *S. aureus* are crucial to its immune evasion. These toxins may create a survival advantage for the bacteria by forming pores into the membrane of target cells, inducing cell death and weakening the host during the first stages of infection. Because of the limited treatment modalities for *S. aureus* infection, the emergence of methicillin-resistant *S. aureus* poses a tremendous public health threat. While the molecular basis of the disease remains unclear, community-associated MRSA infection is closely linked to the presence of a Panton-Valentine leukocidin (PVL), a bipartite toxin consisting of the ~34 kDa LukF-PV and the ~32 kDa LukS-PV proteins (H. F. Chambers. *The New England Journal of Medicine* 352, 1485-1487, 2005). The function of the two PVL components (LukF-PV and LukS-PV) is synergistic and requires a sequence of events at the membrane surface of the target cell (J. Kaneko and Y. Kamio. *Bioscience, Biotechnology, and Biochemistry* 68, 981-1003, 2004). In the first step, the secreted, water-soluble LukF-PV and LukS-PV monomers aggregate on the membrane surface, and subsequently assemble into heterodimers. In a stepwise fashion, these heterodimers further oligomerize into heterotetramers that are characterized by alternating LukF-PV and LukS-PV subunits. These heterotetramers further assemble into an octameric, disc-like structure that is comprised of alternating LukS-PV and LukF-PV subunits in a 1:1 stoichiometry (L. Jayasinghe and H. Bayley. *Protein Sci* 14, 2550-2561, 2005). At this stage, experimental data indicates that PVL exists as an octamer in pre-pore conformation that is not fully functional and not transversing the cell membrane. Subsequently, the pre-pore structure undergoes major conformational changes that result in the formation of a single transmembrane pore that allows the influx of calcium ions, leading to cell death (V. T. Nguyen, Y. Kamio, and H. Higuchi. *The EMBO Journal* 22, 4968-4979, 2003). PVL causes cytolysis resulting in loss of immune cells such as neutrophils and may also cause tissue damage promoting bacterial dissemination. PVL is believed to be involved in pathogenesis of invasive pneumonia and skin infections.

Accordingly, there remains a need in the art for compositions and methods that can safely confer immunity to PVL-expressing *S. aureus*.

BRIEF SUMMARY

The present disclosure provides methods of inducing an immune response against a PVL-expressing *S. aureus*, methods of preventing or treating a PVL-expressing *S. aureus* infections, and compositions for preventing or treating a PVL-expressing *S. aureus* infections. In certain embodiments, the disclosure provides attenuated mutants of LukS-PV and LukF-PV as vaccines for *S. aureus* infections.

Some embodiments include an isolated mutant staphylococcal leukocidin subunit polypeptide comprising a wild-type staphylococcal leukocidin subunit except for one to five amino acid substitutions at conserved residues, which reduce toxicity of the mutant leukocidin subunit relative to the corresponding wild-type leukocidin subunit; where the wild-type leukocidin subunit comprises three consecutive regions designated A-B-C arranged from amino terminus to carboxy terminus, and wherein region B comprises the amino acid sequence of SEQ ID NO: 2.

Also disclosed is the mutant leukocidin subunit described herein, where region A of the wild-type leukocidin subunit comprises the amino acid sequence of SEQ ID NO: 1 and where region C of the wild-type leukocidin subunit comprises the amino acid sequence of SEQ ID NO: 3.

Also disclosed is the mutant leukocidin subunit as described herein, which comprises an amino acid substitution at position K24 of SEQ ID NO: 2. In certain embodiments, K24 is substituted with alanine.

Some embodiments include the mutant leukocidin subunit as described herein, which comprises an amino acid substitution at position S18 of SEQ ID NO: 3. In certain embodiments S18 is substituted with alanine.

Some embodiments include the mutant leukocidin as described herein, which comprises an amino acid substitution at position Y58 of SEQ ID NO:2. In certain embodiments Y58 is substituted with alanine.

Some embodiments include the mutant leukocidin subunit as described herein, which comprises an amino acid substitution at position T11 of SEQ ID NO: 1. In certain embodiments T11 is substituted with phenylalanine.

Some embodiments include the mutant leukocidin subunit as described herein, which comprises an amino acid substitution at position D28 of SEQ ID NO: 2. In certain embodiments D28 is substituted with alanine.

In some embodiments the wild-type leukocidin subunit is a Panton-Valentine leukocidin (PVL) LukS-PV. In certain embodiments, the wild-type leukocidin subunit comprises an amino acid sequence selected from the group consisting of SEQ ID NO: 5, SEQ ID NO: 6 and SEQ ID NO: 15. In some embodiments the mutant LukS-PV subunit contains an amino acid sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In certain embodiments the mutant leukocidin subunit as described herein, comprises the amino acid of SEQ ID NO: 14.

In some embodiments the mutant leukocidin subunit as described herein, comprises a calculated molecular energy between 600 kcal/mol and 7500 kcal/mol, or between 900 kcal/mol and 3900 kcal/mol, or between 2000 kcal/mol and 3650 kcal/mol in complex with a wild-type Panton-Valentine leukocidin (PVL) LukF-PV subunit.

Some embodiments include an isolated mutant staphylococcal leukocidin subunit polypeptide comprising a wild-type staphylococcal leukocidin subunit except for one to five amino acid substitutions at conserved residues, which reduce toxicity of the mutant leukocidin subunit relative to the corresponding wild-type leukocidin subunit; wherein the wild-type leukocidin subunit comprises the amino acid sequence of SEQ ID NO: 4.

In some embodiments the mutant leukocidin subunit as described herein, comprises an amino acid substitution at position K8. In certain embodiments K8 is substituted with alanine.

In some embodiments the mutant leukocidin subunit as described herein, comprises an amino acid substitution at position D28. In certain embodiments D28 is substituted with alanine.

In some embodiments the mutant leukocidin subunit as described herein, comprises an amino acid substitution at position E53. In certain embodiments E53 is substituted with alanine.

In some embodiments the wild-type leukocidin subunit is a Panton-Valentine leukocidin (PVL) LukF-PV. In certain embodiments the wild-type leukocidin subunit comprises an amino acid sequence selected from the group consisting of SEQ ID NO: 16, SEQ ID NO: 21, SEQ ID NO: 22, SEQ ID NO: 23, SEQ ID NO: 24, SEQ ID NO: 25, SEQ ID NO: 26, and SEQ ID NO: 27. In some embodiments, the mutant LukF-PV subunit comprises an amino acid sequence selected from the group consisting of SEQ ID NO: 18, SEQ ID NO: 19, and SEQ ID NO: 20. In one embodiment, the mutant LukF-PV subunit comprises an amino acid sequence of SEQ ID NO: 18.

In some embodiments the mutant leukocidin subunit as described herein, comprises a calculated molecular energy between 900 kcal/mol and 1500 kcal/mol in complex with a wild-type Panton-Valentine leukocidin (PVL) LukS-PV.

Some embodiments include the mutant leukocidin subunit as described herein, which is less toxic in a neutrophil toxicity assay compared to the corresponding wild-type leukocidin subunit.

Some embodiments include the mutant leukocidin subunit as described herein, which does not oligomerize with a wild-type leukocidin component. In certain embodiments, the wild-type leukocidin component is selected from the group consisting of a LukS-PV subunit, a LukF-PV subunit, Gamma hemolysin A, Gamma hemolysin B, Gamma hemolysin C, LukE and LukD subunit, or any combination thereof.

Also disclosed is a polypeptide complex comprising the mutant leukocidin subunits as described herein.

Also disclosed is an isolated polynucleotide comprising a nucleic acid which encodes the mutant leukocidin subunit described herein. In some embodiments, the polynucleotide further comprises a heterologous nucleic acid. In some embodiments, the heterologous nucleic acid comprises a promoter operably associated with the nucleic acid encoding the polypeptide described herein.

Also included is a vector comprising the polynucleotide described herein, or a host cell comprising the vector. In some embodiments, the vector is a plasmid. In some embodiments, the host cell is a bacterium, an insect cell, a mammalian cell, yeast or a plant cell. In certain embodiments, the bacterium is *Escherichia coli.*

Also disclosed is a method of producing a mutant staphylococcal leukocidin subunit polypeptide, comprising culturing the host cell described herein and recovering the polypeptide.

Further disclosed is a composition comprising the mutant leukocidin subunit or the polypeptide complex, as described herein, and a carrier. The composition can further comprise an adjuvant. Further disclosed is a composition comprising an additional staphylococcal antigen. In certain embodiments, the additional staphylococcal antigen is an alpha-hemolysin subunit polypeptide.

Also disclosed is a method of inducing a host immune response against a *Staphylococcus aureus* strain, comprising administering to a subject in need of the immune response an effective amount of the composition described herein. In certain embodiments the immune response is an antibody response. In some embodiments the immune response selected from the group consisting of an innate response, a humoral response, an antibody response a T cell response, and a combination of two or more of said immune responses.

Also disclosed is a method of preventing or treating a Staphylococcal disease or infection in a subject comprising administering to a subject in need thereof the composition described herein. The infection can be localized or systemic infection of skin, soft tissue, blood, or an organ, or is auto-immune in nature, and disease can be a respiratory disease, such as pneumonia. The subject can be an animal, a vertebrate, a mammal, or a human. The composition described herein can be administered via intramuscular injection, intradermal injection, intraperitoneal injection, subcutaneous injection, intravenous injection, oral administration, mucosal administration, intranasal administration, or pulmonary administration.

Also included is a method of producing a vaccine against *S. aureus* infection comprising isolating the mutant leukocidin subunit or the polypeptide complex, as described herein, and combining the mutant leukocidin subunit or polypeptide complex with an adjuvant. In certain embodiments, the method discloses further comprising combining the mutant leukocidin subunit or polypeptide complex with an additional staphylococcal antigen.

(A) Total antibody titers determined by ELISA for individual mouse sera (EC50; i.e. dilution of serum with 50% maximal signal on ELISA plates coated with wild type LukS-PV). (B) Neutralization determined in HL-60 toxin neutralization assay using wild type LukS-PV and LukF-PV toxins. Percent neutralization of wild type toxin is shown at 1:100 dilution of serum from vaccinated mice (sera pooled from 5 mice in each group).

Figure 11:
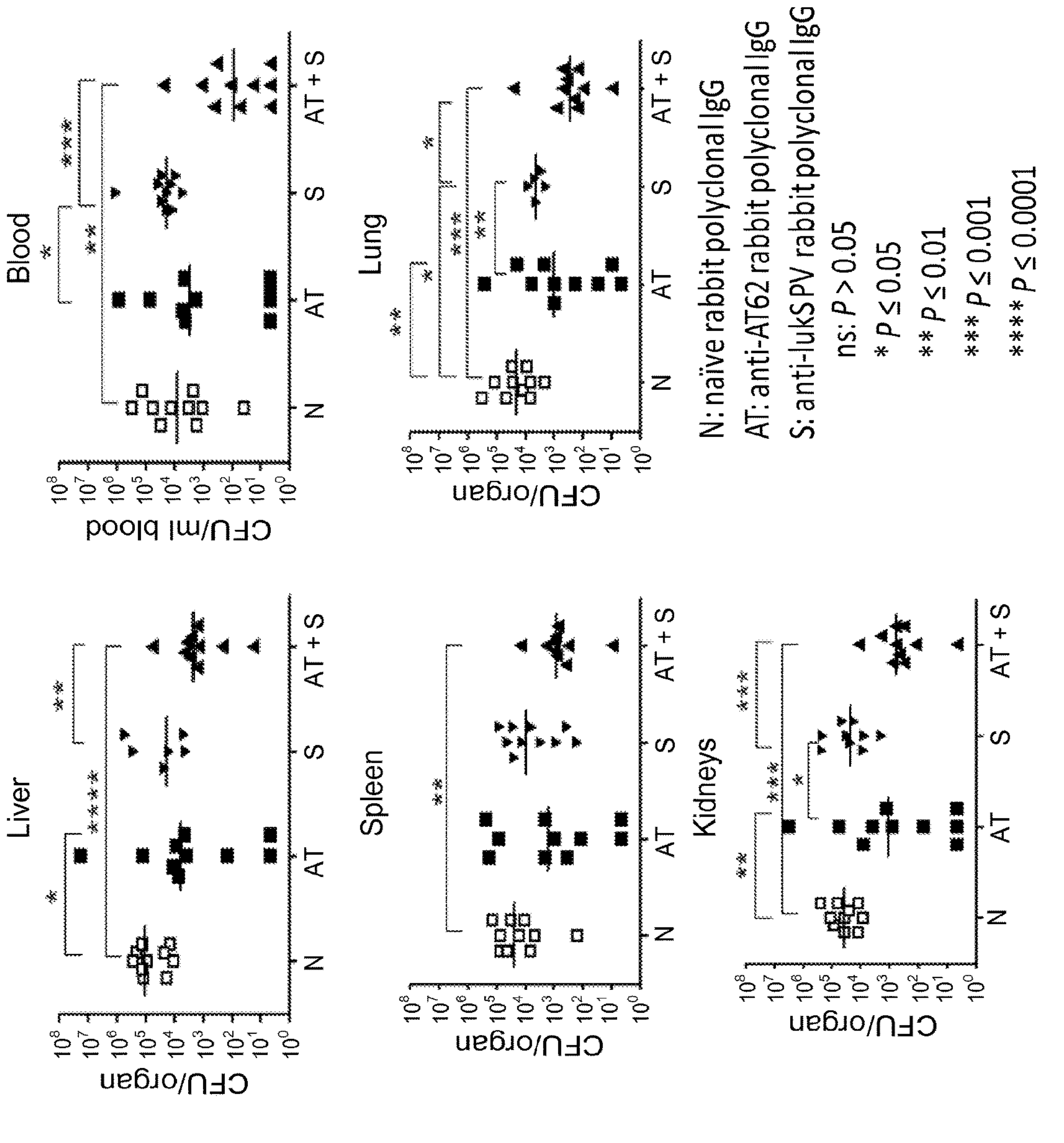

FIG. 11—Bacterial CFU in blood and organs (liver, spleen, lung, and kidneys) after treatment of mice with 2 mg naïve IgG (N), 2 mg AT62-IgG (AT) or the combination of 2 mg AT62-IgG and 0.25 mg of LukS-PV IgG (AT+S).

Figure 12:
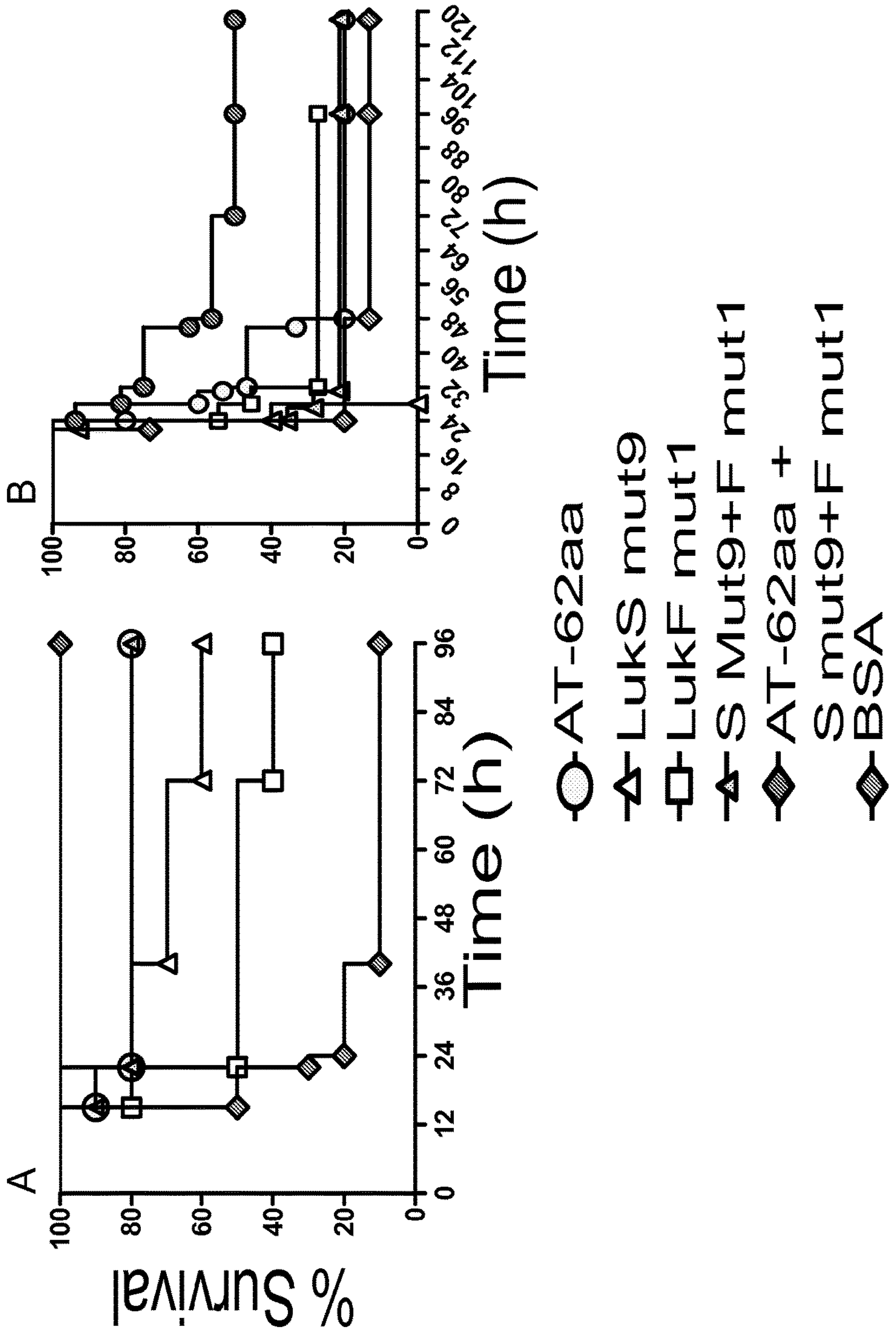

FIG. 12—Survival curves showing protection against (A) bacteremia/sepsis and (B) pneumonia with Luk (LukS Mut 9, LukF Mut1, and LukS Mut 9+LukF Mut1) and Hla (AT-62aa) vaccine candidates as well as the combination of LukS Mut 9+LukF Mut1+AT-62aa and BSA control. No further lethality was observed after the time points shown.

Figure 13:
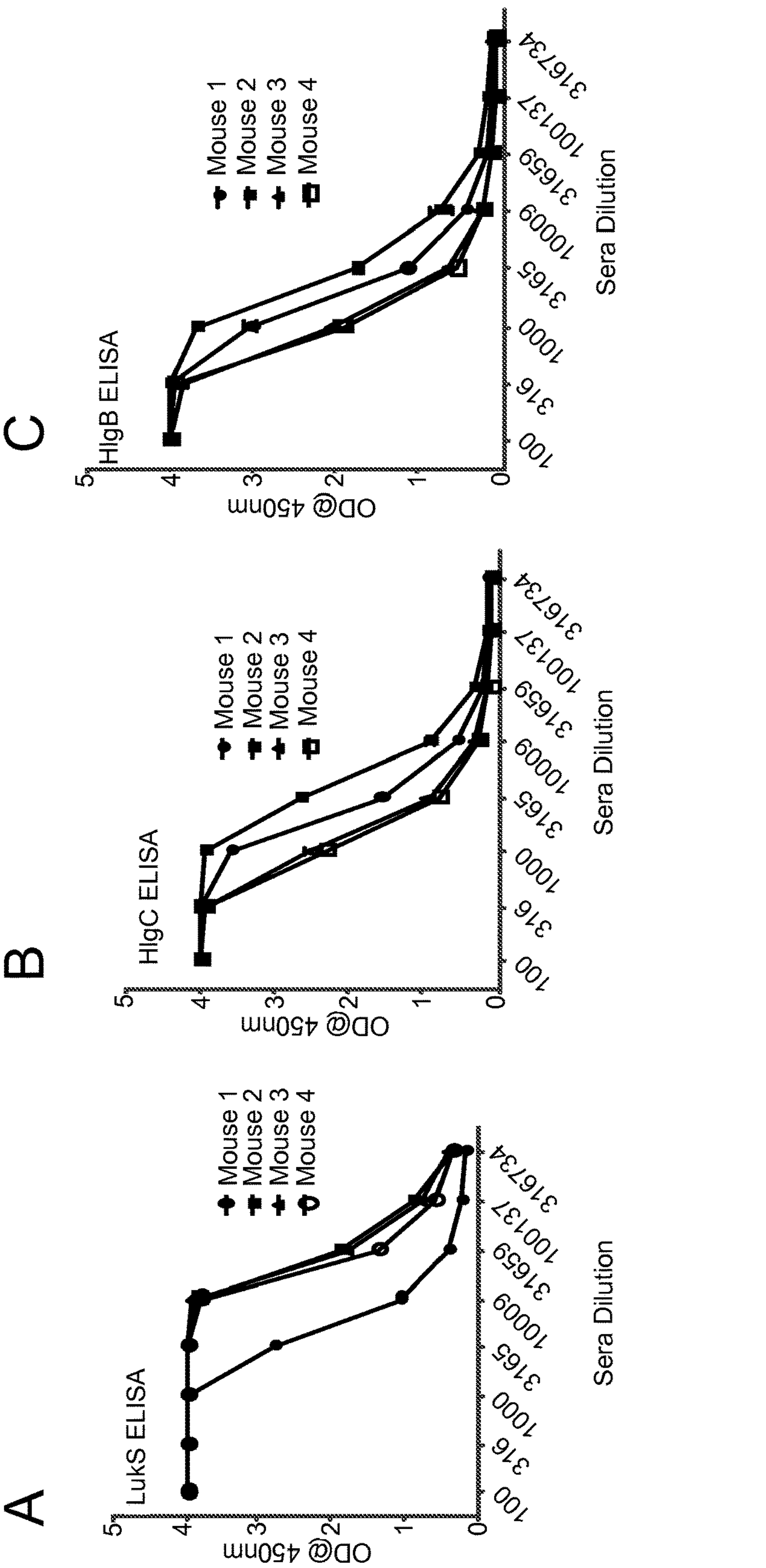

FIG. 13—(A) Specificity of LukS-PV mutant-9 mouse sera to homologous antigen, (B) Cross-reactivity of LukS-PV mutant-9 mouse sera to HlgB antigen, (C) Cross-reactivity of LukS-PV mutant-9 mouse sera to HlgC antigen. (D) Neutralization efficacy of LukS-PV mutant-9 mouse sera against 200 ng/ml of PVL and or gamma-hemolysin toxins in invitro XTT cytotoxicity assay based on human neutrophil cell line HL-60.

Figure 14:
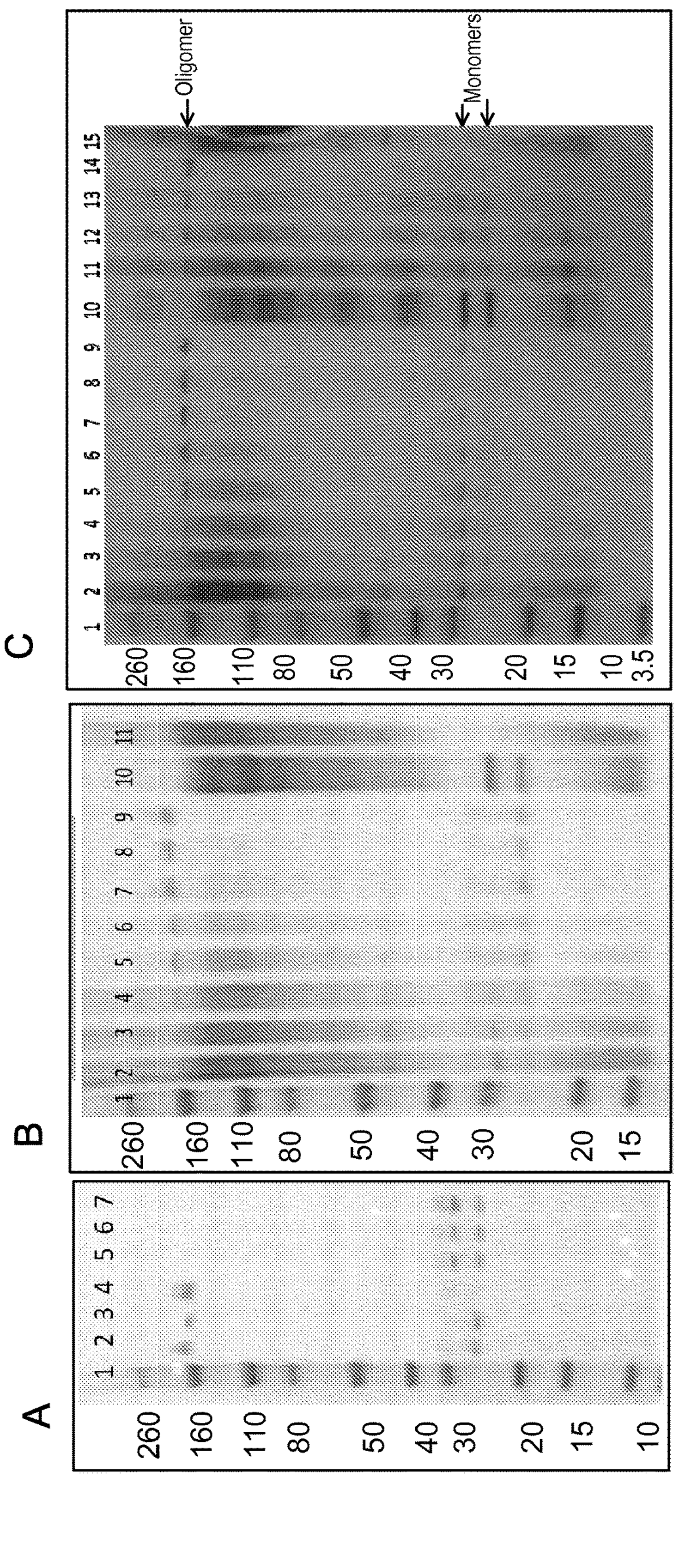

FIG. 14—(A) MPD based oligomerization assay. Lane 1: Molecular weight marker; Lane 2: LukS wt+LukFwt; Lane 3: LukS wt+Lukf mut1; Lane 4: LukS wt+Gamma B; Lane 5: LukF wt+LukS mut9; Lane 6: LukS mut9+LukF mut1; Lane 7: LukS mut9+Gamma B. (B) Inhibition of oligomeric band by anti LukS specific polyclonal antibody. Lane 1: Marker; Lanes 2-8: LukS+LukF+anti-LukS pAbs at 2-fold decreasing concentrations (5.5 mg/ml to 0.85 mg/ml); Lane 9: LukS+LukF without pAbs; Lane 10: LukS+LukF+pAbs without MPD; Lane 11: pAbs+MPD only. (C) Inhibition of oligomeric band formed by LukS-PV+hlgB by anti LukS specific polyclonal antibody. Lane 1: Marker; Lanes 2-8: LukS-PV+hlgB (940 ng each)+anti-LukS pAbs at 2-fold decreasing concentrations (34.5 ug/ml to 0.5 mg/ml); Lane 9: LukS-PV+hlgB without pAbs; Lane 10: LukS-PV+hlgB+pAbs without MPD; Lanes 11-14 Naïve Rabbit pAbs (34.5 ug/ml to 4.3 mg/ml)+LukS-PV+hlgB (940 ng each) and Lane 15: Naïve Rabbit pAbs+MPD only.

DETAILED DESCRIPTION

Disclosed herein are mutant staphylococcal leukocidin subunit polypeptides, e.g., a mutant LukS-PV subunit polypeptide or a mutant LukF-PV subunit polypeptide, compositions comprising one or more mutant leukocidin subunits as disclosed herein, and methods of eliciting an immune response against staphylococci, e.g. *S. aureus*, or treating or preventing a staphylococcal infection in a subject, comprising administering to a subject an effective amount of a mutant staphylococcal leukocidin subunit polypeptide as disclosed herein.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The terms "nucleic acid" or "nucleic acid fragment" refers to any one or more nucleic acid segments, e.g., DNA or RNA fragments, present in a polynucleotide or construct. Two or more nucleic acids of the disclosure can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide," a "protein," an "amino acid chain," an "amino acid sequence," or any other term used to refer to a chain or chains of two or more amino acids, are included in the definition of a "polypeptide," (even though each of these terms can have a more specific meaning) and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The terms "staphylococcal leukocidin subunit," "LukS-PV polypeptide," and "LukF-PV polypeptide," as used herein, encompass mature or full length staphylococcal leukocidin subunits (e.g., LukS-PV or LukF-PV), and fragments, variants or derivatives of mature or full length staphylococcal leukocidin subunits (e.g., LukS-PV and LukF-PV), and chimeric and fusion polypeptides comprising mature or full length staphylococcal leukocidin subunits (e.g., LukS-PV and LukF-PV) or one or more fragments of mature or full length staphylococcal leukocidin subunits (e.g., LukS-PV and LukF-PV). In certain embodiments, staphylococcal leukocidin subunits as disclosed herein are mutant staphylococcal leukocidin subunits, which are reduced in toxicity relative to a corresponding wild-type leukocidin subunit. By "corresponding wild-type leukocidin subunit" is meant the native leukocidin subunit from which the mutant leukocidin subunit was derived.

Pore forming toxins, e.g., single-component alpha-hemolysin and the bi-component hemolysins and leukotoxins, play an important role in staphylococcal immune evasion. These toxins kill key immune cells and cause tissue destruction, thereby often weakening the host during the first stage of infection and promoting bacterial dissemination and metastatic growth. The two PVL components, LukS-PV and LukF-PV, are secreted separately and form the pore-forming octameric complex upon binding of LukS-PV to its receptor and subsequent binding of LukF-PV to LukS-PV (Miles et al., Protein Sci, 2002. 11(4): p. 894-902; Pedelacq et al., Int J Med Microbiol, 2000. 290(4-5): p. 395-401). Targets of PVL include, e.g., polymorphonuclear neutrophils (PMN), monocytes, and macrophages.

Other bi-component toxins have been characterized in *S. aureus*: S components HlgA and HlgC and the F component HlgB for γ-hemolysin; lukE (S) and lukD (F); and lukM (S) and lukF-PV-like (F). Due to their close similarity, these S components can combine with a F component and form an active toxin with different target specificity (Ferreras et al., Biochim Biophys Acta, 1998. 1414(1-2): p. 108-26; Prevost et al., Infect Immun, 1995. 63(10): p. 4121-9). γ-Hemolysin is strongly hemolytic and 90% less leukotoxic than PVL, while PVL is non-hemolytic. However, HlgA or HlgC paired with lukF-PV promotes leukotoxic activity (Prevost et al., Infect Immun, 1995. 63(10): p. 4121-9). Luk and PVL lyse neutrophils, and Hlg is hemolytic (Kaneko et al., Biosci Biotechnol Biochem, 2004. 68(5): p. 981-1003) and was also reported to lyse neutrophils (Malachowa et al., PLoS One, 2011. 6(4): p. e18617). While PVL subunits are phage derived (the F&S leukocidin), Hlg proteins are derived from Hlg locus (hlg) and found in 99% of clinical isolates (Kaleko et al.). Hlg subunits are strongly upregulated during *S. aureus* growth in blood (Malachowa et al.), and Hlg was shown to be involved in survival of *S. aureus* in blood (Malachowa et al., Virulence, 2011. 2(6)). The mutant USA300 Δ-hlgABC has reduced capacity to cause mortality in a mouse bacteremia model (Malachowa et al., PLoS One, 2011. 6(4): p. e18617). Alonzo et al. have shown that LukED toxin is critical for bloodstream infections in mice (Alonzo et al., Mol Microbiol, 2012. 83(2): p. 423-35). Another novel *S. aureus* leukotoxin, LukGH, has also been described, which synergizes with PVL to enhance human PMN lysis (Ventura et al., PLoS One, 2010. 5(7): p. e11634).

The terms “fragment,” “analog,” “derivative,” or “variant” when referring to a staphylococcal leukocidin subunit (e.g., LukS-PV or LukF-PV) of the present disclosure include any polypeptide which retains at least some of the immunogenicity or antigenicity of the source protein. Fragments of staphylococcal leukocidin subunits (e.g., LukS-PV or LukF-PV) as described herein include proteolytic fragments, deletion fragments and in particular, fragments of staphylococcal leukocidin subunits (e.g., LukS-PV or LukF-PV) which exhibit increased solubility during expression, purification, or administration to an animal. Fragments of staphylococcal leukocidin subunits (e.g., LukS-PV or LukF-PV) as described herein further include proteolytic fragments or deletion fragments which exhibit reduced pathogenicity or toxicity when delivered to a subject. Polypeptide fragments further include any portion of the polypeptide which comprises an antigenic or immunogenic epitope of the source polypeptide, including linear as well as three-dimensional epitopes.

An “epitopic fragment” of a polypeptide antigen is a portion of the antigen that contains an epitope. An “epitopic fragment” can, but need not, contain amino acid sequence in addition to one or more epitopes.

The term “variant,” as used herein, refers to a polypeptide that differs from the recited polypeptide due to amino acid substitutions, deletions, insertions, and/or modifications. Non-naturally occurring variants can be produced using art-known mutagenesis techniques. In some embodiments, variant polypeptides differ from an identified sequence by substitution, deletion or addition of three amino acids or fewer. Such variants can generally be identified by modifying a polypeptide sequence, and evaluating the antigenic or pathogenic properties of the modified polypeptide using, for example, the representative procedures described herein. In some embodiments, variants of a wild-type staphylococcal leukocidin subunit (e.g., LukS-PV, or LukF-PV, or both) form a protein complex which is less toxic than the wild-type complex.

Polypeptide variants disclosed herein exhibit at least about 85%, 90%, 94%, 95%, 96%, 97%, 98%, 99% or 99.9% sequence identity with identified polypeptide. Variant polypeptides can comprise conservative or non-conservative amino acid substitutions, deletions or insertions. Variants can comprise staphylococcal leukocidin subunits (e.g., LukS-PV or LukF-PV, or both) identical to a wild-type leukocidin subunit except for at least 1, 2, 3, 4, 5, 6, 7, 8, 9, 10, 15, 20, or more amino acid substitutions, where the substitutions render a leukocidin complex comprising the variant leukocidin subunit less toxic than a corresponding wild-type protein complex. Derivatives of staphylococcal leukocidin subunits (e.g., LukS-PV and LukF-PV) as described herein are polypeptides which have been altered so as to exhibit additional features not found on the native polypeptide. Examples include fusion proteins. An analog is another form of a staphylococcal leukocidin subunit (e.g., LukS-PV and LukF-PV) described herein. An example is a proprotein which can be activated by cleavage of the proprotein to produce an active mature polypeptide.

Variants can also, or alternatively, contain other modifications, whereby, for example, a polypeptide can be conjugated or coupled, e.g., fused to a heterologous amino acid sequence, e.g., a signal (or leader) sequence at the N-terminal end of the protein which co-translationally or post-translationally directs transfer of the protein. The polypeptide can also be conjugated or produced coupled to a linker or other sequence for ease of synthesis, purification or identification of the polypeptide (e.g., 6-His), or to enhance binding of the polypeptide to a solid support. For example, the polypeptide can be conjugated or coupled to an immunoglobulin Fc region. The polypeptide can also be conjugated or coupled to a sequence that imparts or modulates the immune response to the polypeptide (e.g., a T-cell epitope, B-cell epitope, cytokine, chemokine, etc.) and/or enhances uptake and/or processing of the polypeptide by antigen presenting cells or other immune system cells. The polypeptide can also be conjugated or coupled to other polypeptides/epitopes from *Staphylococcus* sp. and/or from other bacteria and/or other viruses to generate a hybrid immunogenic protein that alone or in combination with various adjuvants can elicit protective immunity to other pathogenic organisms. The polypeptide can also be conjugated or coupled to moieties which confer greater stability or improve half life such as, but not limited to albumin, an immunoglobulin Fc region, polyethylene glycol (PEG), and the like. The polypeptide can also be conjugated or coupled to moieties (e.g., immunogenic carbohydrates, e.g., a capsular polysaccharide or a surface polysaccharide) from *Staphylococcus* sp. and/or from other bacteria and/or other viruses to generate a modified immunogenic protein that alone or in combination with one or more adjuvants can enhance and/or synergize protective immunity. In certain embodiments, the polypeptide described herein further comprises an immunogenic carbohydrate. In one embodiment, the immunogenic carbohydrate is a saccharide.

The term “saccharide” throughout this specification may indicate polysaccharide or oligosaccharide and includes both. Polysaccharides of the invention may be isolated from bacteria and may be sized by known methods. For example, full length polysaccharides may be “sized” (e.g., their size may be reduced by various methods such as acid hydrolysis treatment, hydrogen peroxide treatment, sizing by EMULSIFLEX® followed by a hydrogen peroxide treatment to generate oligosaccharide fragments or microfluidization). Polysaccharides can be sized in order to reduce viscosity in polysaccharide samples and/or to improve filterability for conjugated products. Oligosaccharides have a low number of repeat units (e.g., 5-30 repeat units) and are typically hydrolysed polysaccharides. Polysaccharides of the invention may be produced recombinantly.

*S. aureus* capsular antigens are surface associated, limited in antigenic specificity, and highly conserved among clinical isolates. In one embodiment, the immunogenic carbohydrate of the invention is a capsular polysaccharide (CP) of *S. aureus*. In one embodiment, a capsular saccharide may be a full length polysaccharide, however in other embodiments it may be one oligosaccharide unit, or a shorter than native length saccharide chain of repeating oligosaccharide units. Serotyping studies of staphylococcal isolates have revealed several putative capsular serotypes, with types 5 and 8 (CP5 and CP8) being the most prevalent among isolates from clinical infections, accounting for about 25% and 50% of isolates recovered from humans, respectively (O'Riordan and Lee, Clinical Microbiology Reviews, January 2004, p. 218-234, Vol. 17, No. 1; Poutrel and Sutra, J Clin Microbiol. 1993 February; 31(2):467-9). The same isolates were also recovered from poultry, cows, horses and pigs (Tollersrud et al., J Clin Microbiol. 2000 August; 38(8):2998-3003; Cunnion K M et al., Infect Immun. 2001 November; 69(11): 6796-803). Type 5 and 8 capsular polysaccharides purified from the prototype strains Reynolds and Becker, respectively, are structurally very similar to each other and to the capsule made by strain T, described previously by Wu and Park (Wu and Park. 1971. J. Bacteriol. 108:874-884). Type 5 has the structure (→4)-3-O-Ac-β-D-ManNAcA-(1→4)-α-L-FucNAc-(1→3)-β-D-FucNAc-(1→)$_n$ (Fournier, J. M., et al., 1987. Ann. Inst. Pasteur Microbiol. 138:561-567; Moreau, M., et al., 1990. Carbohydr. Res. 201:285-297), and type 8 has the structure (→3)-4-O-Ac-β-D-ManNAcA-(1→3)α-L-FucNAc-(1→3)-β-D-FucNAc-(1→)$_n$ (Fournier, J. M., et al., 1984. Infect Immun. 45:87-93). Type 5 and 8 polysaccharides differ only in the linkages between the sugars and in the sites of O-acetylation of the mannosaminuronic acid residues, yet they are serologically distinct.

Type 5 and 8 CP conjugated to a detoxified recombinant *Pseudomonas aeruginosa* exotoxin A carrier were shown to be highly immunogenic and protective in a mouse model (A Fattom et al., Infect Immun. 1993 March; 61(3): 1023-1032; A Fattom et al., Infect Immun. 1996 May; 64(5): 1659-1665) and passive transfer of the CP5-specific antibodies from the immunized animals induced protection against systemic infection in mice (Lee et al., Infect Immun. 1997 October; 65(10): 4146-4151) and against endocarditis in rats challenged with a serotype 5 *S. aureus* (Shinefield H et al., N Engl J. Med. 2002 Feb. 14; 346(7):491-6). A bivalent CP5 and CP8 conjugate vaccine (StaphVAX®, Nabi Biopharmaceutical) was developed that provided 75% protection in mice against *S. aureus* challenge. The vaccine has been tested on humans (Fattom A I et al., Vaccine. 2004 Feb. 17; 22(7):880-7; Maira-Litrán T et al., Infect Immun. 2005 October; 73(10):6752-62). In certain embodiments, the oligopeptide of the invention is combined with or conjugated to an immunogenic carbohydrate (e.g., CP5, CP8, a CP fragment or a combination thereof).

Immunization with poly-N-acetylglucosamine (PNAG) (McKenney D. et al., Science. 1999 May 28; 284(5419): 1523-7) or poly-N-succinyl glucosamine (PNSG) (Tuchscherr L P. et al., Infect Immun. 2008 December; 76(12): 5738-44. Epub 2008 Sep. 22), both *S. aureus* surface carbohydrates, has been shown to generate at least partial protection against *S. aureus* challenge in experimental animal models. PNSG was identified as the chemical form of the *S. epidermidis* capsular polysaccharide/adhesin (PS/A) which mediates adherence of coagulase-negative staphylococci (CoNS) to biomaterials, serves as the capsule for strains of CoNS that express PS/A, and is a target for protective antibodies. PNSG is also made by *S. aureus*, where it is an environmentally regulated, in vivo-expressed surface polysaccharide and similarly serves as a target for protective immunity (McKenney D. et al., J. Biotechnol. 2000 Sep. 29; 83(1-2): 37-44). In certain embodiments of the invention, the immunogenic carbohydrate is a surface polysaccharide, e.g., poly-N-acetylglucosamine (PNAG), poly-N-succinyl glucosamine (PNSG), a surface polysaccharide fragment or a combination thereof.

Wall Teichoic Acid (WTA) is a prominent polysaccharide widely expressed on *S. aureus* strains (Neuhaus, F. C. and J. Baddiley, Microbiol Mol Biol Rev, 2003. 67(4):686-723) and antisera to WTA have been shown to induce opsonophagocytic killing alone and in presence of complement ((Thakker, M., et al., Infect Immun, 1998. 66(11): 5183-9), and Fattom et al, U.S. Pat. No. 7,754,225). WTA is linked to peptidoglycans and protrudes through the cell wall becoming prominently exposed on non-encapsulated strains such as USA300 responsible for most cases of community acquired MRSA (CA MRSA) in the US (Hidron, A. I., et al., Lancet Infect Dis, 2009. 9(6):384-92).

Lipoteichoic acid (LTA) is a constituent of the cell wall of Gram-positive bacteria, e.g., *Staphylococcus aureus*. LTA may bind to target cells non-specifically through membrane phospholipids, or specifically to CD14 and to Toll-like receptors. Target-bound LTA can interact with circulating antibodies and activate the complement cascade to induce a passive immune kill phenomenon. It also triggers the release from neutrophils and macrophages of reactive oxygen and nitrogen species, acid hydrolases, highly cationic proteinases, bactericidal cationic peptides, growth factors, and cytotoxic cytokines, which may act in synergy to amplify cell damage.

In certain embodiments, a surface polysaccharide is combined with or conjugated to a polypeptide of the disclosure. In certain embodiments the surface polysaccharide is, e.g., poly-N-acetylglucosamine (PNAG), poly-N-succinyl glucosamine (PNSG), Wall Teichoic Acid (WTA), Lipoteichoic acid (LPA), a fragment of any of said surface polysaccharides, or a combination of two or more of said surface polysaccharides.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window and a homologous polypeptide from another isolate. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which is available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The term "epitope," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind its antigen as determined by any method well known in the art. Immunospecific binding excludes non-specific binding but does not necessarily exclude cross-reactivity with other antigens. Whereas all immunogenic epitopes are antigenic, antigenic epitopes need not be immunogenic.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host. Various species exhibit particular bias for certain codons of a particular amino acid.

The term "composition," or "pharmaceutical composition" can include compositions containing immunogenic polypeptides of the disclosure along with e.g., adjuvants or pharmaceutically acceptable carriers, excipients, or diluents, which are administered to an individual already suffering from *S. aureus* infection or an individual in need of immunization against *S. aureus* infection.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the polypeptides, polynucleotides, compositions, and vaccines described herein are pharmaceutically acceptable.

An "effective amount" is that amount the administration of which to an individual, either in a single dose or as part of a series, is effective for treatment or prevention. An amount is effective, for example, when its administration results in a reduced incidence of *S. aureus* infection relative to an untreated individual, as determined, e.g., after infection or challenge with infectious *S. aureus*, including, but is not limited to reduced bacteremia, reduced toxemia, reduced sepsis, reduced symptoms, increased immune response, modulated immune response, or reduced time required for recovery. This amount varies depending upon the health and physical condition of the individual to be treated, the taxonomic group of individual to be treated (e.g., human, non-human primate, primate, etc.), the responsive capacity of the individual's immune system, the extent of treatment or protection desired, the formulation of the vaccine, a professional assessment of the medical situation, and other relevant factors. It is expected that the effective amount will fall in a relatively broad range that can be determined through routine trials. Typically a single dose is from about 10 μg to 10 mg/kg body weight of purified polypeptide or an amount of a modified carrier organism or virus, or a fragment or remnant thereof, sufficient to provide a comparable quantity of recombinantly expressed mutant staphylococcal leukocidin subunit (e.g., LukS-PV or LukF-PV, or both), as described herein. The term "peptide vaccine" or "subunit vaccine" refers to a composition comprising one or more polypeptides described herein, which when administered to an animal are useful in stimulating an immune response against staphylococcal (e.g., *S. aureus*) infection.

The term "subject" is meant any subject, particularly a mammalian subject, for whom diagnosis, prognosis, immunization, or therapy is desired. Mammalian subjects include, but are not limited to, humans, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In one embodiment, the subject is a human subject.

As used herein, a "subject in need thereof" refers to an individual for whom it is desirable to treat, i.e., to prevent, cure, retard, or reduce the severity of staphylococcal (e.g., *S. aureus*) disease symptoms, or result in no worsening of disease cause by *S. aureus* over a specified period of time, or both.

The terms "priming" or "primary" and "boost" or "boosting" as used herein to refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

Polypeptides

Disclosed is an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20 or more amino acid substitutions at conserved residues, which reduce toxicity of the mutant leukocidin subunit relative to the corresponding wild-type leukocidin subunit; where the wild-type leukocidin subunit comprises, consists of, or consists essentially of three consecutive regions designated A-B-C arranged from amino terminus to carboxy terminus, and where region B comprises the amino acid consensus sequence presented here as SEQ ID NO: 2:

```
FQYNIX1LX2X3X4DX5X6X7X8LINX9X10X11LPKX12KIX13

X14X15X16VX17QX18LGYNX19GX20X21X22X23X24X25

X26X27X28X29GX30GX31FX32YSK;
where
```

X1=Glycine(G), Serine(S) or Alanine(A)
X2=Lysine(K), Threonine(T), Serine(S) or Methionine(M)
X3=Threonine(T) or Serine(S)
X4=Asparagine(N) or Lysine(K)
X5=Proline(P), Lysine(K), Serine(S) or Glutamine(Q)
X6=Asparagine(N) or Tyrosine(Y)
X7=Valine(V), Threonine(T) or Isoleucine(I)
X8=Aspartic acid(D), Serine(S) or Phenylalanine(F)
X9=Serine(S) or no amino acid
X10=Isoleucine(I) or no amino acid
X11=Tyrosine(Y), Histidine(H) or Threonine(T)
X12=Asparagine(N) or Threonine(T)
X13=Aspartic acid(D) or Glutamic acid (E)
X14=Serine(S) or Threonine(T)
X15=Valine(V), Threonine(T), Alanine(A) or Isoleucine(I)
X16=Asparagine(N) or Aspartic acid(D)
X17=Serine(S) or Glycine(G)
X18=Threonine(T) or Lysine(K)
X19=Isoleucine(I) or Valine(V)
X20=Glycine(G) or no amino acid
X21=Asparagine(N), Lysine(K) or no amino acid
X22=Phenylalanine(F) or no amino acid
X23=Asparagine(N), Glutamine(Q) or no amino acid
X24=Serine(S), Threonine(T) or no amino acid
X25=Glycine(G), Alanine(A), Valine(V) or no amino acid
X26=Proline(P) or no amino acid
X27=Serine(S), Leucine(L) or no amino acid
X28=Threonine(T), Leucine(L), Isoleucine(I) or no amino acid
X29=Glycine(G), Alanine(A) or no amino acid
X30=Asparagine(N), Serine(S) or Lysine(K)
X31=Serine(S), Alanine(A) or Glutamic acid (E); and
X32=Asparagine(N) or Serine(S).

In some embodiments, region A of the wild-type leukocidin subunit comprises the amino acid consensus sequence presented here as SEQ ID NO: 1:

```
X1X2X3X4SX5X6X7X8X9TQNX10QFX11FX12KDX13KYNKX14AL

X15X16KMQGFIX17SX18TX19X20X21X22X23KX24X25X26X27

X28X29X30KX31X32X33WP;
```

where
X1=Glutamic acid (E), Glutamine(Q) or no amino acid
X2=Aspartic acid(D), Glycine(G) or no amino acid
X3=Threonine(T), Lysine(K), Isoleucine(I), Valine(V) or no amino acid
X4=Serine(S), Threonine(T), Alanine(A) or no amino acid
X5=Aspartic acid(D), Lysine(K), Asparagine(N), Arginine (R) or no amino acid
X6=Lysine(K), Arginine(R) or no amino acid
X7=Tryptophan(W), Leucine(L) or no amino acid
X8=Glycine(G), Alanine(A) or no amino acid
X9=Valine(V), Isoleucine(I) or no amino acid
X10=Isoleucine(I), Valine(V) or no amino acid
X11=Aspartic acid(D), Glycine(G) or no amino acid
X12=Valine(V) or Methionine(M)
X13=Lysine(K), Threonine(T) or Proline(P)
X14=Aspartic acid(D), Asparagine(N) or Valine(V)
X15=Isoleucine(I) or Valine(V)
X16=Leucine(L), Valine(V) or Isoleucine(I)
X17=Asparagine(N), Serine(S) or Lysine(K)
X18=Lysine(K) or Arginine(R)
X19=Threonine(T), Serine(S) or Alanine(A)
X20=Tyrosine(Y) or Phenylalanine(F)
X21=Tyrosine(Y), Serine(S), Asparagine(N) or Threonine (T)
X22=Asparagine(N) or Aspartic acid(D)
X23=Tyrosine(Y), Valine(V), Leucine(L), Phenylalanine(F) or Serine(S)
X24=Asparagine(N), Lysine(K), Glycine(G) or Glutamine (Q)
X25=Threonine(T), Tyrosine(Y), Serine(S), Asparagine(N), Lysine(K) or Arginine(R)
X26=Glycine(G) or no amino acid
X27=Tyrosine(Y) or no amino acid
X28=Aspartic acid(D), Asparagine(N), Glutamic acid (E), Proline(P) or Arginine(R)
X29=Histidine(H), Tyrosine(Y), Leucine(L) or Alanine(A)
X30=Isoleucine(I), Threonine(T), Valine(V) or Asparagine (N)
X31=Alanine(A), Arginine(R) or Serine(S)
X32=Methionine(M), Isoleucine(I) or Leucine(L); and
X33=Arginine(R), Isoleucine(I), Valine(V) or Leucine(L).

In some embodiments, region C of the wild-type leukocidin subunit comprises the amino acid consensus sequence presented here as SEQ ID NO: 3:

```
FX1X2X3X4X5LPPLX6X7SGFNPSFIX8TX9SHEX10X11X12X13

X14X15X16X17X18X19X20X21X22YGRNX23DX24TX25AX26

X27X28X29X30X31X32X33X34X35X36;
where
```

X1=Valine(V) or Alanine(A)
X2=Proline(P) or Aspartic acid(D)
X3=Aspartic acid(D) or Asparagine(N)
X4=Asparagine(N), Serine(S) or Aspartic acid(D)
X5=Glutamic acid (E) or Glutamine(Q)
X6=Valine(V) or Isoleucine(I)
X7=Histidine(H), Glutamine(Q) or Threonine(T)
X8=Alanine(A) or Threonine(T)
X9=Valine(V) or Leucine(L)
X10=Lysine(K) or Arginine(R)
X11=Glycine(G) or Aspartic acid(D)
X12=Serine(S), Lysine(K) or Threonine(T)
X13=Glycine(G), Serine(S) or Lysine(K)
X14=Aspartic acid(D), Glutamic acid (E) or Leucine(L)
X15=Threonine(T), Lysine(K) or Isoleucine(I)
X16=Arginine(R) or no amino acid
X17=Serine(S) or Valine(V)
X18=Glutamic acid (E), Aspartic acid(D) or Asparagine(N)
X19=Phenylalanine(F) or Leucine(L)
X20=Glutamic acid (E) or Lysine(K)
X21=Isoleucine(I) or Phenylalanine(F)
X22=Threonine(T), Serine(S) or Alanine(A)
X23=Methionine(M) or Leucine(L)
X24=Valine(V), Alanine(A), Isoleucine(I) or Threonine(T)
X25=Histidine(H) or Tyrosine(Y)
X26=Threonine(T), Isoleucine(I) or Tyrosine(Y)
X27=Arginine(R), Lysine(K), Valine(V), Leucine(L) or Phenylalanine(F)

X28=Arginine(R), Threonine(T), Phenylalanine(F) or Leucine(L)
X29=Threonine(T), Serine(S), Arginine(R) or Proline(P)
X30=Threonine(T), Histidine(H), Arginine(R), Lysine(K) or Proline(P)
X31=Histidine(H), Arginine(R), Threonine(T), Leucine(L) or Glutamine(Q)
X32=Tyrosine(Y) or no amino acid
X33=Glycine(G) or no amino acid
X34=Asparagine(N) or no amino acid
X35=Serine(S) or no amino acid; and
X36=Tyrosine(Y) or Glycine(G).

In some embodiments the mutant leukocidin subunit comprises amino acid substitutions at positions T11, K24, D28, Y58, S18, or any combination thereof. In certain embodiments, the substitutions can be with any amino acid which maintains the antigenicity of the mutant staphylococcal leukocidin subunit. In certain embodiments T11, K24, D28, Y58, or S18 is substituted with alanine or phenylalanine Also disclosed is the mutant leukocidin subunit, as described herein, which comprises an amino acid substitution at position K24 of SEQ ID NO: 2. The substitution can be with any amino acid which maintains the antigenicity of the mutant staphylococcal leukocidin subunit. In certain embodiments K24 is substituted with alanine Also disclosed is the mutant leukocidin subunit, as described herein, which comprises an amino acid substitution at position S18 of SEQ ID NO: 3. The substitution can be with any amino acid which maintains the antigenicity of the mutant staphylococcal leukocidin subunit. In certain embodiments S18 is substituted with alanine Some embodiments include the mutant leukocidin subunit, as described herein, which comprises an amino acid substitution at position Y58 of SEQ ID NO:2. The substitution can be with any amino acid which maintains the antigenicity of the mutant staphylococcal leukocidin subunit. In certain embodiments Y58 is substituted with alanine.

Some embodiments include the mutant leukocidin subunit, as described herein, which comprises an amino acid substitution at position T11 of SEQ ID NO: 1. The substitution can be with any amino acid which maintains the antigenicity of the mutant staphylococcal leukocidin subunit. In certain embodiments T11 is substituted with phenylalanine Some embodiments include the mutant leukocidin subunit, as described herein, which comprises amino acid substitutions at positions T11 and Y58. The substitutions can be with any amino acid which maintains the antigenicity of the mutant staphylococcal leukocidin subunit. In certain embodiments T11 and Y58 are substituted with phenylalanine and alanine, respectively.

Some embodiments include the mutant leukocidin subunit, as described herein, which comprises amino acid substitutions at positions T11 and S18. The substitutions can be with any amino acid which maintains the antigenicity of the mutant staphylococcal leukocidin subunit. In certain embodiments T11 and S18 are substituted with phenylalanine and alanine, respectively.

Some embodiments include the mutant leukocidin subunit, as described herein, which comprises amino acid substitutions at positions T11, K24, and S18. The substitutions can be with any amino acid which maintains the antigenicity of the mutant staphylococcal leukocidin subunit. In certain embodiments T11 is substituted with phenylalanine, and K24 and S18 are substituted with alanine Also disclosed is the mutant leukocidin subunit, as described herein, which comprises an amino acid substitution at position D28 of SEQ ID NO: 2. The substitution can be with any amino acid which maintains the antigenicity of the mutant staphylococcal leukocidin subunit. In certain embodiments D28 is substituted with alanine Also disclosed is an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20, or more amino acid substitutions at conserved residues, which reduce toxicity of the mutant leukocidin subunit relative to the corresponding wild-type leukocidin subunit; where the wild-type leukocidin is a Panton-Valentine leukocidin (PVL) LukS-PV. In some embodiments, the wild-type LukS-PV comprises an amino acid sequence selected from the group consisting of SEQ ID NO: 5, SEQ ID NO: 15, and SEQ ID NO: 16. In certain embodiments the wild-type LukS-PV comprises an amino acid sequence of SEQ ID NO: 5:

```
mvkkrllaat lslgiitpia tsfheskadn nienigdgae
vvkrtedtss dkwgvtqniq fdfvkdkkyn kdalilkmqg
finskttyyn ykntdhikam rwpfqynigl ktndpnvdli
nylpknkids vnvsqtlgyn iggnfnsgps tggngsfnys
ktisynqqny isevehqnsk svqwgikans fitslgkmsg
hdpnlfvgyk pysqnprdyf vpdnelpplv hsgfnpsfia
tvshekgsgd tsefeitygr nmdvthatrr tthygnsyle
gsrihnafvn rnytvkyevn wktheikvkg hn
```

(precursor protein sequence for LukS-PV. GenBank accession number: NP_058465.1; 28 amino acid signal peptide (amino acids 1-28) is underlined).

In some embodiments the mutant LukS-PV subunit comprises an amino acid sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In certain embodiments the mutant leukocidin subunit as described herein, comprises the amino acid of SEQ ID NO: 14.

Also disclosed is an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20, or more amino acid substitutions at conserved residues, which reduce toxicity of the mutant leukocidin subunit relative to the corresponding wild-type leukocidin subunit; where the wild-type leukocidin subunit comprises, consists of, or consists essentially of the amino acid consensus sequence presented here as SEQ ID NO: 4:

```
NX1VX2YAPKNQNEEFQVQX3TX4GYX5X6GGDIX7IX8X9GLX10
GGX11NGX12X13X14FSETINYKQESYRX15X16X17X18;
where
```

X1=Valine(V), Isoleucine(I) or Alanine(A)
X2=Aspartic acid(D) or Histidine(H)
X3=Asparagine(N) or Glutamine(Q)
X4=Leucine(L) or Valine(V)
X5=Serine(S) or Threonine(T)
X6=Phenylalanine(F) or Tyrosine(Y)

X7=Serine(S) or Asparagine(N)
X8=Serine(S), Isoleucine(I), Asparagine(N) or Threonine (T)
X9=Lysine(K) or Asparagine(N)
X10=Serine(S) or Threonine(T)
X11=Leucine(L) or Glycine(G)
X12=Serine(S) or Asparagine(N)
X13=Glutamic acid (E), Threonine(T) or Lysine(K)
X14=Serine(S) or Alanine(A)
X15=Threonine(T) or no amino acid
X16=Threonine(T) or Serine(S)
X17=Isoleucine(I) or Leucine(L); and
X18=Aspartic acid(D) or Serine(S).

In some embodiments the mutant leukocidin subunit comprises amino acid substitutions at positions K8, D28, E53, or any combination thereof. In certain embodiments, the substitutions can be with any amino acid which maintains the antigenicity of the mutant staphylococcal leukocidin subunit. In certain embodiments K8, D28, or E53 is substituted with alanine Also disclosed is an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20, or more amino acid substitutions at conserved residues, which reduce toxicity of the mutant leukocidin subunit relative to the corresponding wild-type leukocidin subunit; where the wild-type leukocidin is a Panton-Valentine leukocidin (PVL) LukF-PV. In some embodiments the wild-type LukF-PV comprises an amino acid sequence selected from the group consisting of SEQ ID NO: 16, SEQ ID NO: 21, SEQ ID NO: 22, SEQ ID NO: 23, SEQ ID NO: 24, SEQ ID NO: 25, SEQ ID NO: 26, and SEQ ID NO: 27. In certain embodiments the wild-type LukF-PV comprises an amino acid sequence of SEQ ID NO: 16:

```
mkkivkssvv tsiallllsn tvdaaqhitp vsekkvddki
tlykttatsd sdklkisqil tfnfikdksy dkdtlilkaa
gniysgytkp npkdtissqf ywgskynisi nsdsndsvnv
vdyapknqne efqvqqtvgy syggdinisn glsgggngsk
sfsetinykq esyrtsldkr tnfkkigwdv eahkimnngw
gpygrdsyhs tygnemflgs rqsnlnagqn fleyhkmpvl
srgnfnpefi gvlsrkqnaa kkskitvtyq remdrytnfw
nqlhwignny kdenrathts iyevdwenht vklidtqske
knpms
```

(precursor protein sequence for LukF-PV. GenBank accession number: NP_058466.1; 24 amino acid signal peptide (amino acids 1-24) is underlined).

In some embodiments, the mutant LukF-PV subunit comprises an amino acid sequence selected from the group consisting of SEQ ID NO: 18, SEQ ID NO: 19, SEQ ID NO: 20, and SEQ ID NO: 136. In certain embodiments the mutant LukF-PV subunit comprises an amino acid sequence of SEQ ID NO: 18. In certain embodiments the mutant LukF-PV subunit comprises an amino acid sequence of SEQ ID NO: 136.

Also disclosed is a polypeptide complex comprising the mutant leukocidin subunits as described herein. The substitution can be any amino acid that maintains structure and conformation of the mutant leukocidin subunit complex.

In another embodiment, the mutant staphylococcal leukocidin subunit (e.g., LukS-PV or LukF-PV, or both), as described herein, can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenyalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, T7gene10, an avidin/streptavidin/Strep-tag complex, trpE, chloramphenicol acetyltransferase, lacZ ((β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of LukS-PV and/or LukF-PV polypeptide as described herein from a host cell or any useful immunogenic sequence, including but not limited to sequences that encode a T-cell epitope of a microbial pathogen, or other immunogenic proteins and/or epitopes.

In some embodiments, the mutant staphylococcal leukocidin subunit (e.g., LukS-PV or LukF-PV, or both), attached to a heterologous polypeptide, as described herein, can include a peptide linker sequence joining sequences that comprise two or more peptide regions. Suitable peptide linker sequences can be chosen based on their ability to adopt a flexible, extended conformation, or a secondary structure that could interact with joined epitopes, or based on their ability to increase overall solubility of the fusion polypeptide, or based on their lack of electrostatic or water-interaction effects that influence joined peptide regions.

In some embodiments, the mutant staphylococcal leukocidin subunit (e.g., LukS-PV or LukF-PV, or both), as described herein, is isolated. An "isolated" polypeptide is one that has been removed from its natural milieu. The term "isolated" does not connote any particular level of purification. Recombinantly produced mutant staphylococcal leukocidin subunit (e.g., LukS-PV or LukF-PV, or both), as described herein, expressed in non-native host cells is considered isolated for purposes of the disclosure, as is the polypeptide which have been separated, fractionated, or partially or substantially purified by any suitable technique, including by filtration, chromatography, centrifugation, and the like.

Production of the mutant staphylococcal leukocidin subunit (e.g., LukS-PV or LukF-PV, or both), as described herein, can be achieved by culturing a host cell comprising a polynucleotide which operably encodes the polypeptide of the disclosure, and recovering the polypeptide. Determining conditions for culturing such a host cell and expressing the polynucleotide are generally specific to the host cell and the expression system and are within the knowledge of one of skill in the art. Likewise, appropriate methods for recovering the polypeptide of the disclosure are known to those in the art, and include, but are not limited to, chromatography, filtration, precipitation, or centrifugation.

In certain embodiments, the mutant staphylococcal leukocidin subunit, as described herein, comprises a calculated molecular energy of less than 7000 kcal/mol, or less than 4000 kcal/mol, or less than 2000 kcal/mol, or between 600 kcal/mol and 7500 kcal/mol, or between 900 kcal/mol and 3900 kcal/mol, or between 900 kcal/mol and 1500 kcal/mol, or between 2000 kcal/mol and 3650 kcal/mol. Specific calculated molecular energies for the heterodimer complex structure for LukS-PV and LukF-PV mutants are represented in Table 1. These measurements are explained in detail in the examples section.

TABLE 1

Calculated molecular energies for the heterodimer complex structure for LukS-PV and LukF-PV mutants

| LukS-PV Mutants (numbering according to mature (i.e., without signal peptide) wild-type LukS-PV sequence of SEQ ID NO: 6) | Energy (kcal/mol) | LukS-PV Mutants (corresponding numbers according to consensus wild-type LukS-PV sequences of SEQ ID NO: 1, SEQ ID NO: 2 or SEQ ID NO: 3) |
|---|---|---|
| T28F | 2535 | T11F of SEQ ID NO: 1 |
| K97A | 655 | K24A of SEQ ID NO: 2 |
| D101A | 3200 | D28A of SEQ ID NO: 2 |
| Y131A | 1027 | Y58A of SEQ ID NO: 2 |
| S209A | 7399 | S18A of SEQ ID NO: 3 |
| T28F/Y131A | 2032 | T11F/Y58A |
| T28F/S209A | 3187 | T11F/S18A |
| T28F/K97A/S209A | 3595 | T11F/K24A/S18A |
| **LukF-PV Mutants (numbering according to mature (i.e., without signal peptide) wild-type LukF-PV sequence of SEQ ID NO: 17)** | **Energy (kcal/mol)** | **LukF-PV Mutants (corresponding numbers according to consensus wild-type LukF-PV sequence of SEQ ID NO: 4)** |
| K102A | 1209 | K8A |
| D121A | 989 | D28A |
| E147A | 1384 | E53A |
| K102A/D121A/E147A | n/a | K8A/D28A/E53A |

Polynucleotides

The disclosure is further directed to an isolated polynucleotide comprising a nucleic acid encoding an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20, or more amino acid substitutions at conserved residues, which reduce toxicity of the mutant leukocidin subunit relative to the corresponding wild-type leukocidin subunit; where the wild-type leukocidin subunit comprises, consists of, or consists essentially of three consecutive regions designated A-B-C arranged from amino terminus to carboxy terminus, and where region B comprises the amino acid consensus sequence of SEQ ID NO: 2.

Also disclosed is an isolated polynucleotide comprising a nucleic acid encoding an isolated mutant staphylococcal leukocidin subunit polypeptide comprising, consisting of, or consisting essentially of a wild-type staphylococcal leukocidin subunit except for 1, 2, 3, 4, 5, 6, 7, 8, 9, 10, 15, 20, or more amino acid substitutions at conserved residues, which reduce toxicity of the mutant leukocidin subunit relative to the corresponding wild-type leukocidin subunit; where the wild-type leukocidin subunit comprises, consists of, or consists essentially of the amino acid consensus sequence presented here as SEQ ID NO: 4.

In certain embodiments, the isolated polynucleotide as described herein further comprises non-coding regions such as promoters, operators, or transcription terminators as described elsewhere herein. In some embodiments, the disclosure is directed to the polynucleotide as described herein, and further comprising a heterologous nucleic acid. The heterologous nucleic acid can, in some embodiments, encode a heterologous polypeptide fused to the polypeptide as described herein. For example, the isolated polynucleotide as described herein can comprise additional coding regions encoding, e.g., a heterologous polypeptide fused to the polypeptide as described herein, or coding regions encoding heterologous polypeptides separate from the polypeptide as described herein such as, but not limited to, selectable markers, additional immunogens, immune enhancers, and the like.

Also provided are expression constructs, vectors, and/or host cells comprising the polynucleotides described herein.

An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. In certain embodiments of the disclosure a polynucleotide is "recombinant." Isolated polynucleotides or nucleic acids according to the disclosure further include such molecules produced synthetically. The relative degree of purity of a polynucleotide or polypeptide described herein is easily determined by well-known methods.

Codon Optimization

Also included within the scope of the disclosure are genetically engineered polynucleotides encoding the mutant staphylococcal leukocidin subunit (e.g., LukS-PV or LukF-PV, or both), as described herein. Modifications of nucleic acids encoding the mutant staphylococcal leukocidin subunit e.g., (LukS-PV or LukF-PV, or both), as described herein, can readily be accomplished by those skilled in the art, for example, by oligonucleotide-directed site-specific mutagenesis or de novo nucleic acid synthesis.

Some embodiments disclose an isolated polynucleotide comprising a nucleic acid fragment, which encodes the mutant staphylococcal leukocidin subunit (e.g., LukS-PV or LukF-PV, or both), as described herein, where the coding region encoding the polypeptide has been codon-optimized. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence of the coding region. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 2

| | The Standard Genetic Code | | | |
|---|---|---|---|---|
| | T | C | A | G |
| T | TTT Phe(F) | TCT Ser(S) | TAT Tyr(Y) | TGT Cys(C) |
| | TTC Phe(F) | TCC Ser(S) | TAC Tyr(Y) | TGC |
| | TTA Leu(L) | TCA Ser(S) | TAA Ter | TGA Ter |
| | TTG Leu(L) | TCG Ser(S) | TAG Ter | TGG Trp(W) |
| C | CTT Leu(L) | CCT Pro(P) | CAT His(H) | CGT Arg(R) |
| | CTC Leu(L) | CCC Pro(P) | CAC His(H) | CGC Arg(R) |
| | CTA Leu(L) | CCA Pro(P) | CAA Gln(Q) | CGA Arg(R) |
| | CTG Leu(L) | CCG Pro(P) | CAG Gln(Q) | CGG Arg(R) |
| A | ATT Ile(I) | ACT Thr(T) | AAT Asn(N) | AGT Ser(S) |
| | ATC Ile(I) | ACC Thr(T) | AAC Asn(N) | AGC Ser(S) |
| | ATA Ile(I) | ACA Thr(T) | AAA Lys(K) | AGA Arg(R) |
| | **ATG** Met(M) | ACG Thr(T) | AAG Lys(K) | AGG Arg(R) |
| G | GTT Val(V) | GCT Ala(A) | GAT Asp(D) | GGT Gly(G) |
| | GTC Val(V) | GCC Ala(A) | GAC Asp(D) | GGC Gly(G) |
| | GTA Val(V) | GCA Ala(A) | GAA Glu(E) | GGA Gly(G) |
| | GTG Val(V) | GCG Ala(A) | GAG Glu(E) | GGG Gly(G) |

It is to be appreciated that any polynucleotide that encodes a polypeptide in accordance with the disclosure falls within the scope of this disclosure, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms.

Different factors have been proposed to contribute to codon usage preference, including translational selection, GC composition, strand-specific mutational bias, amino acid conservation, protein hydropathy, transcriptional selection and even RNA stability. One factor that determines codon usage is mutational bias that shapes genome GC composition. This factor is most significant in genomes with extreme base composition: species with high GC content (e.g., gram positive bacteria). Mutational bias is responsible not only for intergenetic difference in codon usage but also for codon usage bias within the same genome (Ermolaeva M, *Curr. Issues Mol. Biol.* 3(4):91-97, 2001).

Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The present disclosure relates to a polynucleotide comprising a codon-optimized coding region which encodes the mutant staphylococcal leukocidin subunit polypeptide (e.g., LukS-PV or LukF-PV, or both), as described herein. The codon usage is adapted for optimized expression in a given prokaryotic or eukaryotic host cell.

Codon-optimized polynucleotides are prepared by incorporating codons preferred for use in the genes of a given species into the DNA sequence. Also provided are polynucleotide expression constructs, vectors, host cells comprising polynucleotides comprising codon-optimized coding regions which encode the mutant staphylococcal leukocidin subunit polypeptide (e.g., LukS-PV or LukF-PV, or both), as described herein.

Given the large number of gene sequences available for a wide variety of animal, plant and microbial species, it is possible to calculate the relative frequencies of codon usage. Codon usage tables are readily available, for example, at the "Codon Usage Database" available on the world wide web at kazusa.or.jp/codon (visited Oct. 12, 2011), and these tables can be adapted in a number of ways. (Nakamura, Y., et al., "Codon usage tabulated from the international DNA sequence databases: status for the year 2000" *Nucl. Acids Res.* 28:292, 2000).

By utilizing available tables, one of ordinary skill in the art can apply the frequencies to any given polypeptide sequence, and produce a nucleic acid fragment of a codon-optimized coding region which encodes a desired polypeptide, but which uses codons optimal for a given species. For example, in some embodiments of the disclosure, the coding region is codon-optimized for expression in *E. coli.*

DNA Synthesis

A number of options are available for synthesizing codon optimized coding regions designed by any of the methods described above, using standard and routine molecular biological manipulations well known to those of ordinary skill in the art. In addition, gene synthesis is readily available commercially.

Vectors and Expression Systems

Further disclosed is a vector comprising the polynucleotide as described herein. The term "vector," as used herein, refers to e.g., any of a number of nucleic acids into which a desired sequence can be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct made up of genetic material (i.e., nucleic acids), in which the genetic material is extrachromosomal and in some instances, replicates autonomously. A polynucleotide described herein can be in a circular or linearized plasmid or in any other sort of vector. Procedures for inserting a nucleotide sequence into a vector, e.g., an expression vector, and transforming or transfecting into an appropriate host cell and cultivating under conditions suitable for expression are generally known in the art.

In accordance with one aspect of the disclosure, provided is a vector comprising a nucleic acid sequence encoding the mutant staphylococcal leukocidin subunit (e.g., LukS-PV or LukF-PV, or both), as described herein. In certain embodiments the vector is an expression vector capable of expressing the mutant staphylococcal leukocidin subunit (e.g., LukS-PV or LukF-PV, or both), as described herein in a suitable host cell. The term "expression vector" refers to a vector that is capable of expressing the polypeptide described herein, i.e., the vector sequence contains the regulatory sequences required for transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain embodiments, the host cell is a bacterium, e.g., *E. coli*.

Host cells are genetically engineered (infected, transduced, transformed, or transfected) with vectors of the disclosure. Thus, one aspect of the disclosure is directed to a host cell comprising a vector which contains the polynucleotide as describe herein. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., *E. coli*), transformed with recombinant bacteriophage DNA, plasmid DNA or cosmid DNA. In some embodiments, the plasmids used with *E. coli* use the T7 promoter-driven system regulated by the Lad protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiXl74, pBluescript SK, pbsks, pNH8A, pNH16a, pNH18A, pNH46A (Stratagene), ptrc99a, pKK223-3, pKK243-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences which can be operably joined to an inserted nucleotide sequence encoding the mutant staphylococcal leukocidin subunit (e.g., LukS-PV or LukF-PV, or both), as described herein. As used herein, the term "regulatory sequences" means nucleotide sequences which are necessary for or conducive to the transcription of an inserted sequence coding the mutant staphylococcal leukocidin subunit (e.g., LukS-PV or LukF-PV, or both), as described herein by a host cell and/or which are necessary for or conducive to the translation by a host cell of the resulting transcript into the desired mutant leukocidin subunit (e.g., LukS-PV or LukF-PV, or both). Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of *E. coli*, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, the polynucleotide as described herein can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are confirmed using restriction mapping, DNA sequence analysis, and/or PCR analysis. Bacterial cells harboring the correct plasmid can be stored as cell banks Immunogenic and Pharmaceutical Compositions Further disclosed are compositions, e.g., immunogenic or pharmaceutical compositions, that contain an effective amount of the mutant staphylococcal leukocidin subunit (e.g., LukS-PV or LukF-PV, or both), as described herein, or a polynucleotide encoding the polypeptide of the disclosure. Compositions as described herein can further comprise additional immunogenic components, e.g., as a multivalent vaccine, as well as carriers, excipients or adjuvants.

Compositions as described herein can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the disclosure can be administered directly to the subject. The subjects to be treated can be animals; in particular, human subjects can be treated.

Carriers that can be used with compositions of the disclosure are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions as described herein further include one or more adjuvants, a substance added to an immunogenic composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant. The term "immunogenic carrier" as used herein refers to a first moiety, e.g., a polypeptide or fragment, variant, or derivative thereof which enhances the immunogenicity of a second polypeptide or fragment, variant, or derivative thereof.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or $Th_2$ response into a primarily cellular, or $Th_1$ response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions described herein include, but are not limited to: inert carriers, such as alum, bentonite, latex, and acrylic particles; incomplete Freund's adjuvant, complete Freund's adjuvant; aluminum-based salts such as aluminum hydroxide; Alhydrogel ($Al(OH_3)$); aluminum phosphate ($AlPO_4$); calcium-based salts; silica; any TLR biological ligand(s); IDC-1001 (also known as GLA-SE; glucopyranosyl lipid adjuvant stable emulsion) (Coler et al., PLoS One, 2010. 5(10): p. e13677; Coler et al., PLoS One, 2011. 6(1): p. e16333); CpG (Mullen et al., PLoS One, 2008. 3(8): p. e2940), or any combination thereof. The amount of adjuvant, how it is formulated, and how it is administered all parameters which are well within the purview of a person of ordinary skill in the art.

In some embodiments, a composition of the disclosure further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, the polypeptide described herein can be incorporated as part of a liposome or other particle, or can be delivered in conjunction with a liposome. Liposomes for use in accordance with the disclosure can be formed from standard vesicle-forming lipids, which generally include neutral and negatively charged phospholipids and a sterol, such as cholesterol. A composition comprising a liposome or other particulate suspension as well as the polypeptide as described herein can be administered intravenously, locally, topically, etc. in a dose which varies according to, inter alia, the manner of administration, the polypeptide being delivered, and the stage of the disease being treated.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, the polypeptide as described herein, often at a concentration of 25%-75%.

For aerosol or mucosal administration, the polypeptide as described herein can be supplied in finely divided form, optionally along with a surfactant and, propellant and/or a mucoadhesive, e.g., chitosan. The surfactant must, of course, be pharmaceutically acceptable, and in some embodiments soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some embodiments 0.25-5% by weight. The balance of the composition is ordinarily propellant, although an atomizer can be used in which no propellant is necessary and other percentages are adjusted accordingly. In some embodiments, the immunogenic polypeptides can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

The disclosure is also directed to a method of producing the composition according to the disclosure. In some embodiments, the method of producing the composition comprises (a) isolating a polypeptide according to the disclosure; and (b) adding an adjuvant, carrier and/or excipient to the isolated polypeptide. Some embodiments disclose further combining the polypeptide with other staphylococcal antigens. staphylococcal antigens.

Some embodiments include a multivalent vaccine. A multivalent vaccine of the present disclosure comprises the mutant staphylococcal leukocidin subunit (e.g., LukS-PV or LukF-PV, or both), as described herein, or a polynucleotide encoding one or both subunits, and one or more additional immunogenic components. Such components can be additional immunogens of the same infectious agent, e.g., *S. aureus*, or from other staphylococci, or can be immunogens derived from other infectious agents which can be effectively, conveniently, or economically administered together. In certain embodiments, the mutant staphylococcal leukocidin subunit (e.g., LukS-PV or LukF-PV, or both), as described herein, can be combined with other toxins or other virulent component-based vaccines to make a broad toxin-based multivalent vaccine capable of targeting multiple bacterial virulence determinants. In other embodiments, the mutant staphylococcal leukocidin subunit (e.g., LukS-PV or LukF-PV, or both), as described herein, can be fused to other immunogenic, biologically significant, or protective epitope containing polypeptides to generate a multivalent vaccine in a single chain and induce an immune response against multiple antigens. In yet another embodiment, the mutant staphylococcal leukocidin subunit (e.g., LukS-PV or LukF-PV, or both), as described herein, can be fused to one or more T cell epitopes to induce T cell immunity along with anti PVL antibodies.

Methods of Treatment/Prevention and Regimens

Also provided is a method of treating or preventing *Staphylococcus* infection, e.g., *S. aureus* infection or treating or preventing a disease caused by *Staphylococcus*, e.g, *S. aureus* in a subject, comprising administering to a subject in need thereof a composition as described herein comprising the mutant staphylococcal leukocidin subunit (e.g., LukS-PV or LukF-PV, or both), as described herein, or polynucleotides, vectors, or host cells encoding same. In certain embodiments, the subject is an animal, e.g., a vertebrate, e.g., a mammal, e.g., a human. Some embodiments include a method of inducing an immune response against a *S. aureus* strain, comprising administering to a subject in need of said immune response an effective amount of a composition as described herein comprising the mutant staphylococcal leukocidin subunit (e.g., LukS-PV or LukF-PV, or both), as described herein, or polynucleotides, vectors, or host cells encoding same.

In some embodiments, a subject is administered a composition as described herein comprising the mutant staphylococcal leukocidin subunit (e.g., LukS-PV or LukF-PV, or both), as described herein, or polynucleotides, vectors, or host cells encoding same prophylactically, e.g., as a prophylactic vaccine, to establish or enhance immunity to *Staphylococcus*, e.g., *S. aureus*, in a healthy animal prior to potential or actual exposure to *Staphylococcus*, e.g., *S. aureus* or contraction of a *Staphylococcus*-related symptom, thus preventing disease, alleviating symptoms, reducing symptoms, or reducing the severity of disease symptoms. In one embodiment the disease is a respiratory disease, e.g., pneumonia. Other diseases or conditions to be treated or prevented include, but are not limited to, bacteremia, sepsis, skin infections, wound infections, endocarditis, bone and joint infections, osteomyelitis, and/or meningitis. One or more compositions, polypeptides, polynucleotides, vectors, or host cells as described herein can also be used to treat a subject already exposed to *Staphylococcus*, e.g., *S. aureus*, or already suffering from a *Staphylococcus* related symptom to further stimulate the immune system of the animal, thus reducing or eliminating the symptoms associated with that exposure. As defined herein, "treatment of an animal" refers to the use of one or more compositions, polypeptides, polynucleotides, vectors, or host cells of the disclosure to prevent, cure, retard, or reduce the severity of *S. aureus* symptoms in an animal, and/or result in no worsening of *S. aureus* symptoms over a specified period of time. It is not required that any composition, polypeptide, polynucleotide, a vector, or a host cell as described herein provides total protection against a staphylococcal infection or totally cure or eliminate all *Staphylococcus* related symptoms.

As used herein, "a subject in need of therapeutic and/or preventative immunity" refers to a subject in which it is desirable to treat, i.e., to prevent, cure, retard, or reduce the severity of *Staphylococcus* related symptoms, or result in no worsening of *Staphylococcus* related symptoms over a specified period of time. As used herein, "a subject in need of the immune response" refers to a subject for which an immune response(s) against any of PVL expressing Staphylococcal strains is desired.

Treatment with pharmaceutical compositions comprising an immunogenic composition, polypeptide or polynucleotide as described herein can occur separately or in conjunction with other treatments, as appropriate.

In therapeutic applications, a composition, polypeptide or polynucleotide of the disclosure is administered to a patient in an amount sufficient to elicit an effective innate, humoral or cellular response, or both, to the *S. aureus* PVL derived polypeptide to cure or at least partially arrest symptoms or complications.

An amount adequate to accomplish this is defined as "therapeutically effective dose" or "unit dose." Amounts effective for this use will depend on, e.g., the polypeptide or polynucleotide composition, the manner of administration, the stage and severity of the disease being treated, the weight and general state of health of the patient, and the judgment of the prescribing physician, but generally range for the initial immunization for polypeptide vaccines is (that is for therapeutic or prophylactic administration) from about e.g., 0.1 μg to about 5000 μg of polypeptide, depending upon the patient's response and condition by measuring, for example, antibody levels in the patient's blood. In some embodiments, a priming dose is followed by a boosting dose over a period of time.

In non-limiting embodiments of the disclosure, an effective amount of a composition as disclosed herein produces an elevation of antibody titer to at least 2, 5, 10, 50, 100, 500, 1000, 5000, 10^4, 5×10^4, or 10^5 times the antibody titer prior to administration.

In alternative embodiments, generally for humans an initial immunization (that is for therapeutic or prophylactic administration) is administered followed by boosting dosages in the same dose range pursuant to a boosting regimen over weeks to months depending upon the patient's response and condition by measuring the antibody or T lymphocyte response in the patient's blood.

It must be kept in mind that the polypeptides and compositions as described herein can generally be employed in serious disease states, that is, life-threatening or potentially life threatening situations. In such cases, in view of the minimization of extraneous substances and the relative nontoxic nature of the polypeptides, it is possible and can be felt desirable by the treating physician to administer substantial excesses of these polypeptide compositions.

For therapeutic use, administration should begin at the first sign of *S. aureus* infection or risk factors. In certain embodiments, the initial dose is followed by boosting doses until, e.g., symptoms are substantially abated and for a period thereafter. In frequent infection, loading doses followed by boosting doses can be required.

In certain embodiments, the composition as described herein is delivered to a subject by methods described herein, thereby achieving an effective immune response, and/or an effective therapeutic or preventative immune response. Any mode of administration can be used so long as the mode results in the delivery and/or expression of the desired polypeptide in the desired tissue, in an amount sufficient to generate an immune response to *Staphylococcus*, e.g., *S. aureus*, and/or to generate a prophylactically or therapeutically effective immune response to *Staphylococcus*, e.g., to *S. aureus*, in an animal in need of such response. According to the disclosed methods, a composition described herein can be administered by mucosal delivery, transdermal delivery, subcutaneous injection, intravenous injection, oral administration, pulmonary administration, intramuscular (i.m.) administration, or via intraperitoneal injection. Other suitable routes of administration include, but not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired polypeptide in an amount sufficient to generate an immune response to *Staphylococcus*, e.g., *S. aureus*, and/or to generate a prophylactically or therapeutically effective immune response to *Staphylococcus*, e.g., *S. aureus*, in an animal in need of such response. Administration as described herein can be by e.g., needle injection, or other delivery or devices known in the art.

In some embodiments, a composition comprising the mutant staphylococcal leukocidin subunit (e.g., LukS-PV or LukF-PV, or both), as described herein, or polynucleotides, vectors, or host cells encoding same, stimulate an antibody response or a cell-mediated immune response sufficient for protection of an animal against *Staphylococcus*, e.g., *S. aureus* infection. In other embodiments, a composition comprising the mutant staphylococcal leukocidin subunit (e.g., LukS-PV or LukF-PV, or both), as described herein, or polynucleotides, vectors, or host cells encoding same, stimulate both a humoral and a cell-mediated response, the combination of which is sufficient for protection of an animal against *Staphylococcus*, e.g., *S. aureus* infection. In some embodiments, a composition comprising the mutant staphylococcal leukocidin subunit (e.g., LukS-PV or LukF-PV, or both), as described herein, or polynucleotides, vectors, or host cells encoding same, further stimulates an innate, an antibody, and/or a cellular immune response.

In some embodiments, a composition comprising the mutant staphylococcal leukocidin subunit (e.g., LukS-PV or LukF-PV, or both), as described herein, or polynucleotides, vectors, or host cells encoding same, induce antibody responses to *S. aureus* PVL. In certain embodiments, components that induce T cell responses (e.g., T cell epitopes) are combined with components such as the polypeptides as described herein that primarily induce an antibody response.

Further disclosed is a method for generating, enhancing, or modulating a protective and/or therapeutic immune response to *S. aureus* infection in a subject, comprising administering to a subject in need of therapeutic and/or preventative immunity one or more of the compositions as described herein.

The compositions as described herein can be administered to an animal at any time during the lifecycle of the animal to which it is being administered. In humans, administration of the composition as described herein can, and often advantageously occurs while other vaccines are being administered, e.g., as a multivalent vaccine as described elsewhere herein.

Furthermore, the composition as described herein can be used in any desired immunization or administration regimen; e.g., in a single administration or alternatively as part of periodic vaccination regimes such as annual vaccinations, or as in a prime-boost regime in which composition or polypeptide or polynucleotide of the disclosure is administered either before or after the administration of the same or of a different polypeptide or polynucleotide. Recent studies have indicated that a prime-boost protocol is often a suitable method of administering vaccines. In a prime-boost protocol, one or more compositions as described herein can be utilized in a "prime boost" regimen. An example of a "prime boost" regimen can be found in Yang, Z. et al. *J. Virol.* 77:799-803, 2002, which is incorporated herein by reference in its entirety.

Infections to be treated include, but are not limited to a localized or systemic infection of skin, soft tissue, blood, or an organ or an auto-immune disease. Specific diseases or conditions to be treated or prevented include, but are not limited to, respiratory diseases, e.g., pneumonia, sepsis, skin infections, wound infections, endocarditis, bone and joint infections, osteomyelitis, and/or meningitis.

Immune Correlates

A number of animal models for *S. aureus* infection are known in the art, and can be used with the methods disclosed herein without undue experimentation. For example, a hamster model of methicillin-resistant *Staphylococcus aureus* (MRSA) pneumonia has been described for the testing of antimicrobials. (Verghese A. et al., *Chemotherapy.* 34:497-503 (1988), Kephart P A. et al. J Antimicrob *Chemother.* 21:33-9, (1988)). Further, a model of *S. aureus-induced* pneumonia in adult, immunocompetent C57BL/6J mice is described, which closely mimics the clinical and pathological features of pneumonia in human patients. (Bubeck-Wardenburg J. et al., *Infect Immun.* 75:1040-4 (2007)). Additionally, virulence has been tested in a rat model of *S. aureus* pneumonia as described in McElroy et al. (McElroy M C. et al., *Infect Immun.* 67:5541-4 (1999)). Finally, a standardized and reproducible model of MRSA-induced septic pneumonia to evaluate new therapies was established in sheep. (Enkhbaatar P. et al., *Shock.* 29(5):642-9 (2008)).

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt, I., Brostoff, J. and Male D., Immunology, $6^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

EXAMPLES

Example 1

Molecular Modeling and Design of Vaccine Candidates

This example describes molecular modeling (computer based) techniques for deriving, analyzing and manipulating the structure of Panton-Valentine leukocidin (PVL) LukF-PV and LukS-PV subunits in order to design vaccine candidates.

To develop a vaccine that is composed of attenuated forms of LukF-PV and/or LukS-PV, the subunits were modified to avoid in vivo pore assembly and the cytolytic and inflammatory effects that occur upon pore formation. To identify regions on the LukF-PV and LukS-PV protein surfaces that may be amenable to mutations that abolish pore-formation without disrupting the structural integrity of each subunit, the structure of the LukF-PV/LukS-PV heterodimer and octamer was modeled as described in Aman et al. *J Biomol Struct Dyn* 28, 1-12, 2010. Briefly, LukF-PV and LukS-PV monomers were extracted from the 1PVL and 1T5R crystal structures, respectively. Missing residues in each structure were modeled into the polypeptide. The resulting structures were energy refined using tethered minimization. Since each subunit possesses two interacting faces in the octamer ring-like structure, it was necessary to construct two different LukF-PV/LukS-PV heterodimer models to fully elucidate the binding interactions on each subunit. These two molecular models were identified as $F_R$-$S_L$, and $S_L$-$F_R$. This nomenclature is based on the side-by-side relationship of the LukF-PV and LukS-PV constituents in the octameric ring-like structure. F and S represent the two classes, and subscript R and L denote right and left faces, respectively. If one views the two subunits from inside the channel lumen, in the FR-SL model, the right side of LukF-PV ($F_R$) is bound with the left side of LukS-PV ($S_L$) and alternatively, in the $S_L$-$F_R$ model, the right side of LukS-PV ($S_L$) is bound with the left side of LukF-PV ($F_R$). The Discovery Studio 2.1 (Accelrys, Inc) program running on a Dell Precision 690 with Red Hat Enterprise Linux 4 was used to build, visualize, and analyze the protein models. Simulations were performed in vacuo using a distance-dependent dielectric of 1 and nonbonded interactions limited to within 14 Å in a CHARMM force-field. The template in the model building is disclosed in Aman et al.

Figure 1:
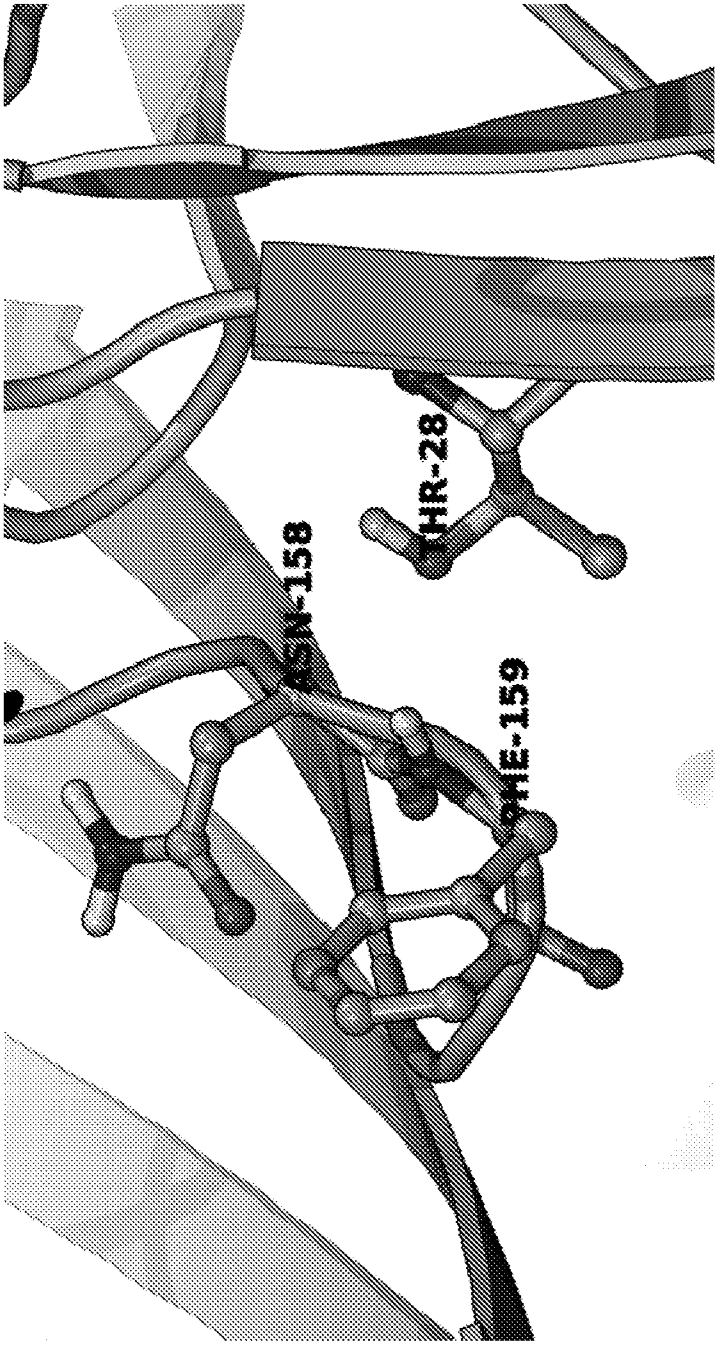
FIG. 1—Interface interactions between Thr28 of LukS-PV and Asn158 and Phe159 of LukF-PV.

The $F_R$-$S_L$ model shows that the Thr28 side chain is tightly packed against the polypeptide backbone of residues Asn158 and Phe159 in the neighboring LukF-PV subunit (FIG. 1).

To identify other interaction sites that may be crucial to oligomerization, molecular modeling as described above was used to scan the $F_R$-$S_L$ and $S_R$-$F_L$ interfaces in the PVL octamer model for hotspots that, if mutated, would significantly shift the monomer-dimer equilibrium constant in favor of monomer. In mature LukS-PV, these sites were Tyr131 and Ser209, which were identified from the $F_R$-$S_L$ interface model and Lys97 and Asp101 from the $S_R$-$F_L$ model. The corresponding sites in mature LukF-PV were Lys102 and Asp121 in the $F_R$-$S_L$ model and Glu147 and Asn220 in the $S_R$-$F_L$ model.

Figure 2:
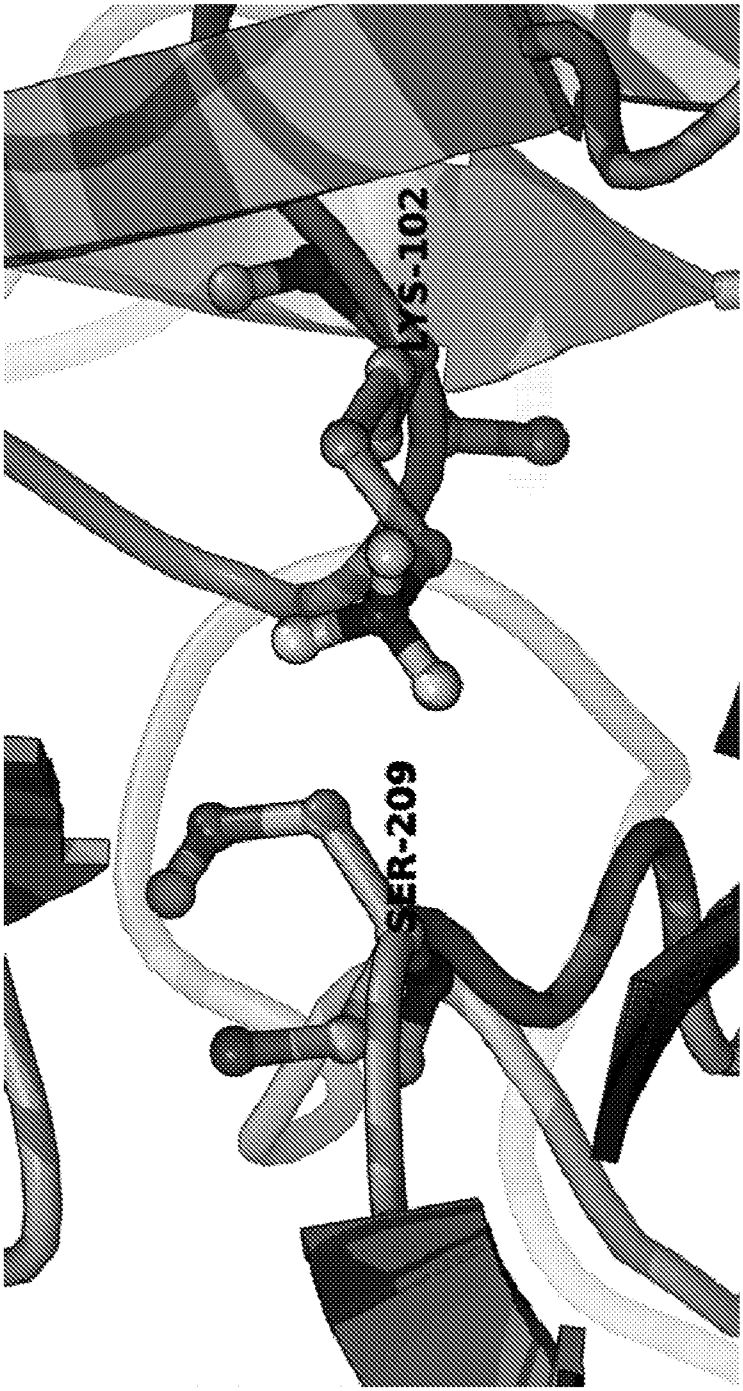
FIG. 2—Interface interaction between Ser209 of LukS-PV and Lys102 of LukF-PV.

As one of the metrics used to determine the effect of each mutant on dimerization, the positions were mutated to alanine in silico for residues outside of Thr28 and to phenylalanine for Thr28. The single- and double-point mutant complexes were energy minimized, and their molecular energies were calculated relative to wild-type. Similar alanine mutations of Lys97, Asp101 and Tyr131 in LukS-PV and of Lys102, Asp121, and Glu147 in LukF-PV in the molecular models resulted in significant increases in the calculated energy of the complex relative to wild-type (see Table 1 above). The most dramatic increase in destabilization energy was observed for the Ser209Ala mutant of LukS-PV. Ser209 connects loop and strand structures in LukS-PV and is buried near the middle of the dimer interface between Ser209 of LukS-PV and Lys 102 of LukF-PV (FIG. 2).

Single point mutations at the above-described sites were predicted to shift the monomer-heterodimer equilibrium of PVL in favor of monomers, and these mutants were selected as candidates for vaccine development.

Thr28 on LukS-PV has been reported in the literature to play a role in dimerization (V. Guillet et al., *The Journal of Biological Chemistry* 279: 41028-41037 (2004)). The potential utility of Thr28 in double mutants was examined. In this preliminary analysis, the double mutants Thr28Phe/Tyr131Ala and Thr28Phe/Ser209Ala as well as a triple mutant Thr28Phe/Tyr131Ala/Ser209Ala was investigated in silico. Based on energy calculations, the Thr28Phe/Ser209Ala mutant followed by the triple mutant had the most significant effect. Table 1 also lists the calculated energy increase in the heterodimer complex structure as a result of the different proposed single and double mutations of LukS-PV.

Example 2

Generation of LukS-PV and LukF-PV Mutants

Mutations were designed based on the octameric model and were introduced into cDNA constructs for LukS-PV and LukF-PV that carried a N-Terminal 6xHis tag for purification purposes. Wild-type LukS-PV and LukF-PV DNA fragments encoding the respective mature protein sequences were synthesized by PCR, treated by BamHI and KpnI restriction enzymes to create cohesive ends, and cloned into pQE30 vector (Qiagen) digested by BamHI and KpnI restriction enzymes. Mutations were introduced into DNA by using the QickChange$^R$ II Site-Directed Mutagenesis Kit (Stratagene). The nucleotide sequence of the plasmid construct encoding the wild-type LukS-PV is presented as SEQ ID NO: 123. The nucleotide sequence of the plasmid construct encoding the mutant (K97A) LukS-PV is presented as SEQ ID NO: 124. The nucleotide sequence of the plasmid construct encoding the mutant (D102A) LukS-PV is presented as SEQ ID NO: 125. The nucleotide sequence of the plasmid construct encoding the mutant (Y131A) LukS-PV is presented as SEQ ID NO: 126. The nucleotide sequence of the plasmid construct encoding the mutant (5209A) LukS-PV is presented as SEQ ID NO: 127. The nucleotide sequence of the plasmid construct encoding the mutant (T28F) LukS-PV is presented as SEQ ID NO: 128. The nucleotide sequence of the plasmid construct encoding the mutant (T28F/Y131A) LukS-PV is presented as SEQ ID NO: 129. The nucleotide sequence of the plasmid construct encoding the mutant (T28F/S209A) LukS-PV is presented as SEQ ID NO: 130. The nucleotide sequence of the plasmid construct encoding the mutant (T28F/K97A/S209A) LukS-PV is presented as SEQ ID NO: 131. The nucleotide sequence of the plasmid construct encoding the wild-type LukF-PV is presented as SEQ ID NO: 132. The nucleotide sequence of the plasmid construct encoding the mutant (K102A) LukF-PV is presented as SEQ ID NO: 133. The nucleotide sequence of the plasmid construct encoding the mutant (D121A) LukF-PV is presented as SEQ ID NO: 134. The nucleotide sequence of the plasmid construct encoding the mutant (E147A) LukF-PV is presented as SEQ ID NO: 135.

A plasmid construct encoding the LukF-PV triple mutant (K102A/D121A/E147A) listed in Table 1 was also generated as described above. The mature protein sequence of the LukF-PV Triple Mutant (Lys102Ala (K102A)/Asp121Ala (D121A)/Glu147Ala (E147A)) is shown below with the mutated amino acids underlined and presented as SEQ ID NO: 136:

```
  1 aqhitpvsek kvddkitlyk ttatsdsdkl kisqiltfnf
    ikdksydkdt lilkaagniy

 61 sgytkpnpkd tissqfywgs kynisinsds ndsvnvvdya
    panqneefqv qqtvgysygg

121 ainisnglsg ggngsksfse tinykqasyr tsldkrtnfk
    kigwdveahk imnngwgpyg

181 rdsyhstygn emflgsrqsn lnagqnfley hkmpvlsrgn
    fnpefigvls rkqnaakksk

241 itvtyqremd rytnfwnqlh wignnykden rathtsiyev
    dwenhtvkli dtqskeknpm

301 s
```

The nucleotide sequence of the plasmid construct encoding the triple mutant (K102A/D121A/E147A) LukF-PV is shown below (cloning sites BamHI and KpnI are underlined, the mutations are double underlined, and the termination codon is in italics) and presented as SEQ ID NO: 137:

```
ATGAGAGGATCGCATCACCATCACCATCACGGATCCGCTCAACATATCAC
ACCTGTAAGTGAGAAAAAGGTTGATGATAAAATTACTTTGTACAAAACAA
CTGCAACATCAGATTCCGATAAGTTAAAAATTTCTCAGATTTTAACTTTT
AATTTTATTAAAGATAAAAGTTATGATAAAGATACATTAATACTCAAAGC
TGCTGGAAACATTTATTCTGGCTATACAAAGCCAAATCCAAAAGACACTA
TTAGTTCTCAATTTTATTGGGGTTCTAAGTACAACATTTCAATTAATTCA
GATTCTAATGACTCAGTAAACGTTGTAGATTATGCACCTGCAAATCAAAA
TGAAGAATTTCAAGTACAACAAACGGTAGGTTATTCTTATGGTGGAGCTA
TTAATATCTCTAACGGCTTATCAGGTGGAGGTAATGGTTCAAAATCTTTT
TCAGAGACAATTAACTATAAACAAGCAAGCTATAGAACTAGCTTAGATAA
AAGAACTAATTTCAAAAAAATTGGTTGGGATGTTGAAGCACATAAAATTA
TGAATAATGGTTGGGGACCATATGGCAGAGATAGTTATCATTCAACTTAT
GGTAATGAAATGTTTTTAGGCTCAAGACAAAGCAACTTAAATGCTGGACA
AAACTTCTTGGAATATCACAAAATGCCAGTGTTATCCAGAGGTAACTTCA
ATCCAGAATTTATTGGTGTCCTATCTCGAAAACAAAACGCTGCAAAAAAA
```

-continued

```
TCAAAAATTACTGTTACTTATCAAAGAGAAATGGATAGATATACAAACTT
TTGGAATCAACTTCACTGGATAGGTAATAATTATAAAGATGAAAATAGAG
CAACTCATACATCAATTTATGAAGTTGATTGGGAAAATCATACAGTTAAA
TTAATAGATACTCAATCTAAGGAAAAAAATCCTATGAGCTAAGGTACC
```

The mutants, which were selected based on structural analysis described above, included five single, two double and one triple mutants of LukS-PV as well as four single and one triple mutants of LukF-PV (Table 1). The mutant proteins along with the His-tagged wild-type subunits were produced in *E. coli* strain XL1-Blue [recA1 endA1 gyrA96 thi-1 hsdR17 supE44 relA1 lac [F' proAB lacIqZΔM15 Tn10 (Tetr)] and purified on a HisTrap™ HP column (GE Healthcare Cat#17-5248-02) used according to the manufacturer's instructions. All proteins were quality controlled by SDS-PAGE (Sodium Dodecyl Sulfate-Polyacrylamide Gel Electrophoresis) using common techniques and western blotting with respective antibodies (LukS-PV: V5184 rabbit polyclonal Ab (Genscript), LukF-PV: 1A11 mA (IBT)).

Figure 7:
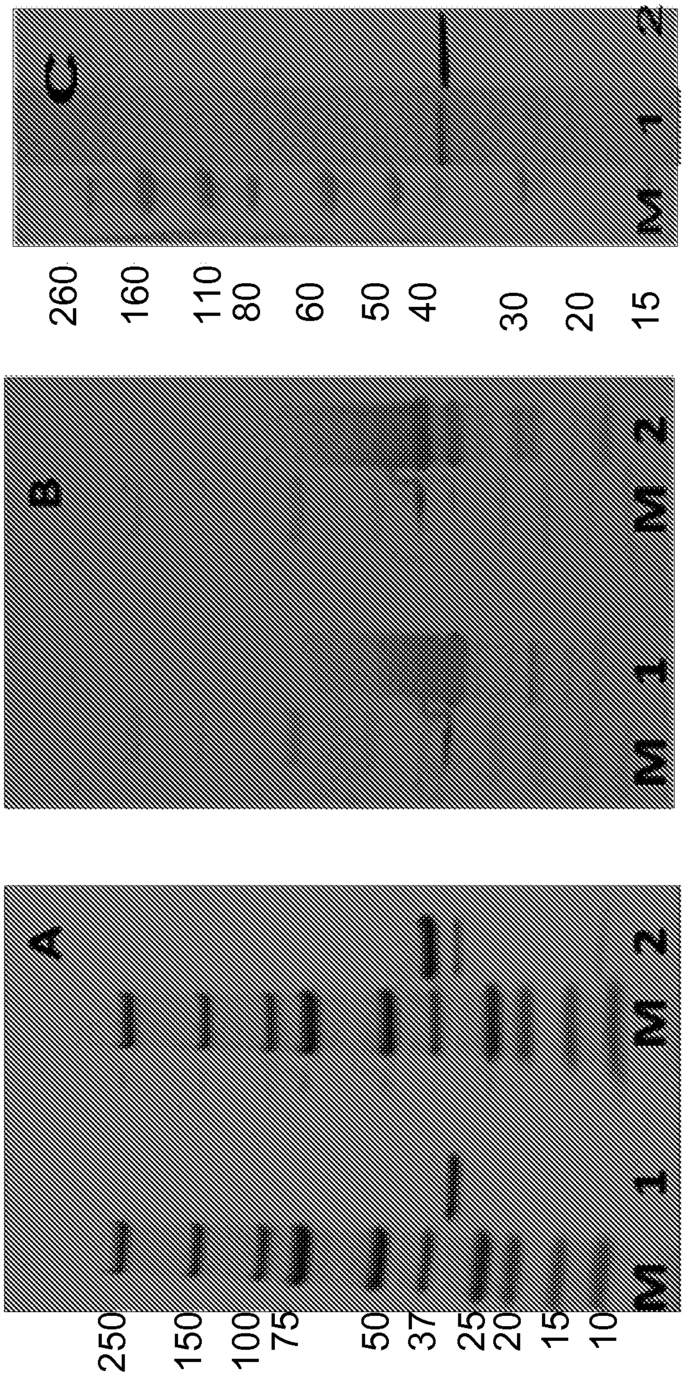
FIG. 7—(A) SDS-PAGE and (B) Western blot analysis of mutant PVL subunits. M: MW marker; Lane 1: LukS-PV Mut9; Lane 2: LukF-PV Mut1. (C) SDS-PAGE (Lane 1) and Western blot (Lane 2) analysis of LukF-PV triple mutant (K102A/D121A/E147A); M: MW marker.

SDS-PAGE and Western blot analysis of LukS-PV Mut9, LukF-PV Mut1 and LukF-PV triple mutant (K102A/D121A/E147A) are shown in FIG. 7A-C.

Example 3

Attenuation of LukS-PV and LukF-PV Mutants

Each of the LukS-PV and LukF-PV mutants were tested in a neutrophil toxicity assay in combination with the wild-type LukF-PV, or LukS-PV, respectively. Using a 96-well round bottom tissue culture plate, the wild-type or mutant LukS-PV or LukF-PV proteins were semi-log diluted in duplicates down the plate in assay media (RPMI, 2% FBS, 5 mM glutamine) followed by addition of $5\times10^5$ DMSO induced HL-60 cells. HL-60 cells were differentiated into neutrophils by treatment with DMSO. The suspension was gently tapped and plates incubated for 48 hours at 37° C. with 5% $CO_2$ and 95% humidity. To determine cellular viability, 20 μL of 2 mg/mL diluted XTT (Sigma-Aldrich, St. Louis, Mo.) was added to each well, incubated for 6 hours at 37° C. with 5% $CO_2$ and 95% humidity, centrifuged and supernatant transferred to an ELISA plate and read to 470 nm. The percent (%) viability was determined as follows: % Viability ═(OD value of Experimental Sample Well/OD value of HL-60 cells without PVL Toxin)×100. The data are presented as % cell survival in FIGS. 3 and 4.

Figure 3:
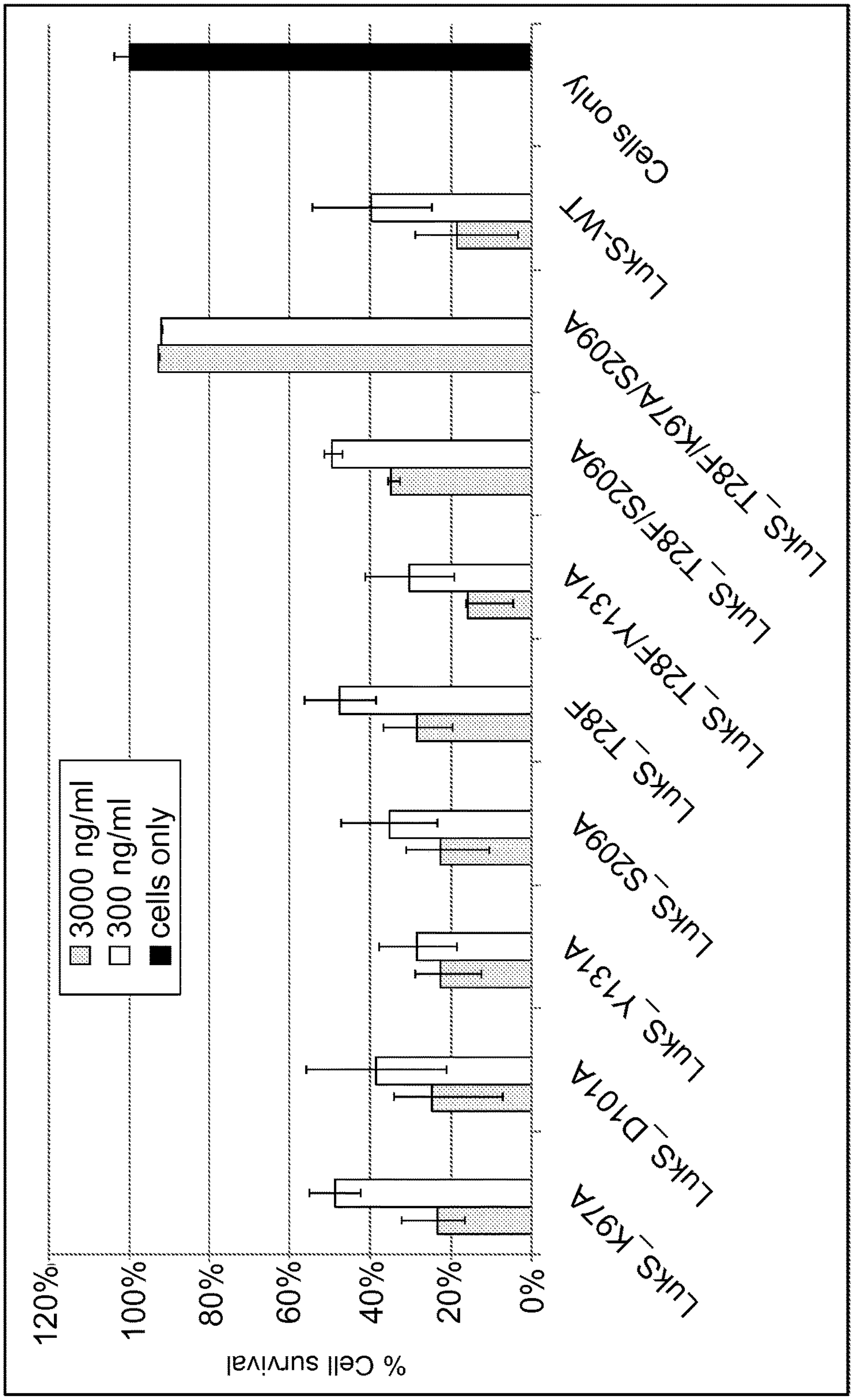
FIG. 3—Percent (%) survival of HL-60 derived neutrophils in the presence of 3000 or 300 ng/ml of LukS-PV mutants (K97A, D101A, S209A, T28F, T28F/Y131A, T28F/S209A, or T28F/K97A/S209A) or the wild-type LukS-PV along with the same concentrations of the wild-type LukF-PV. Cells only bar represents the control with no toxin added. Data are shown as average of 3-5 experiments with standard deviation shown as error bars.

Mutant LukS-PV data showed that while each of the single mutants or double mutants slightly reduced the toxicity of LukS-PV in complex with the wild-type LukF-PV, a triple mutant combining the mutations T28F, K97A, and 5209A led to nearly complete attenuation. In the presence of the triple mutant combined with the wild-type LukF-PV, over 90% of cells remained viable (FIG. 3).

Figure 4:
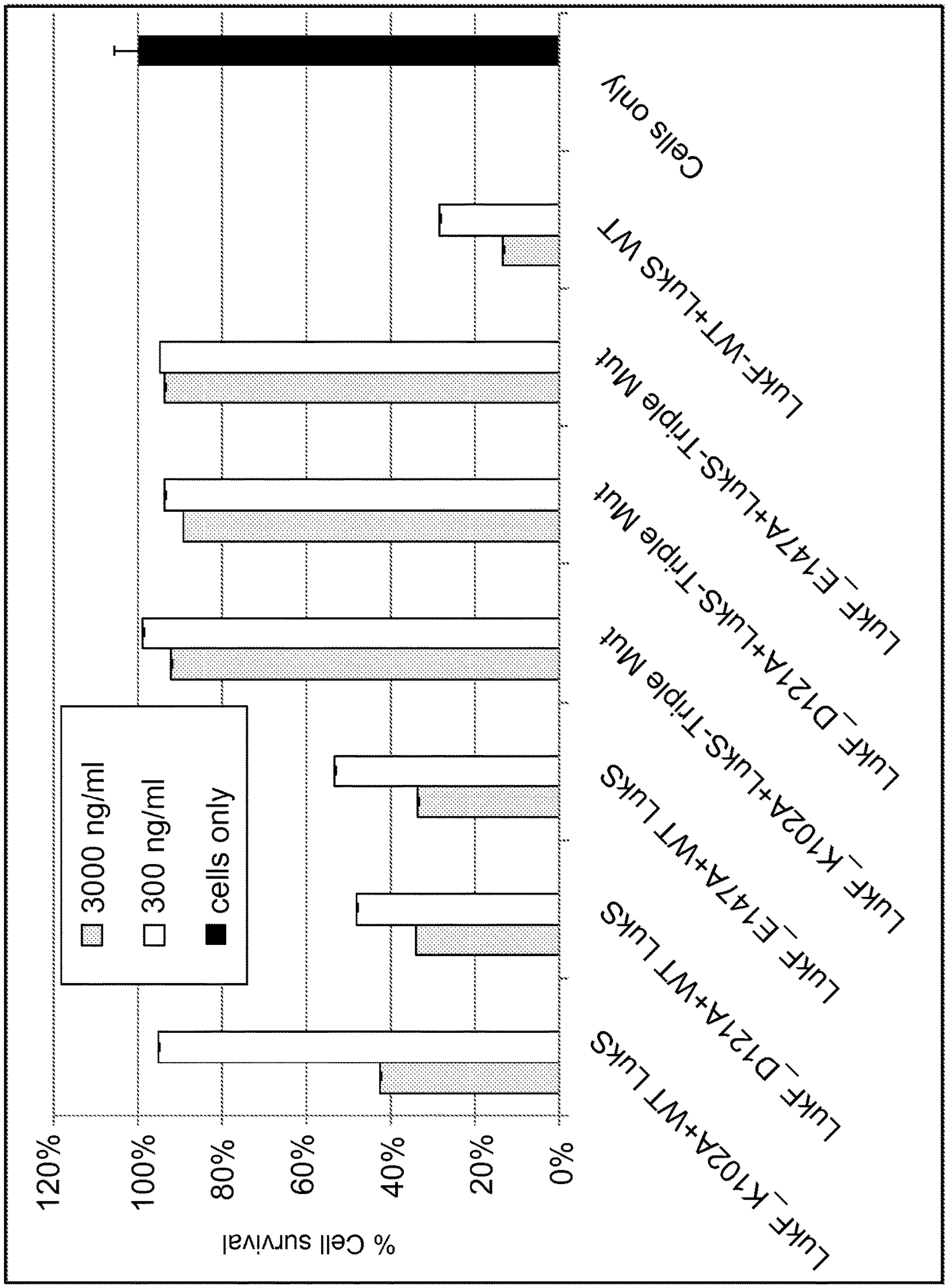
FIG. 4—Percent (%) survival of HL-60 derived neutrophils in the presence of 3000 or 300 ng/ml of LukF-PV mutants (K102A, D121A, or E147A) or the wild-type LukF-PV along with the same concentrations of the wild-type LukS-PV or triple mutant of LukS-PV as defined in FIG. 3. Cells only bar represents the control with no toxin added.

Mutant LukF-PV proteins were tested in a neutrophil toxicity assay as described above, in combination with the wild-type LukS-PV or LukS-PV triple mutant (T28F, K97A, and 5209A). As shown in FIG. 4, each of the single mutations reduced the toxicity of LukF-PV when combined with the wild-type LukS-PV. *Of* the three LukF-PV mutants tested, the K102A mutant showed the highest degree of attenuation with complete loss of toxicity at 300 ng/ml and about 50% reduced toxicity at 3000 ng/ml. When combined with the LukS-PV triple mutant all three LukF-PV mutants (LukF K102A, LukF D121A and LukF E147A) showed complete inactivation.

Example 4

Polyclonal Antibodies to PVL Protect Mice from Lethal Challenge with Community Acquired *S. aureus* Strain USA300 (LAC)

The ability of anti-PVL polyclonal antibodies to protect against bacteremia caused by *S. aureus* USA300 in mice was tested. For this study polyclonal antibodies were generated in rabbits by immunizing with His-tagged protein containing the wild-type sequence of LukS-PV presented by SEQ ID NO: 6 and an N-terminal 6xHis tag. Polyclonal antibodies (total IgG) were purified from hyperimmune serum over a protein G column. Furthermore, specific anti-LukS-PV antibodies were purified from total IgG using AminoLink® Plus Immobilization Kit (Thermoscientific). The Kit included reagents, column and buffers needed to make the affinity column packed with beads. Beads coupled with LukS-PV protein and affinity purification of polyclonal anti-LukS-PV antibody was carried out according to the manufacturer's protocol. Furthermore, to test the ability of anti-LukS-PV antibodies to synergize with anti-α-hemolysin antibodies (Hla), combinations of anti-LukS-PV and anti-Hla polyclonal antibodies were examined. A model as disclosed in Fattom et al., *Infect Immun* 64, 1659-1665, 1996, in which BALB/c mice were challenged via intraperitoneal route with *S. aureus* mixed with Hog-Mucin was applied. Mice were pre-treated with the indicated antibodies 24 hour prior to challenge. Naïve mouse IgG was used as control. After challenge with $5\times10^4$ USA300 and 3% Hog-Mucin (Sigma-Aldrich, St. Louis, Mo.), mice were monitored for morbidity and mortality for 5 days. As shown in Table 3, all mice treated with naïve mouse IgG succumbed to death within 16-20 hours post challenge. In contrast, 3 out of 5 mice who received 50 ug of purified anti-LukS-PV and 2 out of 5 mice who received 2 mg of anti-Hla total IgG survived suggesting that each component contributes to protection. When 2 mg of anti-Hla IgG was combined with 50 or 25 μg of purified anti LukS-PV antibodies, 100% survival was observed. Lower dose of purified anti-LukS-PV (12.5 μg) when added to anti-Hla lead to 80% survival which was higher than the survival achieved by either component alone. These data suggest that vaccination with a combination of LukS-PV or Hla vaccines may lead to additive or synergistic protective effect against *S. aureus* bacteremia.

TABLE 3

Protection against USA300 bacteremia by antibodies to LukS-PV and Hla

| Group # | N | Anti-LukS (affinity Purified) | Anti-Hla (Total IgG) | Naïve mouse IgG | % Survival 16 h | 20 h | 36 h | 48 h | 120 h |
|---|---|---|---|---|---|---|---|---|---|
| 1 | 5 | 50 ug | 2 mg | 0 | 100% | 100% | 100% | 100% | 100% |
| 2 | 5 | 25 ug | 2 mg | 0 | 100% | 100% | 100% | 100% | 100% |
| 3 | 5 | 12.5 ug | 2 mg | 0 | 80% | 80% | 80% | 80% | 80% |
| 4 | 5 | 50 ug | 0 | 0 | 100% | 60% | 60% | 60% | 60% |
| 5 | 5 | 0 | 2 mg | 0 | 60% | 40% | 40% | 40% | 40% |
| 6 | 5 | 0 | 0 | 2 mg | 60% | 0% | 0% | 0% | 0% |

Example 5

Sequence Identity for Staphylococcal Two Component Pore-forming Toxins

The sequence identity between LukS, LukM, LukM, LukE, and HIgA/S was compared. *S. aureus* γ-hemolysin (Hlg), leukocidin (Luk) and PVL are related two-component pore-forming toxins (Kaneko et al., Biosci Biotechnol Biochem, 2004. 68(5): p. 981-1003).

Figure 5:
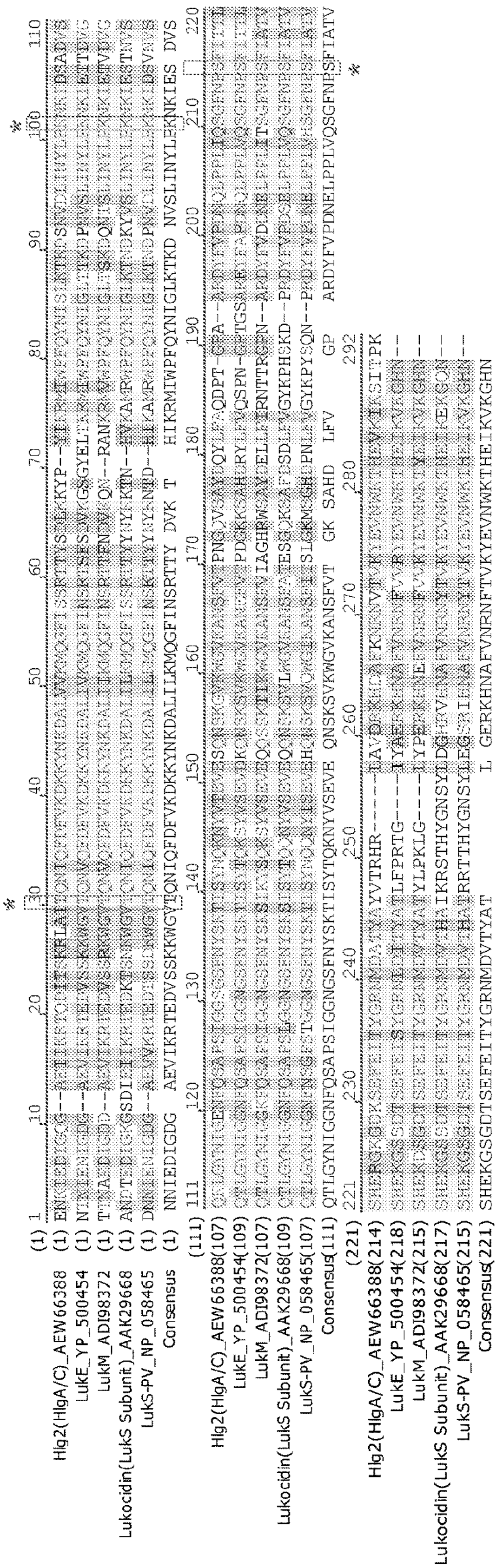
FIG. 5—Alignments of S subunits of leukocidins amino acid sequences. Hlg2(HlgA/C)_AEW66388 (SEQ ID NO: 138); LukE_YP_500454 (SEQ ID NO: 139); Luk-M_ADI98372 (SEQ ID NO: 140); Leucocidin (LukS Subunit)_AAK29668 (SEQ ID NO: 141); LukS-PV_NP_058465 (SEQ ID NO: 142); Consensus (SEQ ID NO: 143).
Figure 6:
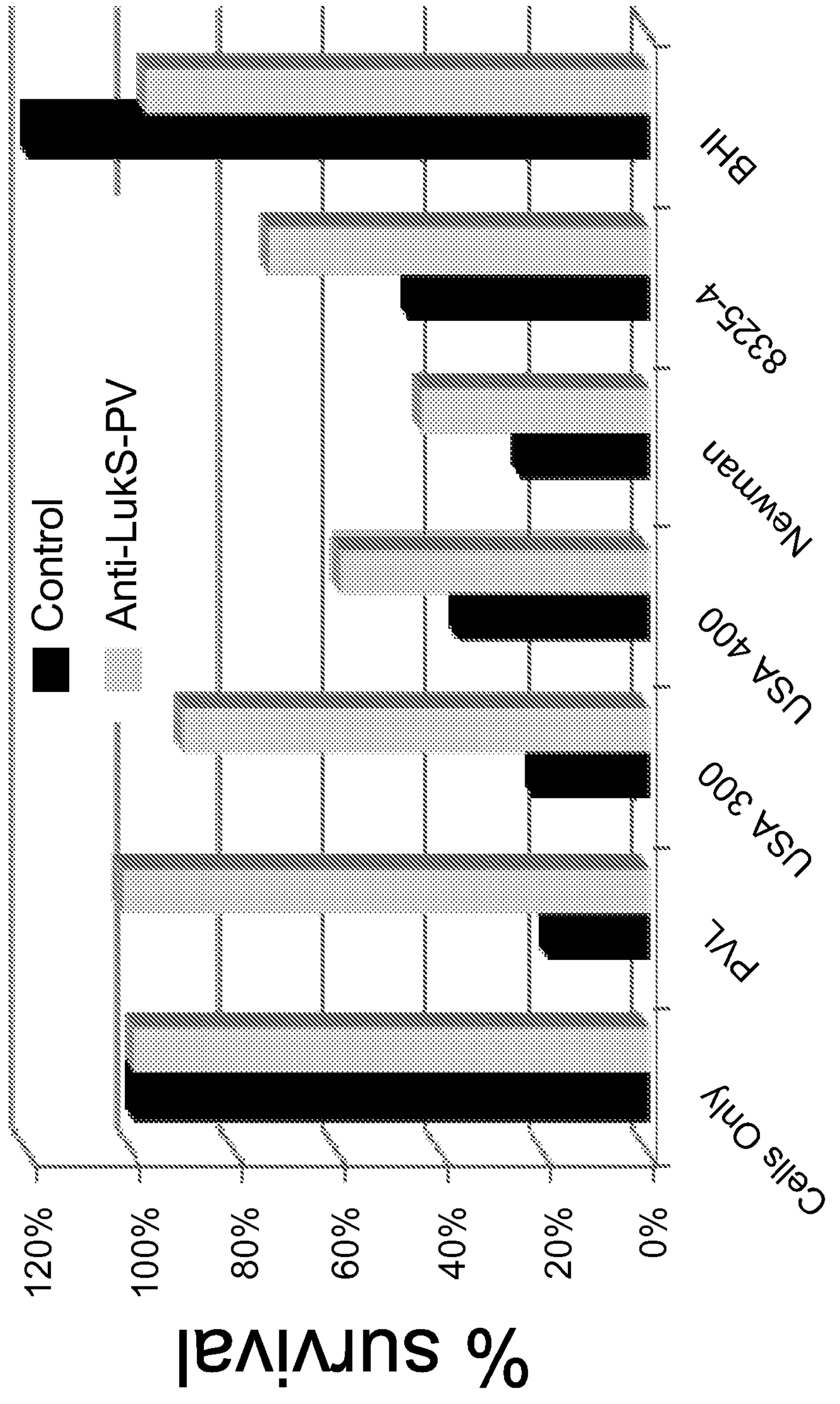
FIG. 6—Percent (%) survival of polymorphonuclear neutrophils (PMN) in supernatants of PVL positive (USA300&400) and PVL negative (Newman, 8325-4) SA strains treated with anti-LukS-PV or control (rabbit total IgG). PVL: purified PVL; BHI: medium control; and Cells only: control with no toxin added.

LukS-PV has high sequence identity with LukS, LukM, LukE, and HIgA/C ranging from 65% to 81% as shown in FIG. 5. All three sites mutagenized in the attenuated triple mutant LukS-PV vaccine candidate tested herein were shown to be conserved throughout the family (shown in box with * in FIG. 5). Similarly, LukF-PV was shown to be highly homologous to LukF, LukD, LukDv, and HlgB, and the sites mutated in the LukS-PV vaccines tested herein were conserved. Consistent with this homology, it was shown that LukS-PV polyclonal antibodies inhibited cytotoxic activity towards PMNs in the supernatants of not only PVL-positive strains (USA300&400) but also in PVL deficient strains such as Newman and 8325-4 (FIG. 6). These data showed that antibodies elicited against PVL subunits showed broader reactivity and neutralized non-PVL leukocidins.

Example 6

In Vitro Structural and Functional Characterization of Mutant Proteins

Functional activity of LukS-PV and LukF-PV mutants disclosed herein was tested in a cytotoxicity assay using HL-60 cells differentiated to neutrophils (Romero-Steiner et al., Clin Diagn Lab Immunol, 1997. 4(4): p. 415-22). To ensure the structural integrity of the mutants, these proteins along with wild-type counterparts were analyzed by circular dichroism (CD) spectrometry. Furthermore, the thermal stability of the proteins was determined using Differential Scanning Fluorimetry (DSF).

Analysis of cytotoxicity: Cellular cytotoxicity was tested using a combination of each mutant subunit with the wild-type form of the other subunit using HL-60 cells (ATCC, Catalog Number CCL-240) differentiated in vitro into neutrophils (Romero-Steiner et al.). The HL-60 cells were propagated in RPMI/15% FBS and 1.6% dimethylsulfoxide (DMSO) for 6 days. The differentiated neutrophil-like cells were harvested and transferred to 96 well plates for PVL toxicity assay at a final density of $5\times10^5$ cells/well. Each PVL subunit (mutant or wild-type) was used at 200 ng/ml. Cells were incubated for 48 hours at 37° C. and cellular viability was evaluated after 16 hours of further incubation with 100 μg/ml of XTT (Sigma-Aldrich) and colorimetric measurement at OD470 nm. Percent viability of the cells was then calculated in comparison to the wells without toxin.

Figure 8A:
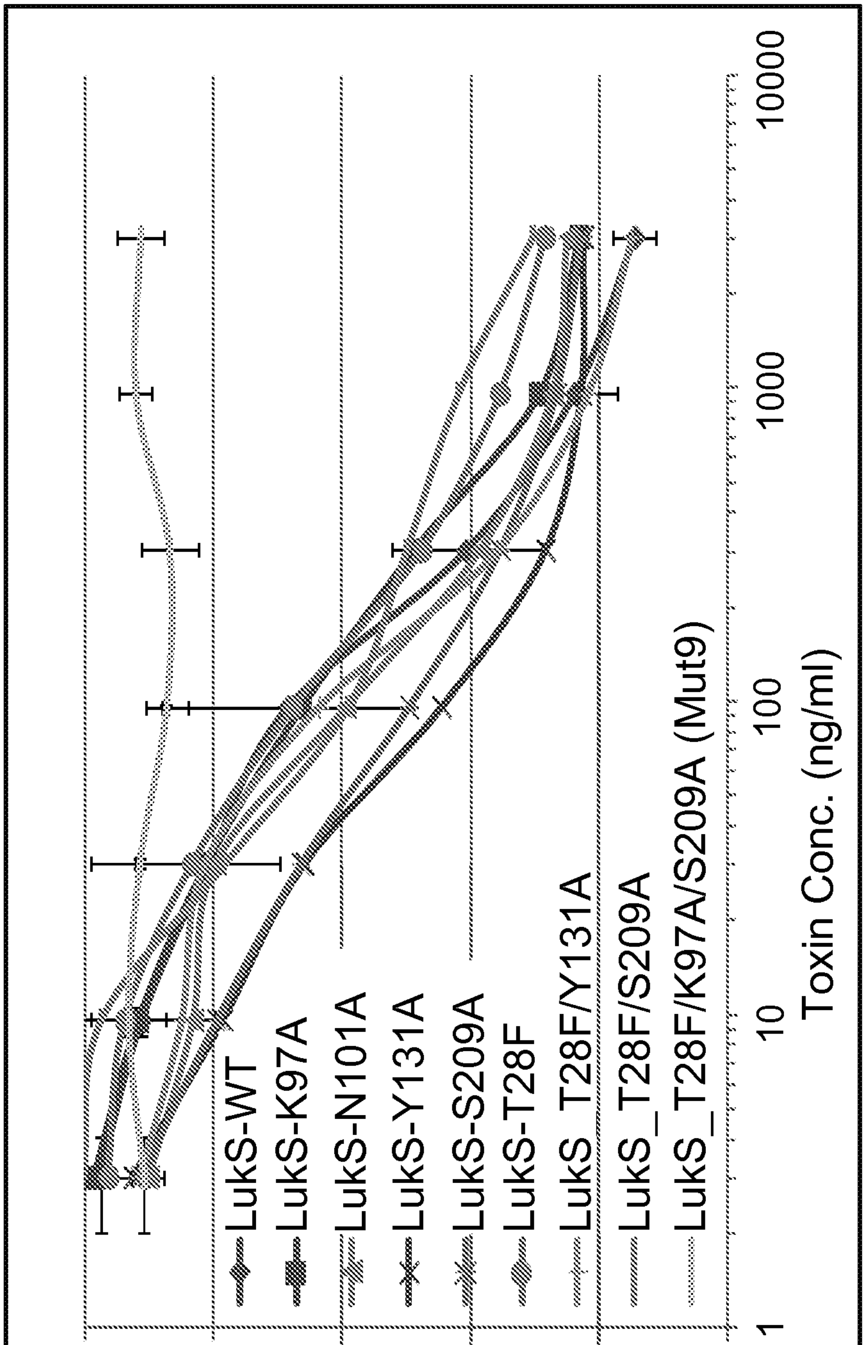
FIG. 8—(A) Percent (%) survival of HL-60 derived neutrophils treated with increasing concentrations of wild-type or mutant LukS in combination with wild-type LukF. Results are from 5 independent experiments. STDV is shown only for wild-type and triple mutant. (B) % survival of HL-60 derived neutrophils treated with increasing concentrations of wild-type or mutant LukF in combination with wild-type LukS or LukS Triple mutant (Mut9). (C) % survival of HL-60 with increasing concentrations of wild-type or triple mutant LukF or LukF mutant 1 in combination with wild-type LukS or LukS Triple mutant (Mut9).
Figure 8B:
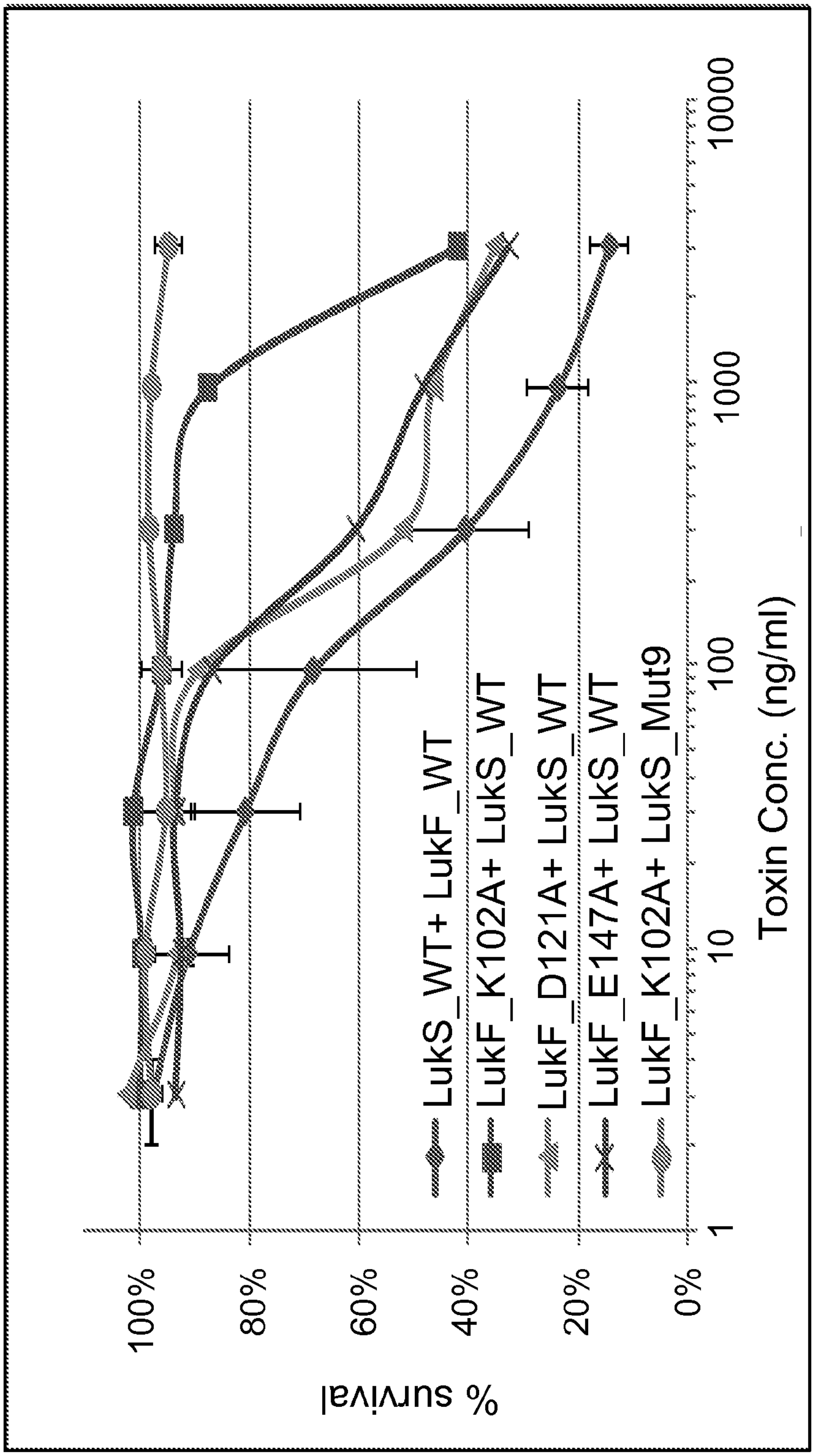
Figure 8C:
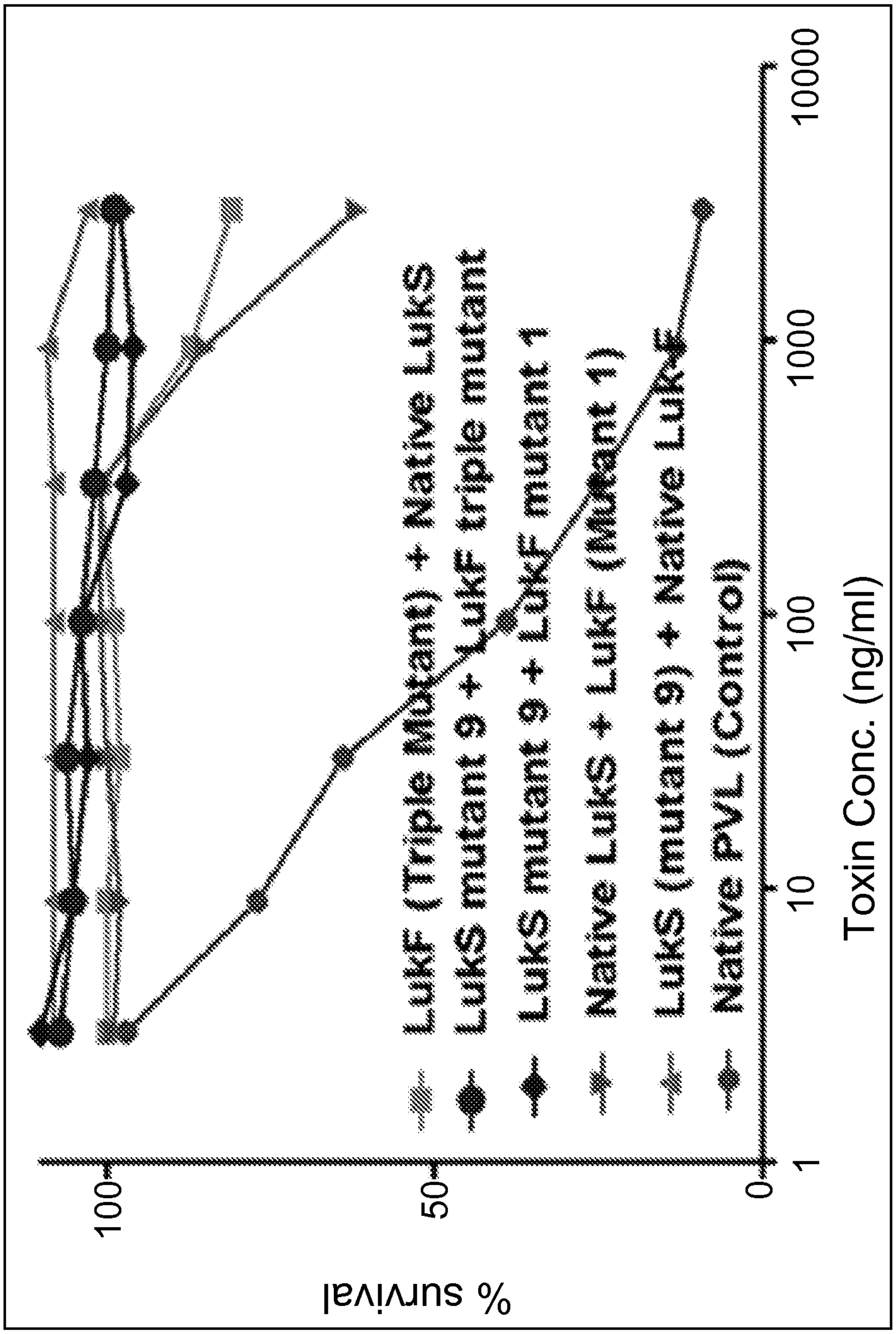

As shown in FIG. 8A, single mutants of LukS-PV did not have a significant impact on toxicity of PVL when the mutant was combined with wild-type LukF, and double mutants slightly reduced the PVL toxicity. However, the triple mutant LukS-PV_T28F/K97A/S209A (denoted as Mut9) was completely attenuated despite combining with wild-type LukF (FIG. 8A). All three single mutants of LukF caused a right shift in dose response curve with the highest attenuation achieved with LukF_K102A (denoted as Mut1) (FIG. 8B). When this mutant was combined with LukS Mut9 no toxicity was observed (FIG. 8B). Low toxicity was observed with LukF mut1 when combined with wild-type LukS toward high concentration. A triple LukF mutant (K102A/D121A/E147A) was constructed and tested. As shown in FIG. 8C, the triple LukF mutant was completely attenuated when combined with wild-type LukS and also with LukS mut9.

Thermal Stability analysis: Thermal stability of LukS-PV and LukF-PV mutant proteins was assessed by Thermofluor (Differential Scanning Fluorimetry) using Sypro Orange as the external fluorescent probe, which binds to hydrophobic residues detecting their exposure during protein unfolding. When heated above critical temperature (>70° C. for LukS and LukF-PV), proteins tend to unfold. This results in increased fluorescence, but if unfolding leads to aggregation the result is a decreased fourescence. This increase and decrease of the fluorescent signal is a means to monitor protein unfolding, calculate the melting temperatures, and compare the thermal stabilities of different proteins under different experimental conditions (Ericsson et al., Anal Biochem, 2006. 357(2): p. 289-98; He et al., J Pharm Sci, 2010. 99(4): p. 1707-20). The results are shown in FIG. 9.

Figure 9A:
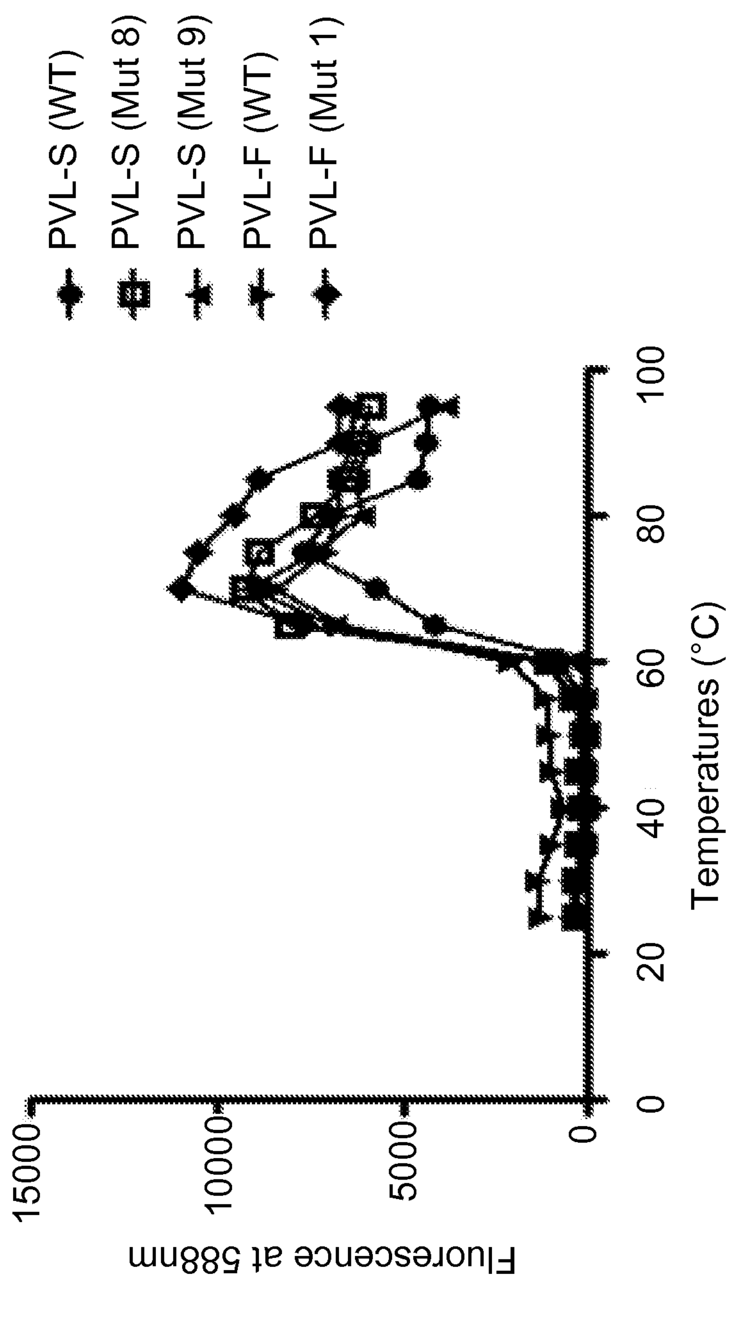
FIG. 9—Thermal unfolding of LukS-PV and LukF-PV proteins as monitored by thermofluor assay using Sypro Orange dye. (A) Plot of fluorescence intensity of PVL proteins (wild-type LukS-PV, LukS-PV Mut 8, LukS-PV Mut 9, wild-type LukF-PV, and LukF-PV Mut 1) at 588 nm against temperature. Data was collected for every 5° C. (B) Plot of unfolded fraction calculated from the thermal denaturation curve for PVL proteins (wild-type LukS-PV, LukS-PV Mut 8, LukS-PV Mut 9, wild-type LukF-PV, and LukF-PV Mut 1).
Figure 9B:
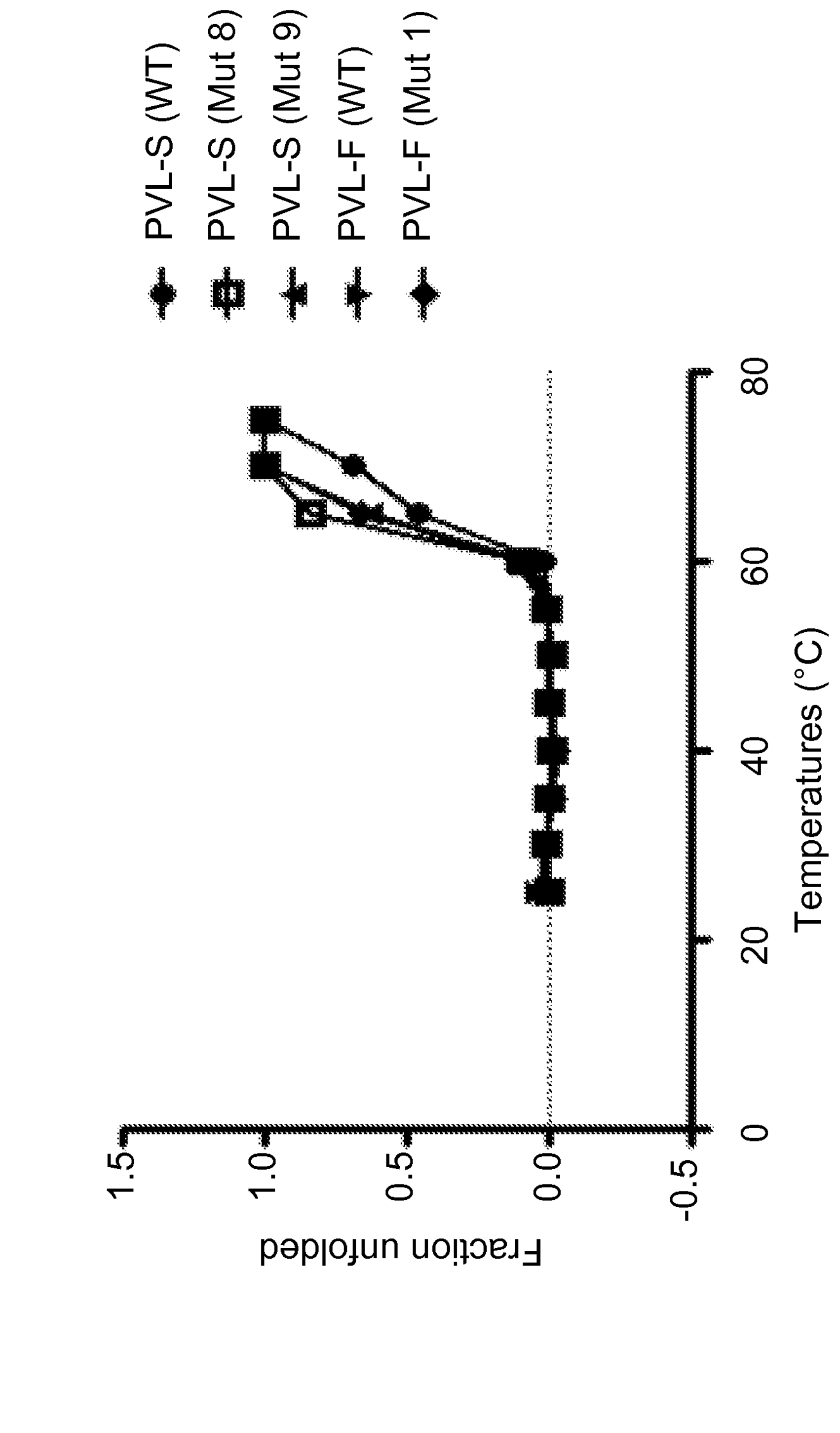

FIG. 9A shows the changes in fluorescent signal of the proteins during thermal unfolding in the presence of dye while FIG. 9B shows the plot of the fraction of unfolded protein based on fitting each protein melting curve using two-state equations as described in Devi et al., Biochemistry, 2006. 45(6): p. 1599-607. Wild-type and mutant proteins of both subunits showed very low background fluorescence when properly folded at 25° C. and retain intensity until 55° C. showing that the proteins were stable. Melting above 55° C. caused an increase in the fluorescent signal, which was due to protein unfolding. This steep increase also supported a highly co-operative unfolding process. LukS-PV wild-type curve was slightly shifted to the right indicating its higher stability. The maximum fluorescence intensity was observed at 75° C. for the LukS-PV wild-type while it was at 70° C. for other mutants. When heated above these temperatures, the fluorescent intensity dropped down for all the proteins indicating an aggregation event was taking place. Therefore, intensity values only up to 75° C. were considered for creating the fraction unfolded protein plot (FIG. 9B). Apparent Tm values from Boltzmann Sigmoid fitting of the data showed that the Tm for all the tested mutants ranged from 62.6 to 63.6, which was similar to wild-type LukS (64.8) and wild-type LukF (62.9) and suggested that that the mutations did not affect the thermal stability of the proteins.

Example 7

Immunogenicity Study in Mice Using Different Clinically Relevant Adjuvants

Immunogenicity and adjuvant studies: An immunogenicity study was performed in mice using different clinically relevant adjuvants including two forms of alum-based adjuvants, Alhydrogel ($Al(OH)_3$) and aluminum phosphate ($AlPO_4$), as well as two novel adjuvants currently in clinical trials IDC-1001 (also known as GLA-SE; glucopyranosyl lipid adjuvant stable emulsion) (Coler et al., PLoS One, 2010. 5(10): p. e13677; Coler et al., PLoS One, 2011. 6(1): p. e16333) and CpG (Mullen et al., PLoS One, 2008. 3(8): p. e2940).

Figure 10A:
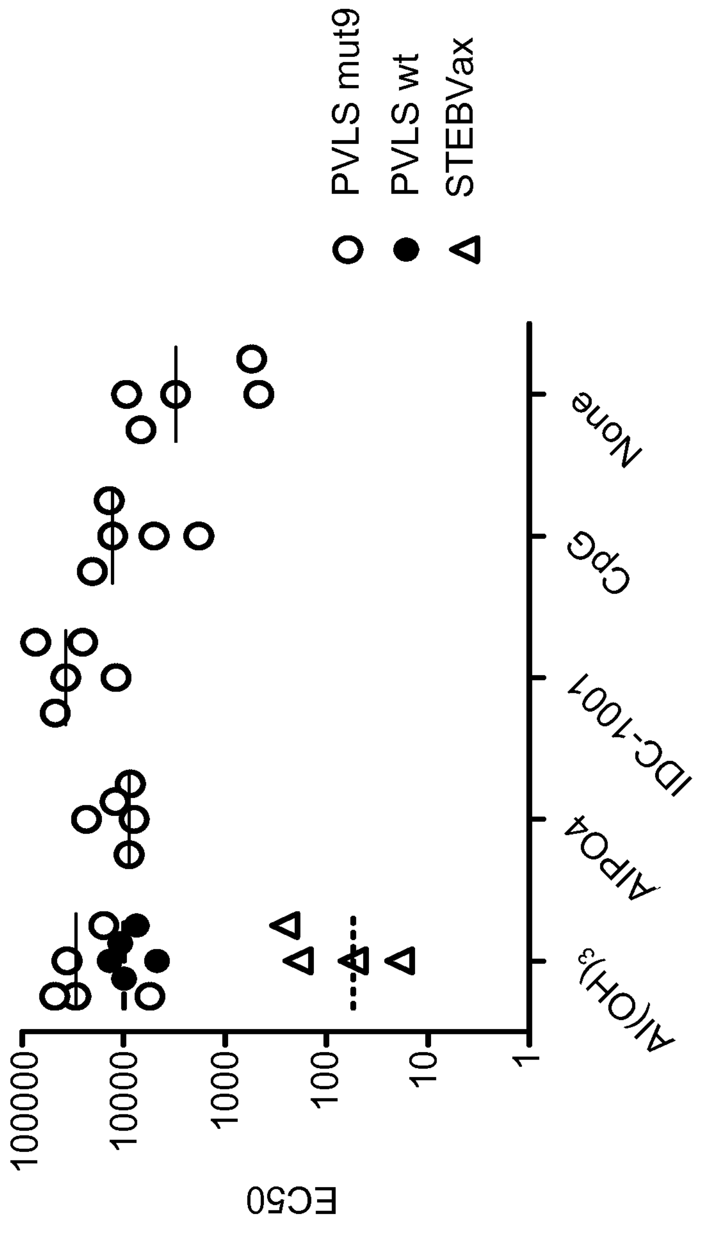
FIG. 10—Immunogenicity of LukS-Mut9, wild-type LukS-PV, and control (STEBVax) in mice with different adjuvants. Doses used: antigens: 10 ug; Al(OH)3: 34 ug, AlPO4: 70 ug, IDC-1001: 20 ug, and CpG: 10 ug/mouse.
Figure 10B:
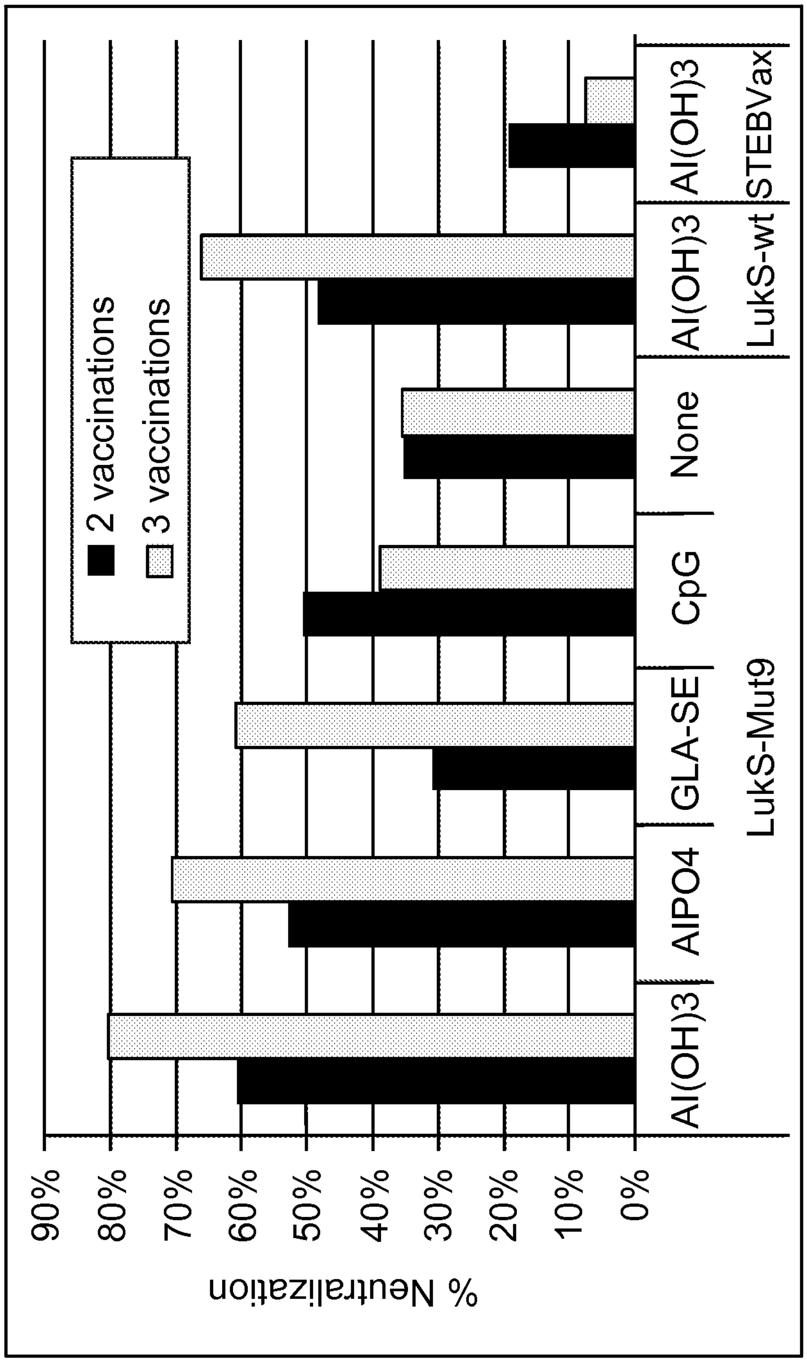

Groups of 5 female BALB/c mice were vaccinated intramuscularly (IM) three times with 5 μg of LukS-PV T28F/K97A/S209A (LukS-Mut9) with each of the adjuvants at 2 week intervals. As controls, the wild-type (wt) LukS-PV as well as an irrelevant antigen (STEBVax; *staph* enterotoxin B vaccine) were combined with Alhydrogel. Mice were bled on days 21 and 35. All tested adjuvants induced robust total antibody response over one log higher than without adjuvant (FIG. 10A). Neutralizing antibody titer was determined using HL-60 derived neutrophils as described above. As shown in FIG. 10B, the highest neutralizing titer was achieved after three vaccinations using the alum-based adjuvants and IDC-1001. The antibody response to LukS-Mut9 was compared to the response to wild-type LukS-PV, and the results supported the conservation of immunological epitopes in the mutant.

Example 8

Efficacy of PVL Vaccine Candidates in Murine Pneumonia and Intraperitoneal Sepsis Models Efficacy studies were performed in murine pneumonia and intraperitoneal sepsis models. Studies were performed to evaluate the efficacy of PVL vaccine candidates alone and in combination with a subunit vaccine for α-hemolysin, AT-62 (Adhikari et al., PLoS One, 2012. 7(6): p. e38567). Initially, passive immunization studies were preformed with lethality and bacterial burden as endpoints using the bacteremia model in mice. Thereafter, proof of concept active immunization studies in both bacteremia/sepsis as well as pneumonia models were performed.

Description of animal models: In the mouse pneumonia model, female BALB/c mice were anesthetized with isoflurane and inoculated intranasally (IN) with a lethal dose (~$2\times10^8$) of USA300 in 50 μl PBS and placed into the cages in a prone position and monitored for morbidity (weight, hunched posture, labored breathing, ruffled fur, impaired mobility) and mortality 4 times a day within the first 48 hours and then once a day until termination of the study. In the bacteremia model, female BALB/c mice were challenged via intra-peritoneal (IP) injection with USA300 in 3% mucin solution as previously described in Fattom et al., Infect Immun, 1996. 64(5): p. 1659-65. Briefly, lypholized hog mucin type III was solubilized to 6% in PBS, sterilized by autoclaving and rapidly cooled on ice. PBS washed, overnight grown bacteria were suspended in PBS at $2\times10^5$ CFU/ml. Bacteria and mucin solution were mixed to achieve the intended challenge dose (see Table 4 below) in 0.5 ml of 3% hog mucin. Mice were monitored for morbidity and mortality twice a day for 7-14 days. Mice were 6 weeks of age for active and 10 weeks for passive immunogenicity studies. To determine bacterial dissemination to organs, mice were euthanized at 12 h after challenge and blood and organs (liver, combined kidneys, lungs and spleen) were aseptically removed, homogenized and taken up in of 500 μl PBS. Blood samples and organ homogenates were streaked in different dilutions on BHI agar plates and CFU was enumerated after ON incubation at 37° C.

Passive immunization studies: The efficacy of rabbit polyclonal antibodies to LukS-PV (LukS-IgG) and Hla (AT62-IgG) alone and in combination was explored in the bacteremia model. Groups of 5 mice were injected IP with different doses of the antibodies, challenged 24 hours later, and monitored for 7 days. As shown in Table 4 (Exp.1), as low as 0.25 mg of LukS-IgG provided full protection. In contrast, 4 mg of AT62-IgG was needed to provide 100% protection with partial efficacy at 2.5 mg (see Table 4 (Exp. 2)).

TABLE 4

Efficacy of passive immunization with rabbit polyclonal antibodies against LukS and Alpha toxin in USA300 bacteremia model

| | Survivor/Total |
|---|---|
| Exp. 1 | |
| 4 mg LukS-IgG | 5/5 |
| 1 mg LukS-IgG | 5/5 |
| 0.25 mg LukS-IgG | 5/5 |
| 4 mg naïve IgG | 0/5 |
| Exp. 2 | |
| 5 mg AT62-IgG | 5/5 |
| 2.5 mg AT62-IgG | 2/5 |
| 1.25 mg AT62-IgG | 1/5 |
| 0.62 mg AT62-IgG | 0/5 |
| 5 mg naïve IgG | 1/5 |

Next, the affinity purified LukS-IgG was combined with a suboptimal dose (2 mg) of AT62-IgG. As shown in Table 5, 50 μg of affinity purified LukS-IgG or 2 mg of AT62-IgG provided partial protection while the combination of the two antibodies at these doses fully protected mice. Full protection was also observed with 2 mg of AT62-IgG and 25 μg of affinity purified LukS-IgG, and 4 out of 5 mice survived with 12.5 μg LukS antibody in the combination with 2 mg of AT62-IgG.

TABLE 5

Combination passive immunization study of rabbit pAb against LukS and Alpha toxin in USA300 bacteremia model

| AT62-IgG | Affinity Pur. LukS-IgG | Naïve IgG | Survivor Total |
|---|---|---|---|
| 2 mg | — | — | 2/5 |
| — | 50 ug | 2 mg | 3/5 |
| 2 mg | 50 ug | — | 5/5 |
| 2 mg | 25 ug | — | 5/5 |
| 2 mg | 12.5 ug | — | 4/5 |
| — | — | 2 mg | 0/5 |

In a set of similar studies, the synergistic effect of pretreatment (24 hours before challenge) with AT62-IgG and LukS-IgG on bacterial dissemination determined 12 hours after USA 300 challenge was tested. As shown in FIG. 11, the two antibodies strongly synergized the reduction of bacterial burden in blood and organs. These data strongly supported that antibodies to LukS and alpha toxin act synergistically in protecting from lethal bacteremia and sepsis.

The efficacy of LukS-PV mut9 and LukF-PV mut1 in combination with alpha toxin vaccine AT-62 was tested in BALB/c mice. Groups of 10 mice were immunized three times IM with 10 μg of each vaccine or BSA (as control) individually or in double or triple combinations at two weeks intervals with $AlPO_4$ in a 1:8 ratio. For the bacteremia/sepsis model, mice were challenged IP on day 42 with 1×LD90 of USA300 ($5\times10^4$ CFU) in 3% mucin and monitored for 7 days. As shown in FIG. 12A, the S and F mutants provided 60% and 40% protection, respectively, and the combination of the two mutant subunits increased protection to 80%, which was similar to AT-62 alone. Full protection was observed when the three antigens were combined together. A similar study was performed in a pneumonia model with a high challenge dose ($2\times10^8$ CFU) of USA300. While none of the individual components provided significant protection, a combination of the two leukocidins with AT-62 led to 50% protection (P=0.0021) (FIG. 12B).

Example 9

Figure 13D:
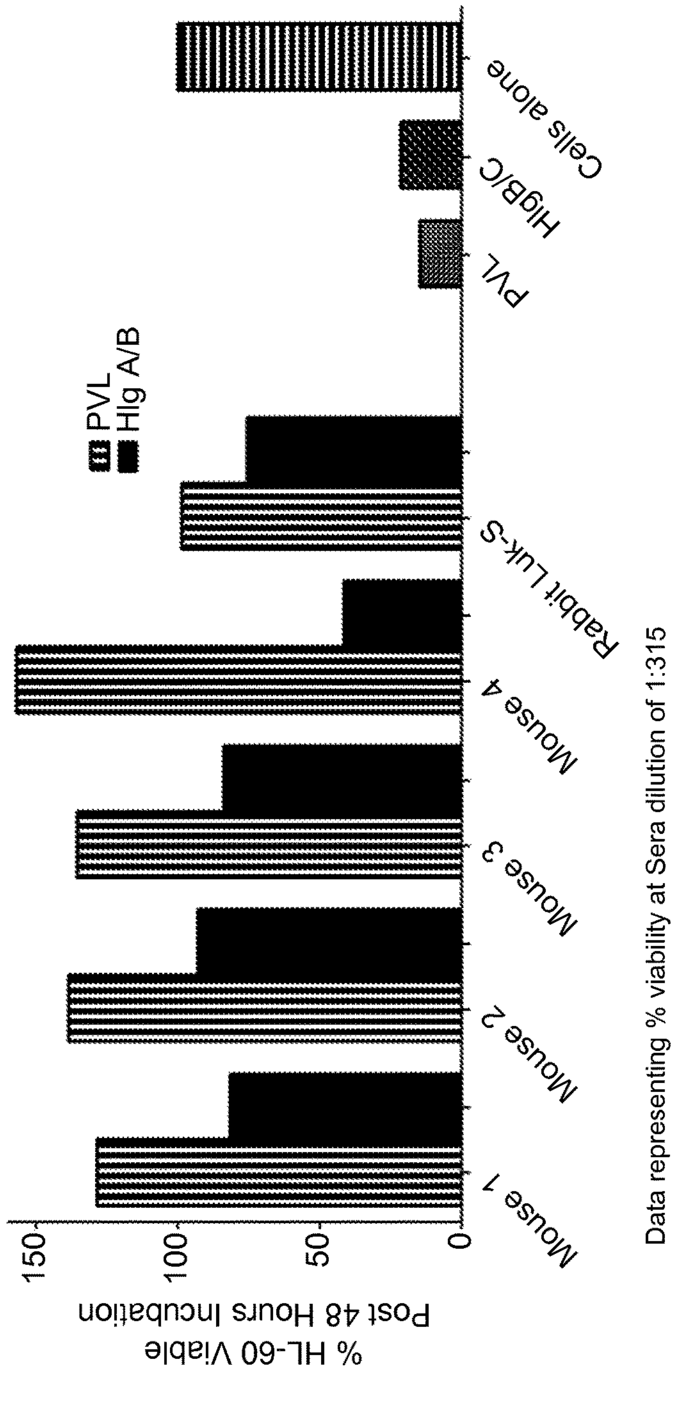

Cross-reactive and Cross-neutralizing Antibody Generated by LukS-PV Mut9 In Vivo An immunogenicity assay was carried out by immunizing the LukS-PV mutant 9 (LukS-PV T28F/K97A/S209A) in a group of 4 mice. Serum samples were collected after the fourth immunization and the antibody titer against wild-type LukS-PV (FIG. 13A), HlgC (FIG. 13B) and HlgB (FIG. 13C) were determined. These results clearly show the presence of cross reactive antibodies for both HlgB and C induced by immunization with LukS-PV mut9. Based on HL-60 cell based neutralization assay, polyclonal anti-LukS-PV mut9 antibody was shown to neutralize both PVL (wild-type LukS-PV+LukF-PV) and Gamma hemolysin (wild type HlgB+HlgC) leukotoxins (FIG. 13D). These experiments further confirmed the induction of cross protective anti-leukotoxin antibodies by immunization with LukS-PV mut9 and supporting the broad spectrum application of this mutant vaccine.

Example 10

Leukocidin Oligomerization and Inhibition of Oligomerization by Antibodies to LukS-PV Oligomerization of the leukocidin components is a required step for cytotoxicity of these toxins. In studies described herein, it was explored whether (i) mutations in LukS-PV or LukF-PV interfere with homologous and/or heterologous oligomerization of the leukocidin components, and (ii) whether antibodies to LukS inhibit homologous and/or heterologous oligomerization. An oligomerization assay for Leukocidin components (PVL and gamma hemolysins) was performed using a 2-methyl-2,4-pentanediol (MPD) based assay as described in Yamashita et al., Proc Natl Acad Sci USA, 2011. 108(42): p. 17314-9. Briefly, equal amounts of both components were incubated together in the presence of 40% MPD for 24 hours at room temperature. Samples were run in a SDS PAGE without boiling and gels were stained with Gel Code Blue™ reagent. For the inhibition of PVL oligomerization, LukS-PV was pre-incubated with rabbit anti-LukS-PV polyclonal antibodies (pAbs) at decreasing concentration for 30 minutes. An equal amount of LukF-PV was added to the mix and incubated at room temperature in the presence of 40% MPD for 24 hours. Samples were analyzed in a SDS PAGE without boiling and gels were stained with Gel Code Blue™ reagent.

As shown in FIG. 14A (Lane 2), wild-type (wt) forms of LukS-PV and LukF-PV formed an oligomeric band of >160 kd. A similar oligomeric band was seen with LukF-PV mutant 1 in combination with wild-type LukS-PV (FIG. 14A, Lane 3). Cross oligomerization between wild-type LukS-PV and gamma hemolysin component B was shown (FIG. 14A, Lane 4). However, LukS-PV mutant 9 did not oligomerize with either wild-type LukF-PV or with LukF-PV mutant 1 (FIG. 14A, Lanes 5 and 6), which is consistent with the attenuated toxicity observed for LukS-PV mutant 9. This mutant also did not oligomerize with wild-type gamma hemolysin B subunit (FIG. 14A, Lane 7), further confirming its safety to use as a vaccine candidate. FIG. 14B, shows the inhibition of oligomerization of wild-type LukS-PV/LukF-PV with rabbit polyclonal anti-LukS antibody in a dose dependent manner. FIG. 14C, showed that rabbit polyclonal anti-LukS antibody was also able to cross inhibit the heterologous oligomerization of LukS-PV+hlgB.

The present disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated mutant staphylococcal leukocidin subunit polypeptide comprising a wild-type staphylococcal leukocidin subunit except for one to five amino acid substitutions at conserved residues, which reduce toxicity of the mutant leukocidin subunit relative to the corresponding wild-type leukocidin subunit;

wherein the wild-type leukocidin subunit comprises the amino acid sequence SEQ ID NO: 6 and wherein the mutant staphylococcal leukocidin subunit polypeptide comprises an amino acid substitution at a position corresponding to K97 of SEQ ID NO: 6, wherein the wild-type leukocidin subunit comprises the amino acid sequence SEQ ID NO: 15 and wherein the mutant staphylococcal leukocidin subunit polypeptide comprises an amino acid substitution at a position corresponding to K125of SEQ ID NO: 15, wherein the wild-type leukocidin subunit comprises the amino acid sequence SEQ ID NO: 17 and wherein the mutant staphylococcal leukocidin subunit polypeptide comprises an amino acid substitution at a position corresponding to K102 of SEQ ID NO: 17, wherein the wild-type leukocidin subunit comprises the amino acid sequence SEQ ID NO: 21 and wherein the mutant staphylococcal leukocidin subunit polypeptide comprises an amino acid substitution at a position corresponding to K126 of SEQ ID NO: 21, wherein the wild-type leukocidin subunit comprises the amino acid sequence SEQ ID NO: 22 and wherein the mutant staphylococcal leukocidin subunit polypeptide comprises an amino acid substitution at a position corresponding to K126 of SEQ ID NO: 22, wherein the wild-type leukocidin subunit comprises the amino acid sequence SEQ ID NO: 23 and wherein the mutant staphylococcal leukocidin subunit polypeptide comprises an amino acid substitution at a position corresponding to K126 of SEQ ID NO: 23, wherein the wild-type leukocidin subunit comprises the amino acid sequence SEQ ID NO: 24 and wherein the mutant staphylococcal leukocidin subunit polypeptide comprises an amino acid substitution at a position corresponding to K128 of SEQ ID NO: 24, wherein the wild-type leukocidin subunit comprises the amino acid sequence SEQ ID NO: 25 and wherein the mutant staphylococcal leukocidin subunit polypeptide comprises an amino acid substitution at a position corresponding to K128 of SEQ ID NO: 25, wherein the wild-type leukocidin subunit comprises the amino acid sequence SEQ ID NO: 26 and wherein the mutant staphylococcal leukocidin subunit polypeptide comprises an amino acid substitution at a position corresponding to K128 of SEQ ID NO: 26, or wherein the wild-type leukocidin subunit comprises the amino acid sequence SEQ ID NO: 27 and wherein the mutant staphylococcal leukocidin subunit polypeptide comprises an amino acid substitution at a position corresponding to K128 of SEQ ID NO: 27.

2. The mutant leukocidin subunit of claim 1, wherein the wild-type leukocidin subunit is a Panton-Valentine leukocidin (PVL) LukS-PV comprising the amino acid sequence SEQ ID NO: 6.

3. The mutant leukocidin subunit of claim 2, wherein the subunit comprises the amino acid sequence SEQ ID NO: 7 or SEQ ID NO: 14.

4. The mutant leukocidin subunit of claim 3 comprising the amino acid sequence SEQ ID NO: 14.

5. The mutant leukocidin subunit of claim 1, wherein the wild-type leukocidin subunit is a Panton-Valentine leukocidin (PVL) LukF-PV comprising the amino acid sequence SEQ ID NO: 17.

6. The mutant leukocidin subunit of claim 5, wherein the subunit comprises the amino acid sequence SEQ ID NO: 18 or SEQ ID NO: 136.

7. The mutant leukocidin subunit of claim 6 comprising the amino acid sequence SEQ ID NO: 18.

8. A composition comprising the mutant leukocidin subunit of claim 1 and a carrier.

9. A method of inducing a host immune response against a *Staphylococcus aureus* strain, comprising administering to a subject in need of the immune response an effective amount of the composition of claim 8.

10. The mutant leukocidin subunit of claim 6 comprising the amino acid sequence SEQ ID NO: 136.

11. A composition comprising the mutant leukocidin subunit of claim 6 and a carrier.

12. A method of inducing a host immune response against a *Staphylococcus aureus* strain, comprising administering to a subject in need of the immune response an effective amount of the composition of claim 11.

13. A composition comprising the mutant leukocidin subunit of claim 3 and a carrier.

14. A method of inducing a host immune response against a *Staphylococcus aureus* strain, comprising administering to a subject in need of the immune response an effective amount of the composition of claim 13.

15. A composition comprising the mutant leukocidin subunit of claim 4 and a carrier.

16. A method of inducing a host immune response against a *Staphylococcus aureus* strain, comprising administering to a subject in need of the immune response an effective amount of the composition of claim 15.

17. A composition comprising the mutant leukocidin subunit of claim 7 and a carrier.

18. A method of inducing a host immune response against a *Staphylococcus aureus* strain, comprising administering to a subject in need of the immune response an effective amount of the composition of claim 17.

19. A composition comprising the mutant leukocidin subunit of claim 10 and a carrier.

20. A method of inducing a host immune response against a *Staphylococcus aureus* strain, comprising administering to a subject in need of the immune response an effective amount of the composition of claim 19.

21. The mutant leukocidin subunit of claim 1, wherein the substituted wild-type lysine (K) is substituted with an alanine (A).

* * * * *